(12) United States Patent
Gurney et al.

(10) Patent No.: US 11,512,128 B2
(45) Date of Patent: *Nov. 29, 2022

(54) VEGF/DLL4 BINDING AGENTS AND USES THEREOF

(71) Applicant: MEREO BIOPHARMA 5, INC., Redwood City, CA (US)

(72) Inventors: Austin L. Gurney, San Francisco, CA (US); Aaron Ken Sato, Burlingame, CA (US); Christopher John Bond, San Mateo, CA (US)

(73) Assignee: MEREO BIOPHARMA 5, INC., Redwood City, CA (US)

( * ) Notice: Subject to any disclaimer, the term of this patent is extended or adjusted under 35 U.S.C. 154(b) by 165 days.

This patent is subject to a terminal disclaimer.

(21) Appl. No.: 16/928,452

(22) Filed: Jul. 14, 2020

(65) Prior Publication Data

US 2021/0061903 A1    Mar. 4, 2021

Related U.S. Application Data

(60) Continuation of application No. 15/847,335, filed on Dec. 19, 2017, now Pat. No. 10,730,940, which is a division of application No. 15/401,543, filed on Jan. 9, 2017, now Pat. No. 9,879,084, which is a division of application No. 15/163,301, filed on May 24, 2016, now Pat. No. 9,574,009, which is a division of application No. 14/476,582, filed on Sep. 3, 2014, now Pat. No. 9,376,488, which is a division of application No. 13/625,417, filed on Sep. 24, 2012, now Pat. No. 8,858,941.

(60) Provisional application No. 61/695,978, filed on Aug. 24, 2012, provisional application No. 61/597,409, filed on Feb. 10, 2012, provisional application No. 61/538,454, filed on Sep. 23, 2011.

(51) Int. Cl.

| A61K 39/395 | (2006.01) |
|---|---|
| C07K 16/22 | (2006.01) |
| C07K 16/28 | (2006.01) |
| A61K 45/06 | (2006.01) |
| A61K 31/4745 | (2006.01) |
| A61K 31/7068 | (2006.01) |
| A61K 39/00 | (2006.01) |
| A61K 45/00 | (2006.01) |
| C07K 16/18 | (2006.01) |
| C07K 16/30 | (2006.01) |

(52) U.S. Cl.
CPC .......... *C07K 16/28* (2013.01); *A61K 31/4745* (2013.01); *A61K 31/7068* (2013.01); *A61K 39/00* (2013.01); *A61K 39/395* (2013.01); *A61K 39/3955* (2013.01); *A61K 45/00* (2013.01); *A61K 45/06* (2013.01); *C07K 16/18* (2013.01); *C07K 16/22* (2013.01); *C07K 16/30* (2013.01); *C07K 16/303* (2013.01); *C07K 16/3046* (2013.01); *A61K 2039/505* (2013.01); *C07K 2317/31* (2013.01); *C07K 2317/56* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 3,773,919 | A | 11/1973 | Boswell et al. |
|---|---|---|---|
| 4,485,045 | A | 11/1984 | Regen |
| 4,544,545 | A | 10/1985 | Ryan et al. |
| 4,816,567 | A | 3/1989 | Cabilly et al. |
| 5,013,556 | A | 5/1991 | Woodle et al. |
| 5,225,539 | A | 7/1993 | Winter |
| 5,545,806 | A | 8/1996 | Lonberg et al. |
| 5,545,807 | A | 8/1996 | Surani et al. |
| 5,569,825 | A | 10/1996 | Lonberg et al. |
| 5,574,009 | A | 11/1996 | Cohen et al. |
| 5,585,089 | A | 12/1996 | Queen et al. |
| 5,625,126 | A | 4/1997 | Lonberg et al. |

(Continued)

FOREIGN PATENT DOCUMENTS

| CA | 2789446 A1 | 8/2011 |
|---|---|---|
| CN | 1176659 A | 3/1998 |

(Continued)

OTHER PUBLICATIONS

Al-Hajj, M., et al., "Prospective Identification of Tumorigenic Breast Cancer Cells," Proceedings of the National Academy of Sciences 100(7):3983-3988, The National Academy of Sciences, United States (2003).

(Continued)

*Primary Examiner* — Christine J Saoud
*Assistant Examiner* — Jon M Lockard
(74) *Attorney, Agent, or Firm* — Sterne, Kessler, Goldstein & Fox P.L.L.C.

(57) ABSTRACT

The present invention relates to VEGF-binding agents, DLL4-binding agents, VEGF/DLL4 bispecific binding agents, and methods of using the agents for treating diseases such as cancer. The present invention provides antibodies that specifically bind human VEGF, antibodies that specifically bind human DLL4, and bispecific antibodies that specifically bind human VEGF and/or human DLL4. The present invention further provides methods of using the agents to inhibit tumor growth. Also described are methods of treating cancer comprising administering a therapeutically effect amount of an agent or antibody of the present invention to a patient having a tumor or cancer.

20 Claims, 12 Drawing Sheets

Figure 2:
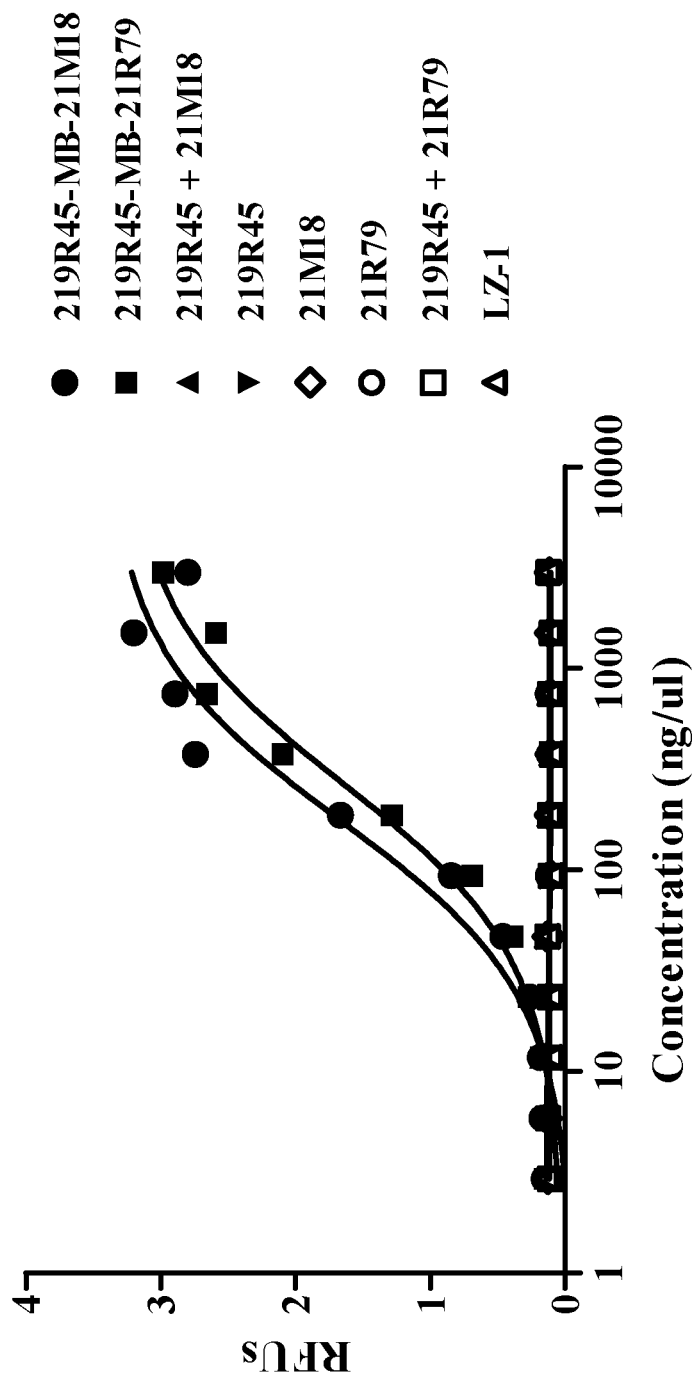

Specification includes a Sequence Listing.

(56) References Cited

U.S. PATENT DOCUMENTS

| | | |
|---|---|---|
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,730,977 A | 3/1998 | Ooka et al. |
| 5,731,168 A | 3/1998 | Carter et al. |
| 5,750,373 A | 5/1998 | Garrard et al. |
| 5,821,333 A | 10/1998 | Carter et al. |
| 5,840,299 A | 11/1998 | Bendig et al. |
| 5,849,869 A | 12/1998 | Artavanis-Tsakonas et al. |
| 6,004,528 A | 12/1999 | Bergstein |
| 6,024,955 A | 2/2000 | Asano et al. |
| 6,121,045 A | 9/2000 | McCarthy et al. |
| 6,262,025 B1 | 7/2001 | Ish-Horowicz et al. |
| 6,342,219 B1 | 1/2002 | Thorpe et al. |
| 6,524,583 B1 | 2/2003 | Thorpe et al. |
| 6,582,959 B2 | 6/2003 | Kim et al. |
| 6,664,098 B1 | 12/2003 | Sakano |
| 6,676,941 B2 | 1/2004 | Thorpe et al. |
| 6,689,744 B2 | 2/2004 | Gao et al. |
| 6,833,441 B2 | 12/2004 | Wang et al. |
| 6,887,468 B1 | 5/2005 | Thorpe et al. |
| 6,984,522 B2 | 1/2006 | Clarke et al. |
| 7,022,499 B2 | 4/2006 | Sakano |
| 7,056,509 B2 | 6/2006 | Thorpe et al. |
| 7,060,269 B1 | 6/2006 | Baca et al. |
| 7,118,890 B2 | 10/2006 | Ish-Horowicz et al. |
| 7,183,076 B2 | 2/2007 | Arathoon et al. |
| 7,227,004 B2 | 6/2007 | Kim |
| 7,354,581 B2 | 4/2008 | Cedarbaum et al. |
| 7,449,182 B2 | 11/2008 | Cedarbaum et al. |
| 7,482,005 B2 | 1/2009 | Kim et al. |
| 7,488,806 B2 | 2/2009 | Papadopoulos et al. |
| 7,531,172 B2 | 5/2009 | Stahl et al. |
| 7,534,868 B1 | 5/2009 | Papadopoulos et al. |
| 7,642,228 B2 | 1/2010 | Carter et al. |
| 7,695,936 B2 | 4/2010 | Carter et al. |
| 7,750,124 B2 | 7/2010 | Gurney et al. |
| 7,754,206 B2 | 7/2010 | Clarke et al. |
| 7,758,859 B2 | 7/2010 | Fuh et al. |
| 7,803,377 B2 | 9/2010 | Yan et al. |
| 7,897,725 B2 | 3/2011 | McCarthy et al. |
| 7,906,116 B2 | 3/2011 | Gill et al. |
| 7,910,098 B2 | 3/2011 | Fuh et al. |
| 7,919,593 B2 | 4/2011 | Papadopoulos et al. |
| 7,951,917 B1 | 5/2011 | Arathoon et al. |
| 8,048,418 B2 | 11/2011 | Noguera-Troise et al. |
| 8,133,857 B2 | 3/2012 | Aikawa |
| 8,192,738 B2 | 6/2012 | Bedian et al. |
| 8,216,571 B2 | 7/2012 | Ramachandra et al. |
| 8,216,805 B2 | 7/2012 | Carter et al. |
| 8,404,233 B2 | 3/2013 | Sunamura et al. |
| 8,512,699 B2 | 8/2013 | Fuh et al. |
| 8,518,887 B2 | 8/2013 | Noguera-Troise et al. |
| 8,557,965 B2 | 10/2013 | Saunders et al. |
| 8,592,562 B2 | 11/2013 | Kannan et al. |
| 8,592,563 B2 | 11/2013 | Bates et al. |
| 8,642,745 B2 | 2/2014 | Arathoon et al. |
| 8,679,785 B2 | 3/2014 | Carter et al. |
| 8,685,401 B2 | 4/2014 | Harris et al. |
| 8,765,125 B2 | 7/2014 | Skokos |
| 8,765,412 B2 | 7/2014 | Arathoon et al. |
| 8,840,886 B2 | 9/2014 | Noguera-Troise et al. |
| 8,858,941 B2 | 10/2014 | Gurney et al. |
| 8,883,145 B2 | 11/2014 | Stagg et al. |
| 8,889,131 B2 | 11/2014 | Aikawa et al. |
| 8,889,133 B2 | 11/2014 | Skokos |
| 9,029,508 B2 | 5/2015 | Ghayur et al. |
| 9,067,986 B2 | 6/2015 | Gurney et al. |
| 9,115,195 B2 | 8/2015 | Chen et al. |
| 9,132,190 B2 | 9/2015 | Benatuil et al. |
| 9,228,020 B2 | 1/2016 | Gurney et al. |
| 9,309,311 B2 | 4/2016 | Gurney et al. |
| 9,376,488 B2 | 6/2016 | Gurney et al. |
| 9,376,497 B2 | 6/2016 | Gurney et al. |
| 9,403,904 B2 | 8/2016 | Smider et al. |
| 9,469,689 B2 | 10/2016 | Chen et al. |
| 9,511,139 B2 | 12/2016 | Stagg et al. |
| 9,574,009 B2 | 2/2017 | Gurney et al. |
| 9,598,483 B2 | 3/2017 | Kim et al. |
| 9,599,620 B2 | 3/2017 | Benner et al. |
| RE46,534 E | 9/2017 | Baldwin et al. |
| 9,873,740 B2 | 1/2018 | Grogan et al. |
| 9,879,084 B2 | 1/2018 | Gurney et al. |
| 9,914,771 B2 | 3/2018 | Gurney et al. |
| RE46,805 E | 4/2018 | Baldwin et al. |
| RE46,816 E | 5/2018 | Baldwin et al. |
| 9,982,042 B2 | 5/2018 | Stagg et al. |
| 994,637 A1 | 6/2018 | Gao et al. |
| 10,730,940 B2 | 8/2020 | Gurney et al. |
| 10,870,693 B2 | 12/2020 | Stagg et al. |
| 11,046,760 B2 | 6/2021 | Murriel et al. |
| 11,339,213 B2 | 5/2022 | Dupont et al. |
| 2002/0028488 A1 | 3/2002 | Singh et al. |
| 2002/0032315 A1 | 3/2002 | Baca et al. |
| 2002/0062010 A1 | 5/2002 | Arathoon et al. |
| 2003/0175877 A1 | 9/2003 | Baker et al. |
| 2003/0180784 A1 | 9/2003 | McCarthy et al. |
| 2004/0123343 A1 | 6/2004 | La et al. |
| 2004/0133357 A1 | 7/2004 | Zhong et al. |
| 2004/0137569 A1 | 7/2004 | Chan et al. |
| 2004/0265307 A1 | 12/2004 | Singh et al. |
| 2004/0265309 A1 | 12/2004 | Kandel et al. |
| 2005/0026831 A1 | 2/2005 | Bodmer et al. |
| 2005/0054036 A1 | 3/2005 | Bates et al. |
| 2005/0059093 A1 | 3/2005 | Bodmer et al. |
| 2005/0079184 A1 | 4/2005 | Hsing-Chang et al. |
| 2005/0089518 A1 | 4/2005 | Clarke et al. |
| 2005/0112121 A1 | 5/2005 | Artavanis-Tsakonas et al. |
| 2005/0137130 A1 | 6/2005 | Bodmer et al. |
| 2005/0170398 A1 | 8/2005 | Van et al. |
| 2005/0232927 A1 | 10/2005 | Clarke et al. |
| 2005/0261477 A1 | 11/2005 | Champion et al. |
| 2005/0276808 A1 | 12/2005 | Cedarbaum |
| 2005/0281822 A1 | 12/2005 | Cedarbaum et al. |
| 2006/0084588 A1 | 4/2006 | Briend et al. |
| 2006/0122373 A1 | 6/2006 | McCarthy et al. |
| 2006/0134080 A1 | 6/2006 | Lyden et al. |
| 2006/0134121 A1 | 6/2006 | Thurston et al. |
| 2006/0204493 A1 | 9/2006 | Huang et al. |
| 2006/0280747 A1 | 12/2006 | Fuh et al. |
| 2007/0004909 A1 | 1/2007 | Johnson et al. |
| 2007/0020267 A1 | 1/2007 | Fuh et al. |
| 2007/0036797 A1 | 2/2007 | Kim et al. |
| 2007/0062010 A1 | 3/2007 | Van Doom |
| 2007/0082846 A1 | 4/2007 | Ish-Horowicz et al. |
| 2007/0098712 A1 | 5/2007 | Arathoon et al. |
| 2007/0105199 A1 | 5/2007 | Yan et al. |
| 2007/0141065 A1 | 6/2007 | Fuh et al. |
| 2007/0154391 A1 | 7/2007 | Kim et al. |
| 2007/0178552 A1 | 8/2007 | Arathoon et al. |
| 2007/0190573 A1 | 8/2007 | Hess et al. |
| 2007/0190647 A1 | 8/2007 | Clarke et al. |
| 2007/0196374 A1 | 8/2007 | Baca et al. |
| 2007/0202102 A1 | 8/2007 | Bizzini et al. |
| 2007/0212354 A1 | 9/2007 | Yung et al. |
| 2007/0213266 A1 | 9/2007 | Gill et al. |
| 2007/0231325 A1 | 10/2007 | Clarke et al. |
| 2007/0287170 A1 | 12/2007 | Davis et al. |
| 2008/0014196 A1 | 1/2008 | Yan |
| 2008/0063635 A1 | 3/2008 | Takahashi et al. |
| 2008/0069820 A1 | 3/2008 | Fuh et al. |
| 2008/0107648 A1 | 5/2008 | Noguera et al. |
| 2008/0175847 A1 | 7/2008 | Yan et al. |
| 2008/0181893 A1 | 7/2008 | Lobov et al. |
| 2008/0181899 A1 | 7/2008 | Papadopoulos et al. |
| 2008/0187532 A1 | 8/2008 | Gurney et al. |
| 2008/0220495 A1 | 9/2008 | McCarthy et al. |
| 2009/0004205 A1 | 1/2009 | Clarke et al. |
| 2009/0017035 A1 | 1/2009 | Papadopoulos et al. |
| 2009/0023591 A1 | 1/2009 | Spanuth |
| 2009/0035308 A1 | 2/2009 | Gill et al. |
| 2009/0142354 A1 | 6/2009 | Papadopoulos et al. |

(56) References Cited

U.S. PATENT DOCUMENTS

| | | |
|---|---|---|
| 2009/0217401 A1 | 8/2009 | Korman et al. |
| 2009/0221549 A1 | 9/2009 | Gerber et al. |
| 2009/0246199 A1 | 10/2009 | Noguera-Troise et al. |
| 2009/0286956 A1 | 11/2009 | McCarthy et al. |
| 2010/0015133 A1 | 1/2010 | Igawa et al. |
| 2010/0076178 A1 | 3/2010 | Ghayur et al. |
| 2010/0086544 A1 | 4/2010 | Mass et al. |
| 2010/0119526 A1 | 5/2010 | Hellstroem |
| 2010/0129356 A1 | 5/2010 | Yan |
| 2010/0150940 A1 | 6/2010 | Adam et al. |
| 2010/0215779 A1 | 8/2010 | Currie et al. |
| 2010/0221250 A1 | 9/2010 | Kim et al. |
| 2010/0260668 A1 | 10/2010 | Ghayur et al. |
| 2010/0266589 A1 | 10/2010 | Hedrick et al. |
| 2010/0272733 A1 | 10/2010 | Bates et al. |
| 2010/0286374 A1 | 11/2010 | Kannan et al. |
| 2010/0316637 A1 | 12/2010 | Gurney et al. |
| 2011/0052575 A1 | 3/2011 | Baca et al. |
| 2011/0052576 A1 | 3/2011 | Ferrara et al. |
| 2011/0076279 A1 | 3/2011 | Ramachandra et al. |
| 2011/0081342 A1 | 4/2011 | Baca et al. |
| 2011/0091372 A1 | 4/2011 | Ghayur et al. |
| 2011/0113865 A1 | 5/2011 | Hess et al. |
| 2011/0117079 A1 | 5/2011 | Benatuil et al. |
| 2011/0123532 A1 | 5/2011 | Gurney et al. |
| 2011/0159009 A1 | 6/2011 | Fuh et al. |
| 2011/0165162 A1 | 7/2011 | Hoey et al. |
| 2011/0172398 A1 | 7/2011 | Borges et al. |
| 2011/0195494 A1 | 8/2011 | Borges et al. |
| 2011/0217237 A1 | 9/2011 | Chen et al. |
| 2011/0306044 A1 | 12/2011 | McCarthy et al. |
| 2012/0116057 A1 | 5/2012 | Kannan et al. |
| 2012/0245151 A1 | 9/2012 | Gavai et al. |
| 2012/0258108 A1 | 10/2012 | Ghayur et al. |
| 2012/0263721 A1 | 10/2012 | Stagg et al. |
| 2012/0288496 A1 | 11/2012 | Gurney et al. |
| 2013/0131076 A1 | 5/2013 | Fernandez et al. |
| 2013/0164295 A1 | 6/2013 | Gurney et al. |
| 2013/0253172 A1 | 9/2013 | Gurney et al. |
| 2013/0266569 A1 | 10/2013 | Gurney et al. |
| 2013/0309250 A1 | 11/2013 | Cogswell et al. |
| 2013/0323248 A1 | 12/2013 | Gros et al. |
| 2013/0323260 A1 | 12/2013 | Walsh et al. |
| 2013/0323265 A1 | 12/2013 | Stagg et al. |
| 2014/0017244 A1 | 1/2014 | Duerr et al. |
| 2014/0093499 A1 | 4/2014 | Gschwind et al. |
| 2014/0134169 A1 | 5/2014 | Kuhnert et al. |
| 2014/0134172 A1 | 5/2014 | Gu et al. |
| 2014/0147443 A9 | 5/2014 | Gurney et al. |
| 2014/0154255 A1 | 6/2014 | Akamatsu et al. |
| 2014/0206853 A1 | 7/2014 | Foltz et al. |
| 2014/0220001 A1 | 8/2014 | Benner et al. |
| 2014/0227252 A1 | 8/2014 | Benner et al. |
| 2014/0348835 A1 | 11/2014 | Gu et al. |
| 2015/0005475 A1 | 1/2015 | Kucia et al. |
| 2015/0098949 A1 | 4/2015 | Gurney et al. |
| 2015/0118232 A1 | 4/2015 | Stagg et al. |
| 2015/0183856 A1 | 7/2015 | Kim et al. |
| 2016/0068596 A1 | 3/2016 | De Sauvage et al. |
| 2016/0176963 A1 | 6/2016 | Maurer et al. |
| 2016/0280774 A1 | 9/2016 | Gurney et al. |
| 2016/0289317 A1 | 10/2016 | Bollag et al. |
| 2016/0362499 A1 | 12/2016 | Gurney et al. |
| 2016/0367667 A1 | 12/2016 | Gurney et al. |
| 2017/0037127 A1 | 2/2017 | Grogan et al. |
| 2017/0044256 A1 | 2/2017 | Grogan et al. |
| 2017/0143825 A1 | 5/2017 | Grogan et al. |
| 2017/0145093 A1 | 5/2017 | Clark et al. |
| 2017/0183406 A1 | 6/2017 | Gurney et al. |
| 2018/0273618 A1 | 9/2018 | Murriel et al. |
| 2018/0346556 A1 | 12/2018 | Stagg et al. |
| 2019/0023776 A1 | 1/2019 | Dupont et al. |
| 2021/0403553 A1 | 12/2021 | Murriel et al. |

FOREIGN PATENT DOCUMENTS

| | | |
|---|---|---|
| CN | 1511850 A | 7/2004 |
| CN | 1558916 A | 12/2004 |
| CN | 1668636 A | 9/2005 |
| EP | 0662827 A1 | 7/1995 |
| EP | 0861894 A1 | 9/1998 |
| EP | 1004669 A1 | 5/2000 |
| EP | 0662827 B1 | 4/2002 |
| EP | 1179541 B1 | 6/2004 |
| EP | 0979281 B1 | 7/2005 |
| EP | 1615036 A1 | 1/2006 |
| EP | 0972041 B1 | 10/2006 |
| EP | 1810979 A1 | 7/2007 |
| EP | 1870459 A1 | 12/2007 |
| EP | 2488204 A1 | 8/2012 |
| EP | 3050963 A1 | 8/2016 |
| EP | 3183267 A1 | 6/2017 |
| EP | 3214095 A1 | 9/2017 |
| EP | 3237448 A1 | 11/2017 |
| EP | 3353210 A1 | 8/2018 |
| EP | 3020731 B1 | 6/2019 |
| GB | 2449354 A | 11/2008 |
| JP | 2008528958 A | 7/2008 |
| JP | 2011505135 A | 2/2011 |
| WO | WO-9219734 A1 | 11/1992 |
| WO | WO-9407474 A1 | 4/1994 |
| WO | WO-9627011 A1 | 9/1996 |
| WO | WO-9701571 A1 | 1/1997 |
| WO | WO-9845331 A2 | 10/1998 |
| WO | WO-9845434 A1 | 10/1998 |
| WO | WO-9850431 A2 | 11/1998 |
| WO | WO-9851799 A1 | 11/1998 |
| WO | WO-9857621 A1 | 12/1998 |
| WO | WO-2000002897 A3 | 1/2000 |
| WO | WO-0006726 A2 | 2/2000 |
| WO | WO-0140466 A2 | 6/2001 |
| WO | WO-0212447 A2 | 2/2002 |
| WO | WO-03041735 A2 | 5/2003 |
| WO | WO-2003042246 A2 | 5/2003 |
| WO | WO-03050502 A2 | 6/2003 |
| WO | WO-2004110490 A2 | 12/2004 |
| WO | WO-2005054426 A2 | 6/2005 |
| WO | WO-2006027693 A2 | 3/2006 |
| WO | WO-2006028936 A2 | 3/2006 |
| WO | WO-2006033386 A1 | 3/2006 |
| WO | WO-2006052128 A1 | 5/2006 |
| WO | WO-2006077265 A1 | 7/2006 |
| WO | WO-2006106905 A1 | 10/2006 |
| WO | WO-2006113665 A2 | 10/2006 |
| WO | WO-2007028110 A2 | 3/2007 |
| WO | WO-2007048037 A2 | 4/2007 |
| WO | WO-2007070671 A2 | 6/2007 |
| WO | WO-2007110205 A2 | 10/2007 |
| WO | WO-2007143689 A2 | 12/2007 |
| WO | WO-2007145840 A2 | 12/2007 |
| WO | WO-2007147901 A1 | 12/2007 |
| WO | WO-2008019144 A2 | 2/2008 |
| WO | WO-2008042236 A2 | 4/2008 |
| WO | WO-2008060705 A2 | 5/2008 |
| WO | WO-2008070042 A2 | 6/2008 |
| WO | WO-2008076379 A2 | 6/2008 |
| WO | WO-2008079326 A2 | 7/2008 |
| WO | WO-2008091222 A1 | 7/2008 |
| WO | WO-2008133706 A2 | 11/2008 |
| WO | WO-2008139202 A1 | 11/2008 |
| WO | WO-2009073160 A1 | 6/2009 |
| WO | WO-2009075565 A1 | 6/2009 |
| WO | WO-2009080251 A1 | 7/2009 |
| WO | WO-2009085209 A2 | 7/2009 |
| WO | WO-2009089004 A1 | 7/2009 |
| WO | WO-2009134776 A2 | 11/2009 |
| WO | WO-2010010153 A1 | 1/2010 |
| WO | WO-2010032060 A1 | 3/2010 |
| WO | WO-2010054010 A1 | 5/2010 |
| WO | WO-2010124009 A2 | 10/2010 |
| WO | WO-2010129304 A2 | 11/2010 |
| WO | WO-2010151770 A1 | 12/2010 |
| WO | WO-2011039368 A2 | 4/2011 |

(56) References Cited

FOREIGN PATENT DOCUMENTS

| WO | WO-2011039370 A1 | 4/2011 |
| --- | --- | --- |
| WO | WO-2011047383 A1 | 4/2011 |
| WO | WO-2011047442 A1 | 4/2011 |
| WO | WO-2011050262 A2 | 4/2011 |
| WO | WO-2011068840 A1 | 6/2011 |
| WO | WO-2011100566 A2 | 8/2011 |
| WO | WO-2011106300 A2 | 9/2011 |
| WO | WO-2011109298 A2 | 9/2011 |
| WO | WO-2012061374 A2 | 5/2012 |
| WO | WO-2012068098 A1 | 5/2012 |
| WO | WO-2012092539 A2 | 7/2012 |
| WO | WO-2013044215 A1 | 3/2013 |
| WO | WO 2013/135602 A2 | 9/2013 |
| WO | WO 2014/062659 A2 | 4/2014 |
| WO | WO-2014049100 A1 | 4/2014 |
| WO | WO-2014071074 A2 | 5/2014 |
| WO | WO-2015130751 A1 | 9/2015 |
| WO | WO 2015/153974 A1 | 10/2015 |
| WO | WO-2020102644 A2 | 5/2020 |

OTHER PUBLICATIONS

Allenspach, E.J., et al., "Notch Signaling in Cancer," Cancer Biology Therapy 1(5):466-476, Landes Biosience, United Kingdom (2002).

Amado, R.G., et al., "Wild-Type KRAS is Required for Panitumumab Efficacy in Patients with Metastatic Colorectal Cancer," Journal of Clinical Oncology 26(10):1626-1634, American Society of Clinical Oncology, United States (2008).

Artavanis-Tsakonas, S., et al., "Notch Signaling: Cell Fate Control and Signal Integration in Development," Science 284(5415):770-776, American Association for the Advancement of Science, United States (1999).

Axelson, H., "Notch Signaling and Cancer: Emerging Complexity," Seminars in Cancer Biology 14(5):317-319, Academic Press, England (2004).

Barbas, C.F. 3rd., et al., "In vitro evolution of a neutralizing human antibody to human immunodeficiency virus type 1 to enhance affinity and broaden strain cross-reactivity," Proceedings of the National Academy of Sciences 91(9):3809-3813, National Academy of Sciences, United States (1994).

Beachy, P.A., et al., "Tissue Repair and Stem Cell Renewal in Carcinogenesis," Nature 432(7015):324-331, Nature Publishing Group, England (2004).

Bellavia, D., et al., "Constitutive Activation of NF-κB and T-cell Leukemia/lymphoma in Notch3 Transgenic Mice," The EMBO Journal 19(13):3337-3348, European Molecular Biology Organization, Germany (2000).

Benvenuti, S., et al., "Oncogenic activation of the RAS/RAF signaling pathway impairs the response of metastatic colorectal cancers to anti-epidermal growth factor receptor antibody therapies," Cancer Research 67(6):2643-2648, American Association for Cancer Research, United States (2007).

Besseyrias, V., et al., "Hierarchy of Notch-Delta interactions promoting T cell lineage commitment and maturation," The Journal of Experimental Medicine 204(2):331-343, The Rockefeller University Press, United States (2007).

Beviglia, L., et al., "Anti-DLL4 reduces tumor growth and tumorigenicity in B-RAF V600E melanomas including those with acquired resistance to B-RAF inhibitors," AACR 103rd Annual Meeting 2012, Mar. 31-Apr. 4, Abstract LB-196, 1 page (2012).

Beviglia, L., et al., "Anti-DLL4 Treatment Inhibits Melanoma Tumor Growth, Recurrence, Metastases and Reduces Frequency of Cancer Stem Cells in a Clinically Relevant Tumor Model in NOD/SCID Mice," Cancer Research 71(8 Suppl.):Abstract 2834, AACR 102nd Annual Meeting 2011, Apr. 2-6, 2011.

Beviglia, L., et al., "In vivo evaluation of anti-tumor activity by an anti-VEGF and anti-DLL4 bispecific antibody in a humanized model of skin graft," AACR 104th Annual Meeting 2013, Abstract 4330, Apr. 6-10, 1 page (2013).

Bloom, J.W., et al., "Intrachain Disulfide Bond in the Core Hinge Region of Human IgG4," Protein Science 6(2):407-415, John Wiley & Sons, Inc., United States (Feb. 1997).

Boerner, P., et al., "Production of Antigen-specific Human Monoclonal Antibodies from in Vitro-primed Human Splenocytes," Journal of Immunology 147(1):86-95, The American Association of Immunologists, United States (1991).

Bonnet, D. and Dick, J.E., "Human acute myeloid leukemia is organized as a hierarchy that originates from a primitive hematopoietic cell," Nature Medicine 3(7):730-737, Nature Publishing Company, United States (1997).

Bray, S.J., "Notch signalling: a simple pathway becomes complex," Nature Reviews Molecular Cell Biology 7(9):678-689, Nature Publishing Group, United States (2006).

Brennan, K. and Brown, A.M., "Is there a Role for Notch Signalling in Human Breast Cancer?," Breast Cancer Research 5(2):69-75, BioMed Central Ltd., United Kingdom (2003).

Brennan, M., et al., "Preparation of Bispecific Antibodies by Chemical Recombination of Monoclonal Immunoglobulin G1 Fragments," Science 229(4708):81-83, American Association for the Advancement of Science, United States (Jul. 1985).

Brorson, K., et al., "Mutational Analysis of Avidity and Fine Specificity of Anti-Levan Antibodies," Journal of Immunology 163(12):6694-6701, American Association of Immunologists, United States (1999).

Brummell, D.A., et al., "Probing the Combining Site of an Anti-Carbohydrate Antibody by Saturation-Mutagenesis: Role of the Heavy-Chain CDR3 Residues," Biochemistry 32(4):1180-1187, American Chemical Society, United States (1993).

Burgess, W.H., et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology 111(5Pt1):2129-2138, The Rockefeller University Press, United States (Nov. 1990).

Burks, E.A., et al., "In vitro Scanning Saturation Mutagenesis of an Antibody Binding Pocket," Proceedings of the National Academy of Sciences USA 94(2):412-417, Plenum Publishing Corporation, United States (1997).

Callahan, R. and Raafat, A., "Notch Signaling in Mammary Gland Tumorigenesis," Journal of Mammary Gland Biology and Neoplasia 6(1):23-36, Kluwer Academic/Plenum Publishers, United States (2001).

Carter, P., "Improving the efficacy of antibody-based cancer therapies," Nature Reviews Cancer 1(2):118-129, Nature Publishing Group, United States (2001).

Chartier, C., et al., "The Hippo Signaling Pathway Mediates BMP Inhibition of Cancer Stem Cells," 2015 AACR Annual meeting, Apr. 18-22, Abstract 2322, 1 page (2015).

Chau, I. and Cunningham, D., "Treatment in advanced colorectal cancer: what, when and how?," British Journal of Cancer 100(11):1704-1719, Nature Publishing Group, United States (2009).

Chen, C., et al., "Generation and Analysis of Random Point Mutations in an Antibody CDR2 Sequence: Many Mutated Antibodies Lose their Ability to Bind Antigen," The Journal of Experimental Medicine 176(3):855-866, Rockefeller University Press, United States (1992).

Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (Nov. 1999).

Chi, A.S., et al., "Angiogenesis as a Therapeutic Target in Malignant Gliomas," Oncologist 14(6):621-636, AlphaMed Press, United States (2009).

Chothia, C. and Lesk, A.M., "Canonical Structures for the Hypervariable Regions of Immunoglobulins," Journal of Molecular Biology 196(4):901-917, Elsevier Science, United States (Aug. 1987).

Chothia, C., et al., "Domain association in immunoglobulin molecules. The packing of variable domains," Journal of Molecular Biology 186(3):651-663, Elsevier Science, England (1985).

(56) References Cited

OTHER PUBLICATIONS

Chowdhury, P.S. and Pastan, I., "Improving Antibody Affinity by Mimicking Somatic Hypermutation in Vitro," Nature Biotechnology 17(6):568-572, Nature Publishing Group, United States (Jun. 1999).

Clackson, T., et al., "Making Antibody Fragments using Phage Display Libraries," Nature 352(6336):624-628, Nature Publishing Group, England (Aug. 1991).

Clarke, M.F., et al., "Cancer stem cells—perspectives on current status and future directions: AACR Workshop on cancer stem cells," Cancer Research 66(19):9339-9344, American Association for Cancer Research, United States (2006).

Claxton, S. and Fruttiger, M., "Periodic Delta-like 4 expression in developing retinal arteries," Gene Expression Pattern 5:123-127, Elsevier B.V., Netherlands (2004).

Cole, S.P.C., et al., "The EBV-Hybridoma Technique and Its Application to Human Lung Cancer," in Monoclonal Antibodies and Cancer Therapy, Reisfeld, R.A. and Sell, S., eds., pp. 77-96, Alan R. Liss, Inc., United States (1985).

Colman, P.M., "Effects of Amino Acid Sequence Changes on Antibody-antigen Interactions," Research in Immunology 145(1):33-36, Elsevier, France (Jan. 1994).

Cubillo, A., et al., "A Ph1b Study of Demcizumab (DEM, anti-DLL4) with Gemcitabine (GEM) in Patients with 1st Line Locally Advanced or Metastatic Pancreatic Cancer," AACR-NCI-EORTC International Conference on Molecular Targets and Cancer Therapeutics, Oct. 19-23, 2013, Poster (2013), 8 pages.

Cubillo, A., et al., "A Phase lb study of demcizumab (DEM, anti-DLL4) with gemcitabine (GEM) in patients with first line locally advanced or metastatic pancreatic cancer," Proceedings of the AACR-NCI-EORTC International Conference on Molecular Targets and Cancer Therapeutics, Oct. 19-23, 2013, Abstract B78, 2 pages (2013).

Dalerba, P., et al., "Phenotypic characterization of human colorectal cancer stem cells," Proceedings of the National Academy of Sciences 104(24):10158-10163, National Academy of Sciences, United States (2007).

Dando, J.S., et al., "Notch/Delta4 interaction in human embryonic liver CD34+ CD38-cells: positive influence on BFU-E production and LTC-IC potential maintenance," Stem Cells 23(4):550-560, John Wiley & Sons, Inc., United States (2005).

Deisenhofer, J., "Crystallographic refinement and atomic models of a human Fc fragment and its complex with fragment B of protein A from *Staphylococcus aureus* at 2.9- and 2.8-A resolution," Biochemistry 20(9):2361-2370, American Chemical Society, United States (1981).

Deonarain, M.P., et al., "Antibodies Targeting Cancer Stem Cells: A New Paradigm in Immunotherapy?," mAbs 1(1):12-25,Taylor & Francis, United States (2009).

Dixit, R., "Cardiovascular Safety of Biologics: Challenges and Opportunities," Medimmune, Safety Pharmacology Society, Annular Meeting Speakers Presentations (Oct. 3, 2012).

Dontu, G., et al., "Role of Notch Signaling in Cell-Fate Determination of Human Mammary Stem/progenitor Cells," Breast Cancer Research 6(6):R605-R615, BioMed Central, England (2004).

Dorsch, M., et al., "Ectopic expression of Delta4 impairs hematopoietic development and leads to lymphoproliferative disease," Blood 100(6):2046-2055, American Society of Hematology, United States (2002).

Dreher, M.L., et al., "Colony assays for antibody fragments expressed in bacteria," Journal of Immunological Methods 139(2):197-205, Elsevier Science, United States (1991).

Duarte, A., et al., "Dosage-sensitive requirement for mouse Dll4 in artery development," Genes & Development 18(20):2474-2478, Cold Spring Harbor Laboratory Press, United States (2004).

Dupont, J. "Anti-Angiogenic Agents and Cardiovascular Effects: Implications for Clinical Development in Cancer," presentation given in Barcelona, Spain on Nov. 4, 2011, 16 pages.

Dupont, J., et al., "A Phase 1b Study of Anti-DLL4 (Delta-Like Ligand 4) Antibody Demcizumab (DEM) with Pemetrexed (PEM) and Carboplatin (CARBO) in Patients with 1st-Line Non-Squamous NSCLC," 2015 European Lung Cancer Conference (ELCC), Geneva, Switzerland, Apr. 15-18, Abstract 114, 2 pages (2015).

Ellisen, L.W., et al., "TAN-1, the Human Homolog of the *Drosophila* Notch Gene is Broken by Chromosomal Translocations in T Lymphoblastic neoplasm," Cell 66(4):649-661, Cell Press, United States (1991).

Engin,F., et al., "Dimorphic effects of Notch signaling in bone homeostasis," Nature Medicine 14(3):299-305, Nature Publishing Group, United States (2008).

English language translation of Oishi, H., et al., "Novel therapeutic strategy for pancreatic cancer targeting Notch signaling pathway," Proceedings of the Japanese Cancer Association 65:311-312, Japan (2006).

English language translation of "Tumor-angiogenesis suppression therapy targeting the Notch signaling pathway," Suizo (Pancreas) 21(3):249, Japan (2006).

Eppstein, D.A., et al., "Biological activity of liposome-encapsulated murine interferon gamma is mediated by a cell membrane receptor," Proceedings of the National Academy of Sciences 82(11):3688-3692, National Academy of Sciences, United States (1985).

European Search Report for EP Application No. EP10824244.7, Munich, Germany, dated Feb. 18, 2013, 6 pages.

Farnie, G. and Clarke, R.B., "Mammary stem cells and breast cancer—role of Notch signalling," Stem Cell Reviews and Reports 3(2):169-175, Humana Press, United States (2007).

Farnie, G., et al., "Novel cell culture technique for primary ductal carcinoma in situ: role of Notch and epidermal growth factor receptor signaling pathways," Journal of the National Cancer Institute 99(8):616-627, Oxford University Press, United Kingdom (2007).

Fischer, M., et al., "Anti-DLL4 Inhibits Growth and Reduces Tumor-Initiating Cell Frequency in Colorectal Tumors with Oncogenic KRAS Mutations," Cancer Research 71(5):1520-1525, American Association for Cancer Research, United States (2011).

Fleming, R.J., et al., "The NOTCH receptor and its ligands," Trends in Cell Biology 7(11):437-441, Elsevier Science Ltd., The Netherlands (1997).

Fre, S., et al., "Notch Signals Control the Fate of Immature Progenitor Cells in the Intestine," Nature 435(7044):964-968, Nature Publishing Group, United States (2005).

Fung, E., et al., "Delta-like 4 induces notch signaling in macrophages: implications for inflammation," Circulation 115(23):2948-2956, American Heart Association, Inc., United States (2007).

Gagnon, M.L., et al., "Identification of a natural soluble neuropilin-1 that binds vascular endothelial growth factor: In vivo expression and antitumor activity," Proceedings of the National Academy of Sciences 97(6):2573-2578, National Academy of Sciences, United States (2000).

Gale, N.W., et al., "Haploinsufficiency of Delta-like 4 Ligand Results in Embryonic Lethality due to Major Defects in arterial and Vascular Development," Proceedings of the National Academy of Sciences 101(45):15949-15954, National Academy of Sciences, United States (2004).

Gallahan, D., et al., "A new common integration region (int-3) for mouse mammary tumor virus on mouse chromosome 17," Journal of Virology 61(1):218-220, American Society for Microbiology, United States (1987).

Gallahan, D., et al., "Expression of a Truncated Int3 Gene in Developing Secretory Mammary Epithelium Specifically Retards Lobular Differentiation Resulting in Tumorigenesis," Cancer Research 56(8):1775-1785, American Association for Cancer Research, United States (1996).

Garber, K., "Notch Emerges as New Cancer Drug Target," Journal of the national Cancer Institute 99(17):1284-1285, Oxford University Press, United States (2007).

Goding, J.W., "Production of Monoclonal Antibodies," in Monoclonal Antibodies: Principles and Practice, 2nd ed., pp. 59-103, Academic Press Inc., London (1986).

Gracian, A.C., et al., "A phase 1b study of the anticancer stem cell agent demcizumab (DEM) and gemcitabine (GEM) with or without

(56) References Cited

OTHER PUBLICATIONS paclitaxel protein bound particles (nab-paclitaxel) in patients with pancreatic cancer," 2014 Gastrointestinal Cancers Symposium, Abstract 279, 2 pages (2014).
Gray-Schopfer, V.C., et al., "The Role of B-RAF in Melanoma," Cancer Metastasis Reviews 24(1):165-183, Springer Science + Business Media, Inc., Netherlands (2005).
Gridley, T., "Notch Signaling During Vascular Development," Proceedings of the National Academy of Sciences 98(10):5377-5378, National Academy of Sciences, United States (2001).
Gridley, T. "Notch signaling in vascular development and physiology," Development 134(15):2709-2718, (2007).
Gronberg, B.H., et al., "Phase III Study by the Norwegian Lung Cancer Study Group: Pemetrexed Plus Carboplatin Compared with Gemcitabine Plus Carboplatin as First-line Chemotherapy in Advanced Non-small-cell Lung Cancer," Journal of Clinical Oncology 27(19):3217-3224, American Society of Clinical Oncology, United States (2009).
Gruber, M., et al., "Efficient Tumor Cell Lysis Mediated by a Bispecific Single Chain Antibody Expressed in *Escherichia coli*," The Journal of Immunology 152(11):5368-5374, The American Association of Immunologists, Inc., United States (1994).
Gurney, A. and Hoey, T., "Anti-DLL4, a Cancer Therapeutic with Multiple Mechanisms of Action," Vascular Cell 3, 4 pages, BioMed Central, United States (2011).
Hainaud, P., et al., "The role of the vascular endothelial growth factor-Delta-like 4 ligand/Notch4-ephrin B2 cascade in tumor vessel remodeling and endothelial cell functions," Cancer Research 66(17):8501-8510, American Association for Cancer Research, United States (2006).
Hallahan, A.R., et al., "The SmoA1 Mouse Model Reveals that Notch Signaling is Critical for the Growth and Survival of Sonic Hedgehog-Induced Medulloblastomas," Cancer Research 64(21):7794-7800, American Association for Cancer Research, United States (2004).
Han, W., et al., "A soluble form of human Delta-like-1 inhibits differentiation of hematopoietic progenitor cells," Blood 95(5):1616-1625, The American Society of Hematology, United States (2000).
Harlow, E. and Lane, D., eds., "Immunoassays," in Antibodies: A Laboratory Manual, 14:553-612, Cold Spring Harbor Laboratory, United States (1988).
Harper, J.A., et al., "Notch Signaling in Development and Disease," Clinical Genetics 64(6):461-472, Blackwell Publishing, United States (2003).
Harrington, L.S., et al., "Regulation of multiple angiogenic pathways by Dll4 and Notch in human umbilical vein endothelial cells," Microvascular Research 75(2):144-154, Elsevier Science, United States (2008).
Harris, W.J., "Production of Humanized Monoclonal Antibodies for in vivo Imaging and Therapy," Biochemical Society Transactions 23(4):1035-1038, Portland Press on the Behalf of the Biochemical Society, England (1995).
Hawkins, R.E., et al., "Selection of phage antibodies by binding affinity. Mimicking affinity maturation," Journal of Molecular Biology 226(3):889-896, Elsevier Science, United States (1992).
Hellström, M., et al., "Dll4 signalling through Notch1 regulates formation of tip cells during angiogenesis," Nature 445(7129):776-780, Nature Publishing Group, United States (2007).
Henning, K., et al., "mNotch1 signaling and erythropoietin cooperate in erythroid differentiation of multipotent progenitor cells and upregulate beta-globin," Experimental Hematology 35(9):1321-1332, Elsevier Science, United States (2007).
Hermentin, P. and Seiler, F.R., "Investigations with Monoclonal Antibody Drug (Anthracycline) Conjugates," Behring Institute Research Communications 82:197-215, Behringwerke Ag, Germany (1988).
Hidalgo, M., et al., "A Phase 1b Study of the Anti-Cancer Stem Cell Agent Demcizumab (DEM, anti-DLL4) and Gemcitabine (GEM) with or without Nab-Paclitaxvel in Patients with Pancreatic Cancer," European Society for Medical Oncology 2014 Congress, Sep. 17 and Sep. 28, Poster 616PD, 1 page (2014).

Hidalgo, M., et al., "A Phase 1b Study of the Anti-Cancer Stem Cell Agent Demcizumab (DEM, Anti-DLL4) and Gemcitabine (GEM) with or without Paclitaxel Protein Bound Particles (Nab-Paclitaxel) in pts with Pancreatic Cancer," 2015 ASCO Annual Meeting, Abstract 4118, 3 pages (2015).
Hidalgo, M., et al., "Pre-Clinical and Clinical Activity of Anti-DLL4 (Demcizumab) in Combination with Gemcitabine Plus nab-Paclitaxel in Pancreatic Cancer," 26th EORTC-NCI-AACR Symposium on Molecular Targets and Cancer Therapeutics Preclinical Models Poster Session, Abstract 166, 2 pages (Nov. 2014).
Hoey, T., et al., "DLL4 blockade inhibits tumor growth and reduces tumor-initiating cell frequency," Cell Stem Cell 5(2):168-177, Elsevier Science, United States (2009).
Hofmann, J.J. and Iruela-Arispe, M.L., "Notch signaling in blood vessels: who is talking to whom about what?," Circulation Research 100(11):1556-1568, American Heart Association, Inc., United States (2007).
Holash, J., et al., "Inhibitors of growth factor receptors, signaling pathways and angiogenesis as therapeutic molecular agents," Cancer Metastasis Rev 25:243-252, Dordrecht, Netherlands (2006).
Holash, J., et al., "VEGF-Trap: A VEGF Blocker with Potent Antitumor Effects," Proceedings of the National Academy of Sciences USA 99(17):11393-11398, National Academy of Sciences, United States (2002).
Holm, P., et al., "Functional Mapping and Single Chain Construction of the Anti-cytokeratin 8 Monoclonal Antibody TS1," Molecular Immunology 44(6):1075-1084, Pergamon Press, England (Feb. 2007).
Hoogenboom, H.R. and Winter, G., "By-Passing Immunisation. Human Antibodies from Synthetic Repertoires of Germline VH Gene Segments Rearranged in vitro," Journal of Molecular Biology 227(2):381-388, Elsevier, England (1992).
Hope, K.J., et al., "Acute myeloid leukemia originates from a hierarchy of leukemic stem cell classes that differ in selfrenewal capacity," Nature Immunology 5(7):738-743, Nature Publishing Group,United States (2004).
Hopfer, O., et al., "The Notch Pathway in Ovarian Carcinomas and Adenomas," British Journal of Cancer 93(6):709-718, Nature Publishing Group on behalf of Cancer Research UK, England (2005).
Humphreys, D.P., et al., "Formation of dimeric Fabs in *Escherichia coli*: effect of hinge size and isotype, presence of interchain disulphide bond, Fab' expression levels, tail piece sequences and growth conditions," Journal of Immunological Methods 209(2):193-202, Elsevier Science, Netherlands (1997).
Hurle, M.R. and Gross, M., "Protein engineering techniques for antibody humanization," Current Opinion in Biotechnology 5(4):428-433, (1994).
Hurwitz, H.I., et al., "Phase I Trial of Pazopanib in Patients with Advanced Cancer," Clinical Cancer Research 15(12):4220-4227, American Association for Cancer Research, United States (2009).
Hwang, K.J., et al., "Hepatic uptake and degradation of unilamellar sphingomyelin/cholesterol liposomes: a kinetic study," Proceedings of the National Academy of Sciences 77(7):4030-4034, National Academy of Sciences, United States (1980).
International Preliminary Report on Patentability and Written Opinion for International Application No. PCT/US2010/53064, International Searching Authority, dated Feb. 14, 2011, 7 pages.
International Preliminary Report on Patentability for Application No. PCT/US2016/053316, International Searching Authority, dated Apr. 5, 2018, 11 pages.
International Preliminary Report on Patentability for International Application No. PCT/US2013/065015, The International Bureau of WIPO, Switzerland, dated Apr. 22, 2014, 17 pages.
International Search Report for International Application No. PCT/US16/53316, ISA/US, Alexandria, Virginia, dated Feb. 21, 2017, 7 pages.
International Search Report for International Application No. PCT/US2010/53064, dated Feb. 14, 2011, 3 Pages.
International Search Report for International Application No. PCT/US2015/024251, ISA/US, Alexandria, Virginia, United States, dated Jul. 16, 2015, 4 pages.

(56) References Cited

OTHER PUBLICATIONS

International Search Report for International Patent Application No. PCT/US11/60773, International Searching Authority, Alexandria, Virginia, United States, dated Mar. 26, 2012, 3 pages.

International Search Report for International Patent Application No. PCT/US2007/020889, United States Patent and Trademark Office, United States, dated Apr. 9, 2008, 5 pages.

International Search Report with the Written Opinion of the International Searching Authority for International application No. PCT/US10/32625, United States Patent and Trademark Office, United States, dated Dec. 17, 2010, 11 pages.

International Search Report with the Written Opinion of the International Searching Authority for International application No. PCT/US12/56886, United States Patent and Trademark Office, United States, dated Feb. 28, 2013, 8 pages.

International Search Report with the Written Opinion of the International Searching Authority for International application No. PCT/US15/58327, United States Patent and Trademark Office, United States, dated May 19, 2016, 12 pages.

International Search Report with Written Opinion for International Application No. PCT/US2010/58511, International Searching Authority, United States, dated Mar. 3, 2011, 9 pages.

Ishiko, E., et al., "Notch signals inhibit the development of erythroid/megakaryocytic cells by suppressing GATA-1 activity through the induction of HES1," The Journal of Biological Chemistry 280(6):4929-4939, American Society for Biochemistry and Molecular Biology, United States (2005).

Iso, T., et al., "Notch Signaling in Vascular Development," Arteriosclerosis, Thrombosis, and Vascular Biology 23(4):543-553, American Heart Association, Inc., United States (2003).

Izzedine, H., et al., "Management of Hypertension In Angiogenesis Inhibitor-Treated Patients," Annals of Oncology 20(5):807-815, Oxford University Press, England (2009).

Jackson, J.R., et al., "In vitro antibody maturation. Improvement of a high affinity, neutralizing antibody against IL-1 beta," The Journal of Immunology 154(7):3310-3319, The American Association of Immunologists, Inc., United States (1995).

Janda, C.Y., "Structural Basis of Wnt Recognition by Frizzled," Science 337(6090):59-64, American Association for the Advancement of Science, United States (2012).

Janeway, Jr., et al., "Immunobiology, The Immune System in Health and Disease," Edition 4:579-581, Current Biology Publications (1999).

Jang, Y.-J., et al., "The Structural Basis for DNA Binding by an Anti-DNA Autoantibody," Molecular Immunology 35(18):1207-1217, Pergamon Press, England (1998).

Jarriault, S., et al., "Signalling Downstream of Activated Mammalian Notch," Nature 377(6547):355-358, Nature Publishing Group, United States (1995).

Jeffries, S. and Capobianco, A.J., "Neoplastic transformation by Notch requires nuclear localization," Molecular and Cellular Biology 20(11):3928-3941, American Society for Microbiology, United States (2000).

Jemal, A., et al., "Cancer Statistics, 2003," CA—A Cancer Journal for Clinicians 53(1):05-26, American Cancer Society, United States (2003).

Jhappan, C., et al., "Expression of an Activated Notch-Related int-3 Transgene Interferes with Cell Differentiation and Induces Neoplastic Transformation in Mammary and Salivary Glands," Genes & Development 6(3):345-355, Cold Spring Harbor Laboratory Press, United States (1992).

Jimeno, A., et al., "Phase 1 study of REGN421 (R)/SAR153192, a fully-human delta-like ligand 4 (Dll4) monoclonal antibody (mAb), in patients with advanced solid tumors," ASCO University 2013 ASCO Annual Meeting accessed at http://meetinglibrary.asco.org/content/113836-132, 2 pages.

Jones, P.T., et al., "Replacing the Complementarity-determining Regions in a Human Antibody with those from a Mouse," Nature 321(6069):522-525, Nature Publishing Group, England (May 1986).

Kim, E.S., et al., "Potent VEGF blockade causes regression of coopted vessels in a model of neuroblastoma," Proceedings of the National Academy of Sciences 99(17):11399-11404, National Academy of Sciences, United States (2002).

Kingsman, A.J., et al., "Replication in *Saccharomyces cerevisiae* of Plasmid pBR313 Carrying DNA from the Yeast Trpl Region," Gene 7(2):141-152, Elsevier/North-Holland Biomedical Press, Netherlands (Oct. 1979).

Kobayashi, H., et al., "Tryptophan H33 Plays an Important Role in Pyrimidine (6-4) Pyrimidone Photoproduct Binding by a High-Affinity Antibody," Protein Engineering Design and Selection 12(10):879-884, Oxford University Press, United States (1999).

Kohler, G. and Milstein, C., "Continuous Cultures of Fused Cells Secreting Antibody of Predefined Specificity," Nature 256(5517):495-497, Macmillan Journals Ltd., England (Aug. 1975).

Kopper, L. and Hajdu, M., "Tumor Stem Cells," Pathology Oncology Research 10(2):69-73, Aranyi Lajos Foundation, Hungary (2004).

Kostelny, S.A., et al., "Formation of a Bispecific Antibody by the Use of Leucine Zippers," The Journal of Immunology 148(5):1547-1553, American Association of Immunologists, United States (Mar. 1992).

Krebs, L.T., et al., "Haploinsufficient Lethality and Formation of Arteriovenous Malformations in Notch Pathway Mutants," Genes & Development 18(20):2469-2473, Cold Spring Harbor Laboratory Press, United States (2004).

Krebs, L.T., et al., "Notch Signaling is Essential for Vascular Morphogenesis in Mice," Genes & Development 14(11):1343-1352, Cold Spring Harbor Laboratory Press, United States (2000).

Kuo, C.J., et al., "Comparative evaluation of the antitumor activity of antiangiogenic proteins delivered by gene transfer," Proceedings of the National Academy of Sciences 98(8):4605-4610, National Academy of Sciences, United States (2001).

Lapidot, T., et al., "A Cell Initiating Human Acute Myeloid Leukaemia After Transplantation Into SCID Mice," Nature 367(6464):645-648, Nature Publishing Group, United States (1994).

Lauret, E., et al., "Membrane-Bound Delta-4 Notch Ligand Reduces the Proliferative Activity of Primitive Human Hematopoietic CD34+ CD38low Cells while Maintaining their LTC-IC Potential," Leukemia 18(4):788-797, Nature Publishing Group, United States (2006).

Lazar, E., et al., "Transforming Growth Factor α: Mutation of Aspartic Acid 47 and Leucine 48 Results in Different Biological Activities," Molecular and Cellular Biology 8(3):1247-1252, American Society for Microbiology, United States (Mar. 1988).

Lee, H.S., et al., "Generation and Characterization of a Novel Single-gene-encoded Single-chain Immunoglobulin Molecule with Antigen Binding Activity and Effector Functions," Molecular Immunology 36(1):61-71, Elsevier Science Ltd., Netherlands (Jan. 1999).

Leethanakul, C., et al., "Distinct Pattern of Expression of Differentiation and Growth-Related Genes in Squamous Cell Carcinomas of the Head and Neck Revealed By the Use of Laser Capture Microdissection and cDNA Arrays," Oncogene 19(28):3220-3224, Nature Publishing Group, United States (2000).

Lenihan, D.J., "How is cardiac toxicity defined and what impact does this have on cancer outcome or drug development," PowerPoint Presentation from the DIA Meeting, 42 slides (2011).

Leong, K.G. and Karsan, A., "Recent Insights into the Role of Notch Signaling in Tumorigenesis," Blood 107(6):2223-2233, The American Society of Hematology, United States (2006).

Li, J.L. and Harris A.L., "Notch Signaling from Tumor Cells: A New Mechanism of Angiogenesis," Cancer Cell 8(1):pp. 1-3, Cell Press, United States (2005).

Li, X., et al., "Notch3 Signaling is Required for the Development of Pulmonary Arterial Hypertension," Nature Medicine 15(11):1289-1297, Nature Publishing Company, United States (2009).

Lievre, A., et al., "KRAS Mutation Status Is Predictive of Response to Cetuximab Therapy in Colorectal Cancer," Cancer Research 66(8):3992-3995, American Association for Cancer Research, United States (2006).

Limbourg, A., et al., "Notch ligand Delta-like 1 is essential for postnatal arteriogenesis," Circulation Research 100(3):363-371, American Heart Association, Inc., United States (2007).

(56) References Cited

OTHER PUBLICATIONS

Liu, S., et al., "Mammary stem cells, self-renewal pathways, and carcinogenesis," Breast Cancer Research 7(3):86-95, BioMed Central, England (2005).

Liu, Z.J., et al., "Inhibition of endothelial cell proliferation by Notch 1 signaling is mediated by repressing MAPK and P14K/Akt pathways and requires MAML1," Federation of American Societies for Experimental Biology 20:E201-E210, American Society for Experimental Biology, United States (2006).

Liu, Z.J., et al., "Regulation of Notch1 and Dll4 by vascular endothelial growth factor in arterial endothelial cells: implications for modulating arteriogenesis and angiogenesis," Molecular and Cellular Biology 23(1):14-25, American Society for Microbiology, United States (2003).

Lobov, I.B., et al., "Delta-like ligand 4 (Dll4) is induced by VEGF as a negative regulator of angiogenic sprouting," Proceedings of the National Academy of Sciences 104(9):3219-3224, National Academy of Sciences, United States (2007).

Lu, K.V., and Bergers, G., "Mechanisms of evasive resistance to anti-VEGF therapy in glioblastoma," CNS Oncology 2(1):49-65, Future Medicine, Inc., United States (2013).

Luca, V.C., et al., "Structural basis for Notch1 engagement of Delta-like 4," Science, 347(6224):847-853, American Association for the Advancement of Science, United States (2015).

Maccallum, R.M., et al., "Antibody-antigen Interactions: Contact Analysis and Binding Site Topography," Journal of Molecular Biology 262(5):732-745, Academic Press, England (Oct. 1996).

Maeda, H., et al., "Construction of Reshaped Human Antibodies with HIV-Neutralizing Activity," Human Antibodies and Hybridomas 2(3):124-134, Butterworth-Heinemann, United Kingdom (1991).

Mailhos, C., et al., "Delta4, an Endothelial Specific Notch Ligand Expressed at Sites of Physiological and Tumor Angiogenesis," Differentiation 69:135-144, Elsevier, England (2001).

Marks, J.D., et al., "By-Passing Immunization: Building High Affinity Human Antibodies by Chain Shuffling," Biotechnology 10(7):779-783, Nature Publishing Company, United States (Jul. 1992).

Marks, J.D., et al., "By-passing Immunization. Human Antibodies from V-gene Libraries Displayed on Phage," Journal of Molecular Biology 222(3):581-597, Academic Press Limited, United States (Dec. 1991).

Mazella, J., et al., "Expression of Delta-like protein 4 in the human endometrium," Endocrinology 149(1):15-19, Association for the Study of Internal Secretions, United States (2008).

McAuliffe, S.M., et al., "Targeting Notch, a Key Pathway for Ovarian Cancer Stem Cells, Sensitizes Tumors to Platinum Therapy," Proceedings of the National Academy of Sciences USA 109(43):E2939-E2948, National Academy of Sciences, United States (2012) with Supporting Information.

McCafferty, J., et al., "Phage Antibodies: Filamentous Phage Displaying Antibody Variable Domains," Nature 348(6301):552-554, Nature Publishing Group, London (Dec. 1990).

McKeage, M., et al., "A Phase 1b Study of Demcizumab plus Pemetrexed and Carboplatin in Patients with 1st line Non-Squamous Non-Small Cell Lung Cancer (NSCLC)," 24th EORTC-NCI-AACR Symposium on Molecular Targets and Cancer Therapeutics, Nov. 6-9, 2012, Poster (2012), 9 pages.

McKeage, M., et al., "A Phase 1b study of demcizumab (DEM, anti-DLL4) plus pemetrexed and carboplatin in patients with first line stage IIIb/IV non-squamous non-small cell lung cancer," Proceedings of the AACR-NCI-EORTC International Conference on Molecular Targets and Cancer Therapeutics, Oct. 19-23, 2013, Abstract A71, 2 pages (2013).

McKeage, M., et al., "Phase 1b Study of Demcizumab plus Pemetrexed and Carboplatin in Patients with 1st line Non-Small Cell Lung Cancer (NSCLC)," AACR-NCI-EORTC International Conference on Molecular Targets and Cancer Therapeutics, Oct. 19-23, 2013, Poster (2013), 8 pages.

McKeage, M.J., et al., "A phase 1b study of the anticancer stem cell agent demcizumab (DEM), pemetrexed (PEM), and carboplatin (CARBO) in pts with first-line nonsquamous NSCLC," 2014 ASCO Annual Meeting, Abstract 2544, 2 pages (2014).

McKeage, M.J., et al., "A Phase 1b Study of the Anti-Cancer Stem Cell Agent Demcizumab (DEM), Pemetrexed (PEM) and Carboplatin (CARBO) inPatients with 1st Line Non-Squamous Non-Small Cell Lung Cancer (NSCLC)," 2015 ASCO Annual Meeting, Abstract 8045, 2 pages (2015).

Merchant, A.M., et al., "An Efficient Route to Human Bispecific IgG," Nature Biotechnology 16(7):677-681, Nature Publishing Group, United States (1998).

Miele, L. and Osborne, B., "Arbiter of Differentiation and Death: Notch Signaling Meets Apoptosis," Journal of Cellular Physiology 181(3):393-409, Wiley-Liss, Inc., United States (1999).

Miele, L., "Notch Signaling," Clinical Cancer Research 12:1074-1077, The American Association for Cancer Research, United States (2006 ).

Milano, J., et al., "Modulation of Notch Processing By D-Secretase Inhibitors Causes Intestinal Goblet Cell Metaplasia And Induction of Genes Known to Specify Gut Secretory Lineage Differentiation," Toxicological Sciences 82(1):341-358, Oxford University Press, United States (2004).

Milstein, C. and Cuello, A.C., "Hybrid Hybridomas and their Use in Immunohistochemistry," Nature 305(5934):537-540, Nature Publishing Group, England (Oct. 1983).

Morimoto, K., and Inouye K., "Single-step purification of F(ab')2 mu fragments of mouse monoclonal antibodies (immunoglobulins G1) by hydrophobic interaction high-performance liquid chromatography using TSKgel Phenyl-5PW," Journal of Biochemical and Biophysical Methods 24(1-2):107-117, Elsevier/North-Holland Biomedical Press, Netherlands (1993).

Morrison, S.J., et al., "Hematopoietic Stem Cells: Challenges to Expectations," Current Opinion in Immunology 9(2):216-221, Elsevier Science, United States (1997).

Morrison, S.J.,et al., "Regulatory Mechanisms in Stem Cell Biology," Cell 88(3):287-298, Elsevier Science, United States (1997).

Morrison, S.J.,et al., "The Biology of Hematopoietic Stem Cells," Annual Review of Cell and Developmental Biology 11:35-71, Annual Reviews, United States (1995).

Morrison, S.J.,et al., "Transient Notch activation initiates an irreversible switch from neurogenesis to gliogenesis by neural crest stem cells," Cell 101(5):499-510, Elsevier Science, United States (2000).

Morrison, S.L., et al., "Chimeric Human Antibody Molecules: Mouse Antigen-binding Domains with Human Constant Region Domains," Proceedings of the National Academy of Sciences USA 81(21):6851-6855, National Academy of Sciences, United States (Nov. 1984).

Nam, Y., et al., "Notch Signaling as a Therapeutic Target," Current Opinion in Chemical Biology 6(4):501-509, Elsevier Science, United States (2002).

NCT00744562, "A Phase 1 Dose Escalation Study of OMP-21M18 in Subjects With Solid Tumors," ClinicalTrials.gov archive, accessed at http://clinicaltrials.gov/archiveiNCT00744562/2008_10_06, accessed on Feb. 2, 2012, 4 pages.

NCT01189929, "A Phase 1b Study of Gemcitabine Plus OMP-21M18 as 1st-line Treatment in Subjects With Locally Advanced or Metastatic Pancreatic Cancer" as updated on Aug. 26, 2010, ClinicalTrials.gov archive, accessed at https://clinicaltrials.gov/archives/NCT01189929/2010_08_26, accessed on Apr. 20, 2015, 5 pages.

NCT01189929, "A Phase 1b Study of Gemcitabine Plus OMP-21M18 as 1st-line Treatment in Subjects With Locally Advanced or Metastatic Pancreatic Cancer" as updated on Dec. 15, 2011, ClinicalTrials.gov archive, accessed at https://clinicaltrials.gov/archives/NCT01189929/2011_12_15, accessed on Apr. 20, 2015, 5 pages.

NCT01189968, "A Phase 1b Study of Carboplatin and Pemetrexed Plus OMP-21M18 as 1st-line Treatment in Subjects with Non-Squamous Non-Small Cell Lung Cancer" as updated on Aug. 26, 2010, ClinicalTrials.gov archive, accessed at https://clinicaltrials.gov/archive/NCT01189968/2010_08_26, accessed on Apr. 20, 2015, 5 pages.

NCT01189968, "A Phase 1b Study of Carboplatin and Pemetrexed Plus OMP-21M18 as 1st-line Treatment in Subjects with Non-Squamous Non-Small Cell Lung Cancer" as updated on Dec. 15,

(56) References Cited

OTHER PUBLICATIONS

2011, ClinicalTrials.gov archive, accessed at https://clinicaltrials.gov/archive/NCT01189968/2011_12_15, accessed on Apr. 20, 2015, 5 pages.
NCT01189968, "A Phase 1b Study of Carboplatin and Permetrexed Plus OMP-21M18 as 1st-line Treatment in Subject With Non-Squamous Non-Small Cell Lung Cancer," ClinicalTrials.gov archive, accessed at http://clinicaltrials.gov/archive/NCT01189968/2010_10_28, accessed on Feb. 7, 2012, 4 pages.
Nickoloff, B.J., et al., "Notch Signaling as a Therapeutic Target in Cancer: a New Approach to the Development of Cell Fate Modifying Agents," Oncogene 22(42):6598-6608, Nature Publishing Group, England (2003).
Noguera, I., et al., "Delta-like ligand 4 (Dll4) is critical for tumor growth and angiogenesis," Proceedings of the Annual Meeting of American Association for Cancer Research 47:1342, American Association for Cancer Research, United States (2006).
Noguera, I., et al., "Expression of Delta-like 4 (Dll4) ligand in mouse tumor models," Proceedings of the Annual Meeting of the American Association for Cancer Research 46(Suppl5):1104, American Association for CancerResearch, United States (2005).
Noguera-Troise, I., et al., "Blockade of Dll4 inhibits tumour growth by promoting non-productive angiogenesis," Nature 444(7122):1032-1037, Nature Publishing Group, United States (2006).
Nohaile, M.J., et al., "Altering dimerization specificity by changes in surface electrostatics," Proceedings of the National Academy of Sciences 98(6):3109-3114, National Academy of Sciences, United States (2001).
Novotný, J. and Haber, E., "Structural invariants of antigen binding: comparison of immunoglobulin VL-VH and VL-VL domain dimers," Proceedings of the National Academy of Sciences 82(14):4592-4596, National Academy of Sciences, United States (1985).
Oishi, H., et al., "Novel therapeutic strategy for pancreatic cancer targeting Notch signaling pathway," Proceedings of the Japanese Cancer Association 65:311-312, (2006).
OncoMed Pharmaceuticals, Press Release, "Clinical Cancer Research Publishes OncoMed Data Demonstrating Anti-Cancer Activity for Anti-DLL4 (Demcizumab) in Pancreatic Cancer," Sep. 6, 2012, 2 pages.
OncoMed Pharmaceuticals Press Release, "OncoMed and Lilly Enter Clinical Supply Agreement to Evaluate the Combination of Demcizumab and Alimta(R) (pemetrexed for injection) in Lung Cancer," Apr. 2, 2015, 4 pages.
OncoMed Pharmaceuticals, Press Release, "OncoMed Announces Abstracts Accepted at the 2014 ASCO Annual Meeting," Apr. 23, 2014, 2 pages.
OncoMed Pharmaceuticals Press Release, "OncoMed Announces Abstracts Accepted for Presentation at the 2015 ASCO Annual Meeting," Apr. 21, 2015, 2 pages.
OncoMed Pharmaceuticals, Press Release, "OncoMed Anti-Cancer Stem Cell Antibody OMP-21M18 Demonstrates Potent Activity in Preclinical Studies Against Human Colon Cancer Tumors Regardless of KRAS Mutation Status," Mar. 1, 2011, 3 pages.
OncoMed Pharmaceuticals, Press Release, "OncoMed's Demcizumab Phase 1b Clinical Trials Show Encouraging Safety and Anti-Tumor Activity at ESMO," Sep. 28, 2014, 3 pages.
OncoMed Pharmaceuticals Press Release, "OncoMed Doses First Patient in Phase 1 Clinical Trial of Novel Anti-DLL4/VEGF Bispecific Antibody," Jan. 5, 2015, 2 pages.
OncoMed Pharmaceuticals Press Release, "OncoMed Highlights Immuno-Oncology Discoveries During 2015 Research & Development Day," Apr. 29, 2015, 3 pages.
OncoMed Pharmaceuticals Press Release, "OncoMed Initiates Dosing in Phase 2 Clinical Trial of Demcizumab for the Treatment of Non-Small Cell Lung Cancer," Feb. 4, 2015, 3 pages.
OncoMed Pharmaceuticals Press Release, "OncoMed Initiates Dosing in Randomized Phase 2 Clinical Trial of Demcizumab in Pancreatic Cancer Patients," Apr. 22, 2015, 3 pages.
OncoMed Pharmaceuticals, Press Release, "OncoMed Pharmaceuticals Announces Presentations of Anti-Notch2/3 and Demcizumab Clinical Data at EORTC-NCI-AACR Meeting," Nov. 9, 2012, 3 pages.
OncoMed Pharmaceuticals, Press Release, "OncoMed Pharmaceuticals Initiates Phase 1b/2 Clinical Trial of Demcizuman (Anti-DLL4) in Combination with Paclitaxel in Ovarian Cancer," Sep. 19, 2013, 3 pages.
OncoMed Pharmaceuticals Press Release, "OncoMed Pharmaceuticals Presents Data From Clinical Trials of Four Novel Anti-Cancer Stem Cell (Anti-CSC) Therapeutics at the AACR-NCI-EORTC International Conference on Molecular Targets and Cancer Therapeutics in Boston, Oct. 19-23, 2013," Oct. 21, 2013, 4 pages.
OncoMed Pharmaceuticals, Press Release, "OncoMed Pharmaceuticals Presents Data From Demcizumab Phase 1b Clinical Study in Pancreatic Cancer at the 2014 Gastrointestinal Cancers Symposium," Jan. 17, 2014, 3 pages.
OncoMed Pharmaceuticals Press Release, "OncoMed Pharmaceuticals Recaps New Data Presented at AACR," Apr. 3, 2012, 2 pages.
OncoMed Pharmaceuticals Press Release, "OncoMed Pharmaceuticals to Present Data From Clinical Trials of Four Novel Anti-Cancer Stem Cell (Anti-CSC) Therapeutics in Five Posters at the AACR-NCI-EORTC International Conference on Molecular Targets and Cancer Therapeutics in Boston, Oct. 19-23, 2013," Oct. 14, 2013, 4 pages.
OncoMed Pharmaceuticals Press Release, "OncoMed Pharmaceuticals to Present Data from Two Clinical Programs in Advanced Pancreatic Cancer at the 2014 Gastrointestinal Cancers Symposium," Jan. 9, 2014, 2 pages.
OncoMed Pharmaceuticals Press Release, "OncoMed Pharmaceuticals to Review Key ASCO Data for Demcizumab and Tarextumab During Conference Call on Tuesday, Jun. 2, 2015," May 28, 2015, 2 pages.
OncoMed Pharmaceuticals, Press Release, "OncoMed Pharmaceuticals Updates Phase 1b Data for Demcizumab With Pemetrexed and Carboplatin in Patients With First-Line Stage IIIb/IV Non-Small Cell Lung Cancer at the AACR-NCO-EORTC International Conference on Molecular Targets and Cancer Therapeutics in Boston, Oct. 19-23, 2013," Oct. 20, 2013, 3 pages.
OncoMed Pharmaceuticals Press Release, "OncoMed Presents Data From Phase 1b Trial of Demcizumab in Pancreatic Cancer at the 2015 ASCO Annual Meeting," Jun. 1, 2015, 3 pages.
OncoMed Pharmaceuticals Press Release, "OncoMed Presents Data on Clinical and Preclinical Anti-Cancer Stem Cell Programs at American Association for Cancer Research Annual Meeting," Apr. 21, 2015, 3 pages.
OncoMed Pharmaceuticals, Press Release, "OncoMed Presents Data on Multiple Anti-Cancer Stem Cell Programs at American Association for Cancer Research Annual Meeting," Apr. 8, 2014, 4 pages.
OncoMed Pharmaceuticals Press Release, "OncoMed Presents Demcizumab Data From Phase 1b Clinical Trial in Non-Small Cell Lung Cancer Patients at the European Lung Cancer Conference," Apr. 16, 2015, 3 pages.
OncoMed Pharmaceuticals Press Release, "OncoMed Presents New Clinical and Biomarker Data From Its Tarextumab and Demcizumab Clinical Trials at the EORTC-NCI-AACR Symposium," Nov. 21, 2014, 3 pages.
OncoMed Pharmaceuticals Press Release, "OncoMed Presents New Data in Six Anti-Cancer Stem Cell Programs at AACR," Apr. 9, 2013, 3 pages.
OncoMed Pharmaceuticals Press Release, "OncoMed Presents Updated Demcizumab Data in Non-Small Cell Lung Cancer at the 2015 ASCO Annual Meeting," Jun. 1, 2015, 3 pages.
OncoMed Pharmaceuticals Press Release, "OncoMed to Present Clinical and Preclinical Data at the 26th EORTC-NCI-AACR Symposium on Molecular Targets and Cancer Therapeutics Meeting," Oct. 30, 2014, 2 pages.
OncoMed Pharmaceuticals Press Release, "OncoMed to Present Clinical Data for Demcizumab at the European Lung Cancer Conference," Apr. 9, 2015, 2 pages.

(56) References Cited

OTHER PUBLICATIONS

OncoMed Pharmaceuticals Press Release, "OncoMed to Present Data From Three Clinical Studies at the 2014 ASCO Annual Meeting," May 14, 2014, 4 pages.

OncoMed Pharmaceuticals Press Release, "OncoMed to Present New and Emerging Data from Demcizumab (anti-DLL4, OMP-21M18) and Tarextumab (anti-Notch2/3, OMP-59R5) Clinical Studies at the European Society for Medical Oncology 2014 Congress," Sep. 17, 2014, 2 pages.

OncoMed Pharmaceuticals Press Release, "OncoMed To Present New Data in Six Anti-Cancer Stem Cell Programs at AACR," Apr. 2, 2013, 2 pages.

Parks, A.L., et al., "Structure-function analysis of delta trafficking, receptor binding and signaling in *Drosophila*," Genetics 174(4):1947-1961, Genetics Society of America, United States (2006).

Parr, C., et al., "The Possible Correlation of Notch-1 and Notch-2 with Clinical Outcome and Tumour Clinicopathological Parameters in Human Breast Cancer," International Journal of Molecular Medicine 14(5):779-786, Spandidos Publications, Greece (2004).

Patel, N.S., et al., "Up-regulation of delta-like 4 ligand in human tumor vasculature and the role of basal expression in endothelial cell function," Cancer Research 65(19):8690-8697, American Association for Cancer Research, United States (2005).

Paul, W.E., "Immunogenicity and Antigen Structure," in Fundamental Immunology, Third Edition, pp. 242, Raven Press, United States (1993).

Pear, W.S. and Aster, J.C., "T Cell Acute Lymphoblastic Leukemia/Lymphoma: a Human Cancer Commonly Associated with Aberrant NOTCH1 Signaling," Current Opinion in Hematology 11(6):426-433, Lippincott Williams & Wilkins, United States (2004).

Pear, W.S., et al., "Exclusive development of T cell neoplasms in mice transplanted with bone marrow expressing activated Notch alleles," The Journal of Experimental Medicine 183(5):2283-2291, the Rockefeller University Press, United States (1996).

Phng, L.K., et al., "Nrarp coordinates endothelial Notch and Wnt signaling to control vessel density in angiogenesis," Developmental Cell 16(1):70-82, Elsevier Science, United States (2009).

Pisano, C., et al., "Undersulfated, low-molecular-weight glycol-split heparin as an antiangiogenic VEGF antagonist," Glycobiology 15(2):1C-6C, Oxford University Press, England (2005).

Mochizuki, K., et al., "Delta-like Ligand 4 Identifies a Previously Uncharacterized Population of Inflammatory Dendritic Cells That Plays Important Roles in Eliciting Allogeneic T Cell Responses in Mice," in: The Journal of Immunology 190(7):3772-3782, American Association of Immunologists, Bethesda, MD (Apr. 2013).

Nimmagadda, S., et al., "Expression pattern of Dll4 during chick embryogenesis," Histochem Cell Biol 128(2):147-152, Springer-Verlag, Germany (2007).

Oie, E., et al., "Activation of Notch signaling in cardiomyocytes during post-infarction remodeling," Scandinavian Cardiovascular Journal 44(6):359-366, Informa Healthcare, England (2010).

Politi, K., et al., "Notch in Mammary Gland Development and Breast Cancer," Seminars in Cancer Biology 14(5):341-347, Academic Press, United States (2004).

Portolano, S., et al., "Lack of Promiscuity in Autoantigen-Specific H and L Chain Combinations as Revealed by Human H and L Chain 'Roulette'," The Journal of Immunology 150(3):880-887, The American Association of Immunologists, United States (1993).

Presta, L.G., et al., "Humanization of an Antibody Directed Against IgE," The Journal of Immunology 151(5):2623-2632, The American Association of Immunologists, Inc., United States (Sep. 1993).

Purow, B.W., et al., "Expression of Notch-1 and its Ligands, Delta-like-1 and Jagged-1, is Critical for Glioma Cell Survival and Proliferation," Cancer Research 65(6):2353-2363, American Association for Cancer Research, United States (2005).

Yeh, E.T., "Cardiotoxicity Induced By Chemotherapy and Antibody Therapy," Annual Review of Medicine 57: 485-498, Annual Reviews, United States (2006).

Rae, F.K., et al., "Novel Association of a Diverse Range of Genes with Renal Cell Carcinoma as Identified by differential Display," International Journal of Cancer 88(5):726-732, John Wiley & Sons, Inc., United States (2000).

Rao, P.K., et al., "Isolation and characterization of the notch ligand delta4," Experimental Cell Research 260(2):379-386, Elsevier Science, United States (2000).

Rehman, A.O. and Wang, C-U, "Notch signaling in the regulation of tumor angiogenesis," TRENDS in Cell Biology 16(6):293-300, Elsevier Ltd., England (2006).

Response to Office Action dated Jan. 2, 2009, dated Jul. 2, 2009, in U.S. Appl. No. 11/607,780, Clarke, et al., filed Dec. 1, 2006.

Reya, T., et al., "Stem Cells, Cancer, and Cancer Stem Cells," Nature 414(6859):105-111, Nature Publishing Group, England (2001).

Ridgway, J., et al., "Inhibition of Dll4 signalling inhibits tumour growth by deregulating angiogenesis," Nature 444(7122):1083-1087, Nature Publishing Group, United States (2006).

Riechmann, L., et al., "Reshaping Human Antibodies for Therapy," Nature 332(6162):323-327, Nature Publishing Group, United States (Mar. 1988).

Rizzo, P., et al., "Rational Targeting of Notch Signaling in Cancer," Oncogene 27(38):5124-5131, Nature Publishing Group, England (Sep. 2008).

Robey, E., et al., "An Activated form of Notch Influences the Choice between CD4 and CD8 T Cell Lineages," Cell 87(3):483-492, Elsevier Science, United States (1996).

Rudikoff, S., et al., "Single Amino Acid Substitution Altering Antigen-binding Specificity," Proceedings of the National Academy of Sciences of the United States of America 79(6):1979-1983, National Academy of Sciences, Washington (Mar. 1982).

Sainson, R.C. and Harris, A.L., "Anti-Dll4 therapy: can we block tumour growth by increasing angiogenesis?," 13(9):389-395, Elsevier Science, United States (2007).

Sal-Man, N. and Shai, Y., "Arginine mutations within a transmembrane domain of Tar, an *Escherichia coli* aspartate receptor, can drive homodimer dissociation and heterodimer association in vivo," Biochemical Journal 385(Pt1):29-36, Portland Press, United Kingdom (2005).

Scehnet, J.S., et al., "Inhibition of Dll4-mediated signaling induces proliferation of immature vessels and results in poor tissue perfusion," Blood 109(11):4753-4760, American Society of Hematology, United Science (2007).

Schier, R., et al., "Identification of functional and structural amino-acid residues by parsimonious mutagenesis," Gene 169(2):147-155, Elsevier Science B.V., Netherlands (1996).

Schmidt, C., "Drug Makers Chase Cancer Stem Cells," Nature Biotechnology 26(4):366-367, Nature Publishing Group, United States (2008).

Shalaby, M.R., et al., "Development of Humanized Bispecific Antibodies Reactive with Cytotoxic Lymphocytes and Tumor Cells Overexpressing the HER2 Protooncogene," The Journal of Experimental Medicine 175(1):217-225, The Rockefeller University Press, United States (Jan. 1992).

Shawber, C.J., et al., "Notch Signaling in Primary Endothelial Cells," Annals of the New York Academy of Sciences 995:162-170, New York Academy of Sciences, United States (2003).

Sheets, M.D., et al., "Efficient Construction of a Large Nonimmune Phage Antibody Library: The Production of High-affinity Human Single-chain Antibodies to Protein Antigens," Proceedings of the National Academy of Sciences 95(11):6157-6162, The National Academy of Sciences, Unites States (1998).

Shields, J.M., et al., "Lack of Extracellular Signal-Regulated Kinase Mitogen-Activated Protein Kinase Signaling Shows A New Type of Melanoma," Cancer Research 67(4):1502-1512, American Association for Cancer Research, United States (2007).

Shutter, J. R., et al., "Dll4, a Novel Notch Ligand Expressed in Arterial Endothelium," Genes & Development 14(11):1313-1318, Cold Spring Harbor Laboratory Press, United States (2000).

Sica, D.A., "Angiogenesis Inhibitors and Hypertension," US Cardiovascular Disease 79-80, Touch Briefings, United States (2007).

Siekmann, A.F. and Lawson, N.D., "Notch signalling limits angiogenic cell behaviour in developing zebrafish arteries," Nature 445(7129):781-784, Nature Publishing Group, United States (2007).

(56) References Cited

OTHER PUBLICATIONS

Siena, S., et al., "Biomarkers predicting clinical outcome of epidermal growth factor receptor-targeted therapy in metastatic colorectal cancer," Journal of the National Cancer Institute 101(19):1308-1324, Oxford University Press, England (2009).

Sims, M.J., et al., "A Humanized CD18 Antibody can Block Function without Cell Destruction," The Journal of Immunology 151(4):2296-2308, The American Association of Immunologists, United States (Aug. 1993).

Skolnick, "From Genes to Protein Stucture and Function: Novel Applications of Computational Approaches in the Genomic era," Trends in Biotechnology 18:34-39, Elsevier Science Publishers, London (Jan. 2000).

Smith, D.C., et al., "A First-in-Human, Phase I Trial of the Anti-Dll4 Antibody (OMP-21M18) Targeting Cancer Stem Cells (CSCs) in Patients with Advanced Solid Tumors," http://www.oncomed.com/news/pr/studylposterfinalNov10.pdf, accessed Feb. 2, 2012, 1 page.

Smith, D.C., et al., "A Phase I Dose Escalation and Expansion Study of the Anticancer Stem Cell Agent Demcizumab (Anti-DLL4) in Patients with Previously Treated Solid Tumors," Clinical Cancer Research 20(24):6295-6303, American Association for Cancer Research, United States (2014).

Smith, D.C., et al., "A First-in-Human, Phase I Trial of the Anti-DLL4 Antibody (OMP-21M18) Targeting Cancer Stem Cells (CSC) in Patients with Advanced Solid Tumors," European Journal of Cancer Supplement 8(7):73, Abstract 222, 1 page (2010).

Smith, G.H., et al., "Constitutive Expression of a Truncated INT3 Gene in Mouse Mammary Epithelium Impairs Differentiation and Functional Development," Cell Growth & Differentiation 6(5):563-577, The American Association for Cancer Research, United States (1995).

Soriano J.V., et al., "Expression of an Activated Notch4(int-3) Oncoprotein Disrupts Morphogenesis and Induces an Invasive Phenotype in Mammary Epithelial Cells in vitro," International Journal of Cancer 86(5):652-659, John Wiley & Sons, United States (2000).

International Preliminary Report on Patentability, including the Written Opinion of the International Searching Authority, for International Application No. PCT/US2016/049703, dated Mar. 6, 2018, 12 pages.

Srivastava, M., et al., "Dual Targeting of Delta-Like Ligand 4 (DLL4) and Programmed Death 1 (PD1) Inhibits Tumor Growth and Generates Enhanced Long-Term Immunological Memory," 2015 AACR Annual Meeting, Apr. 19, Abstract 255, 1 page (2015).

Stinchcomb, D.T., et al., "Isolation and Characterisation of a Yeast Chromosomal Replicator," Nature 282(5734):39-43, Nature Publishing Group, England (Nov. 1979).

Sugimoto, A. et al., "Delta-4 Notch Ligand Promotes Erythroid Differentiation of Human Umbilical Cord Blood CD34+ Cells," Experimental Hematology 34(4):424-432, Elsevier Science Inc, Netherlands (2006).

Sullivan, D.C. and Bicknell, R., "New molecular pathways in angiogenesis," British Journal of Cancer 89:228-231, Cancer Research UK, United Kingdom (2003).

Supplementary European Search Report issued in the corresponding European Patent Application No. 07838966, European Patent Office, Munich, Germany, dated Apr. 6, 2010.

Suresh, M.R., et al., "Bispecific Monoclonal Antibodies from Hybrid Hybridomas," Methods in Enzymology 121:210-228, Academic Press Inc., United States (1986).

Suzuki, T., et al., "Imbalanced Expression of TAN-1 and Human Notch4 in Endometrial Cancers," International Journal of Oncology 17(6):1131-1139, Spandidos Publications, Greece (2000).

Takeda, T. and Kohno, M., "Brain Natriuretic Peptide in Hypertension," Hypertension Research 18(4):259-266, Nature Publishing Group, England (1995).

Tannock, I.F. and Hill R.P., "Influence of Tumor Microenvironment," in The Basic Science of Oncology, 3rd Edition, pp. 357-358, McGraw-Hill, United States (1998).

Tavares, M.J., et al., "Inhibition of Vascular Endothelium by the Notch-Ligand Delta-4 Unveils a Novel Therapeutic Target," Abstract#1944, Poster Board Session: 115-11, Blood 102(11):531a, American Society of Hematology, United States, 3 pages(2003).

Tax, F.E., et al., "Sequence of C. Elegans Lag-2 Reveals a Cell-signalling Domain Shared with delta and Serrate of *Drosophila*," Nature 368(6467):150-154, The National Academy of Sciences, United States (Mar. 1994).

Thelu, J., et al., "Notch Signalling is Linked to Epidermal Cell Differentiation Level in Basal Cell Carcinoma, Psoriasis and Wound Healing," BMC Dermatology 2(1):7, BioMed Central, England, 12 pages(2002).

Thurston, G., and Gale, N.W., "Vascular Endothelial Growth Factor and Other Signaling Pathways in Developmental and Pathologic Angiogenesis," International Journal of Hematology 80:7-20, The Japanese Society of Hematology, Japan (2004).

Thurston, G., et al., "The Delta paradox: DLL4 blockade leads to more tumour vessels but less tumour growth," Nature Reviews Cancer 7(5):327-331, Nature Publishing Group, United States (2007).

Ton, N.C. and Jayson, G.C., "Resistance to Anti-VEGF Agents," Current Pharmaceutical Design 10:51-64, Bentham Science Publishers Ltd., Netherlands (2004).

Traunecker, A., et al., "Bispecific Single Chain Molecules (Janusins) Target Cytotoxic Lymphocytes on HIV Infected Cells," The EMBO Journal 10(12):3655-3659, Oxford University Press, United Kingdom (Dec. 1991).

Tutt, A., et al., "Trispecific F(ab')3 Derivatives that use Cooperative Signaling via the TCR/CD3 Complex and CD2 to Activate and Redirect Resting Cytotoxic T Cells," The Journal of Immunology 147:60-69, The American Association of Immunologists, United States (Jul. 1991).

Unknown Author., "Tumor angiogenesis suppression therapy targeting the Notch signaling pathway," Suizo (Pancreas) 21(3):249, (2006).

Urlaub, G. and Chasin, L.A., "Isolation of Chinese Hamster Cell Mutants Deficient in Dihydrofolate Reductase Activity," Proceedings of the National Academy of Sciences USA 77(7):4216-4220, National Academy of Sciences, United States (Jul. 1980).

Uyttendaele, H., et al., "Notch4 and Wnt-1 Proteins Function to Regulate Branching Morphogenesis of Mammary Epithelial Cells in an Opposing Fashion," Developmental Biology 196(2):204-217, Elsevier Inc., Netherlands (1998).

Van Es, J.H., and Clevers, H., "Notch and Wnt Inhibitors as Potential New Drugs for Intestinal Neoplastic Disease," Trends in Molecular Medicine 11(11):496-502, Elsevier Inc., Netherlands (2005).

Van Limpt, V., et al., "SAGE Analysis of Neuroblastoma Reveals a High Expression of the Human Homologue of the *Drosophila* Delta Gene," Medical and Pediatric Oncology 35(6):554-558, Wiley-Liss, Inc., United States (2000).

Vaswani, S.K. and Hamilton, R.G., "Humanized antibodies as potential therapeutic drugs," Annals of Allergy, Asthma & Immunology 81(2):105-115, American College of Allergy, Asthma, & Immunology, United States (1998).

Vaughan, T.J., et al., "Human Antibodies with Sub-nanomolar Affinities Isolated from a Large non-Immunized Phage Display Library," Nature Biotechnology 14(3):309-314, Nature Publishing Co., United States (1996).

Verhoeyen, M., et al., "Reshaping Human Antibodies: Grafting an Antilysozyme Activity," Science 239(4847):1534-1536, American Association for the Advancement of Science, United States (Mar. 1988).

Vincke, C., and Muyldermans, S., "Introduction to Heavy Chain Antibodies and Derived Nanobodies," Methods in Molecular Biology 911:15-26, Springer Science + Business Media, Germany (2012).

Wang, J.C., et al., "Primitive human hematopoietic cells are enriched in cord blood compared with adult bone marrow or mobilized peripheral blood as measured by the quantitative in vivo SCID-repopulating cell assay," Blood 89(11):3919-3924, American Society of Hematology, United States (1997).

(56) References Cited

OTHER PUBLICATIONS

Ward, E.S., "Antibody engineering using *Escherichia coli* as host," Advances in Pharmacology 24:1-20, Academic Press, United States (1993).

Weijzen, S., et al., "Activation of Notch-1 Signaling Maintains the Neoplastic Phenotype in Human Ras-Transformed Cells," Nature Medicine 8(9):979-986, Nature Publishing Group, United States (2002).

Weng, A.P., et al., "Activating Mutations of NOTCH1 in Human T Cell Acute Lymphoblastic Leukemia," Science 306(5694):269-271, American Association for the Advancement of Science, United States (2004).

Weng, A.P., et al., "Growth Suppression of Pre-T Acute Lymphoblastic Leukemia Cells by Inhibition of Notch Signaling," Molecular and Cellular Biology 23(2):655-664, American Society for Microbiology, United States (2003).

Williams, C.K., et al., "Up-regulation of the Notch ligand Delta-like 4 inhibits VEGF-induced endothelial cell function," Blood 107(3):931-939, American Society of Hematology, United States (2006).

Wilson, A. and Radtke, F., "Multiple Functions of Notch Signaling in Self-renewing Organs and Cancer," FEBS Letters 580(12):2860-2868, Elsevier Science, United States (May 2006).

Wong, O.K., et al., "Voreloxin (formerly SNS-595) is a potent DNA intercalator and topoisomerase II poison that induces cell cycle dependent DNA damage and rapid apoptosis in cancer cell lines," 24th EORTC-NCI-AACR Symposium, Nov. 9, Poster 169, 1 page (2012).

Written Opinion for International Application No. PCT/US16/53316, ISA/US, Alexandria, Virginia, dated Feb. 21, 2017, 9 pages.

Written Opinion for International Application No. PCT/US2015/024251, ISA/US, Alexandria, Virginia, United States, dated Jul. 16, 2015, 7 pages.

Written Opinion of the International Searching Authority for International application No. PCT/US2007/020889, United States Patent and Trademark Office, United States, dated Apr. 9, 2008, 4 pages.

Written Opinion of the International Searching Authority for International Patent Application No. PCT/US11/60773, International Searching Authority, Alexandria, Virginia, United States, dated Mar. 26, 2012, 5 pages.

Wu, C., et al., "Simultaneous Targeting of Multiple Disease Mediators by a Dual-variable-domain Immunoglobulin," Nature Biotechnology 25(11):1290-1297, Nature Publishing Co., United States (2007).

Wu, H., et al., "Humanization of a Murine Monoclonal Antibody by Simultaneous Optimization of Framework and CDR Residues," Journal of Molecular Biology 294(1):151-162, Elsevier, England (Nov. 1999).

Xu, A., et al., "Regions of *Drosophila* Notch that Contribute to Ligand Binding and the Modulatory Influence of Fringe," The Journal of Biological Chemistry 280(34):30158-30165, American Society for Biochemistry and Molecular Biology, United States (2005).

Yan, M., et al., "Chronic DLL4 blockade induces vascular neoplasms," Nature 463(7282):E6-E7, Macmillan Publishers Limited, England (2010).

Yan, Wei., "Design and Engineering of Fc Heterodimers for the Production of Bispecific Antibodies," Symposium Abstract, Keystone Symposia on Molecular and Cellular Biology, Accelerating Life Science Discovery, Mar. 27-Apr. 1, 2009, Whistler, British Columbia.

Yan, Wei, The Design and Engineering of Fc Heterodimers for the Production of Bispecific Antibodies and Other Heterodirner Fusion Proteins, Symposium Abstract, 20th Annual International Conference, Antibody Engineering, Antibody Engineering and Immunotherapeutics for the 21st Century, Dec. 6-10, 2009, San Diego, California.

Yan, Wei, "The Design and Engineering of Fc Heterodimers for the Production of Bispecific Antibodies," Symposium Abstract, Eleventh Annual Phage Display of Antibodies and Peptides, Approaches for 2nd Generation Biologics, Apr. 6-Apr. 7, 2009, Boston, Massachusetts.

Yan, X.Q., et al., "A novel Notch ligand, Dll4, induces T-cell leukemia/lymphoma when overexpressed in mice by retroviral-mediated gene transfer," Blood 98(13):3793-3799, American Society of Hematology, United States (2001).

Yelton, D.E., "Affinity maturation of the BR96 anti-carcinoma antibody by codon-based mutagenesis," The Journal of Immunology 155(4):1994-2004, The American Association of Immunologists, United States (1995).

Yen, W., et al., "Targeting Cancer Stem Cells and Vasculature by a Novel Anti-Delta-Like 4 Ligand (DLL4) Antibody for Treatment of Triple Negative Breast Cancer," Cancer Research 69(Suppl.)(24):788s-789s, Abstract 5071, American Association for Cancer Research, United Sates (2009).

Yen, W.C., at al., "Targeting Cancer Stem Cells and Vasculature by a Novel Anti-Dll4 Antibody Inhibits Pancreatic Tumor Growth and Delays Tumor Recurrence," Presented at the 100th Annual Meeting of the American Association for Cancer Research in Denver, Colorado on Apr. 18-22, 2009.

Yen, W-C., et al., "Anti-DLL4 (demcizumab) inhibits tumor growth and reduces cancer stem cell frequency in patient-derived ovarian cancer xenografts," AACR 104th Annual Meeting 2013, Abstract 3725, Apr. 6-10, 1 page (2013).

Yen, W.C., et al., "Anti-DLL4 has broad spectrum activity in pancreatic cancer dependent on targeting DLL4-Notch signaling in both tumor and vasculature cells," Clinical Cancer Research 18(19):5374-5386, American Association for Cancer Research, United States (2012).

Yen, W-C., et al., "Dual targeting of DLL4 and VEGF signaling by a novel bispecific antibody inhibits tumor growth and reduces cancer stem cell frequency," AACR Annual Meeting 2014, Apr. 5-9, 2014, Abstract 207, 1 page (2014).

Yen, W-C., et al., "Targeting cancer stem cells by an anti-DLL4 antibody inhibits epithelial-to-mesenchymal transition, delays tumor recurrence and overcomes drug resistance in breast and pancreatic cancer," AACR 103rd Annual Meeting 2012, Mar. 31-Apr. 4, Abstract 3357, 1 page (2013).

Yen, W-C., et al., "The combination of gemcitabine/nab-paclitaxel and anti-DLL4 (demcizumab) produces synergistic growth inhibition, delays tumor recurrence and reduces tumor initiating cells in pancreatic cancer," American Association for Cancer Research Annual Meeting 2014, Abstract 1898, 1 page (2014).

Yoneya, T., et al., "Molecular Cloning of Delta-4, A New Mouse and Human Notch Ligand," Journal of Biochemistry 129(1):27-34, Japanese Biochemical Society, Japan (2001).

Zagouras, P., et al., "Alterations in Notch Signaling in Neoplastic Lesions of the Human Cervix," Proceedings of the National Academy of Sciences 92(14):6414-6418, National Academy of Sciences, United States (1995).

Brekke, O.H. and Sandlie, I., "Therapeutic Antibodies for Human Diseases at the Dawn of the Twenty-First Century," Nature reviews. Drug Discovery 2(1):52-62, Nature Publishing Group, England (2003).

Carter, P., "Bispecific Human IgG by Design," Journal of Immunological Methods 248(1-2):7-15, Elsevier, Netherlands (2001).

Germain, C., et al.,, "Redirecting Nk Cells Mediated Tumor Cell Lysis by a New Recombinant Bifunctional Protein," Protein Engineering, Design & Selection 21(11):665-672, Oxford University Press, England (2008).

Kufer, P., et al., "A Revival of Bispecific Antibodies," Trends in Biotechnology 22(5):238-244, Elsevier Science Publishers, England (May 2004).

Kumar, S. and Nussinov, R., "Relationship Between Ion Pair Geometries and Electrostatic Strengths in Proteins," Biophysical Journal 83(3):1595-1612, Cell Press, United States (Sep. 2002).

Li, J.L., et al., "DLL4-notch Signaling Mediates Tumor Resistance to Anti-VEGF Therapy in Vivo," Cancer Research 71(18):6073-6083, American Association for Cancer Research, United States (Sep. 2011).

Lu, D., et al., "A Fully Human Recombinant IgG-like Bispecific Antibody to Both the Epidermal Growth Factor Receptor and the

(56) References Cited

OTHER PUBLICATIONS

Insulin-like Growth Factor Receptor for Enhanced Antitumor Activity," The Journal of Biological Chemistry 280(20):19665-19672, American Society for Biochemistry and Molecular Biology, United States (May 2005).

Paul, W.E., "Structure and Function of Immunoglobulins," in Fundamental Immunology, Third Edition, pp. 292-295, Raven Press, New York, United States (1993).

Presta, L.G., "Molecular Engineering and Design of Therapeutic Antibodies," Current Opinion in Immunology 20(4):460-470, Elsevier, England (2008).

Xie, Z., et al., "A New Format of Bispecific Antibody: Highly Efficient Heterodimerization, Expression and Tumor Cell Lysis," Journal of Immunological Methods 296(1-2):95-101, Elsevier, Netherlands (2005).

Zuo, Z., et al., "An Efficient Route to the Production of an IgG-like Bispecific Antibody," Protein Engineering 13(5):361-367, Oxford University Press, England (May 2000).

Non-Final Office Action dated May 31, 2017, in U.S. Appl. No. 15/401,543, Gurney, et al., filed Jan. 9, 2017, 6 pages.

Cohn et al., "Bevacizumab and weekly taxane chemotherapy demonstrates activity in refractory ovarian cancer," Gynecologic Oncology 102 (2006) 134-139.

Li et al., "Targeting DLL4 in tumors shows preclinical activity but potentially significant toxicity," Future Oncol., 2010, 6(7), 1099-1103.

Lobov et al., "The DLL4/Notch pathway controls post angiogenic blood vessel remodeling and regression by modulating vasoconstriction and blood flow," Blood. Jun. 16, 2011, 117(24):6728-37. doi: 10/1182/blood-2010-08-302067. Epub Apr. 15, 2011.

Osherovich, Lev. "Notch nicked again," SciBX 4(6): doi:10.1038/scibx.2011.151, Published online Feb. 10, 2011.

Thurston and Kitajewski, "VEGF and Delta-Notch: interacting signalling pathways in tumour angiogenesis," Br J Cancer. Oct. 21, 2008; 99(8):1204-9. doi: 10.1038/sj.bjc.6604484. Epub Sep. 30, 2008.

Yan, M. "Therapeutic promise and challenges of targeting DLL4/NOTCH1," Vasc Cell. Aug. 8, 2011; 3:17; doi: 10.1186/2045-824X-3-17.

Yan and Plowman, "Delta-like 4/Notch signaling and its therapeutic implications," Clin Cancer Res. Dec. 15, 2007, 13(24):7243-6.

Hu et al., "Biological roles of the Delta family Notch ligand DLL4 in tumor and endothelial cells in ovarian cancer," Cancer Res. Sep. 15, 2011; 71(18); 6030-9. Doi: 10.1158/0008-5472.CAN-10-2719. Epub Jul. 27, 2011.

Jenkins et al., "MEDI0639: a novel therapeutic antibody targeting Dll4 modulates endothelial cell function and angiogenesis in vivo," Mol Cancer Ther. Aug. 2012; 11(8)1650-60. Doi: 10.1158/1535-7163.MCT-11-1027. Epub Jun. 7, 2012.

NCT01952249, "A Study of Demcizumab Plus Paclitaxel in Subjects With Platinum Resistant Ovarian (SIERRA)," ClinicalTrials.gov archive, accessed at https://clinicaltrials.gov/ct2/show/NCT01952249, accessed on Jun. 27, 2022, first posted Sep. 27, 2013, last updated posted Sep. 9, 2020, 6 pages.

Figure 1A

| Bispecific Antibody | Anti-VEGF binding region | | | | | |
|---|---|---|---|---|---|---|
| | Heavy Chain | | | | | |
| | CDR1 | CDR2 | CDR3 | CDR1 | CDR2 | CDR3 |
| | | | | Anti-DLL4 binding region | | |
| | | | | Heavy Chain | | |
| 219R45-MB-21M18 | NYWMH (SEQ ID NO:17) | DINPSNGRTSYKEKFKR (SEQ ID NO:18) | HYDDKYYPLMDY (SEQ ID NO:19) | TAYYIH (SEQ ID NO:13) | YISSYNGATNYNQKFKG (SEQ ID NO:15) | RDYDYDVGMDY (SEQ ID NO:16) |
| 219R45-MB-21R79 | NYWMH (SEQ ID NO:17) | DINPSNGRTSYKEKFKR (SEQ ID NO:18) | HYDDKYYPLMDY (SEQ ID NO:19) | TAYYIH (SEQ ID NO:13) | YIANYNRATNYNQKFKG (SEQ ID NO:14) | RDYDYDVGMDY (SEQ ID NO:16) |
| 219R45-MB-21R75 | NYWMH (SEQ ID NO:17) | DINPSNGRTSYKEKFKR (SEQ ID NO:18) | HYDDKYYPLMDY (SEQ ID NO:19) | TAYYIH (SEQ ID NO:13) | YIAGYKDATNYNQKFKG (SEQ ID NO:59) | RDYDYDVGMDY (SEQ ID NO:16) |
| 219R45-MB-21R83 | NYWMH (SEQ ID NO:17) | DINPSNGRTSYKEKFKR (SEQ ID NO:18) | HYDDKYYPLMDY (SEQ ID NO:19) | TAYYIH (SEQ ID NO:13) | YISNYNRATNYNQKFKG (SEQ ID NO:65) | RDYDYDVGMDY (SEQ ID NO:16) |

| Bispecific Antibody | Anti-VEGF and Anti-DLL4 binding regions | | |
|---|---|---|---|
| | Light Chain | | |
| | CDR1 | CDR2 | CDR3 |
| 219R45-MB-21M18 | RASESVDNYGISFMK (SEQ ID NO:20) | AASNQGS (SEQ ID NO:21) | QQSKEVPWTFGG (SEQ ID NO:22) |
| 219R45-MB-21R79 | RASESVDNYGISFMK (SEQ ID NO:20) | AASNQGS (SEQ ID NO:21) | QQSKEVPWTFGG (SEQ ID NO:22) |
| 219R45-MB-21R75 | RASESVDNYGISFMK (SEQ ID NO:20) | AASNQGS (SEQ ID NO:21) | QQSKEVPWTFGG (SEQ ID NO:22) |
| 219R45-MB-21R83 | RASESVDNYGISFMK (SEQ ID NO:20) | AASNQGS (SEQ ID NO:21) | QQSKEVPWTFGG (SEQ ID NO:22) |

Figure 1B

| Bispecific Antibody | Anti-VEGF binding region | | Anti-DLL4 binding region | |
|---|---|---|---|---|
| | Heavy Chain Variable Region | Light Chain Variable Region | Heavy Chain Variable Region | Light Chain Variable Region |
| 219R45-MB-21M18 | SEQ ID NO:11 | SEQ ID NO:12 | SEQ ID NO:9 | SEQ ID NO:12 |
| 219R45-MB-21R79 | SEQ ID NO:11 | SEQ ID NO:12 | SEQ ID NO:10 | SEQ ID NO:12 |
| 219R45-MB-21R75 | SEQ ID NO:11 | SEQ ID NO:12 | SEQ ID NO:58 | SEQ ID NO:12 |
| 219R45-MB-21R83 | SEQ ID NO:11 | SEQ ID NO:12 | SEQ ID NO:64 | SEQ ID NO:12 |

Figure 1C

| Bispecific Antibody | Anti-VEGF binding region | | Anti-DLL4 binding region | |
|---|---|---|---|---|
| | Heavy Chain | Light Chain | Heavy Chain | Light Chain |
| 219R45-MB-21M18 | SEQ ID NO:3 SEQ ID NO:7 | SEQ ID NO:4 SEQ ID NO:8 | SEQ ID NO:1 SEQ ID NO:5 | SEQ ID NO:4 SEQ ID NO:8 |
| 219R45-MB-21R79 | SEQ ID NO:3 SEQ ID NO:7 | SEQ ID NO:4 SEQ ID NO:8 | SEQ ID NO:2 SEQ ID NO:6 | SEQ ID NO:4 SEQ ID NO:8 |
| 219R45-MB-21R75 | SEQ ID NO:3 SEQ ID NO:7 | SEQ ID NO:4 SEQ ID NO:8 | SEQ ID NO:57 SEQ ID NO:56 | SEQ ID NO:4 SEQ ID NO:8 |
| 219R45-MB-21R83 | SEQ ID NO:3 SEQ ID NO:7 | SEQ ID NO:4 SEQ ID NO:8 | SEQ ID NO:63 SEQ ID NO:62 | SEQ ID NO:4 SEQ ID NO:8 |

SEQUENCE LISTING

<160> NUMBER OF SEQ ID NOS: 80

<210> SEQ ID NO 1
<211> LENGTH: 464
<212> TYPE: PRT
<213> ORGANISM: Artificial sequence
<220> FEATURE:
<223> OTHER INFORMATION: 21M18 Heavy chain with signal sequence

<400> SEQUENCE: 1

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ser Ser Tyr Asn Gly Ala Thr Asn Tyr Asn

```
                65                  70                  75                  80
            Gln Lys Phe Lys Gly Arg Val Thr Phe Thr Thr Asp Thr Ser Thr Ser
                            85                  90                  95

Thr Ala Tyr Met Glu Leu Arg Ser Leu Arg Ser Asp Asp Thr Ala Val
                        100                 105                 110

Tyr Tyr Cys Ala Arg Asp Tyr Asp Tyr Val Gly Met Asp Tyr Trp
                    115                 120                 125

Gly Gln Gly Thr Leu Val Thr Val Ser Ser Ala Ser Thr Lys Gly Pro
                130                 135                 140

Ser Val Phe Pro Leu Ala Pro Cys Ser Arg Ser Thr Ser Glu Ser Thr
            145                 150                 155                 160

Ala Ala Leu Gly Cys Leu Val Lys Asp Tyr Phe Pro Glu Pro Val Thr
                            165                 170                 175

Val Ser Trp Asn Ser Gly Ala Leu Thr Ser Gly Val His Thr Phe Pro
                        180                 185                 190

Ala Val Leu Gln Ser Ser Gly Leu Tyr Ser Leu Ser Ser Val Val Thr
                    195                 200                 205

Val Pro Ser Ser Asn Phe Gly Thr Gln Thr Tyr Thr Cys Asn Val Asp
                210                 215                 220

His Lys Pro Ser Asn Thr Lys Val Asp Lys Thr Val Glu Arg Lys Cys
            225                 230                 235                 240

Cys Val Glu Cys Pro Pro Cys Pro Ala Pro Pro Val Ala Gly Pro Ser
                            245                 250                 255

Val Phe Leu Phe Pro Pro Lys Pro Lys Asp Thr Leu Met Ile Ser Arg
                        260                 265                 270

Thr Pro Glu Val Thr Cys Val Val Val Asp Val Ser His Glu Asp Pro
                    275                 280                 285

Glu Val Gln Phe Asn Trp Tyr Val Asp Gly Val Glu Val His Asn Ala
                290                 295                 300

Lys Thr Lys Pro Arg Glu Glu Gln Phe Asn Ser Thr Phe Arg Val Val
            305                 310                 315                 320

Ser Val Leu Thr Val Val His Gln Asp Trp Leu Asn Gly Lys Glu Tyr
                            325                 330                 335

Lys Cys Lys Val Ser Asn Lys Gly Leu Pro Ala Pro Ile Glu Lys Thr
                        340                 345                 350

Ile Ser Lys Thr Lys Gly Gln Pro Arg Glu Pro Gln Val Tyr Thr Leu
                    355                 360                 365

Pro Pro Ser Arg Glu Glu Met Thr Lys Asn Gln Val Ser Leu Thr Cys
                370                 375                 380

Leu Val Glu Gly Phe Tyr Pro Ser Asp Ile Ala Val Glu Trp Glu Ser
            385                 390                 395                 400

Asn Gly Gln Pro Glu Asn Asn Tyr Lys Thr Thr Pro Pro Met Leu Asp
                            405                 410                 415

Ser Asp Gly Ser Phe Phe Leu Tyr Ser Glu Leu Thr Val Asp Lys Ser
                        420                 425                 430

Arg Trp Gln Gln Gly Asn Val Phe Ser Cys Ser Val Met His Glu Ala
                    435                 440                 445

Leu His Asn His Tyr Thr Gln Lys Ser Leu Ser Leu Ser Pro Gly Lys
                450                 455                 460

<210> SEQ ID NO 2
<211> LENGTH: 464
<212> TYPE: PRT
<213> ORGANISM: Artificial sequence
```

```
<220> FEATURE:
<223> OTHER INFORMATION: 21R79 Heavy chain with signal sequence

<400> SEQUENCE: 2

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ala Asn Tyr Asn Arg Ala Thr Asn Tyr Asn
65                  70                  75                  80

Gln Lys Phe Lys Gly Arg Val Thr Phe Thr Asp Thr Ser Thr Ser
            85                  90                  95

Thr Ala Tyr Met Glu Leu Arg Ser Leu Arg Ser Asp Asp Thr Ala Val
                100                 105                 110

Tyr Tyr Cys Ala Arg Asp Tyr Asp Tyr Asp Val Gly Met Asp Tyr Trp
            115                 120                 125

Gly Gln Gly Thr Leu Val Thr Val Ser Ser Ala Ser Thr Lys Gly Pro
130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Glu Gly Phe Tyr Pro Ser Asp Ile Ala Val Glu Trp Glu Ser
385                 390                 395                 400
```

```
Asn Gly Gln Pro Glu Asn Asn Tyr Lys Thr Thr Pro Pro Met Leu Asp
            405                 410                 415

Ser Asp Gly Ser Phe Phe Leu Tyr Ser Glu Leu Thr Val Asp Lys Ser
        420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
        450                 455                 460

<210> SEQ ID NO 3
<211> LENGTH: 466
<212> TYPE: PRT
<213> ORGANISM: Artificial sequence
<220> FEATURE:
<223> OTHER INFORMATION: 219R45 Heavy chain with signal sequence

<400> SEQUENCE: 3

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Tyr Trp Met His Trp Val Arg Gln Ala Pro Gly Gln Gly Leu
    50                  55                  60

Glu Trp Met Gly Asp Ile Asn Pro Ser Asn Gly Arg Thr Ser Tyr Lys
65                  70                  75                  80

Glu Lys Phe Lys Arg Arg Val Thr Leu Ser Val Asp Lys Ser Ser Ser
                85                  90                  95

Thr Ala Tyr Met Glu Leu Ser Ser Leu Arg Ser Glu Asp Thr Ala Val
            100                 105                 110

Tyr Phe Cys Thr Ile His Tyr Asp Asp Lys Tyr Tyr Pro Leu Met Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300
```

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
            325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Lys Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
            405                 410                 415

Leu Lys Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 4
<211> LENGTH: 238
<212> TYPE: PRT
<213> ORGANISM: Artificial sequence
<220> FEATURE:
<223> OTHER INFORMATION: Light chain with signal sequence

<400> SEQUENCE: 4

Met Val Leu Gln Thr Gln Val Phe Ile Ser Leu Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Ser Cys Arg Ala Ser Glu Ser
        35                  40                  45

Val Asp Asn Tyr Gly Ile Ser Phe Met Lys Trp Phe Gln Gln Lys Pro
    50                  55                  60

Gly Gln Pro Pro Lys Leu Leu Ile Tyr Ala Ala Ser Asn Gln Gly Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
            100                 105                 110

Gln Gln Ser Lys Glu Val Pro Trp Thr Phe Gly Gly Gly Thr Lys Val
            115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 5
<211> LENGTH: 445
<212> TYPE: PRT
<213> ORGANISM: Artificial sequence
<220> FEATURE:
<223> OTHER INFORMATION: 21M18 Heavy chain without predicted signal
      sequence

<400> SEQUENCE: 5

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys

```
305                 310                 315                 320
Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
                340                 345                 350

Arg Glu Glu Met Thr Lys Asn Gln Val Ser Leu Thr Cys Leu Val Glu
                355                 360                 365

Gly Phe Tyr Pro Ser Asp Ile Ala Val Glu Trp Glu Ser Asn Gly Gln
                370                 375                 380

Pro Glu Asn Asn Tyr Lys Thr Thr Pro Pro Met Leu Asp Ser Asp Gly
385                 390                 395                 400

Ser Phe Phe Leu Tyr Ser Glu Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
                435                 440                 445

<210> SEQ ID NO 6
<211> LENGTH: 445
<212> TYPE: PRT
<213> ORGANISM: Artificial sequence
<220> FEATURE:
<223> OTHER INFORMATION: 21R79 Heavy chain without predicted signal
      sequence

<400> SEQUENCE: 6

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
                35                  40                  45

Gly Tyr Ile Ala Asn Tyr Asn Arg Ala Thr Asn Tyr Asn Gln Lys Phe
50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser Ala Ser Thr Lys Gly Pro Ser Val Phe
                115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Asn Phe Gly Thr Gln Thr Tyr Thr Cys Asn Val Asp His Lys Pro
                195                 200                 205

Ser Asn Thr Lys Val Asp Lys Thr Val Glu Arg Lys Cys Cys Val Glu
                210                 215                 220
```

```
Cys Pro Pro Cys Pro Ala Pro Pro Val Ala Gly Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
        260                 265                 270

Phe Asn Trp Tyr Val Asp Gly Val Glu Val His Asn Ala Lys Thr Lys
    275                 280                 285

Pro Arg Glu Glu Gln Phe Asn Ser Thr Phe Arg Val Val Ser Val Leu
    290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
        340                 345                 350

Arg Glu Glu Met Thr Lys Asn Gln Val Ser Leu Thr Cys Leu Val Glu
    355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Met Leu Asp Ser Asp Gly
385                 390                 395                 400

Ser Phe Phe Leu Tyr Ser Glu Leu Thr Val Asp Lys Ser Arg Trp Gln
            405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
    435                 440                 445

<210> SEQ ID NO 7
<211> LENGTH: 447
<212> TYPE: PRT
<213> ORGANISM: Artificial sequence
<220> FEATURE:
<223> OTHER INFORMATION: 21R79 Heavy chain without predicted signal
      sequence

<400> SEQUENCE: 7

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Asp Ile Asn Pro Ser Asn Gly Arg Thr Ser Tyr Lys Glu Lys Phe
    50                  55                  60

Lys Arg Arg Val Thr Leu Ser Val Asp Lys Ser Ser Ser Thr Ala Tyr
65                  70                  75                  80

Met Glu Leu Ser Ser Leu Arg Ser Glu Asp Thr Ala Val Tyr Phe Cys
                85                  90                  95

Thr Ile His Tyr Asp Asp Lys Tyr Tyr Pro Leu Met Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Thr Val
            180                 185                 190

Pro Ser Ser Asn Phe Gly Thr Gln Thr Tyr Thr Cys Asn Val Asp His
            195                 200                 205

Lys Pro Ser Asn Thr Lys Val Asp Lys Thr Val Glu Arg Lys Cys Cys
        210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Phe Arg Val Val Ser
290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                325                 330                 335

Ser Lys Thr Lys Gly Gln Pro Arg Glu Pro Gln Val Tyr Thr Leu Pro
            340                 345                 350

Pro Ser Arg Glu Lys Met Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Met Leu Lys Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 8
<211> LENGTH: 217
<212> TYPE: PRT
<213> ORGANISM: Artificial sequence
<220> FEATURE:
<223> OTHER INFORMATION: Light chain without predicted signal sequence

<400> SEQUENCE: 8

Asp Ile Val Met Thr Gln Ser Pro Asp Ser Leu Ala Val Ser Leu Gly
1               5                   10                  15

Glu Arg Ala Thr Ile Ser Cys Arg Ala Ser Glu Ser Val Asp Asn Tyr
            20                  25                  30

Gly Ile Ser Phe Met Lys Trp Phe Gln Gln Lys Pro Gly Gln Pro Pro
        35                  40                  45

Lys Leu Leu Ile Tyr Ala Ala Ser Asn Gln Gly Ser Gly Val Pro Asp
    50                  55                  60
```

-continued

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Ser Lys
            85                  90                  95

Glu Val Pro Trp Thr Phe Gly Gly Gly Thr Lys Val Glu Ile Lys Arg
            100                 105                 110

Thr Val Ala Ala Pro Ser Val Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 9
<211> LENGTH: 119
<212> TYPE: PRT
<213> ORGANISM: Artificial sequence
<220> FEATURE:
<223> OTHER INFORMATION: 21M18 Heavy chain variable region

<400> SEQUENCE: 9

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ser Ser Tyr Asn Gly Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
            85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 10
<211> LENGTH: 119
<212> TYPE: PRT
<213> ORGANISM: Artificial sequence
<220> FEATURE:
<223> OTHER INFORMATION: 21R79 Heavy chain variable region

<400> SEQUENCE: 10

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr

```
                20                  25                  30
Tyr Ile His Trp Val Lys Gln Ala Pro Gly Gln Gly Leu Glu Trp Ile
            35                  40                  45
Gly Tyr Ile Ala Asn Tyr Asn Arg Ala Thr Asn Tyr Asn Gln Lys Phe
        50                  55                  60
Lys Gly Arg Val Thr Phe Thr Thr Asp Thr Ser Thr Ser Thr Ala Tyr
65                  70                  75                  80
Met Glu Leu Arg Ser Leu Arg Ser Asp Asp Thr Ala Val Tyr Tyr Cys
                85                  90                  95
Ala Arg Asp Tyr Asp Tyr Asp Val Gly Met Asp Tyr Trp Gly Gln Gly
                100                 105                 110
Thr Leu Val Thr Val Ser Ser
            115

<210> SEQ ID NO 11
<211> LENGTH: 121
<212> TYPE: PRT
<213> ORGANISM: Artificial sequence
<220> FEATURE:
<223> OTHER INFORMATION: 21R79 Heavy chain variable region

<400> SEQUENCE: 11

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asn Tyr
                20                  25                  30
Trp Met His Trp Val Arg Gln Ala Pro Gly Gln Gly Leu Glu Trp Met
            35                  40                  45
Gly Asp Ile Asn Pro Ser Asn Gly Arg Thr Ser Tyr Lys Glu Lys Phe
        50                  55                  60
Lys Arg Arg Val Thr Leu Ser Val Asp Lys Ser Ser Ser Thr Ala Tyr
65                  70                  75                  80
Met Glu Leu Ser Ser Leu Arg Ser Glu Asp Thr Ala Val Tyr Phe Cys
                85                  90                  95
Thr Ile His Tyr Asp Asp Lys Tyr Tyr Pro Leu Met Asp Tyr Trp Gly
                100                 105                 110
Gln Gly Thr Leu Val Thr Val Ser Ser
            115                 120

<210> SEQ ID NO 12
<211> LENGTH: 111
<212> TYPE: PRT
<213> ORGANISM: Artificial sequence
<220> FEATURE:
<223> OTHER INFORMATION: Light chain variable region

<400> SEQUENCE: 12

Asp Ile Val Met Thr Gln Ser Pro Asp Ser Leu Ala Val Ser Leu Gly
1               5                   10                  15
Glu Arg Ala Thr Ile Ser Cys Arg Ala Ser Glu Ser Val Asp Asn Tyr
                20                  25                  30
Gly Ile Ser Phe Met Lys Trp Phe Gln Gln Lys Pro Gly Gln Pro Pro
            35                  40                  45
Lys Leu Leu Ile Tyr Ala Ala Ser Asn Gln Gly Ser Gly Val Pro Asp
        50                  55                  60
Arg Phe Ser Gly Ser Gly Ser Gly Thr Asp Phe Thr Leu Thr Ile Ser
65                  70                  75                  80
```

Ser Leu Gln Ala Glu Asp Val Ala Val Tyr Tyr Cys Gln Gln Ser Lys
            85                  90                  95

Glu Val Pro Trp Thr Phe Gly Gly Gly Thr Lys Val Glu Ile Lys
            100                 105                 110

<210> SEQ ID NO 13
<211> LENGTH: 6
<212> TYPE: PRT
<213> ORGANISM: Artificial sequence
<220> FEATURE:
<223> OTHER INFORMATION: 21R75, 21R79, 21R83, and 21M18 Heavy chain CDR1

<400> SEQUENCE: 13

Thr Ala Tyr Tyr Ile His
1               5

<210> SEQ ID NO 14
<211> LENGTH: 17
<212> TYPE: PRT
<213> ORGANISM: Artificial sequence
<220> FEATURE:
<223> OTHER INFORMATION: 21R79 Heavy chain CDR2

<400> SEQUENCE: 14

Tyr Ile Ala Asn Tyr Asn Arg Ala Thr Asn Tyr Asn Gln Lys Phe Lys
1               5                   10                  15

Gly

<210> SEQ ID NO 15
<211> LENGTH: 17
<212> TYPE: PRT
<213> ORGANISM: Artificial sequence
<220> FEATURE:
<223> OTHER INFORMATION: 21M18 Heavy chain CDR2

<400> SEQUENCE: 15

Tyr Ile Ser Ser Tyr Asn Gly Ala Thr Asn Tyr Asn Gln Lys Phe Lys
1               5                   10                  15

Gly

<210> SEQ ID NO 16
<211> LENGTH: 11
<212> TYPE: PRT
<213> ORGANISM: Artificial sequence
<220> FEATURE:
<223> OTHER INFORMATION: 21R75, 21R79, 21R83, and 21M18 Heavy chain CDR3

<400> SEQUENCE: 16

Arg Asp Tyr Asp Tyr Asp Val Gly Met Asp Tyr
1               5                   10

<210> SEQ ID NO 17
<211> LENGTH: 5
<212> TYPE: PRT
<213> ORGANISM: Artificial sequence
<220> FEATURE:
<223> OTHER INFORMATION: 219R45 Heavy chain CDR1

<400> SEQUENCE: 17

Asn Tyr Trp Met His
1               5

<210> SEQ ID NO 18
<211> LENGTH: 17
<212> TYPE: PRT

-continued

<213> ORGANISM: Artificial sequence
<220> FEATURE:
<223> OTHER INFORMATION: 219R45 Heavy chain CDR2

<400> SEQUENCE: 18

Asp Ile Asn Pro Ser Asn Gly Arg Thr Ser Tyr Lys Glu Lys Phe Lys
1               5                   10                  15

Arg

<210> SEQ ID NO 19
<211> LENGTH: 12
<212> TYPE: PRT
<213> ORGANISM: Artificial sequence
<220> FEATURE:
<223> OTHER INFORMATION: 219R45 Heavy chain CDR3

<400> SEQUENCE: 19

His Tyr Asp Asp Lys Tyr Tyr Pro Leu Met Asp Tyr
1               5                   10

<210> SEQ ID NO 20
<211> LENGTH: 15
<212> TYPE: PRT
<213> ORGANISM: Artificial sequence
<220> FEATURE:
<223> OTHER INFORMATION: Light chain CDR1

<400> SEQUENCE: 20

Arg Ala Ser Glu Ser Val Asp Asn Tyr Gly Ile Ser Phe Met Lys
1               5                   10                  15

<210> SEQ ID NO 21
<211> LENGTH: 7
<212> TYPE: PRT
<213> ORGANISM: Artificial sequence
<220> FEATURE:
<223> OTHER INFORMATION: Light chain CDR2

<400> SEQUENCE: 21

Ala Ala Ser Asn Gln Gly Ser
1               5

<210> SEQ ID NO 22
<211> LENGTH: 12
<212> TYPE: PRT
<213> ORGANISM: Artificial sequence
<220> FEATURE:
<223> OTHER INFORMATION: Light chain CDR3

<400> SEQUENCE: 22

Gln Gln Ser Lys Glu Val Pro Trp Thr Phe Gly Gly
1               5                   10

<210> SEQ ID NO 23
<211> LENGTH: 522
<212> TYPE: PRT
<213> ORGANISM: Homo sapiens

<400> SEQUENCE: 23

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60
Phe Gln Ala Val Val Ser Pro Gly Pro Cys Thr Phe Gly Thr Val Ser
65                  70                  75                  80
Thr Pro Val Leu Gly Thr Asn Ser Phe Ala Val Arg Asp Asp Ser Ser
                85                  90                  95
Gly Gly Gly Arg Asn Pro Leu Gln Leu Pro Phe Asn Phe Thr Trp Pro
                100                 105                 110
Gly Thr Phe Ser Leu Ile Ile Glu Ala Trp His Ala Pro Gly Asp Asp
            115                 120                 125
Leu Arg Pro Glu Ala Leu Pro Pro Asp Ala Leu Ile Ser Lys Ile Ala
    130                 135                 140
Ile Gln Gly Ser Leu Ala Val Gly Gln Asn Trp Leu Leu Asp Glu Gln
145                 150                 155                 160
Thr Ser Thr Leu Thr Arg Leu Arg Tyr Ser Tyr Arg Val Ile Cys Ser
                165                 170                 175
Asp Asn Tyr Tyr Gly Asp Asn Cys Ser Arg Leu Cys Lys Lys Arg Asn
            180                 185                 190
Asp His Phe Gly His Tyr Val Cys Gln Pro Asp Gly Asn Leu Ser Cys
    195                 200                 205
Leu Pro Gly Trp Thr Gly Glu Tyr Cys Gln Gln Pro Ile Cys Leu Ser
    210                 215                 220
Gly Cys His Glu Gln Asn Gly Tyr Cys Ser Lys Pro Ala Glu Cys Leu
225                 230                 235                 240
Cys Arg Pro Gly Trp Gln Gly Arg Leu Cys Asn Glu Cys Ile Pro His
                245                 250                 255
Asn Gly Cys Arg His Gly Thr Cys Ser Thr Pro Trp Gln Cys Thr Cys
            260                 265                 270
Asp Glu Gly Trp Gly Gly Leu Phe Cys Asp Gln Asp Leu Asn Tyr Cys
    275                 280                 285
Thr His His Ser Pro Cys Lys Asn Gly Ala Thr Cys Ser Asn Ser Gly
    290                 295                 300
Gln Arg Ser Tyr Thr Cys Thr Cys Arg Pro Gly Tyr Thr Gly Val Asp
305                 310                 315                 320
Cys Glu Leu Glu Leu Ser Glu Cys Asp Ser Asn Pro Cys Arg Asn Gly
                325                 330                 335
Gly Ser Cys Lys Asp Gln Glu Asp Gly Tyr His Cys Leu Cys Pro Pro
            340                 345                 350
Gly Tyr Tyr Gly Leu His Cys Glu His Ser Thr Leu Ser Cys Ala Asp
    355                 360                 365
Ser Pro Cys Phe Asn Gly Gly Ser Cys Arg Glu Arg Asn Gln Gly Ala
    370                 375                 380
Asn Tyr Ala Cys Glu Cys Pro Pro Asn Phe Thr Gly Ser Asn Cys Glu
385                 390                 395                 400
Lys Lys Val Asp Arg Cys Thr Ser Asn Pro Cys Ala Asn Gly Gly Gln
                405                 410                 415
Cys Leu Asn Arg Gly Pro Ser Arg Met Cys Arg Cys Arg Pro Gly Phe
            420                 425                 430
Thr Gly Thr Tyr Cys Glu Leu His Val Ser Asp Cys Ala Arg Asn Pro
    435                 440                 445
Cys Ala His Gly Gly Thr Cys His Asp Leu Glu Asn Gly Leu Met Cys
    450                 455                 460

```
Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly
        515                 520

<210> SEQ ID NO 24
<211> LENGTH: 496
<212> TYPE: PRT
<213> ORGANISM: Homo sapiens

<400> SEQUENCE: 24

Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
            180                 185                 190

Gln Pro Ile Cys Leu Ser Gly Cys His Glu Gln Asn Gly Tyr Cys Ser
        195                 200                 205

Lys Pro Ala Glu Cys Leu Cys Arg Pro Gly Trp Gln Gly Arg Leu Cys
210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
            260                 265                 270

Thr Cys Ser Asn Ser Gly Gln Arg Ser Tyr Thr Cys Thr Cys Arg Pro
        275                 280                 285

Gly Tyr Thr Gly Val Asp Cys Glu Leu Glu Leu Ser Glu Cys Asp Ser
290                 295                 300

Asn Pro Cys Arg Asn Gly Gly Ser Cys Lys Asp Gln Glu Asp Gly Tyr
305                 310                 315                 320
```

His Cys Leu Cys Pro Pro Gly Tyr Tyr Gly Leu His Cys Glu His Ser
            325                 330                 335

Thr Leu Ser Cys Ala Asp Ser Pro Cys Phe Asn Gly Gly Ser Cys Arg
            340                 345                 350

Glu Arg Asn Gln Gly Ala Asn Tyr Ala Cys Glu Cys Pro Pro Asn Phe
            355                 360                 365

Thr Gly Ser Asn Cys Glu Lys Lys Val Asp Arg Cys Thr Ser Asn Pro
            370                 375                 380

Cys Ala Asn Gly Gly Gln Cys Leu Asn Arg Gly Pro Ser Arg Met Cys
385                 390                 395                 400

Arg Cys Arg Pro Gly Phe Thr Gly Thr Tyr Cys Glu Leu His Val Ser
            405                 410                 415

Asp Cys Ala Arg Asn Pro Cys Ala His Gly Gly Thr Cys His Asp Leu
            420                 425                 430

Glu Asn Gly Leu Met Cys Thr Cys Pro Ala Gly Phe Ser Gly Arg Arg
            435                 440                 445

Cys Glu Val Arg Thr Ser Ile Asp Ala Cys Ala Ser Ser Pro Cys Phe
            450                 455                 460

Asn Arg Ala Thr Cys Tyr Thr Asp Leu Ser Thr Asp Thr Phe Val Cys
465                 470                 475                 480

Asn Cys Pro Tyr Gly Phe Val Gly Ser Arg Cys Glu Phe Pro Val Gly
            485                 490                 495

<210> SEQ ID NO 25
<211> LENGTH: 128
<212> TYPE: PRT
<213> ORGANISM: Homo sapiens

<400> SEQUENCE: 25

Ser Gly Val Phe Gln Leu Gln Leu Gln Glu Phe Ile Asn Glu Arg Gly
1               5                   10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
            35                  40                  45

Thr Phe Gly Thr Val Ser Thr Pro Val Leu Gly Thr Asn Ser Phe Ala
        50                  55                  60

Val Arg Asp Asp Ser Ser Gly Gly Gly Arg Asn Pro Leu Gln Leu Pro
65                  70                  75                  80

Phe Asn Phe Thr Trp Pro Gly Thr Phe Ser Leu Ile Ile Glu Ala Trp
            85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
            115                 120                 125

<210> SEQ ID NO 26
<211> LENGTH: 63
<212> TYPE: PRT
<213> ORGANISM: Homo sapiens

<400> SEQUENCE: 26

Trp Leu Leu Asp Glu Gln Thr Ser Thr Leu Thr Arg Leu Arg Tyr Ser
1               5                   10                  15

Tyr Arg Val Ile Cys Ser Asp Asn Tyr Tyr Gly Asp Asn Cys Ser Arg
            20                  25                  30

```
Leu Cys Lys Lys Arg Asn Asp His Phe Gly His Tyr Val Cys Gln Pro
         35                  40                  45

Asp Gly Asn Leu Ser Cys Leu Pro Gly Trp Thr Gly Glu Tyr Cys
 50                  55                  60

<210> SEQ ID NO 27
<211> LENGTH: 232
<212> TYPE: PRT
<213> ORGANISM: Homo sapiens

<400> SEQUENCE: 27

Met Asn Phe Leu Leu Ser Trp Val His Trp Ser Leu Ala Leu Leu Leu
  1               5                  10                  15

Tyr Leu His His Ala Lys Trp Ser Gln Ala Ala Pro Met Ala Glu Gly
                 20                  25                  30

Gly Gly Gln Asn His His Glu Val Val Lys Phe Met Asp Val Tyr Gln
             35                  40                  45

Arg Ser Tyr Cys His Pro Ile Glu Thr Leu Val Asp Ile Phe Gln Glu
 50                  55                  60

Tyr Pro Asp Glu Ile Glu Tyr Ile Phe Lys Pro Ser Cys Val Pro Leu
 65                  70                  75                  80

Met Arg Cys Gly Gly Cys Cys Asn Asp Glu Gly Leu Glu Cys Val Pro
                 85                  90                  95

Thr Glu Glu Ser Asn Ile Thr Met Gln Ile Met Arg Ile Lys Pro His
                100                 105                 110

Gln Gly Gln His Ile Gly Glu Met Ser Phe Leu Gln His Asn Lys Cys
            115                 120                 125

Glu Cys Arg Pro Lys Lys Asp Arg Ala Arg Gln Glu Lys Lys Ser Val
130                 135                 140

Arg Gly Lys Gly Lys Gly Gln Lys Arg Lys Arg Lys Lys Ser Arg Tyr
145                 150                 155                 160

Lys Ser Trp Ser Val Tyr Val Gly Ala Arg Cys Cys Leu Met Pro Trp
                165                 170                 175

Ser Leu Pro Gly Pro His Pro Cys Gly Pro Cys Ser Glu Arg Arg Lys
            180                 185                 190

His Leu Phe Val Gln Asp Pro Gln Thr Cys Lys Cys Ser Cys Lys Asn
        195                 200                 205

Thr Asp Ser Arg Cys Lys Ala Arg Gln Leu Glu Leu Asn Glu Arg Thr
210                 215                 220

Cys Arg Cys Asp Lys Pro Arg Arg
225                 230

<210> SEQ ID NO 28
<211> LENGTH: 206
<212> TYPE: PRT
<213> ORGANISM: Homo sapiens

<400> SEQUENCE: 28

Ala Pro Met Ala Glu Gly Gly Gly Gln Asn His His Glu Val Val Lys
  1               5                  10                  15

Phe Met Asp Val Tyr Gln Arg Ser Tyr Cys His Pro Ile Glu Thr Leu
                 20                  25                  30

Val Asp Ile Phe Gln Glu Tyr Pro Asp Glu Ile Glu Tyr Ile Phe Lys
             35                  40                  45

Pro Ser Cys Val Pro Leu Met Arg Cys Gly Gly Cys Cys Asn Asp Glu
 50                  55                  60
```

-continued

```
Gly Leu Glu Cys Val Pro Thr Glu Glu Ser Asn Ile Thr Met Gln Ile
 65                  70                  75                  80

Met Arg Ile Lys Pro His Gln Gly Gln His Ile Gly Glu Met Ser Phe
                 85                  90                  95

Leu Gln His Asn Lys Cys Glu Cys Arg Pro Lys Lys Asp Arg Ala Arg
            100                 105                 110

Gln Glu Lys Lys Ser Val Arg Gly Lys Gly Lys Gly Gln Lys Arg Lys
        115                 120                 125

Arg Lys Lys Ser Arg Tyr Lys Ser Trp Ser Val Tyr Val Gly Ala Arg
    130                 135                 140

Cys Cys Leu Met Pro Trp Ser Leu Pro Gly Pro His Pro Cys Gly Pro
145                 150                 155                 160

Cys Ser Glu Arg Arg Lys His Leu Phe Val Gln Asp Pro Gln Thr Cys
                165                 170                 175

Lys Cys Ser Cys Lys Asn Thr Asp Ser Arg Cys Lys Ala Arg Gln Leu
            180                 185                 190

Glu Leu Asn Glu Arg Thr Cys Arg Cys Asp Lys Pro Arg Arg
        195                 200                 205
```

<210> SEQ ID NO 29
<211> LENGTH: 1395
<212> TYPE: DNA
<213> ORGANISM: Artificial sequence
<220> FEATURE:
<223> OTHER INFORMATION: 21M18 Heavy chain nucleotide sequence (13B Version 1)

<400> SEQUENCE: 29

| | | | | | |
|---|---|---|---|---|---|
| atgaagcacc | tgtggttctt | tctgctgctg | gtggccgctc | ccagatgggt | gctgtcccag | 60 |
| gtgcagctgg | tgcagtctgg | cgccgaagtg | aagaaacctg | gcgcctccgt | gaagatctcc | 120 |
| tgcaaggcct | ccggctactc | cttcaccgct | tactacatcc | actgggtcaa | gcaggcccct | 180 |
| gggcagggcc | tggaatggat | cggctacatc | tcctcctaca | cggcgccac | caactacaac | 240 |
| cagaaattca | gggccgcgt | gaccttcacc | accgacacct | ccacctccac | cgcctacatg | 300 |
| gaactgcggt | ccctgcggag | cgacgacacc | gccgtgtact | actgcgccag | agactacgac | 360 |
| tacgacgtgg | gcatggacta | ctggggccag | ggcaccctgg | tcaccgtgtc | ctctgcctcc | 420 |
| accaagggcc | catccgtgtt | ccctctggcc | ccttgctccc | ggtccacctc | tgagtctacc | 480 |
| gccgctctgg | gctgcctggt | gaaggactac | ttccctgagc | ctgtgaccgt | gtcctggaac | 540 |
| tctggcgccc | tgacctctgg | cgtgcacacc | ttccctgccg | tgctgcagtc | ctccggcctg | 600 |
| tactccctgt | ctagcgtggt | gaccgtgcct | tcctccaact | tcggcaccca | gacctacacc | 660 |
| tgtaacgtga | accacaagcc | ttccaacacc | aaggtggaca | agaccgtgga | gcggaagtgc | 720 |
| tgcgtggagt | gccctccttg | tcctgctcct | cctgtggctg | cccttctgt | gttcctgttc | 780 |
| cctccaaagc | ctaaggacac | cctgatgatc | tcccggaccc | ctgaagtgac | ctgcgtggtg | 840 |
| gtggacgtgt | cccacgagga | ccctgaggtg | cagttcaatt | ggtacgtgga | cggcgtggag | 900 |
| gtgcacaacg | ccaagaccaa | gcctcgggag | gaacagttca | actccacctt | ccgggtggtg | 960 |
| tctgtgctga | ccgtggtgca | ccaggactgg | ctgaacggca | agaatacaa | gtgcaaggtg | 1020 |
| tccaacaagg | gcctgcctgc | ccctatcgaa | aagaccatca | gcaagaccaa | gggccagcct | 1080 |
| cgcgagcctc | aggtgtacac | cctgcctccc | agcggaag | aaatgaccaa | gaaccaggtg | 1140 |
| tccctgacct | gtctggtgga | gggcttctac | ccttccgata | tcgccgtgga | gtgggagtct | 1200 |

| aacggccagc ctgagaacaa ctacaagacc acccctccta tgctggactc cgacggctcc | 1260 |
| ttcttcctgt actccgaact gaccgtggac aagtcccggt ggcagcaggg caacgtgttc | 1320 |
| tcctgctccg tgatgcacga ggccctgcac aaccactaca cccagaagtc cctgtccctg | 1380 |
| tctcctggca agtag | 1395 |

<210> SEQ ID NO 30
<211> LENGTH: 1395
<212> TYPE: DNA
<213> ORGANISM: Artificial sequence
<220> FEATURE:
<223> OTHER INFORMATION: 21R79 Heavy chain nucleotide sequence (13B Version 1)

<400> SEQUENCE: 30

| atgaagcacc tgtggttctt tctgctgctg gtggccgctc ccagatgggt gctgtcccag | 60 |
| gtgcagctgg tgcagtctgg cgccgaagtg aagaaacctg gcgcctccgt gaagatctcc | 120 |
| tgcaaggcct ccggctactc cttcaccgcc tactacatcc actgggtgaa acaggcacca | 180 |
| ggccagggac tggaatggat cggctatatc gccaactaca ccgggccac caactacaac | 240 |
| cagaaattca gggccgcgt gaccttcacc accgacacct ccacctccac agcctacatg | 300 |
| gaactgcggt ccctgcggag cgacgacacc gccgtgtact actgcgccag agactacgac | 360 |
| tacgacgtgg gcatggacta ctggggccag ggcaccctgg tgacagtgtc ctccgcctcc | 420 |
| accaagggcc cctccgtgtt ccctctggcc ccttgctccc ggtccacctc tgagtctacc | 480 |
| gccgctctgg gctgcctggt gaaggactac ttccctgagc ctgtgaccgt gtcctggaac | 540 |
| tctggcgccc tgacctctgg cgtgcacacc ttccctgccg tgctgcagtc ctccggcctg | 600 |
| tactccctgt ctagcgtggt gaccgtgcct tcctccaact cggcaccca gacctacacc | 660 |
| tgtaacgtgg accacaagcc ttccaacacc aaggtggaca agaccgtgga gcggaagtgc | 720 |
| tgcgtggagt gccctccttg tcctgctcct cctgtggctg ccttctgt gttcctgttc | 780 |
| cctccaaagc ctaaggacac cctgatgatc tcccggaccc ctgaagtgac ctgcgtggtg | 840 |
| gtggacgtgt cccacgagga ccctgaggtg cagttcaatt ggtacgtgga cggcgtggag | 900 |
| gtgcacaacg ccaagaccaa gcctcgggag gaacagttca ctccaccttt ccgggtggtg | 960 |
| tctgtgctga ccgtggtgca ccaggactgg ctgaacggca agaatacaa gtgcaaggtg | 1020 |
| tccaacaagg gcctgcctgc ccctatcgaa aagaccatca gcaagaccaa gggccagcct | 1080 |
| cgcgagcctc aggtgtacac cctgcctccc agccgggaag aaatgaccaa gaaccaggtg | 1140 |
| tccctgacct gtctggtgga gggcttctac ccttccgata tcgccgtgga gtgggagtct | 1200 |
| aacggccagc ctgagaacaa ctacaagacc acccctccta tgctggactc cgacggctcc | 1260 |
| ttcttcctgt actccgaact gaccgtggac aagtcccggt ggcagcaggg caacgtgttc | 1320 |
| tcctgctccg tgatgcacga ggccctgcac aaccactaca cccagaagtc cctgtccctg | 1380 |
| tctcctggca agtag | 1395 |

<210> SEQ ID NO 31
<211> LENGTH: 1395
<212> TYPE: DNA
<213> ORGANISM: Artificial sequence
<220> FEATURE:
<223> OTHER INFORMATION: 21R79 Heavy chain nucleotide sequence (13B Version 2)

<400> SEQUENCE: 31

| atgaagcacc tatggttctt tctattatta gtggccgctc cccgttgggt gttatcgcag | 60 |

```
gttcagctag ttcagtctgg agcggaagtt aagaaacctg gagcatccgt gaaataagt      120 tgcaaggcat ccggttactc gttcaccgca tactatatcc actgggttaa acaggcacca     180
ggacagggac ttgaatggat cggatatatc gctaattata atagagctac aaactataac    240
caaaaattca aggacgcgt gactttcaca actgacacct caacctcgac agcatacatg      300
gaattacggt ccctacggtc tgacgacact gccgtttact attgcgctag agattatgat    360
tatgatgttg gaatggacta ttggggccag ggaacactgg tgacagtgtc ttctgcatcc    420
actaagggac catccgtgtt cccttttggcc ccttgctctc gttcgacctc tgaatcgact    480
gccgctctgg gatgcctcgt gaaagattac ttccctgagc ctgtgaccgt tcctggaac     540 tcgggcgccc taacctctgg cgtgcacaca ttccctgccg tgctacagtc ttctggccta    600
tactctttat cttcggttgt taccgtacct tcttctaact tcggaaccca aacttacacc    660
tgtaacgtag accacaagcc ttcgaacacc aaggtggaca agactgttga gcgaaagtgc    720
tgcgttgagt gccctccatg tcctgcacct cctgtggctg gccttctgt gttcctgttc     780 cctccaaaac ctaaggacac tctaatgatc tctcggactc ctgaggtgac ttgcgtggtt    840
gtggacgtgt cccacgagga ccctgaggtg cagttcaatt ggtacgtgga cggagtcgag    900
gtgcacaatg caaagaccaa gcctcgggag gaacagttca actccaccttt ccgggtggtt   960 tctgtgttga ccgttgtgca ccaagactgg ctgaacggca agaatacaa gtgcaaggtg     1020 tccaacaagg cctgcctgc ccctatcgaa aagaccatca gcaagaccaa gggccagcct    1080
cgcgagcctc aggtgtacac cctgcctccc agccgggaag aaatgaccaa gaaccaggtg   1140
tccctgacct gtctggtgga gggcttctac ccttccgaca tcgccgttga gtgggagtct    1200
aacggacagc cggagaacaa ctacaagact acgcctccaa tgctggactc cgacggctcc   1260
ttcttcctgt actccgaact gaccgtggac aagtcccggt ggcagcaggg caacgtgttc   1320
tcatgctccg taatgcacga agccttgcac aatcactaca ctcaaaagtc cctatcctta   1380
tctcctggca agtag                                                      1395
```

<210> SEQ ID NO 32
<211> LENGTH: 1401
<212> TYPE: DNA
<213> ORGANISM: Artificial sequence
<220> FEATURE:
<223> OTHER INFORMATION: 219R45 Heavy chain nucleotide sequence (13A
      Version 1)

<400> SEQUENCE: 32

```
atgaagcatc tgtggttttt cctgttgctc gtggcggcac ccagatgggt gttgtcccaa      60
gtgcagctgg tccagagcgg ggctgaggtg aagaaacccg gagcaagcgt aaaagtatcg     120
tgtaaggcct cggggtacac gtttacaaac tactggatgc attgggtgcg gcaggctccg     180 ggacagggt tggaatggat gggtgacatt aaccccctcaa atggcagaac atcatataag    240
gaaaagttca acgccgcgt cacactctcc gtggacaagt caagctcgac tgcgtacatg    300
gaactttcgt cgctgaggtc ggaggacacg gcagtgtact tttgcaccat ccattatgat    360
gacaagtatt acccctctgat ggattattgg ggtcagggta cgttggtcac cgtctccagc    420
gcgtcgacga aaggtccctc ggtatttccc ctcgcccct gctcgaggtc gacatccgaa    480
tcaacagctg ccctcggctg cctggtcaaa gactacttcc cagagccggt aacggtgtcg    540
tggaactcgg gagcgcttac gtccggagtc cacacatttc cggcggtact gcaatcctcg   600
ggactgtatt cgttgtcgtc agtggtgact gtcccgtcct ccaatttcgg gactcagacc    660
```

```
tatacgtgca acgtcgacca caaaccctca acaccaagg tggataagac agtggagcgc      720
aagtgctgcg tggagtgtcc cccgtgtccg gcacccctg tcgccggacc ctcagtctt      780 ttgtttccgc cgaagcccaa agatacactc atgatctcaa gaacgcccga ggtaacatgc      840
gtggtggtcg atgtaagcca cgaggatcca gaagtacaat tcaattggta tgtagacggg      900
gtcgaggtcc ataacgcaaa gacgaaaccg agggaagagc agttcaattc gactttccgg      960
gtggtgtcgg tgcttacagt cgtacatcag gactggttga acgggaagga gtacaagtgt     1020
aaagtatcga ataagggcct tccagcgccg attgaaaaga ccatctccaa gaccaaagga     1080
cagccacgag agccgcaagt ctatacgctt cctcccagcc gagaaaagat gactaaaaac     1140
caggtatcgc ttacgtgtct cgtcaagggt ttctacccct cggacatcgc ggtggaatgg     1200
gagagcaatg gacaaccgga aaacaactac aagacgacac cgcctatgtt gaaaagcgat     1260
ggatcgtttt tcctctattc gaaactcacg gtcgataagt cacggtggca gcaggggaat     1320
gtgttctcct gttcagtgat gcacgaggcg ctccacaatc actataccca gaaaagcctg     1380
tcactttccc cgggaaaatg a                                               1401

<210> SEQ ID NO 33
<211> LENGTH: 1401
<212> TYPE: DNA
<213> ORGANISM: Artificial sequence
<220> FEATURE:
<223> OTHER INFORMATION: 219R45 Heavy chain nucleotide sequence (13A
      Version 2)

<400> SEQUENCE: 33
atgaagcacc tctggttctt cctgctcctc gtggctgctc ctcggtgggt cctctcccaa       60
gtgcagctgg tccagagcgg ggctgaggtg aagaaacccg agcttccgt caaagtctcc      120 tgtaaggctt ccggatacac ctttaccaac tattggatgc actgggtgcg gcaggctcct      180
ggacaagggc tggaatggat gggagacatc aatccttcca atggcagaac ctcctacaag      240
gaaaaattca acggcgggt cacactctcc gtggacaagt ctagctccac agcttacatg      300
gaactctcct ccctgcggtc cgaagacaca gctgtctact tctgcaccat ccactacgac      360
gacaagtact accctctgat ggactactgg ggccagggaa ccctggtcac cgtgtccagc      420
gcttccacaa aaggaccctc cgtctttccc ctcgcccct gctcccgtc cacatccgaa      480 tcaacagctg ccctcggctg cctggtcaaa gactacttcc cagagcctgt cacagtgtcc      540
tggaactccg gagctctcac atccggagtc cacacatttc ctgctgtgct ccaatcctcc      600
ggactgtatt ccctctcctc cgtggtgaca gtgccttcct ccaatttcgg gacacagacc      660
tatacatgca acgtggacca caaaccctcc aacaccaaag tcgataagac agtggagcgc      720
aagtgctgcg tggagtgtcc ccttgtcct gctccccctg tggctggacc ttccgtctt      780 ctgtttcctc ctaaacctaa agacaccctc atgatctccc ggaccccga ggtcacatgc      840 gtggtcgtcg atgtgagcca cgaggacccc gaagtccaat taattggta tgtggacggg      900 gtggaggtcc ataacgctaa gaccaaacct agggaagagc agttcaattc cactttccgg      960
gtggtgtccg tgctgaccgt cgttcatcag gactggctca acgggaaaga atacaaatgc     1020
aaagtctcta ataagggcct ccctgctcct attgaaaaaa caatttccaa aacaaaagga     1080
caacctcggg agcctcaagt ctacacactg ccaccttccc gggaaaaaat gacaaaaaat     1140
caagtctccc tcacatgtct cgtcaaggga ttctaccctt ccgacattgc tgtggaatgg     1200
gaatccaatg gacaacctga aaacaactac aagcaacac ctcctatgct caaaagcgat     1260
```

```
gggtccttttt tcctctattc caaactcaca gtcgataagt ctcggtggca gcagggggaat    1320 gtgttctcct gttccgtgat gcacgaggct ctccacaatc actatacccca gaaaagcctg    1380 tccctctccc ctggaaaatg a                                                1401
```

<210> SEQ ID NO 34
<211> LENGTH: 717
<212> TYPE: DNA
<213> ORGANISM: Artificial sequence
<220> FEATURE:
<223> OTHER INFORMATION: Light chain nucleotide sequence

<400> SEQUENCE: 34

```
atggtgctgc agacccaggt gttcatctcc ctgctgctgt ggatctccgg cgcctacggc     60
gacatcgtga tgacccagtc cccagactcc ctggctgtgt ctctgggaga gcggccacc    120 atctcttgca gagcctccga gtccgtggac aactacggca tctccttcat gaagtggttc    180
cagcagaagc ccggccagcc cccaaagctg ctgatctacg ccgcctccaa ccagggatct    240
ggcgtgcccg accggttctc tggatccggc tctggcaccg actttaccct gaccatcagc    300
tccctgcagg ccgaggacgt ggccgtgtac tactgccagc agtccaaaga ggtgcccctgg   360 accttcggcg gaggcaccaa ggtggaaatc aagcggaccg tggccgctcc ctccgtgttc    420
atcttcccac cctccgacga gcagctgaag tccggaaccg cctccgtcgt gtgcctgctg    480
aacaacttct accccgcga ggccaaggtg cagtggaagg tggacaacgc cctgcagtcc    540
ggcaactccc aggaatccgt caccgagcag gactccaagg acagcaccta ctccctgtcc    600
tccaccctga ccctgtccaa ggccgactac gagaagcaca aggtgtacgc ctgcgaagtg    660
acccaccagg gcctgtccag ccccgtgacc aagtccttca ccgggggcga gtgttag       717
```

<210> SEQ ID NO 35
<211> LENGTH: 357
<212> TYPE: DNA
<213> ORGANISM: Artificial sequence
<220> FEATURE:
<223> OTHER INFORMATION: 21M18 Heavy chain variable region nucleotide
      sequence

<400> SEQUENCE: 35

```
caggtgcagc tggtgcagtc tggcgccgaa gtgaagaaac tggcgcctc cgtgaagatc      60 tcctgcaagg cctccggcta ctccttcacc gcttactaca tccactgggt caagcaggcc    120
cctgggcagg gctggaatg gatcggctac atctcctcct acaacggcgc caccaactac    180
aaccagaaat tcaagggccg cgtgaccttc accaccgaca cctccacctc caccgcctac    240
atggaactgc ggtccctgcg gagcgacgac accgccgtgt actactgcgc cagagactac    300
gactacgacg tgggcatgga ctactgggc cagggcaccc tggtcaccgt gtcctct       357
```

<210> SEQ ID NO 36
<211> LENGTH: 357
<212> TYPE: DNA
<213> ORGANISM: Artificial sequence
<220> FEATURE:
<223> OTHER INFORMATION: 21R79 Heavy chain variable region nucleotide
      sequence (13B)

<400> SEQUENCE: 36

```
caggtgcagc tggtgcagtc tggcgccgaa gtgaagaaac tggcgcctc cgtgaagatc      60 tcctgcaagg cctccggcta ctccttcacc gcctactaca tccactgggt gaaacaggca    120
```

| ccaggccagg gactggaatg gatcggctat atcgccaact acaaccgggc caccaactac | 180 |
| aaccagaaat tcaagggccg cgtgaccttc accaccgaca cctccacctc cacagcctac | 240 |
| atggaactgc ggtccctgcg gagcgacgac accgccgtgt actactgcgc cagagactac | 300 |
| gactacgacg tgggcatgga ctactggggc cagggcaccc tggtgacagt gtcctcc | 357 |

```
<210> SEQ ID NO 37
<211> LENGTH: 357
<212> TYPE: DNA
<213> ORGANISM: Artificial sequence
<220> FEATURE:
<223> OTHER INFORMATION: 21R79 Heavy chain variable region nucleotide
      sequence

<400> SEQUENCE: 37
```

| caggttcagc tagttcagtc tggagcggaa gttaagaaac tggagcatc cgtgaaaata | 60 |
| agttgcaagg catccggtta ctcgttcacc gcatactata tccactgggt taaacaggca | 120 |
| ccaggacagg gacttgaatg gatcggatat atcgctaatt ataatagagc tacaaactat | 180 |
| aaccaaaaat tcaaggacg cgtgactttc acaactgaca cctcaacctc gacagcatac | 240 |
| atggaattac ggtccctacg gtctgacgac actgccgttt actattgcgc tagagattat | 300 |
| gattatgatg ttggaatgga ctattggggc cagggaacac tggtgacagt gtcttct | 357 |

```
<210> SEQ ID NO 38
<211> LENGTH: 363
<212> TYPE: DNA
<213> ORGANISM: Artificial sequence
<220> FEATURE:
<223> OTHER INFORMATION: 219R45 Heavy chain variable region nucleotide
      sequence

<400> SEQUENCE: 38
```

| caagtgcagc tggtccagag cggggctgag gtgaagaaac ccggagcaag cgtaaaagta | 60 |
| tcgtgtaagg cctcggggta cacgtttaca aactactgga tgcattgggt gcggcaggct | 120 |
| ccgggacagg ggttggaatg gatgggtgac attaaccct caaatggcag aacatcatat | 180 |
| aaggaaaagt tcaaacgccg cgtcacactc tccgtggaca gtcaagctc gactgcgtac | 240 |
| atggaactt cgtcgctgag gtcggaggac acggcagtgt acttttgcac catccattat | 300 |
| gatgacaagt attaccctct gatggattat tggggtcagg gtacgttggt caccgtctcc | 360 |
| agc | 363 |

```
<210> SEQ ID NO 39
<211> LENGTH: 363
<212> TYPE: DNA
<213> ORGANISM: Artificial sequence
<220> FEATURE:
<223> OTHER INFORMATION: 219R45 Heavy chain variable region nucleotide
      sequence

<400> SEQUENCE: 39
```

| caagtgcagc tggtccagag cggggctgag gtgaagaaac ccggagcttc cgtcaaagtc | 60 |
| tcctgtaagg cttccggata cacctttacc aactattgga tgcactgggt gcggcaggct | 120 |
| cctggacaag gctggaatg gatggagac atcaatcctt ccaatggcag aacctcctac | 180 |
| aaggaaaaat tcaaacggcg ggtcacactc tccgtggaca gtctagctc cacagcttac | 240 |
| atggaactct cctcccctgcg gtccgaagac acagctgtct acttctgcac catccactac | 300 |
| gacgacaagt actaccctct gatggactac tggggccagg gaaccctggt caccgtgtcc | 360 |

```
agc                                                                    363
```

<210> SEQ ID NO 40
<211> LENGTH: 333
<212> TYPE: DNA
<213> ORGANISM: Artificial sequence
<220> FEATURE:
<223> OTHER INFORMATION: Light chain variable region nucleotide sequence

<400> SEQUENCE: 40

```
gacatcgtga tgacccagtc cccagactcc ctggctgtgt ctctgggaga gcgggccacc    60
atctcttgca gagcctccga gtccgtggac aactacggca tctccttcat gaagtggttc   120
cagcagaagc ccggccagcc cccaaagctg ctgatctacg ccgcctccaa ccagggatct   180
ggcgtgcccg accggttctc tggatccggc tctggcaccg actttaccct gaccatcagc   240
tccctgcagg ccgaggacgt ggccgtgtac tactgccagc agtccaaaga ggtgccctgg   300
accttcggcg gaggcaccaa ggtggaaatc aag                                 333
```

<210> SEQ ID NO 41
<211> LENGTH: 330
<212> TYPE: PRT
<213> ORGANISM: Homo sapiens

<400> SEQUENCE: 41

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 42
<211> LENGTH: 326
<212> TYPE: PRT
<213> ORGANISM: Homo sapiens

<400> SEQUENCE: 42

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
```

```
                    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 43
<211> LENGTH: 377
<212> TYPE: PRT
<213> ORGANISM: Homo sapiens

<400> SEQUENCE: 43

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
                100                 105                 110

Arg Cys Pro Glu Pro Lys Ser Cys Asp Thr Pro Pro Pro Cys Pro Arg
            115                 120                 125

Cys Pro Glu Pro Lys Ser Cys Asp Thr Pro Pro Pro Cys Pro Arg Cys
        130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
                180                 185                 190

Val Val Asp Val Ser His Glu Asp Pro Glu Val Gln Phe Lys Trp Tyr
            195                 200                 205

Val Asp Gly Val Glu Val His Asn Ala Lys Thr Lys Pro Arg Glu Glu
        210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
                260                 265                 270

Pro Arg Glu Pro Gln Val Tyr Thr Leu Pro Pro Ser Arg Glu Glu Met
            275                 280                 285

Thr Lys Asn Gln Val Ser Leu Thr Cys Leu Val Lys Gly Phe Tyr Pro
        290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335
```

```
Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
            355                 360                 365

Lys Ser Leu Ser Leu Ser Pro Gly Lys
            370                 375

<210> SEQ ID NO 44
<211> LENGTH: 327
<212> TYPE: PRT
<213> ORGANISM: Homo sapiens

<400> SEQUENCE: 44

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 45
<211> LENGTH: 8
<212> TYPE: PRT
<213> ORGANISM: Artificial sequence
<220> FEATURE:
<223> OTHER INFORMATION: FLAG peptide

<400> SEQUENCE: 45

Asp Tyr Lys Asp Asp Asp Asp Lys
1               5

<210> SEQ ID NO 46
<211> LENGTH: 464
<212> TYPE: PRT
<213> ORGANISM: Artificial sequence
<220> FEATURE:
<223> OTHER INFORMATION: Parental 21R79 Heavy chain

<400> SEQUENCE: 46

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ala Asn Tyr Asn Arg Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala

```
                290                 295                 300
Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
                340                 345                 350

Ile Ser Lys Thr Lys Gly Gln Pro Arg Glu Pro Gln Val Tyr Thr Leu
                355                 360                 365

Pro Pro Ser Arg Glu Glu Met Thr Lys Asn Gln Val Ser Leu Thr Cys
                370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Pro Gly Lys
                450                 455                 460

<210> SEQ ID NO 47
<211> LENGTH: 466
<212> TYPE: PRT
<213> ORGANISM: Artificial sequence
<220> FEATURE:
<223> OTHER INFORMATION: Parental 219R45 Heavy chain

<400> SEQUENCE: 47

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
                35                  40                  45

Thr Asn Tyr Trp Met His Trp Val Arg Gln Ala Pro Gly Gln Gly Leu
50                  55                  60

Glu Trp Met Gly Asp Ile Asn Pro Ser Asn Gly Arg Thr Ser Tyr Lys
65                  70                  75                  80

Glu Lys Phe Lys Arg Arg Val Thr Leu Ser Val Asp Lys Ser Ser Ser
                85                  90                  95

Thr Ala Tyr Met Glu Leu Ser Ser Leu Arg Ser Glu Asp Thr Ala Val
                100                 105                 110

Tyr Phe Cys Thr Ile His Tyr Asp Asp Lys Tyr Tyr Pro Leu Met Asp
                115                 120                 125

Tyr Trp Gly Gln Gly Thr Leu Val Thr Val Ser Ala Ser Thr Lys
                130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
```

```
                195                 200                 205
Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
            275                 280                 285

Asp Pro Glu Val Gln Phe Asn Trp Tyr Val Asp Gly Val Glu Val His
            290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
            370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
    450                 455                 460

Gly Lys
465

<210> SEQ ID NO 48
<211> LENGTH: 445
<212> TYPE: PRT
<213> ORGANISM: Artificial sequence
<220> FEATURE:
<223> OTHER INFORMATION: Parental 21R79 Heavy chain without signal
      sequence

<400> SEQUENCE: 48

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ala Asn Tyr Asn Arg Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80
```

```
Met Glu Leu Arg Ser Leu Arg Ser Asp Asp Thr Ala Val Tyr Tyr Cys
                 85                  90                  95

Ala Arg Asp Tyr Asp Tyr Asp Val Gly Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Met Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 49
<211> LENGTH: 447
<212> TYPE: PRT
<213> ORGANISM: Artificial sequence
<220> FEATURE:
<223> OTHER INFORMATION: Parental 219R45 Heavy chain without signal
      sequence

<400> SEQUENCE: 49
```

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Trp Met His Trp Val Arg Gln Ala Pro Gly Gln Gly Leu Glu Trp Met
             35                  40                  45

Gly Asp Ile Asn Pro Ser Asn Gly Arg Thr Ser Tyr Lys Glu Lys Phe
         50                  55                  60

Lys Arg Arg Val Thr Leu Ser Val Asp Lys Ser Ser Ser Thr Ala Tyr
 65                  70                  75                  80

Met Glu Leu Ser Ser Leu Arg Ser Glu Asp Thr Ala Val Tyr Phe Cys
                 85                  90                  95

Thr Ile His Tyr Asp Asp Lys Tyr Tyr Pro Leu Met Asp Tyr Trp Gly
             100                 105                 110

Gln Gly Thr Leu Val Thr Val Ser Ser Ala Ser Thr Lys Gly Pro Ser
         115                 120                 125

Val Phe Pro Leu Ala Pro Cys Ser Arg Ser Thr Ser Glu Ser Thr Ala
     130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                 165                 170                 175

Val Leu Gln Ser Ser Gly Leu Tyr Ser Leu Ser Ser Val Val Thr Val
             180                 185                 190

Pro Ser Ser Asn Phe Gly Thr Gln Thr Tyr Thr Cys Asn Val Asp His
         195                 200                 205

Lys Pro Ser Asn Thr Lys Val Asp Lys Thr Val Glu Arg Lys Cys Cys
     210                 215                 220

Val Glu Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                 245                 250                 255

Pro Glu Val Thr Cys Val Val Val Asp Val Ser His Glu Asp Pro Glu
             260                 265                 270

Val Gln Phe Asn Trp Tyr Val Asp Gly Val Glu Val His Asn Ala Lys
         275                 280                 285

Thr Lys Pro Arg Glu Glu Gln Phe Asn Ser Thr Phe Arg Val Val Ser
     290                 295                 300

Val Leu Thr Val Val His Gln Asp Trp Leu Asn Gly Lys Glu Tyr Lys
305                 310                 315                 320

Cys Lys Val Ser Asn Lys Gly Leu Pro Ala Pro Ile Glu Lys Thr Ile
                 325                 330                 335

Ser Lys Thr Lys Gly Gln Pro Arg Glu Pro Gln Val Tyr Thr Leu Pro
             340                 345                 350

Pro Ser Arg Glu Glu Met Thr Lys Asn Gln Val Ser Leu Thr Cys Leu
         355                 360                 365

Val Lys Gly Phe Tyr Pro Ser Asp Ile Ala Val Glu Trp Glu Ser Asn
     370                 375                 380

Gly Gln Pro Glu Asn Asn Tyr Lys Thr Thr Pro Pro Met Leu Asp Ser
385                 390                 395                 400

Asp Gly Ser Phe Phe Leu Tyr Ser Lys Leu Thr Val Asp Lys Ser Arg
                 405                 410                 415
```

Trp Gln Gln Gly Asn Val Phe Ser Cys Ser Val Met His Glu Ala Leu
               420                 425                 430

His Asn His Tyr Thr Gln Lys Ser Leu Ser Leu Ser Pro Gly Lys
               435                 440                 445

<210> SEQ ID NO 50
<211> LENGTH: 357
<212> TYPE: DNA
<213> ORGANISM: Artificial sequence
<220> FEATURE:
<223> OTHER INFORMATION: Parental 21R79 Heavy chain variable region

<400> SEQUENCE: 50
caagtgcagc tcgtgcagtc agggcggag gtcaagaagc cgggagcatc ggtcaaaatc    60
tcgtgtaagg cctcggggta ctcctttact gcgtattaca tccattgggt aaagcaggcg   120
ccagggcagg gattggagtg gattgggtat atcgccaatt acaatcgcgc gacgaactat   180
aaccagaaat tcaagggaag ggtgaccttc acaacggata tcgacatc gacggcctac    240 atggaacttc gcagcctgcg atcagatgac acggcggtat actattgcgc aagagattac   300
gactatgatg tgggaatgga ctattgggt caaggtactc tggtcacagt ctcctcc     357

<210> SEQ ID NO 51
<211> LENGTH: 363
<212> TYPE: DNA
<213> ORGANISM: Artificial sequence
<220> FEATURE:
<223> OTHER INFORMATION: Parental 219R45 Heavy chain variable region

<400> SEQUENCE: 51
caggtacagc tcgtgcaatc gggggcagag gtcaaaaagc ccggtgcgtc ggtaaaggtc    60
agctgcaaag cgtcaggtta tacattcacg aattactgga tgcattgggt cagacaggcc   120
cctggacaag gcttgaatg gatgggagat atcaatccgt cgaacggacg gactagctat   180
aaggagaagt ttaagaggcg cgtaacactg tcggtggaca atcgtcctc aacgccctac    240 atggagttgt catccctgcg gtcggaagat acggcggtct acttctgtac tatccactat   300
gacgataagt actacccgct tatggactac tgggtcagg gaacattggt aaccgtgagc    360
agc                                                                 363

<210> SEQ ID NO 52
<211> LENGTH: 1392
<212> TYPE: DNA
<213> ORGANISM: Artificial sequence
<220> FEATURE:
<223> OTHER INFORMATION: Parental 21R79 Heavy chain with signal sequence

<400> SEQUENCE: 52
atgaaacact tgtggttttt cctcttgctc gtggcagctc ctcggtgggt actttcacaa    60
gtgcagctcg tgcagtcagg gcggaggtc aagaagccgg gagcatcggt caaaatctcg   120
tgtaaggcct cggggtactc ctttactgcg tattacatcc attgggtaaa gcaggcgcca   180 gggcaggat tggagtggat tgggtatatc gccaattaca atcgcgcgac gaactataac   240
cagaaattca gggaagggt gaccttcaca acggatatcg acatcgacgg cctacatg    300 gaacttcgca gcctgcgatc agatgacacg gcggtatact attgcgcaag agattacgac   360
tatgatgtgg aatggactat tggggtcaa ggtactctgg tcacagtctc tccgccagc   420 accaagggcc ctagcgtctt ccctctggct ccctgcagca ggagcaccag cgagagcaca   480
gccgccctgg gctgcctggt caaggactac ttccccgaac cggtgacggt gtcgtggaac   540

```
tcaggcgctc tgaccagcgg cgtgcacacc ttcccagctg tcctacagtc ctcaggactc      600
tactccctca gcagcgtggt gaccgtgccc tccagcaact tcggcaccca gacctacacc      660
tgcaacgtag atcacaagcc cagcaacacc aaggtggaca agacagttga gcgcaaatgt      720
tgtgtcgagt gcccaccgtg cccagcacca cctgtggcag gaccgtcagt cttcctcttc      780
cccccaaaac ccaaggacac cctcatgatc tcccggaccc ctgaggtcac gtgcgtggtg      840
gtggacgtga gccacgaaga cccgaggtc cagttcaact ggtacgtgga cggcgtggag       900
gtgcataatg ccaagacaaa gccacgggag gagcagttca acagcacgtt ccgtgtggtc      960
agcgtcctca ccgttgtgca ccaggactgg ctgaacggca aggagtacaa gtgcaaggtc     1020
tccaacaaag gcctcccagc ccccatcgag aaaaccatct ccaaaaccaa agggcagccc     1080
cgagaaccac aggtgtacac cctgccccca tcccgggagg agatgaccaa gaaccaggtc     1140
agcctgacct gcctggtcaa aggcttctac cccagcgaca tcgccgtgga gtgggagagc     1200
aatgggcagc cggagaacaa ctacaagacc acacctccca tgctggactc cgacggctcc     1260
ttcttcctct acagcaagct caccgtggac aagagcaggt ggcagcaggg gaacgtcttc     1320
tcatgctccg tgatgcatga ggctctgcac aaccactaca cgcagaagag cctctccctg     1380
tctccgggta aa                                                        1392
```

<210> SEQ ID NO 53
<211> LENGTH: 1398
<212> TYPE: DNA
<213> ORGANISM: Artificial sequence
<220> FEATURE:
<223> OTHER INFORMATION: Parental 219R45 Heavy chain with signal
      sequence

<400> SEQUENCE: 53

```
atgaaacacc tctggttctt tttgctcctg gtggcagctc ccgatgggt gcttagccag        60 gtacagctcg tgcaatcggg ggcagaggtc aaaaagcccg tgcgtcggt aaaggtcagc       120 tgcaaagcgt caggttatac attcacgaat tactggatgc attgggtcag acaggcccct      180
ggacaagggc ttgaatggat gggagatatc aatccgtcga acggacggac tagctataag      240
gagaagttta gaggcgcgt aacactgtcg gtggacaaat cgtcctcaac ggcctacatg       300
gagttgtcat ccctgcggtc ggaagatacg gcggtctact tctgtactat ccactatgac      360
gataagtact acccgcttat ggactactgg ggtcagggaa cattggtaac cgtgagcagc      420
gcgtccacaa agggcccta gcgtcttccct ctggctccct gcagcaggag caccagcgag     480
agcacagccg ccctgggctg cctggtcaag gactacttcc ccgaaccggt gacggtgtcg      540
tggaactcag gcgctctgac cagcggcgtg cacaccttcc cagctgtcct acagtcctca      600
ggactctact ccctcagcag cgtggtgacc gtgccctcca gcaacttcgg cacccagacc      660
tacacctgca acgtagatca caagcccagc aacaccaagg tggacaagac agttgagcgc      720
aaatgttgtg tcgagtgccc accgtgccca gcaccacctg tggcaggacc gtcagtcttc      780
ctcttccccc caaaacccaa ggacaccctc atgatctccc ggacccctga ggtcacgtgc      840
gtggtggtgg acgtgagcca cgaagacccc gaggtccagt tcaactggta cgtggacggc     900
gtggaggtgc ataatgccaa gacaaagcca cgggaggagc agttcaacag cacgttccgt      960
gtggtcagcg tcctcaccgt tgtgcaccag gactggctga acggcaagga gtacaagtgc     1020
aaggtctcca acaaaggcct cccagccccc atcgagaaaa ccatctccaa aaccaaaggg     1080
cagccccgag aaccacaggt gtacaccctg cccccatccc gggaggagat gaccaagaac     1140
```

```
caggtcagcc tgacctgcct ggtcaaaggc ttctacccca gcgacatcgc cgtggagtgg    1200
gagagcaatg ggcagccgga gaacaactac aagaccacac ctcccatgct ggactccgac    1260
ggctccttct tcctctacag caagctcacc gtggacaaga gcaggtggca gcagggaac     1320 gtcttctcat gctccgtgat gcatgaggct ctgcacaacc actacacgca gaagagcctc    1380
tccctgtctc cgggtaaa                                                  1398
```

<210> SEQ ID NO 54
<211> LENGTH: 333
<212> TYPE: DNA
<213> ORGANISM: Artificial sequence
<220> FEATURE:
<223> OTHER INFORMATION: Parental 21R79 and 219R45 light chain variable
      region

<400> SEQUENCE: 54

```
gacatcgtga tgacccagtc ccctgactcc ctggctgtgt ccctgggcga gagggccacc    60
atctcctgca gagccagcga atccgtcgat aattatggca tttcctttat gaagtggttc    120
cagcagaaac caggacagcc tcctaagctg ctcatttacg ctgcatccaa ccaagggtcc    180
ggggtccctg acaggttctc cggcagcggg tccggaacag atttcactct caccatcagc    240
agcctgcagg ctgaagatgt ggctgtctat tactgtcagc aaagcaagga ggtgccttgg    300
acattcggag agggaccaa ggtggaaatc aaa                                  333
```

<210> SEQ ID NO 55
<211> LENGTH: 717
<212> TYPE: DNA
<213> ORGANISM: Artificial sequence
<220> FEATURE:
<223> OTHER INFORMATION: Parental 21R79 and 219R45 light chain

<400> SEQUENCE: 55

```
atggtgctcc agacccaggt cttcatttcc ctgctgctct ggatcagcgg agcctacggg    60
gacatcgtga tgacccagtc ccctgactcc ctggctgtgt ccctgggcga gagggccacc    120
atctcctgca gagccagcga atccgtcgat aattatggca tttcctttat gaagtggttc    180
cagcagaaac caggacagcc tcctaagctg ctcatttacg ctgcatccaa ccaagggtcc    240
ggggtccctg acaggttctc cggcagcggg tccggaacag atttcactct caccatcagc    300
agcctgcagg ctgaagatgt ggctgtctat tactgtcagc aaagcaagga ggtgccttgg    360
acattcggag agggaccaa ggtggaaatc aaacgtacgg tggctgcccc ctccgtcttc    420
atcttccccc cagcgatga gcagctgaaa agcggcactg ccagcgtggt gtgcctgctg    480
aataacttct atcccgggga ggccaaagtg cagtggaagg tggataacgc cctccaaagc    540
ggcaactccc aggagagcgt cacagagcag gacagcaagg acagcaccta cagcctcagc    600
agcaccctga ccctgagcaa agccgactac gagaaacaca agtctacgc ctgcgaagtc    660 acccatcagg gcctgagcag ccccgtcaca aagagcttca caggggcga gtgttga       717
```

<210> SEQ ID NO 56
<211> LENGTH: 445
<212> TYPE: PRT
<213> ORGANISM: Artificial sequence
<220> FEATURE:
<223> OTHER INFORMATION: 21R75 Heavy chain without signal sequence

<400> SEQUENCE: 56

Gln Val Gln Leu Val Gln Ser Gly Ala Glu Val Lys Lys Pro Gly Ala

-continued

```
1               5                   10                  15
Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
            35                  40                  45

Gly Tyr Ile Ala Gly Tyr Lys Asp Ala Thr Asn Tyr Asn Gln Lys Phe
            50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Thr Ala Val Tyr Tyr Cys
            85                  90                  95

Ala Arg Asp Tyr Asp Tyr Asp Val Gly Met Asp Tyr Trp Gly Gln Gly
            100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
            195                 200                 205

Ser Asn Thr Lys Val Asp Lys Thr Val Glu Arg Lys Cys Cys Val Glu
            210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
            260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
            290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
            325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Glu
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Glu Leu Thr Val Asp Lys Ser Arg Trp Gln
            405                 410                 415

Gln Gly Asn Val Phe Ser Cys Ser Val Met His Glu Ala Leu His Asn
            420                 425                 430
```

His Tyr Thr Gln Lys Ser Leu Ser Leu Ser Pro Gly Lys
        435                 440                 445

<210> SEQ ID NO 57
<211> LENGTH: 464
<212> TYPE: PRT
<213> ORGANISM: Artificial sequence
<220> FEATURE:
<223> OTHER INFORMATION: 21R75 Heavy chain with signal sequence

<400> SEQUENCE: 57

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ala Gly Tyr Lys Asp Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
        275                 280                 285

Glu Val Gln Phe Asn Trp Tyr Val Asp Gly Val Glu Val His Asn Ala
    290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
            355                 360                 365

Pro Pro Ser Arg Glu Glu Met Thr Lys Asn Gln Val Ser Leu Thr Cys
370                 375                 380

Leu Val Glu Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Glu Leu Thr Val Asp Lys Ser
            420                 425                 430

Arg Trp Gln Gln Gly Asn Val Phe Ser Cys Ser Val Met His Glu Ala
            435                 440                 445

Leu His Asn His Tyr Thr Gln Lys Ser Leu Ser Leu Ser Pro Gly Lys
            450                 455                 460

<210> SEQ ID NO 58
<211> LENGTH: 119
<212> TYPE: PRT
<213> ORGANISM: Artificial sequence
<220> FEATURE:
<223> OTHER INFORMATION: 21R75 Heavy chain variable region

<400> SEQUENCE: 58

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
        35                  40                  45

Gly Tyr Ile Ala Gly Tyr Lys Asp Ala Thr Asn Tyr Asn Gln Lys Phe
    50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
            100                 105                 110

Thr Leu Val Thr Val Ser Ser
        115

<210> SEQ ID NO 59
<211> LENGTH: 17
<212> TYPE: PRT
<213> ORGANISM: Artificial sequence
<220> FEATURE:
<223> OTHER INFORMATION: 21R75 Heavy chain CDR2

<400> SEQUENCE: 59

Tyr Ile Ala Gly Tyr Lys Asp Ala Thr Asn Tyr Asn Gln Lys Phe Lys
1               5                   10                  15

Gly

<210> SEQ ID NO 60
<211> LENGTH: 1392
<212> TYPE: DNA
<213> ORGANISM: Artificial sequence
<220> FEATURE:
<223> OTHER INFORMATION: 21R75 Heavy chain with signal sequence

```
<400> SEQUENCE: 60
atgaagcacc tgtggttctt tctgctgctg gtggccgctc ccagatgggt gctgtcccag      60
gtgcagctgg tgcagtctgg cgccgaagtg aagaaacctg gcgcctccgt gaagatctcc     120
tgcaaggcct ccggctactc cttcaccgcc tactacatcc actgggtcaa gcaggcccct     180
ggacagggcc tggaatggat cggctatatc gccggctaca aggacgccac caactacaac     240
cagaaattca gggcagagt gaccttcacc accgacacct ccacctctac cgcctacatg      300
gaactgcggt ccctgcggag cgacgacacc gccgtgtact actgcgccag agactacgac     360
tacgacgtgg gcatggacta ctggggccag ggcacactcg tgaccgtgtc ctctgcttcc     420
accaagggcc cctccgtgtt tcctctggcc ccttgctcca gatccacctc cgagtctacc     480
gccgctctgg gctgcctcgt gaaggactac ttccccgagc ccgtgacagt gtcttggaac     540
tctggcgccc tgacctccgg cgtgcacacc tttccagctg tgctgcagtc ctccggcctg     600
tactccctgt cctccgtcgt gactgtgccc tcctccaact tcggcaccca gacctacacc     660
tgtaacgtgg accacaagcc ctccaacacc aaggtggaca gaccgtgga acggaagtgc      720 tgcgtggaat gccccccttg tcctgcccct cctgtggctg gcctagcgt gttcctgttc       780 cccccaaagc ccaaggacac cctgatgatc tcccggaccc ccgaagtgac ctgcgtggtg     840
gtggatgtgt cccacgagga ccccgaggtg cagttcaatt ggtacgtgga cggcgtggaa     900
gtgcacaacg ccaagaccaa gcccagagag aacagttca actccaccct tccgggtggtg    960 tccgtgctga ccgtggtgca tcaggactgg ctgaacggca agagtacaa gtgcaaggtg     1020 tccaacaagg gcctgcctgc ccccatcgaa aagaccatct ctaagaccaa gggacagccc    1080
cgcgagcccc aggtgtacac actgcctcca tcccgggaag atgaccaa gaaccaggtg     1140 tccctgacct gtctggtgga aggcttctac ccctccgata tcgccgtgga atgggagtcc    1200
aacggccagc ccgagaacaa ctacaagacc acccccccca tgctggactc cgacggctca    1260
ttcttcctgt acagcgagct gacagtggac aagtccggt ggcagcaggg caacgtgttc      1320
tcctgctccg tgatgcacga ggccctgcac aaccactaca cccagaagtc cctgtccctg    1380
agccccggca ag                                                         1392

<210> SEQ ID NO 61
<211> LENGTH: 1392
<212> TYPE: DNA
<213> ORGANISM: Artificial sequence
<220> FEATURE:
<223> OTHER INFORMATION: 21R75 Heavy chain with signal sequence

<400> SEQUENCE: 61
atgaagcacc tgtggttctt tctgctgctg gtggccgctc ccagatgggt gctgtcccag      60
gttcagctag ttcagtctgg agcggaagtt aagaaacctg gagcatccgt gaaaataagt     120
tgcaaggcat ccggttactc gttcaccgca tactatatcc actgggttaa acaggcacca     180
ggacagggac ttgaatggat cggatatatc gctggatata agatgctac aaactataac      240 caaaaattca aggacgcgt gactttcaca actgacacct caacctcgac agcatacatg      300
gaattacggt ccctacggtc tgacgacact gccgtttact attgcgctag agattatgat     360
tatgatgttg gaatggacta ttggggccag ggaacactgg tgacagtgtc ttctgcatcc     420
actaagggac catccgtgtt cccttttggcc ccttgctctc gttcgacctc tgaatcgact    480
gccgctctgg gatgcctcgt gaaagattac ttccctgagc ctgtgaccgt tcctggaac     540 tcgggcgccc taacctctgg cgtgcacaca ttccctgccg tgctacagtc ttctggccta     600
```

```
tactctttat cttcggttgt taccgtacct tcttctaact tcggaaccca aacttacacc    660
tgtaacgtag accacaagcc ttcgaacacc aaggtggaca agactgttga gcgaaagtgc    720
tgcgttgagt gccctccatg tcctgcacct cctgtggctg gcccttctgt gttcctgttc    780
cctccaaaac ctaaggacac tctaatgatc tctcggactc ctgaggtgac ttgcgtggtt    840
gtggacgtgt cccacgagga ccctgaggtg cagttcaatt ggtacgtgga cggagtcgag    900
gtgcacaatg caaagaccaa gcctcgggag gaacagttca actccacctt ccgggtggtt    960
tctgtgttga ccgttgtgca ccaagactgg ctgaacggca agaatacaa gtgcaaggtg   1020 tccaacaagg gcctgcctgc ccctatcgaa aagaccatca gcaagaccaa gggccagcct   1080
cgcgagcctc aggtgtacac cctgcctccc agccgggaag aaatgaccaa gaaccaggtg   1140
tccctgacct gtctggtgga gggcttctac ccttccgaca tcgccgttga gtgggagtct   1200
aacggacagc cggagaacaa ctacaagact acgcctccaa tgctggactc cgacggctcc   1260
ttcttcctgt actccgaact gaccgtggac aagtcccggt ggcagcaggg caacgtgttc   1320
tcatgctccg taatgcacga agccttgcac aatcactaca ctcaaaagtc cctatcctta   1380
tctcctggca ag                                                      1392
```

<210> SEQ ID NO 62
<211> LENGTH: 445
<212> TYPE: PRT
<213> ORGANISM: Artificial sequence
<220> FEATURE:
<223> OTHER INFORMATION: 21R83 Heavy chain without signal sequence

<400> SEQUENCE: 62

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
                20                  25                  30

Tyr Ile His Trp Val Lys Gln Ala Pro Gly Gln Gly Leu Glu Trp Ile
            35                  40                  45

Gly Tyr Ile Ser Asn Tyr Asn Arg Ala Thr Asn Tyr Asn Gln Lys Phe
        50                  55                  60

Lys Gly Arg Val Thr Phe Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Tyr Asp Tyr Asp Val Gly Met Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Asn Phe Gly Thr Gln Thr Tyr Thr Cys Asn Val Asp His Lys Pro
        195                 200                 205

Ser Asn Thr Lys Val Asp Lys Thr Val Glu Arg Lys Cys Cys Val Glu
```

```
                210                 215                 220
Cys Pro Pro Cys Pro Ala Pro Val Ala Gly Pro Ser Val Phe Leu
225                 230                 235                 240

Phe Pro Pro Lys Pro Lys Asp Thr Leu Met Ile Ser Arg Thr Pro Glu
            245                 250                 255

Val Thr Cys Val Val Val Asp Val Ser His Glu Asp Pro Glu Val Gln
                260                 265                 270

Phe Asn Trp Tyr Val Asp Gly Val Glu Val His Asn Ala Lys Thr Lys
            275                 280                 285

Pro Arg Glu Glu Gln Phe Asn Ser Thr Phe Arg Val Val Ser Val Leu
290                 295                 300

Thr Val Val His Gln Asp Trp Leu Asn Gly Lys Glu Tyr Lys Cys Lys
305                 310                 315                 320

Val Ser Asn Lys Gly Leu Pro Ala Pro Ile Glu Lys Thr Ile Ser Lys
                325                 330                 335

Thr Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Glu
            355                 360                 365

Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Met Leu Asp Ser Asp Gly
385                 390                 395                 400

Ser Phe Phe Leu Tyr Ser Glu Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
            435                 440                 445

<210> SEQ ID NO 63
<211> LENGTH: 464
<212> TYPE: PRT
<213> ORGANISM: Artificial sequence
<220> FEATURE:
<223> OTHER INFORMATION: 21R83 Heavy chain with signal sequence

<400> SEQUENCE: 63

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Ala Ser Gly Tyr Ser Phe
        35                  40                  45

Thr Ala Tyr Tyr Ile His Trp Val Lys Gln Ala Pro Gly Gln Gly Leu
    50                  55                  60

Glu Trp Ile Gly Tyr Ile Ser Asn Tyr Asn Arg Ala Thr Asn Tyr Asn
65                  70                  75                  80

Gln Lys Phe Lys Gly Arg Val Thr Phe Thr Thr Asp Thr Ser Thr Ser
                85                  90                  95

Thr Ala Tyr Met Glu Leu Arg Ser Leu Arg Ser Asp Asp Thr Ala Val
            100                 105                 110

Tyr Tyr Cys Ala Arg Asp Tyr Asp Tyr Asp Val Gly Met Asp Tyr Trp
        115                 120                 125

Gly Gln Gly Thr Leu Val Thr Val Ser Ser Ala Ser Thr Lys Gly Pro
```

```
                130              135              140
Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Val Val Thr
        195                 200                 205

Val Pro Ser Ser Asn Phe Gly Thr Gln Thr Tyr Thr Cys Asn Val Asp
    210                 215                 220

His Lys Pro Ser Asn Thr Lys Val Asp Lys Thr Val Glu Arg Lys Cys
225                 230                 235                 240

Cys Val Glu Cys Pro Pro Cys Pro Ala Pro Val Ala Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Asp Val Ser His Glu Asp Pro
    275                 280                 285

Glu Val Gln Phe Asn Trp Tyr Val Asp Gly Val Glu Val His Asn Ala
290                 295                 300

Lys Thr Lys Pro Arg Glu Glu Gln Phe Asn Ser Thr Phe Arg Val Val
305                 310                 315                 320

Ser Val Leu Thr Val Val His Gln Asp Trp Leu Asn Gly Lys Glu Tyr
                325                 330                 335

Lys Cys Lys Val Ser Asn Lys Gly Leu Pro Ala Pro Ile Glu Lys Thr
            340                 345                 350

Ile Ser Lys Thr Lys Gly Gln Pro Arg Glu Pro Gln Val Tyr Thr Leu
        355                 360                 365

Pro Pro Ser Arg Glu Glu Met Thr Lys Asn Gln Val Ser Leu Thr Cys
    370                 375                 380

Leu Val Glu Gly Phe Tyr Pro Ser Asp Ile Ala Val Glu Trp Glu Ser
385                 390                 395                 400

Asn Gly Gln Pro Glu Asn Asn Tyr Lys Thr Thr Pro Pro Met Leu Asp
                405                 410                 415

Ser Asp Gly Ser Phe Phe Leu Tyr Ser Glu Leu Thr Val Asp Lys Ser
            420                 425                 430

Arg Trp Gln Gln Gly Asn Val Phe Ser Cys Ser Val Met His Glu Ala
        435                 440                 445

Leu His Asn His Tyr Thr Gln Lys Ser Leu Ser Leu Ser Pro Gly Lys
    450                 455                 460

<210> SEQ ID NO 64
<211> LENGTH: 119
<212> TYPE: PRT
<213> ORGANISM: Artificial sequence
<220> FEATURE:
<223> OTHER INFORMATION: 21R83 Heavy chain variable region

<400> SEQUENCE: 64

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Ser Phe Thr Ala Tyr
            20                  25                  30

Tyr Ile His Trp Val Lys Gln Ala Pro Gly Gln Gly Leu Glu Trp Ile
```

```
              35                  40                  45
Gly Tyr Ile Ser Asn Tyr Asn Arg Ala Thr Asn Tyr Asn Gln Lys Phe
         50                  55                  60

Lys Gly Arg Val Thr Phe Thr Thr Asp Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Tyr Asp Tyr Asp Val Gly Met Asp Tyr Trp Gly Gln Gly
             100                 105                 110

Thr Leu Val Thr Val Ser Ser
         115

<210> SEQ ID NO 65
<211> LENGTH: 17
<212> TYPE: PRT
<213> ORGANISM: Artificial sequence
<220> FEATURE:
<223> OTHER INFORMATION: 21R83 Heavy chain CDR2

<400> SEQUENCE: 65

Tyr Ile Ser Asn Tyr Asn Arg Ala Thr Asn Tyr Asn Gln Lys Phe Lys
 1               5                  10                  15

Gly

<210> SEQ ID NO 66
<211> LENGTH: 1392
<212> TYPE: DNA
<213> ORGANISM: Artificial sequence
<220> FEATURE:
<223> OTHER INFORMATION: 21R83 Heavy chain with signal sequence

<400> SEQUENCE: 66
atgaagcacc tgtggttctt tctgctgctg gtggccgctc ccagatgggt gctgtcccag      60
gtgcagctgg tgcagtctgg cgccgaagtg aagaaacctg gcgcctccgt gaagatctcc     120
tgcaaggcct ccggctactc cttcaccgcc tactacatcc actgggtcaa gcaggcccct     180
ggacagggcc tggaatggat cggctacatc tccaactaca accgggccac caattacaac     240
cagaaattca agggccgcgt gaccttcacc accgacacct ctacctctac cgcctacatg     300
gaactgcggt ccctgcggag cgacgacacc gccgtgtact actgcgccag agactacgac     360
tacgacgtgg gcatggacta ctggggccag ggcacactcg tgaccgtgtc tagcgcttcc     420
accaagggcc cctccgtgtt cctctggcc ccttgctcca gatccacctc cgagtctacc     480
gccgctctgg gctgcctcgt gaaggactac ttccccgagc ccgtgacagt gtcctggaac     540
tctggcgctc tgacctccgg cgtgcacacc tttccagctg tgctgcagtc ctccggcctg     600
tactccctgt cctccgtcgt gactgtgccc tcctccaact cggcaccca gacctacacc     660 tgtaacgtgg accacaagcc ctccaacacc aaggtggaca gaccgtgga acggaagtgc     720 tgcgtggaat gcccccttg tcctgcccct cctgtgctg gcctagcgt gttcctgttc     780 cccccaaagc ccaaggacac cctgatgatc tcccggaccc ccgaagtgac ctgcgtggtg     840
gtggatgtgt cccacgagga ccccgaggtg cagttcaatt ggtacgtgga cggcgtggaa     900
gtgcacaacg ccaagaccaa gccagagag gaacagttca ctccaccttt ccgggtggtg     960
tccgtgctga ccgtggtgca tcaggactgg ctgaacggca agagtacaa gtgcaaggtg    1020 tccaacaagg gcctgcctgc ccccatcgaa aagaccatct ctaagaccaa gggacagccc    1080
cgcgagcccc aggtgtacac actgcctcca tcccgggaag agatgaccaa gaaccaggtg    1140
```

| tccctgacct gtctggtgga aggcttctac ccctccgata tcgccgtgga atgggagtcc | 1200 |
| aacggccagc ccgagaacaa ctacaagacc acccccccca tgctggactc cgacggctca | 1260 |
| ttcttcctgt acagcgagct gacagtggac aagtcccggt ggcagcaggg caacgtgttc | 1320 |
| tcctgctccg tgatgcacga ggccctgcac aaccactaca cccagaagtc cctgtccctg | 1380 |
| agccccggca ag | 1392 |

<210> SEQ ID NO 67
<211> LENGTH: 1392
<212> TYPE: DNA
<213> ORGANISM: Artificial sequence
<220> FEATURE:
<223> OTHER INFORMATION: 21R75 Heavy chain with signal sequence

<400> SEQUENCE: 67

| atgaagcacc tgtggttctt tctgctgctg gtggccgctc ccagatgggt gctgtcccag | 60 |
| gttcagctag ttcagtctgg agcggaagtt aagaaacctg gagcatccgt gaaaataagt | 120 |
| tgcaaggcat ccggttactc gttcaccgca tactatatcc actgggttaa acaggcacca | 180 |
| ggacagggac ttgaatggat cggatatatc gctggatata agatgctac aaactataac | 240 |
| caaaaattca aggacgcgt gactttcaca actgacacct caacctcgac agcatacatg | 300 |
| gaattacggt ccctacggtc tgacgacact gccgtttact attgcgctag agattatgat | 360 |
| tatgatgttg aatggacta ttggggccag ggaacactgg tgacagtgtc ttctgcatcc | 420 |
| actaagggac catccgtgtt ccctttggcc ccttgctctc gttcgacctc tgaatcgact | 480 |
| gccgctctgg gatgcctcgt gaaagattac ttccctgagc ctgtgaccgt tcctggaac | 540 |
| tcgggcgccc taacctctgg cgtgcacaca ttccctgccg tgctacagtc ttctggccta | 600 |
| tactctttat cttcggttgt taccgtacct tcttctaact tcggaaccca aacttacacc | 660 |
| tgtaacgtag accacaagcc ttcgaacacc aaggtggaca agactgttga gcgaaagtgc | 720 |
| tgcgttgagt gccctccatg tcctgcacct cctgtggctg gccttctgt gttcctgttc | 780 |
| cctccaaaac ctaaggacac tctaatgatc tctcggactc ctgaggtgac ttgcgtggtt | 840 |
| gtggacgtgt cccacgagga ccctgaggtg cagttcaatt ggtacgtgga cggagtcgag | 900 |
| gtgcacaatg caaagaccaa gcctcgggag gaacagttca actccacctt ccgggtggtt | 960 |
| tctgtgttga ccgttgtgca ccaagactgg ctgaacggca agaatacaa gtgcaaggtg | 1020 |
| tccaacaagg gcctgcctgc ccctatcgaa aagaccatca gcaagaccaa gggccagcct | 1080 |
| cgcgagcctc aggtgtacac cctgcctccc agcggaagg aaatgaccaa gaaccaggtg | 1140 |
| tccctgacct gtctggtgga gggcttctac ccttccgaca tcgccgttga gtgggagtct | 1200 |
| aacggacagc cggagaacaa ctacaagact acgcctccaa tgctggactc cgacggctcc | 1260 |
| ttcttcctgt actccgaact gaccgtggac aagtcccggt ggcagcaggg caacgtgttc | 1320 |
| tcatgctccg taatgcacga agccttgcac aatcactaca ctcaaaagtc cctatcctta | 1380 |
| tctcctggca ag | 1392 |

<210> SEQ ID NO 68
<211> LENGTH: 357
<212> TYPE: DNA
<213> ORGANISM: Artificial sequence
<220> FEATURE:
<223> OTHER INFORMATION: 21R75 Heavy chain variable region

<400> SEQUENCE: 68

```
caggtgcagc tggtgcagtc tggcgccgaa gtgaagaaac ctggcgcctc cgtgaagatc    60
tcctgcaagg cctccggcta ctccttcacc gcctactaca tccactgggt caagcaggcc   120
cctggacagg gcctggaatg gatcggctat atcgccggct acaaggacgc caccaactac   180
aaccagaaat tcaagggcag agtgaccttc accaccgaca cctccacctc taccgcctac   240
atggaactgc ggtccctgcg gagcgacgac accgccgtgt actactgcgc cagagactac   300
gactacgacg tgggcatgga ctactggggc cagggcacac tcgtgaccgt gtcctct      357

<210> SEQ ID NO 69
<211> LENGTH: 357
<212> TYPE: DNA
<213> ORGANISM: Artificial sequence
<220> FEATURE:
<223> OTHER INFORMATION: 21R75 Heavy chain variable region

<400> SEQUENCE: 69
caggttcagc tagttcagtc tggagcggaa gttaagaaac ctggagcatc cgtgaaaata    60
agttgcaagg catccggtta ctcgttcacc gcatactata tccactgggt taaacaggca   120
ccaggacagg gacttgaatg gatcggatat atcgctggat ataaagatgc tacaaactat   180
aaccaaaaat tcaaggacg cgtgactttc acaactgaca cctcaacctc gacagcatac   240
atggaattac ggtccctacg gtctgacgac actgccgttt actattgcgc tagagattat   300
gattatgatg ttggaatgga ctattggggc cagggaacac tggtgacagt gtcttct      357

<210> SEQ ID NO 70
<211> LENGTH: 357
<212> TYPE: DNA
<213> ORGANISM: Artificial sequence
<220> FEATURE:
<223> OTHER INFORMATION: 21R83 Heavy chain variable region

<400> SEQUENCE: 70
caggtgcagc tggtgcagtc tggcgccgaa gtgaagaaac ctggcgcctc cgtgaagatc    60
tcctgcaagg cctccggcta ctccttcacc gcctactaca tccactgggt caagcaggcc   120
cctggacagg gcctggaatg gatcggctac atctccaact acaaccgggc caccaattac   180
aaccagaaat tcaagggccg cgtgaccttc accaccgaca cctctacctc taccgcctac   240
atggaactgc ggtccctgcg gagcgacgac accgccgtgt actactgcgc cagagactac   300
gactacgacg tgggcatgga ctactggggc cagggcacac tcgtgaccgt gtctagc      357

<210> SEQ ID NO 71
<211> LENGTH: 357
<212> TYPE: DNA
<213> ORGANISM: Artificial sequence
<220> FEATURE:
<223> OTHER INFORMATION: 21R75 Heavy chain variable region

<400> SEQUENCE: 71
caggttcagc tagttcagtc tggagcggaa gttaagaaac ctggagcatc cgtgaaaata    60
agttgcaagg catccggtta ctcgttcacc gcatactata tccactgggt taaacaggca   120
ccaggacagg gacttgaatg gatcggatat atcgctggat ataaagatgc tacaaactat   180
aaccaaaaat tcaaggacg cgtgactttc acaactgaca cctcaacctc gacagcatac   240
atggaattac ggtccctacg gtctgacgac actgccgttt actattgcgc tagagattat   300
gattatgatg ttggaatgga ctattggggc cagggaacac tggtgacagt gtcttct      357
```

<210> SEQ ID NO 72
<211> LENGTH: 1395
<212> TYPE: DNA
<213> ORGANISM: Artificial sequence
<220> FEATURE:
<223> OTHER INFORMATION: 21R83 Heavy chain with signal sequence

<400> SEQUENCE: 72

| | | | | | |
|---|---|---|---|---|---|
| atgaagcacc | tatggttctt | tctattatta | gtggccgctc | ccgttgggt | gttatcgcag | 60 |
| gttcagctag | ttcagtctgg | agcggaagtt | aagaaacctg | agcatccgt | gaaaataagt | 120 |
| tgcaaggcat | ccggttactc | gttcaccgca | tactatatcc | actgggttaa | acaggcacca | 180 |
| ggacagggac | ttgaatggat | cggatatatc | tccaattata | atagagctac | aaactataac | 240 |
| caaaaattca | aggacgcgt | gactttcaca | actgacacct | caacctcgac | agcatacatg | 300 |
| gaattacggt | ccctacggtc | tgacgacact | gccgtttact | attgcgctag | agattatgat | 360 |
| tatgatgttg | aatggacta | ttggggccag | ggaacactgg | tgacagtgtc | ttctgcatcc | 420 |
| actaagggac | catccgtgtt | ccctttggcc | ccttgctctc | gttcgacctc | tgaatcgact | 480 |
| gccgctctgg | gatgcctcgt | gaaagattac | ttccctgagc | ctgtgaccgt | tcctggaac | 540 |
| tcgggcgccc | taacctctgg | cgtgcacaca | ttccctgccg | tgctacagtc | ttctggccta | 600 |
| tactctttat | cttcggttgt | taccgtacct | tcttctaact | tcggaaccca | aacttacacc | 660 |
| tgtaacgtag | accacaagcc | ttcgaacacc | aaggtggaca | agactgttga | gcgaaagtgc | 720 |
| tgcgttgagt | gccctccatg | tcctgcacct | cctgtggctg | gcccttctgt | gttcctgttc | 780 |
| cctccaaaac | ctaaggacac | tctaatgatc | tctcggactc | ctgaggtgac | ttgcgtggtt | 840 |
| gtggacgtgt | cccacgagga | ccctgaggtg | cagttcaatt | ggtacgtgga | cggagtcgag | 900 |
| gtgcacaatg | caaagaccaa | gcctcgggag | gaacagttca | actccaccttt | ccgggtggtt | 960 |
| tctgtgttga | ccgttgtgca | ccaagactgg | ctgaacggca | agaatacaa | gtgcaaggtg | 1020 |
| tccaacaagg | cctgcctgc | ccctatcgaa | aagaccatca | gcaagaccaa | gggccagcct | 1080 |
| cgcgagcctc | aggtgtacac | cctgcctccc | agccggaag | aaatgaccaa | gaaccaggtg | 1140 |
| tccctgacct | gtctggtgga | gggcttctac | ccttccgaca | tcgccgttga | gtgggagtct | 1200 |
| aacggacagc | cggagaacaa | ctacaagact | acgcctccaa | tgctggactc | cgacggctcc | 1260 |
| ttcttcctgt | actccgaact | gaccgtggac | aagtcccggt | ggcagcaggg | caacgtgttc | 1320 |
| tcatgctccg | taatgcacga | agccttgcac | aatcactaca | ctcaaaagtc | cctatcctta | 1380 |
| tctcctggca | agtag | | | | | 1395 |

<210> SEQ ID NO 73
<211> LENGTH: 357
<212> TYPE: DNA
<213> ORGANISM: Artificial sequence
<220> FEATURE:
<223> OTHER INFORMATION: 21R83 Heavy chain variable region

<400> SEQUENCE: 73

| | | | | | |
|---|---|---|---|---|---|
| caggttcagc | tagttcagtc | tggagcggaa | gttaagaaac | ctggagcatc | cgtgaaaata | 60 |
| agttgcaagg | catccggtta | ctcgttcacc | gcatactata | tccactgggt | taaacaggca | 120 |
| ccaggacagg | gacttgaatg | gatcggatat | atctccaatt | ataatagagc | tacaaactat | 180 |
| aaccaaaaat | tcaaggacg | cgtgactttc | acaactgaca | cctcaacctc | gacagcatac | 240 |
| atggaattac | ggtccctacg | gtctgacgac | actgccgttt | actattgcgc | tagagattat | 300 |
| gattatgatg | ttgaatgga | ctattgggc | cagggaacac | tggtgacagt | gtcttct | 357 |

<210> SEQ ID NO 74
<211> LENGTH: 1395
<212> TYPE: DNA
<213> ORGANISM: Artificial sequence
<220> FEATURE:
<223> OTHER INFORMATION: 21R75 Heavy chain with signal sequence

<400> SEQUENCE: 74

| | |
|---|---|
| atgaagcacc tatggttctt tctattatta gtggccgctc ccgttgggt gttatcgcag | 60 |
| gttcagctag ttcagtctgg agcggaagtt aagaaacctg gagcatccgt gaaaataagt | 120 |
| tgcaaggcat ccggttactc gttcaccgca tactatatcc actgggttaa acaggcacca | 180 |
| ggacagggac ttgaatggat cggatatatc gctggatata agatgctac aaactataac | 240 |
| caaaaattca aggacgcgt gactttcaca actgacacct caacctcgac agcatacatg | 300 |
| gaattacggt ccctacggtc tgacgacact gccgtttact attgcgctag agattatgat | 360 |
| tatgatgttg aatggacta ttggggccag ggaacactgg tgacagtgtc ttctgcatcc | 420 |
| actaagggac catccgtgtt ccctttggcc ccttgctctc gttcgacctc tgaatcgact | 480 |
| gccgctctgg gatgcctcgt gaaagattac ttccctgagc ctgtgaccgt ttcctggaac | 540 |
| tcgggcgccc taacctctgg cgtgcacaca ttccctgccg tgctacagtc ttctggccta | 600 |
| tactctttat cttcggttgt taccgtacct tcttctaact tcggaaccca aacttacacc | 660 |
| tgtaacgtag accacaagcc ttcgaacacc aaggtgaca gactgttga gcgaaagtgc | 720 |
| tgcgttgagt gcctccatg tcctgcacct cctgtggctg cccttctgt gttcctgttc | 780 |
| cctccaaaac ctaaggacac tctaatgatc tctcggactc tgaggtgac ttgcgtggtt | 840 |
| gtggacgtgt cccacgagga ccctgaggtg cagttcaatt ggtacgtgga cggagtcgag | 900 |
| gtgcacaatg caaagaccaa gcctcgggag gaacagttca actccacctt ccgggtggtt | 960 |
| tctgtgttga ccgttgtgca ccaagactgg ctgaacggca agaatacaa gtgcaaggtg | 1020 |
| tccaacaagg gcctgcctgc cctatcgaa aagaccatca gcaagaccaa gggccagcct | 1080 |
| cgcgagcctc aggtgtacac cctgcctccc agccgggaag aaatgaccaa gaaccaggtg | 1140 |
| tccctgacct gtctggtgga gggcttctac ccttccgaca cgccgttga gtgggagtct | 1200 |
| aacggacagc cggagaacaa ctacaagact acgcctccaa tgctggactc cgacggctcc | 1260 |
| ttcttcctgt actccgaact gaccgtggac aagtcccggt ggcagcaggg caacgtgttc | 1320 |
| tcatgctccg taatgcacga agccttgcac aatcactaca ctcaaaagtc cctatcctta | 1380 |
| tctcctggca agtag | 1395 |

<210> SEQ ID NO 75
<211> LENGTH: 1395
<212> TYPE: DNA
<213> ORGANISM: Artificial sequence
<220> FEATURE:
<223> OTHER INFORMATION: 21M18 Heavy chain

<400> SEQUENCE: 75

| | |
|---|---|
| atgaagcacc tatggttctt tctattatta gtggccgctc ccgttgggt gttatcgcag | 60 |
| gttcagctag ttcagtctgg agcggaagtt aagaaacctg gagcatccgt gaaaataagt | 120 |
| tgcaaggcat ccggttactc gttcaccgca tactatatcc actgggttaa acaggcacca | 180 |
| ggacagggac ttgaatggat cggatatatc tcctcttata tggagctac aaactataac | 240 |
| caaaaattca aggacgcgt gactttcaca actgacacct caacctcgac agcatacatg | 300 |
| gaattacggt ccctacggtc tgacgacact gccgtttact attgcgctag agattatgat | 360 |

```
tatgatgttg aatggacta ttggggccag ggaacactgg tgacagtgtc ttctgcatcc        420
actaagggac catccgtgtt cccttttggcc ccttgctctc gttcgacctc tgaatcgact      480
gccgctctgg gatgcctcgt gaaagattac ttccctgagc ctgtgaccgt tcctggaac       540 tcgggcgccc taacctctgg cgtgcacaca ttccctgccg tgctacagtc ttctggccta      600
tactctttat cttcggttgt taccgtacct tcttctaact tcggaaccca aacttacacc      660
tgtaacgtag accacaagcc ttcgaacacc aaggtggaca agactgttga gcgaaagtgc      720
tgcgttgagt gccctccatg tcctgcacct cctgtggctg gcccttctgt gttcctgttc      780
cctccaaaac ctaaggacac tctaatgatc tctcggactc tgaggtgac ttgcgtggtt       840 gtggacgtgt cccacgagga ccctgaggtg cagttcaatt ggtacgtgga cggagtcgag      900
gtgcacaatg caaagaccaa gcctcgggag gaacagttca actccacctt ccgggtggtt      960
tctgtgttga ccgttgtgca ccaagactgg ctgaacggca agaatacaa gtgcaaggtg      1020 tccaacaagg gcctgcctgc ccctatcgaa aagaccatca gcaagaccaa gggccagcct    1080
cgcgagcctc aggtgtacac cctgcctccc agccgggaag aaatgaccaa gaaccaggtg    1140
tccctgacct gtctggtgga gggcttctac ccttccgaca tcgccgttga gtgggagtct    1200
aacggacagc cggagaacaa ctacaagact acgcctccaa tgctggactc cgacggctcc    1260
ttcttcctgt actccgaact gaccgtggac aagtcccggt ggcagcaggg caacgtgttc    1320
tcatgctccg taatgcacga agccttgcac aatcactaca ctcaaaagtc cctatcctta    1380
tctcctggca agtag                                                      1395

<210> SEQ ID NO 76
<211> LENGTH: 351
<212> TYPE: DNA
<213> ORGANISM: Artificial sequence
<220> FEATURE:
<223> OTHER INFORMATION: 21M18 Heavy chain variable region

<400> SEQUENCE: 76
cagctagttc agtctggagc ggaagttaag aaacctggag catccgtgaa aataagttgc        60
aaggcatccg gttactcgtt caccgcatac tatatccact gggttaaaca ggcaccagga      120
cagggacttg aatggatcgg atatatctcc tcttataatg gagctacaaa ctataaccaa      180
aaattcaaag gacgcgtgac tttcacaact gacacctcaa cctcgacagc atacatggaa      240
ttacggtccc tacggtctga cgacactgcc gtttactatt gcgctagaga ttatgattat      300
gatgttggaa tggactattg gggccaggga acactggtga cagtgtcttc t             351

<210> SEQ ID NO 77
<211> LENGTH: 1392
<212> TYPE: DNA
<213> ORGANISM: Artificial sequence
<220> FEATURE:
<223> OTHER INFORMATION: 21R75 Heavy chain with signal sequence

<400> SEQUENCE: 77
atgaagcacc tgtggttctt tctgctgctg gtggccgctc ccagatgggt gctgtctcag        60
gtgcagctgg tgcagtctgg cgccgaagtg aagaaacctg gcgcctccgt gaagatctcc      120
tgcaaggcct ccggctactc cttcaccgcc tactacatcc actgggtcaa gcaggcccct      180
ggacagggcc tggaatggat cggctatatc gccggctaca aggacgccac caactacaac      240
cagaaattca agggcagagt gaccttcacc accgacacct ccacctctac cgcctacatg      300
```

```
gaactgcggt ccctgcggag cgacgacacc gccgtgtact actgcgccag agactacgac    360
tacgacgtgg gcatggacta ctggggccag ggcacactcg tgaccgtgtc ctctgcttcc    420
accaagggcc cctccgtgtt tcctctggcc ccttgctcca gatccacctc cgagtctacc    480
gccgctctgg gctgcctcgt gaaggactac ttccccgagc ccgtgacagt gtcttggaac    540
tctggcgccc tgacctccgg cgtgcacacc tttccagctg tgctgcagtc ctccggcctg    600
tactccctgt cctccgtcgt gactgtgccc tcctccaact cggcaccca gacctacacc    660 tgtaacgtgg accacaagcc ctccaacacc aaggtggaca gaccgtgga acggaagtgc    720 tgcgtggaat gccccccttg tcctgcccct cctgtggctg ccctagcgt gttcctgttc    780 cccccaaagc ccaaggacac cctgatgatc tcccggaccc ccgaagtgac ctgcgtggtg    840
gtggatgtgt cccacgagga ccccgaggtg cagttcaatt ggtacgtgga cggcgtggaa    900
gtgcacaacg ccaagaccaa gcccagagag gaacagttca actccacctt ccgggtggtg    960
tccgtgctga ccgtggtgca tcaggactgg ctgaacggca agagtacaa gtgcaaggtg   1020 tccaacaagg gcctgcctgc ccccatcgaa aagaccatct ctaagaccaa gggacagccc   1080
cgcgagcccc aggtgtacac actgcctcca tcccgggaag agatgaccaa gaaccaggtg   1140
tccctgacct gtctggtgga aggcttctac ccctccgata tcgccgtgga atgggagtcc   1200
aacggccagc ccgagaacaa ctacaagacc accccccca tgctggactc cgacggctca   1260
ttcttcctgt acagcgagct gacagtggac aagtcccggt ggcagcaggg caacgtgttc   1320
tcctgctccg tgatgcacga ggccctgcac aaccactaca cccagaagtc cctgtccctg   1380
agccccggca ag                                                         1392
```

<210> SEQ ID NO 78
<211> LENGTH: 1392
<212> TYPE: DNA
<213> ORGANISM: Artificial sequence
<220> FEATURE:
<223> OTHER INFORMATION: 21R83 Heavy chain with signal sequence

<400> SEQUENCE: 78

```
atgaagcacc tgtggttctt tctgctgctg gtggccgctc ccagatgggt gctgtctcag     60
gtgcagctgg tgcagtctgg cgccgaagtg aagaaacctg gcgcctccgt gaagatctcc    120
tgcaaggcct ccggctactc cttcaccgcc tactacatcc actgggtcaa gcaggcccct    180
ggacagggcc tggaatggat cggctacatc tccaactaca ccggccacc caattacaac    240 cagaaattca gggccgcgt gaccttcacc accgacacct ctacctctac cgcctacatg    300
gaactgcggt ccctgcggag cgacgacacc gccgtgtact actgcgccag agactacgac    360
tacgacgtgg gcatggacta ctggggccag ggcacactcg tgaccgtgtc tagcgcttcc    420
accaagggcc cctccgtgtt tcctctggcc ccttgctcca gatccacctc cgagtctacc    480
gccgctctgg gctgcctcgt gaaggactac ttccccgagc ccgtgacagt gtcctggaac    540
tctggcgctc tgacctccgg cgtgcacacc tttccagctg tgctgcagtc ctccggcctg    600
tactccctgt cctccgtcgt gactgtgccc tcctccaact cggcaccca gacctacacc    660 tgtaacgtgg accacaagcc ctccaacacc aaggtggaca gaccgtgga acggaagtgc    720 tgcgtggaat gccccccttg tcctgcccct cctgtggctg ccctagcgt gttcctgttc    780 cccccaaagc ccaaggacac cctgatgatc tcccggaccc ccgaagtgac ctgcgtggtg    840
gtggatgtgt cccacgagga ccccgaggtg cagttcaatt ggtacgtgga cggcgtggaa    900
gtgcacaacg ccaagaccaa gcccagagag gaacagttca actccacctt ccgggtggtg    960
```

```
tccgtgctga ccgtggtgca tcaggactgg ctgaacggca aagagtacaa gtgcaaggtg      1020
tccaacaagg gcctgcctgc ccccatcgaa aagaccatct ctaagaccaa gggacagccc      1080
cgcgagcccc aggtgtacac actgcctcca tcccgggaag agatgaccaa gaaccaggtg      1140
tccctgacct gtctggtgga aggcttctac ccctccgata tcgccgtgga atgggagtcc      1200
aacggccagc ccgagaacaa ctacaagacc accccccca tgctggactc cgacggctca       1260
ttcttcctgt acagcgagct gacagtggac aagtcccggt ggcagcaggg caacgtgttc      1320
tcctgctccg tgatgcacga ggccctgcac aaccactaca cccagaagtc cctgtccctg      1380
agccccggca ag                                                         1392

<210> SEQ ID NO 79
<211> LENGTH: 5
<212> TYPE: PRT
<213> ORGANISM: Artificial sequence
<220> FEATURE:
<223> OTHER INFORMATION: Alt 21R75, 21R79, 21R83, and 21M18 Heavy chain
      CDR1

<400> SEQUENCE: 79

Ala Tyr Tyr Ile His
1               5

<210> SEQ ID NO 80
<211> LENGTH: 17
<212> TYPE: PRT
<213> ORGANISM: Artificial sequence
<220> FEATURE:
<223> OTHER INFORMATION: Anti-DLL4 heavy chain CDR2 consensus sequence
<220> FEATURE:
<221> NAME/KEY: MISC_FEATURE
<222> LOCATION: (3)..(3)
<223> OTHER INFORMATION: Xaa is serine or alanine
<220> FEATURE:
<221> NAME/KEY: MISC_FEATURE
<222> LOCATION: (4)..(4)
<223> OTHER INFORMATION: Xaa is serine, asparagine, or glycine
<220> FEATURE:
<221> NAME/KEY: MISC_FEATURE
<222> LOCATION: (6)..(6)
<223> OTHER INFORMATION: Xaa is asparagine or lysine
<220> FEATURE:
<221> NAME/KEY: MISC_FEATURE
<222> LOCATION: (7)..(7)
<223> OTHER INFORMATION: Xaa is lysine, arginine, or aspartic acid

<400> SEQUENCE: 80

Tyr Ile Xaa Xaa Tyr Xaa Xaa Ala Thr Asn Tyr Asn Gln Lys Phe Lys
1               5                   10                  15

Gly
```

VEGF/DLL4 BINDING AGENTS AND USES THEREOF

CROSS-REFERENCE TO RELATED APPLICATIONS

This application is a continuation of U.S. application Ser. No. 15/847,335, filed Dec. 19, 2017, now U.S. Pat. No. 10,730,940, which is a divisional of U.S. application Ser. No. 15/401,543, filed Jan. 9, 2017, now U.S. Pat. No. 9,879,084, which is a divisional of U.S. application Ser. No. 15/163,301, filed May 24, 2016, now U.S. Pat. No. 9,574,009, which is a divisional of U.S. application Ser. No. 14/476,582, filed Sep. 3, 2014, now U.S. Pat. No. 9,376,488, which is a divisional of U.S. application Ser. No. 13/625,417, filed Sep. 24, 2012, now U.S. Pat. No. 8,858,941, which claims the benefit of U.S. Provisional Application No. 61/538,454, filed Sep. 23, 2011, U.S. Provisional Application No. 61/597,409, filed Feb. 10, 2012, and U.S. Provisional Application No. 61/692,978, filed Aug. 24, 2012, each of which is hereby incorporated by reference herein in its entirety.

REFERENCE TO A SEQUENCE LISTING SUBMITTED ELECTRONICALLY VIA EFS-WEB

The content of the electronically submitted sequence listing (Name: 4488_0840009_SeqListing_ST25.txt, Size: 141,360 bytes; and Date of Creation: Jul. 6, 2020) is herein incorporated by reference in its entirety.

FIELD OF THE INVENTION

The present invention generally relates to antibodies and other agents that bind VEGF, DLL4, or both VEGF and DLL4, particularly anti-VEGF/anti-DLL4 bispecific antibodies, as well as to methods of using the antibodies or other agents for the treatment of diseases such as cancer.

BACKGROUND OF THE INVENTION

Angiogenesis plays an important role in the pathogenesis of a number of disorders, including solid tumors and metastasis. The production of new blood vessels is essential for providing oxygen and nutrients for the growth and spread of a tumor, and therefore angiogenesis is a good target for cancer therapeutics.

Angiogenesis involves a family of proteins acting as angiogenic activators, including vascular endothelial growth factor (VEGF-A), VEGF-B, VEGF-C, VEGF-E, and their respective receptors (VEGFR-1, VEGFR-2, and VEGFR-3). VEGF-A, also referred to as VEGF or vascular permeability factor (VPF), exists in several isoforms that arise from alternative splicing of mRNA of a single VEGF gene, with $VEGF_{165}$ being the most biologically relevant isoform.

Anti-VEGF antibodies have been shown to suppress the growth of tumor cells in vitro and in vivo. A humanized anti-VEGF monoclonal antibody, bevacizumab (AVASTIN) has been developed and approved in the United States as a cancer therapeutic.

The Notch signaling pathway is a universally conserved signal transduction system. It is involved in cell fate determination during development including embryonic pattern formation and post-embryonic tissue maintenance. In addition, Notch signaling has been identified as a critical factor in the maintenance of hematopoietic stem cells.

The Notch pathway has been linked to the pathogenesis of both hematologic and solid tumors and cancers. Numerous cellular functions and microenvironmental cues associated with tumorigenesis have been shown to be modulated by Notch pathway signaling, including cell proliferation, apoptosis, adhesion, and angiogenesis (Leong et al., 2006, *Blood*, 107:2223-2233). In addition, Notch receptors and/or Notch ligands have been shown to play potential oncogenic roles in a number of human cancers, including acute myelogenous leukemia, B cell chronic lymphocytic leukemia, Hodgkin lymphoma, multiple myeloma, T-cell acute lymphoblastic leukemia, brain cancer, breast cancer, cervical cancer, colon cancer, lung cancer, pancreatic cancer, prostate cancer, and skin cancer. (Leong et al., 2006, *Blood*, 107:2223-2233).

Delta-like 4 ligand (DLL4) is an important component of the Notch pathway and has been identified as a target for cancer therapy. DLL4 is a Notch ligand, characterized by an N-terminal domain, a Delta/Serrate/Lag-2 (DSL) domain and tandem EGF-like repeats within the extracellular domain. It has been reported that DLL4 is induced by VEGF and that DLL4 may act as a negative feedback regulator for vascular proliferation.

Anti-DLL4 antibodies have been shown to enhance angiogenic sprouting and branching which leads to non-productive angiogenesis and decreased tumor growth (Noguera-Troise et al., 2006, *Nature*, 444:1032-1037). In addition, an anti-DLL4 antibody, 21M18, has been shown to inhibit tumor growth and reduce the frequency of cancer stem cells in xenograft tumor models (Hoey et al., 2009, *Cell Stem Cell*, 5:168-177; U.S. Pat. No. 7,750,124).

Although there have been significant strides in development of monoclonal antibodies for use in cancer treatments, there is still great potential for further improvements. One class of antibody molecules with the promise of enhanced potency and/or reduced side effects (e.g., toxicity) is bispecific antibodies.

Early bispecific molecules were mainly generated using chemical cross-linking of two antibodies, or were hybrid hybridomas or "quadromas". One success of the quadroma format is triomabs, which are mouse/rat combinations that demonstrate a preferential species-specific heavy/light chain pairing. More recently, advances in antibody engineering have provided a wide variety of new antibody formats, including, but not limited to, tandem scFv (bi-scFv), diabodies, tandem diabodies (tetra-bodies), single chain diabodies, and dual variable domain antibodies.

It is one of the objectives of the present invention to provide improved molecules for cancer treatment, particularly bispecific antibodies that specifically bind human VEGF and human DLL4.

SUMMARY OF THE INVENTION

The present invention provides binding agents, such as antibodies, that bind VEGF, DLL4, or both VEGF and DLL4 (VEGF/DLL4-binding agents), as well as compositions, such as pharmaceutical compositions, comprising the binding agents. Binding agents that bind VEGF or DLL4, as well as at least one additional antigen or target, and pharmaceutical compositions of such binding agents, are also provided. In certain embodiments, the binding agents are novel polypeptides, such as antibodies, antibody fragments, and other polypeptides related to such antibodies. In certain embodiments, the binding agents are antibodies that specifically bind human VEGF. In some embodiments, the binding agents are antibodies that specifically bind human DLL4. In some embodiments, the binding agents are bispecific antibodies that specifically bind human VEGF and human DLL4. The invention further provides methods of inhibiting the growth of a tumor by administering the binding agents to a subject with a tumor. The invention further provides methods of treating cancer by administering the binding agents to a subject in need thereof. In some embodiments, the methods of treating cancer or inhibiting tumor growth comprise targeting cancer stem cells with the binding agents. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor.

In one aspect, the invention provides a binding agent, such as an antibody, that specifically binds human VEGF. In some embodiments, the binding agent inhibits binding of VEGF to at least one VEGF receptor. In some embodiments, the binding agent inhibits binding of VEGF to VEGFR-1 and/or VEGFR-2. In some embodiments, the binding agent modulates angiogenesis. In certain embodiments, the antibody or other binding agent further specifically binds to and/or inhibits human DLL4 in addition to human VEGF.

In some embodiments, the binding agent is an antibody which comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the binding agent is an antibody that comprises a heavy chain variable region having at least 80% sequence identity to SEQ ID NO:11; and/or a light chain variable region having at least 80% sequence identity to SEQ ID NO:12. In certain embodiments, the binding agent comprises a heavy chain variable region having at least 90% sequence identity to SEQ ID NO:11; and/or a light chain variable region having at least 90% sequence identity to SEQ ID NO:12. In certain embodiments, the binding agent comprises a heavy chain variable region having at least 95% sequence identity to SEQ ID NO:11; and/or a light chain variable region having at least 95% sequence identity to SEQ ID NO:12. In certain embodiments, the binding agent is an antibody that comprises a heavy chain variable region of SEQ ID NO:11; and/or a light chain variable region of SEQ ID NO:12.

In some embodiments, the binding agent is antibody 219R45, 219R45-MB-21M18, 219R45-MB-21R79, 219R45-MB-21R75, or 219R45-MB-21R83.

In another aspect, the invention provides a binding agent, such as an antibody, that specifically binds human DLL4. In some embodiments, the binding agent inhibits binding of DLL4 to at least one Notch receptor. In some embodiments, the binding agent inhibits binding of DLL4 to Notch1, Notch2, Notch3, and/or Notch4. In some embodiments, the binding agent inhibits Notch signaling. In some embodiments, the binding agent promotes unproductive angiogenesis. In certain embodiments, the antibody or other binding agent further specifically binds to and/or inhibits human VEGF in addition to human DLL4.

In some embodiments, the binding agent is an antibody that binds human DLL4 and comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the antibody comprises a heavy chain CDR1 comprising TAYYIH (SEQ ID NO:13) or AYYIH (SEQ ID NO:79), a heavy chain CDR2 comprising YIANYNRATNYNQKFKG (SEQ ID NO:14), and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the binding agent is an antibody that comprises a heavy chain variable region having at least 90% or at least 95% sequence identity to SEQ ID NO:10; and/or a light chain variable region having at least 90% or at least 95% sequence identity to SEQ ID NO:12. In certain embodiments, the binding agent is an antibody that comprises a heavy chain variable region of SEQ ID NO:10; and a light chain variable region of SEQ ID NO:12.

In some embodiments, the binding agent is antibody 21R79 or antibody 219R45-MB-21R79.

In some embodiments, the binding agent is an antibody which comprises a heavy chain CDR1 comprising TAYYIH (SEQ ID NO:13) or AYYIH (SEQ ID NO:79), a heavy chain CDR2 comprising YIAGYKDATNYNQKFKG (SEQ ID NO:59), and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the binding agent is an antibody that comprises a heavy chain variable region having at least 90% or at least 95% sequence identity to SEQ ID NO:58; and/or a light chain variable region having at least 90% or at least 95% sequence identity to SEQ ID NO:12. In certain embodiments, the binding agent is an antibody that comprises a heavy chain variable region of SEQ ID NO:58; and a light chain variable region of SEQ ID NO:12.

In some embodiments, the binding agent is antibody 21R75 or antibody 219R45-MB-21R75.

In some embodiments, the binding agent is an antibody which comprises a heavy chain CDR1 comprising TAYYIH (SEQ ID NO:13) or AYYIH (SEQ ID NO:79), a heavy chain CDR2 comprising YISNYNRATNYNQKFKG (SEQ ID NO:65), and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the binding agent is an antibody that comprises a heavy chain variable region having at least 90% or at least 95% sequence identity to SEQ ID NO:64; and/or a light chain variable region having at least 90% or at least 95% sequence identity to SEQ ID NO:12. In certain embodiments, the binding agent is an antibody that comprises a heavy chain variable region of SEQ ID NO:64; and a light chain variable region of SEQ ID NO:12.

In some embodiments, the binding agent is antibody 21R83 or antibody 219R45-MB-21R83.

In certain embodiments of each of the aforementioned aspects or embodiments, as well as other aspects and/or embodiments described elsewhere herein, the binding agent is a bispecific antibody. In some embodiments, the bispecific antibody specifically binds human VEGF and a second target. In some embodiments, the bispecific antibody specifically binds human DLL4 and a second target. In some embodiments, the bispecific antibody specifically binds both human VEGF and human DLL4. In some embodiments, the bispecific antibody modulates angiogenesis. In certain embodiments, the bispecific antibody inhibits Notch signaling. In some embodiments, the bispecific antibody modulates angiogenesis and inhibits Notch signaling. In some embodiments, the bispecific antibody reduces the number of frequency of cancer stem cells. In certain embodiments, the bispecific antibody comprises two identical light chains. In certain embodiments the bispecific antibody is an IgG antibody (e.g., IgG2).

In some embodiments, the bispecific antibody comprises: a first antigen-binding site that specifically binds human VEGF, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19). In some embodiments, the bispecific antibody further comprises: a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises: a first antigen-binding site that specifically binds human VEGF, wherein the first antigen-binding site comprises (a) a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the bispecific antibody comprises: a first antigen-binding site that specifically binds human DLL4, wherein the first antigen-binding site comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises: a first antigen-binding site that specifically binds human DLL4, wherein the first antigen-binding site comprises a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16). In some embodiments, the bispecific antibody further comprises: a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the the bispecific antibody comprises: a first antigen-binding site that specifically binds human DLL4, wherein the first antigen-binding site comprises (a) a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13), a heavy chain CDR2 comprising YISSYNGATNYNQKFKG (SEQ ID NO:15), and a heavy chain CDR3 comprising RDYDYDVGMDY (SEQ ID NO:16); and wherein both the first and second antigen-binding sites comprise a light chain CDR1 comprising RASESVDNYG- ISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the a bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13), a heavy chain CDR2 comprising YISNYNRATNYNQKFKG (SEQ ID NO:65), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In some embodiments, the bispecific antibody that specifically binds human VEGF, and comprises: a heavy chain variable region having at least 90% sequence identity to SEQ ID NO:11, and/or a light chain variable region having at least 90% sequence identity to SEQ ID NO:12. In some embodiments, the bispecific antibody specifically binds human VEGF, and comprises: a heavy chain variable region having at least 95% sequence identity to SEQ ID NO:11, and/or a light chain variable region having at least 95% sequence identity to SEQ ID NO:12.

In some embodiments, the bispecific antibody specifically binds human DLL4, and comprises: a heavy chain variable region having at least 90% sequence identity to SEQ ID NO:9, SEQ ID NO:10, SEQ ID NO:58, or SEQ ID NO:64; and/or a light chain variable region having at least 90% sequence identity to SEQ ID NO:12. In some embodiments, the bispecific antibody specifically binds human DLL4, and comprises: a heavy chain variable region having at least 95% sequence identity to SEQ ID NO:9, SEQ ID NO:10, SEQ ID NO:58, or SEQ ID NO:64; and/or a light chain variable region having at least 95% sequence identity to SEQ ID NO:12.

In some embodiments, the bispecific antibody specifically binds human VEGF and human DLL4, and comprises: (a) a first heavy chain variable region having at least 90% sequence identity to SEQ ID NO:11; (b) a second heavy chain variable region having at least 90% sequence identity to SEQ ID NO:9, SEQ ID NO:10, SEQ ID NO:58, or SEQ ID NO:64; and (c) a first and a second light chain variable region having at least 90% sequence identity to SEQ ID NO:12. In some embodiments, the VEGF/DLL4 bispecific antibody comprises (a) a first heavy chain variable region having at least 95% sequence identity to SEQ ID NO:11; (b) a second heavy chain variable region having at least 95% sequence identity to SEQ ID NO:9; and (c) a first and a second light chain variable region having at least 95% sequence identity to SEQ ID NO:12. In some embodiments, the VEGF/DLL4 bispecific antibody comprises (a) a first heavy chain variable region having at least 95% sequence identity to SEQ ID NO:11; (b) a second heavy chain variable region having at least 95% sequence identity to SEQ ID NO:10; and (c) a first and a second light chain variable region having at least 95% sequence identity to SEQ ID NO:12. In some embodiments, the VEGF/DLL4 bispecific antibody comprises (a) a first heavy chain variable region having at least 95% sequence identity to SEQ ID NO:11; (b) a second heavy chain variable region having at least 95% sequence identity to SEQ ID NO:58; and (c) a first and a second light chain variable region having at least 95% sequence identity to SEQ ID NO:12. In some embodiments, the VEGF/DLL4 bispecific antibody comprises (a) a first heavy chain variable region having at least 95% sequence identity to SEQ ID NO:11; (b) a second heavy chain variable region having at least 95% sequence identity to SEQ ID NO:64; and (c) a first and a second light chain variable region having at least 95% sequence identity to SEQ ID NO:12.

In some embodiments, the VEGF/DLL4-binding agent is a bispecific antibody comprising (a) a first antigen-binding site that binds human VEGF with a $K_D$ between about 0.1 nM and about 1.0 nM and (b) a second antigen-binding site that specifically binds human DLL4 with a $K_D$ between about 0.1 nM and about 20 nM. In certain embodiments, the bispecific antibody comprises two identical light chains.

In some embodiments, the VEGF/DLL4-binding agent is a bispecific antibody selected from the group consisting of 219R45-MB-21M18, 219R45-MB-21R79, 219R45-MB-21R75, and 219R45-MB-21R83.

In certain embodiments of each of the aforementioned aspects, as well as other aspects and/or embodiments described elsewhere herein, the binding agent or antibody is isolated.

In another aspect, the invention provides a polypeptide selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:46, SEQ ID NO:47, SEQ ID NO:48, SEQ ID NO:49, SEQ ID NO:56, SEQ ID NO:57, SEQ ID NO:58, SEQ ID NO:62, SEQ ID NO:63, and SEQ ID NO:64. In some embodiments, the polypeptide is isolated. In certain embodiments, the polypeptide is substantially pure. In certain embodiments, the polypeptide is an antibody or part of an antibody, such as an antibody fragment.

In another aspect, the invention provides isolated polynucleotide molecules comprising a polynucleotide that encodes the binding agents and/or polypeptides of each of the aforementioned aspects, as well as other aspects and/or embodiments described herein. In some embodiments, the polynucleotide comprises a sequence selected from the group consisting of: SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:50, SEQ ID NO:51, SEQ ID NO:52, SEQ ID NO:53, SEQ ID NO:54, SEQ ID NO:55, SEQ ID NO:60, SEQ ID NO:61, SEQ ID NO:66, SEQ ID NO:67, SEQ ID NO:68, SEQ ID NO:69, SEQ ID NO:70, SEQ ID NO:71, SEQ ID NO:72, SEQ ID NO:73, and SEQ ID NO:74. The invention further provides expression vectors that comprise the polynucleotides, as well as cells that comprise the expression vectors and/or the polynucleotides. In some embodiments, the cell is a prokaryotic cell or a eukaryotic cell.

In other aspects, the invention provides methods of inhibiting growth of a tumor, comprising contacting the tumor with an effective amount of an antibody (or other binding agent) that binds VEGF, DLL4, or both VEGF and DLL4, including each of those antibodies (or other binding agents) described herein.

In another aspect, the invention provides a method of inhibiting the growth of a tumor in a subject, comprising administering to the subject a therapeutically effective amount of an antibody (or other binding agent) that binds VEGF, DLL4, or both VEGF and DLL4, including each of those antibodies (or other binding agents) described herein.

In another aspect, the invention provides a method of modulating angiogenesis in a subject, comprising administering to the subject a therapeutically effective amount of an antibody (or other binding agent) that binds VEGF, DLL4, or both VEGF and DLL4, including each of those antibodies (or other binding agents) described herein.

In another aspect, the invention provides a method of reducing the tumorigenicity of a tumor in a subject, comprising administering to the subject a therapeutically effective amount of an antibody (or other binding agent) that binds VEGF, DLL4, or both VEGF and DLL4, including each of those antibodies (or other binding agents) described herein.

In another aspect, the invention provides a method of reducing the tumorigenicity of a tumor in a subject by reducing the frequency of cancer stem cells in the tumor, comprising administering to the subject a therapeutically effective amount of an antibody (or other binding agent) that binds VEGF, DLL4, or both VEGF and DLL4, including each of those antibodies (or other binding agents) described herein.

In other aspects, the invention provides methods of treating cancer in a subject, comprising administering to the subject a therapeutically effective amount of an antibody (or other binding agent) that binds VEGF, DLL4, or both VEGF and DLL4, including each of those antibodies (or other binding agents) described herein.

Pharmaceutical compositions comprising a binding agent (e.g., antibody) described herein and a pharmaceutically acceptable carrier are further provided, as are cell lines that express and/or produce the binding agents. Methods of treating cancer and/or inhibiting tumor growth in a subject (e.g., a human) comprising administering to the subject an effective amount of a composition comprising the binding agents are also provided.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisages the explicit exclusion of one or more of any of the group members in the claimed invention.

BRIEF DESCRIPTIONS OF THE DRAWINGS

FIGS. 1A, 1B, and 1C. FIG. 1A) Heavy chain and light chain CDRs of anti-VEGF/anti-DLL4 bispecific antibodies 219R45-MB-21M18, 219R45-MB-21R79, 219R45-MB-21R75, and 219R45-MB-21R83; FIG. 1B) Heavy chain and light chain variable region SEQ ID NOs; FIG. 1C) Heavy chain and light chain SEQ ID NOs.

FIG. 2. HTRF assay for simultaneous binding of bispecific antibodies to human VEGF and human DLL4. Results are reported in Relative Fluorescence Units (RFU), which represent the ratio of the relative fluorescence intensity at 665 nm to the relative fluorescence intensity at 620 nm. 219R45-MB-21M18 (-●-); 219R45-MB-21R79 (-■-); 219R45 plus 21M18 (-▲-); 219R45 plus 21R79 (-□-); 219R45 (-▼-); 21M18 (-◇-); 21R79 (-○-); control antibody LZ-1 (-Δ-).

Figure 3:
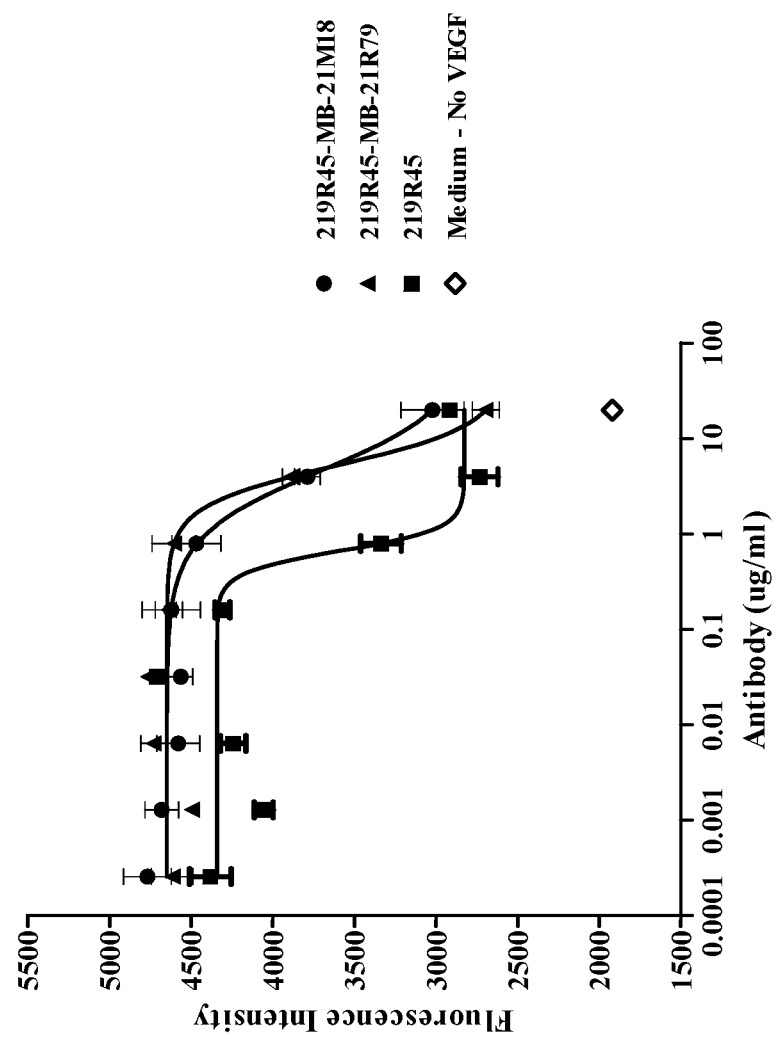

FIG. 3. Inhibition of VEGF-induced HUVEC proliferation by anti-VEGF/anti-DLL4 bispecific antibodies. Fluorescence intensity is read using an excitation wavelength of 530 nm and an emission wavelength of 590. 219R45-MB-21M18 (-●-); 219R45-MB-21R79 (-▲-); 219R45 (-■-); Medium with no VEGF (-◇-).

Figure 4:
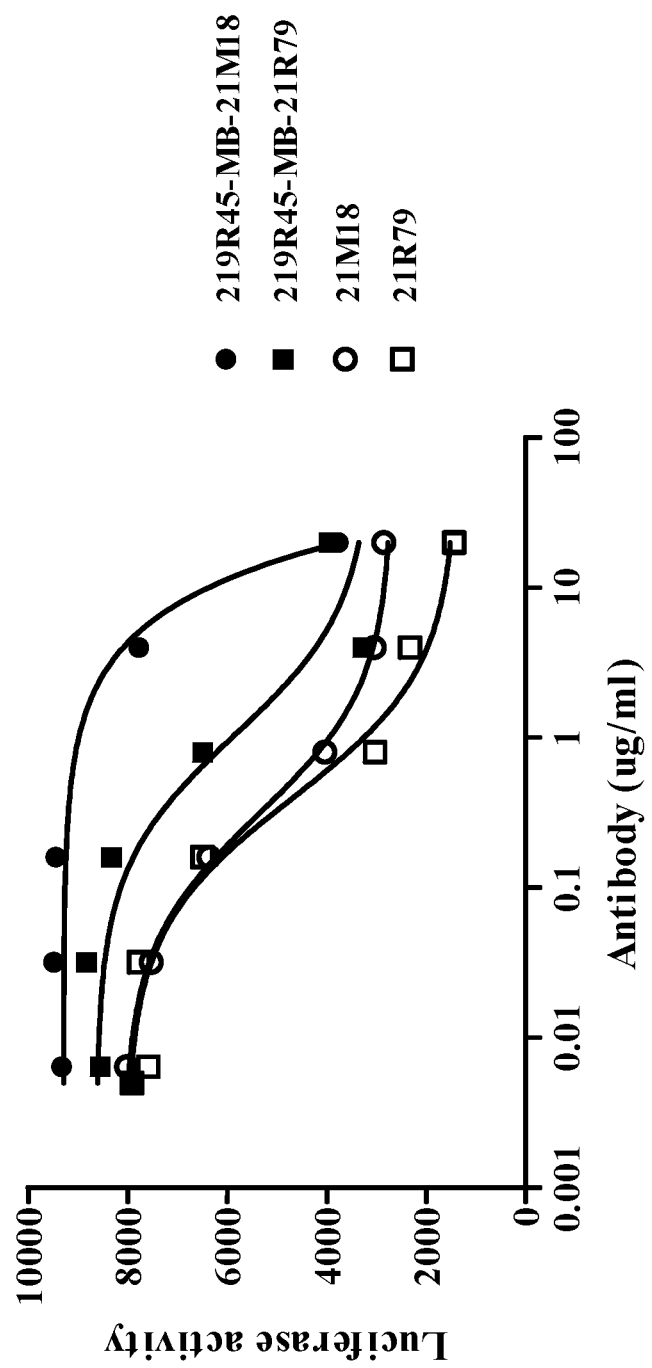

FIG. 4. Inhibition of DLL4-induced Notch signaling by anti-VEGF/anti-DLL4 bispecific antibodies. Luciferase activity was measured using a dual luciferase assay kit with firefly luciferase activity normalized to Renilla luciferase activity. 219R45-MB-21M18 (-●-); 219R45-MB-21R79 (-■-); 21M18 (-○-); 21R79 (-□-).

Figure 5:
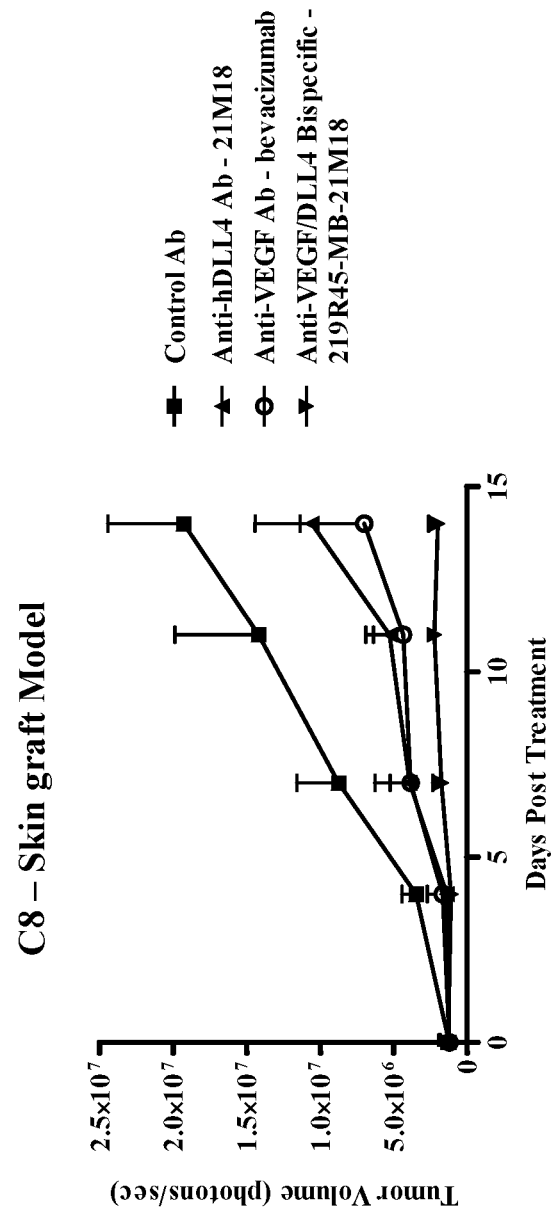

FIG. 5. Inhibition of colon tumor growth in vivo by an anti-VEGF/anti-DLL4 bispecific antibody. OMP-C8 colon tumor cells were injected subcutaneously into a human skin graft in NOD/SCID mice. Mice were treated with control antibody (-■-), anti-hDLL4 antibody 21M18 (-▲-), anti-VEGF antibody bevacizumab (-○-), or anti-VEGF/anti-DLL4 bispecific antibody 219R45-MB-21M18 (-▼-). Data is shown as tumor volume (photons/sec) over days post-treatment. Antibodies were administered intraperitoneally at a dose of 25 mg/kg once a week.

Figure 6:
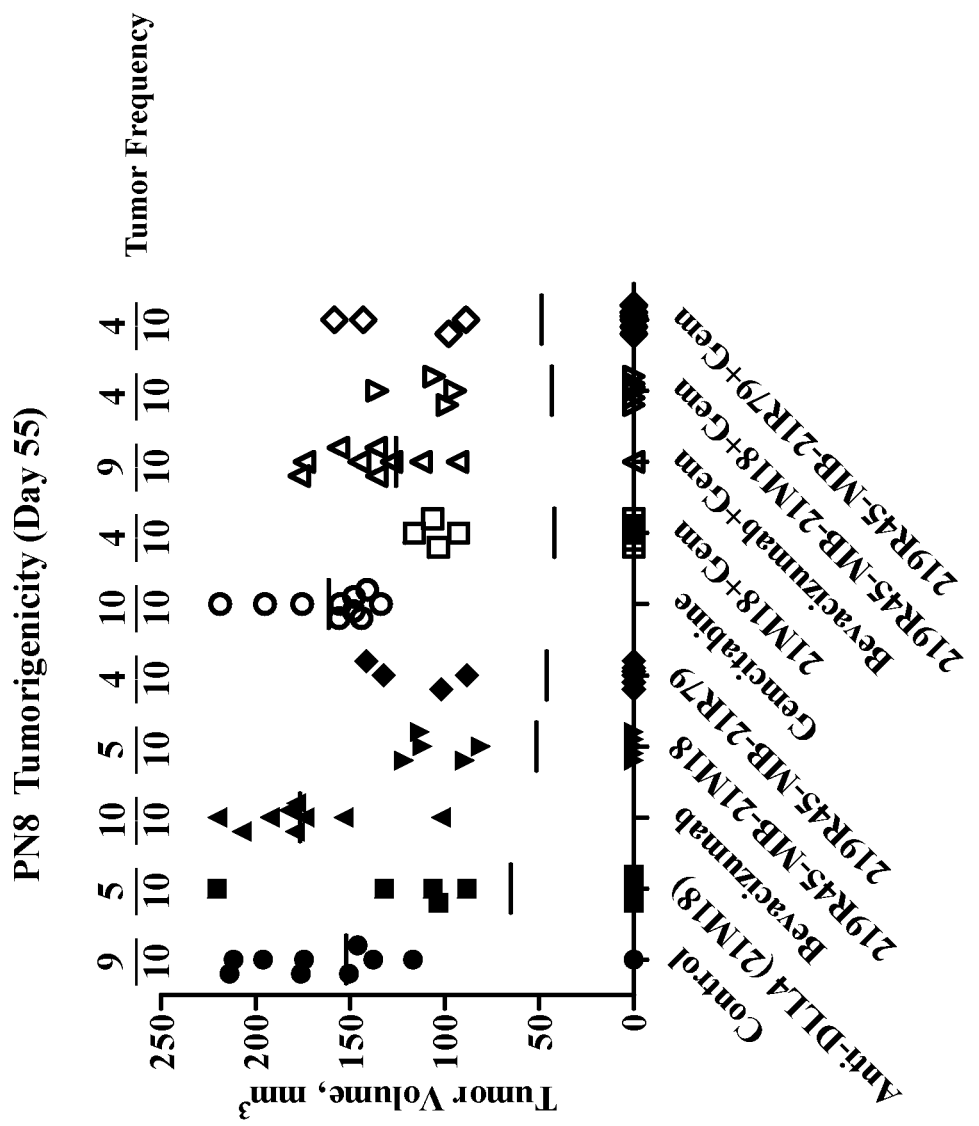

FIG. 6. Tumorigenicity of pancreatic tumor cells after treatment with anti-VEGF/anti-DLL4 bispecific antibodies. OMP-PN8 tumor cells from mice treated with control antibody, anti-hDLL4 antibody 21M18, anti-VEGF antibody bevacizumab, or anti-VEGF/anti-DLL4 bispecific antibodies 219R45-MB-21M18 or 219R45-MB-21R79 with or without gemcitabine were processed to single cell suspensions, and serially transplanted into mice. 90 cells from each treatment group were injected subcutaneously into NOD/SCID mice. Tumors were allowed to grow with no treatment. Data is shown as tumor volume ($mm^3$) on day 55. Tumor frequency is shown as number of tumors over total number of mice injected in each group.

Figure 7:
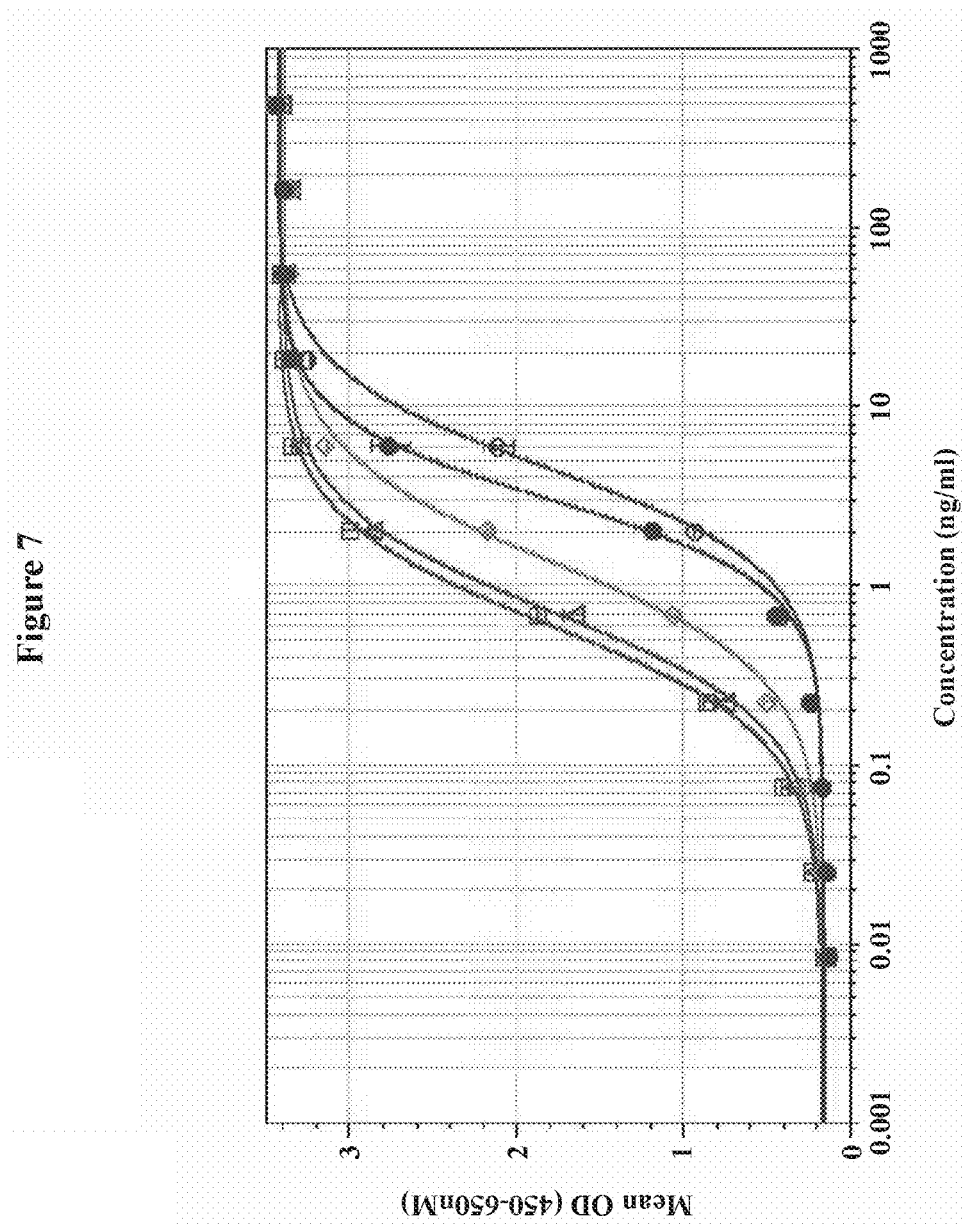

FIG. 7. Bispecific antibody ELISA. Bispecific antibodies 219R45-MB-21M18, 219R45-MB-21R79, 219R45-MB-21R75, and 219R45-MB-21R83 were diluted in blocking buffer (1× PBS, 0.1% gelatin, 0.1% Polysorbate-20, pH 7.4) containing 2 µg/ml biotin-DLL4-hFc. The antibodies were serially diluted 3-fold from 500 ng/ml to 0.008 ng/ml. The antibody samples were incubated for 2 hours in blocking buffer containing the biotin-DLL4-hFc. After incubation, the antibody samples were transferred to a VEGF-coated assay plate (100 ul/well) and incubated for 2 hours. Streptavidin-HRP was added to each well and incubated for 1 hr. TMB substrate was added to the wells with a 10 minute color development and the reaction was stopped with 2M sulfuric acid. Absorbance was read at 450-650 nm and the data analyzed using the 4-parameter fit within the Softmax Pro analysis program.

Figure 8:
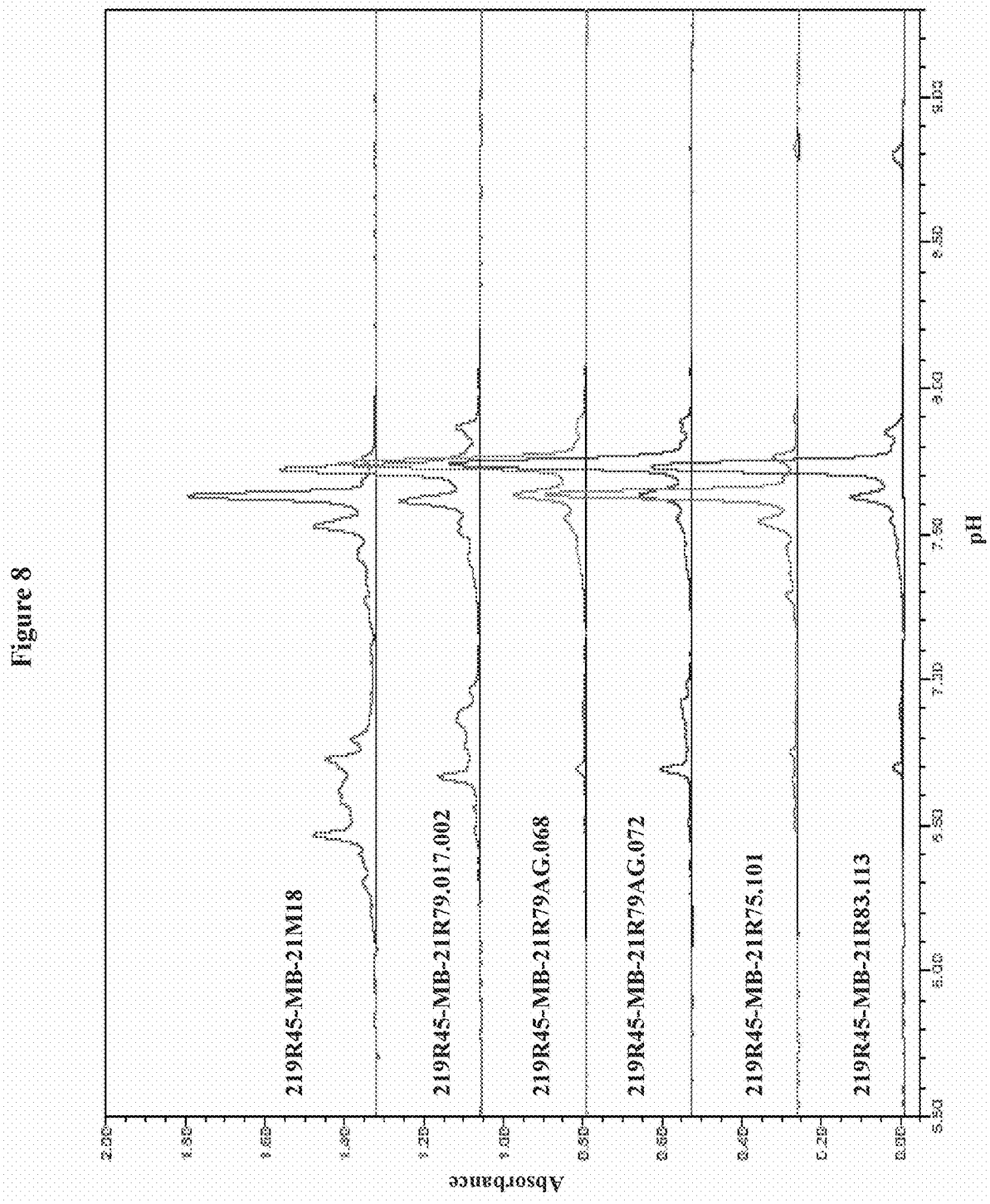

FIG. 8. Imaged capillary isoelectric focusing of anti-VEGF/anti-DLL4 bispecific antibodies.

Figure 9:
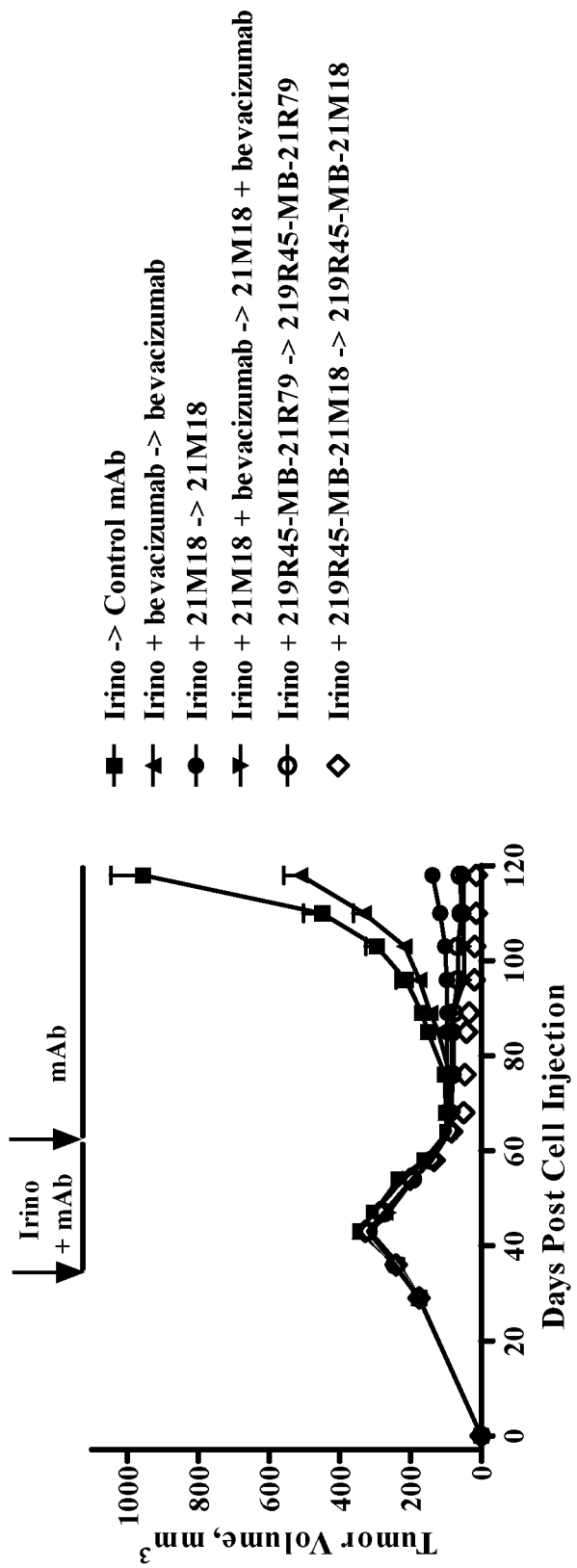

FIG. 9. Inhibition of colon tumor growth by anti-VEGF/anti-DLL4 bispecific antibodies in tumor recurrence model. OMP-C8 colon tumor cells were injected subcutaneously in NOD/SCID mice. Mice were treated with control antibody (-■-), anti-hDLL4 antibody 21M18 (-●-), anti-VEGF antibody bevacizumab (-▲-), a combination of 21M18 and bevacizumab (-▼-), anti-VEGF/anti-DLL4 bispecific antibody 219R45-MB-21M18 (-◇-), or anti-VEGF/anti-DLL4 bispecific antibody 219R45-MB-21R79 (-○-), all in combination with irinotecan. Antibodies 21M18 and bevacizumab were administered intraperitoneally at a dose of 7.5 mg/kg once a week, bispecific antibodies 219R45-MB-21M18 and 219R45-MB-21R79 were administered intraperitoneally at a dose of 15 mg/kg once a week, and irinotecan was administered for the first 4 weeks at a dose of 45 mg/kg. Data are shown as tumor volume (mm$^3$) over days post-treatment.

Figure 10:
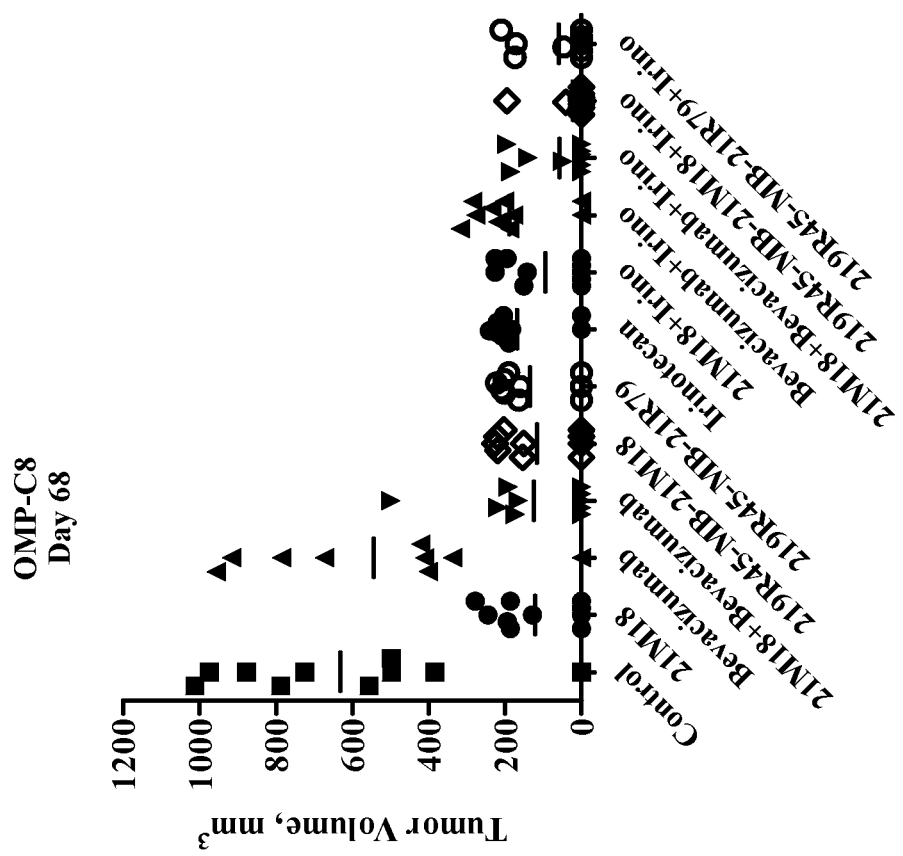

FIG. 10. Tumorigenicity of OMP-C3 colon tumor cells after treatment with anti-VEGF/anti-DLL4 bispecific antibodies. Tumors from mice treated with control antibody, anti-hDLL4 antibody 21M18, anti-VEGF antibody bevacizumab, a combination of 21M18 and bevacizumab, or anti-VEGF/anti-DLL4 bispecific antibodies 219R45-MB-21M18 or 219R45-MB-21R79 with or without irinotecan were processed to single cell suspensions, and serially transplanted into mice. 150 cells from each treatment group were injected subcutaneously into NOD/SCID mice. Tumors were allowed to grow with no treatment. Data are shown as tumor volume (mm$^3$) on day 68.

Figure 11B:
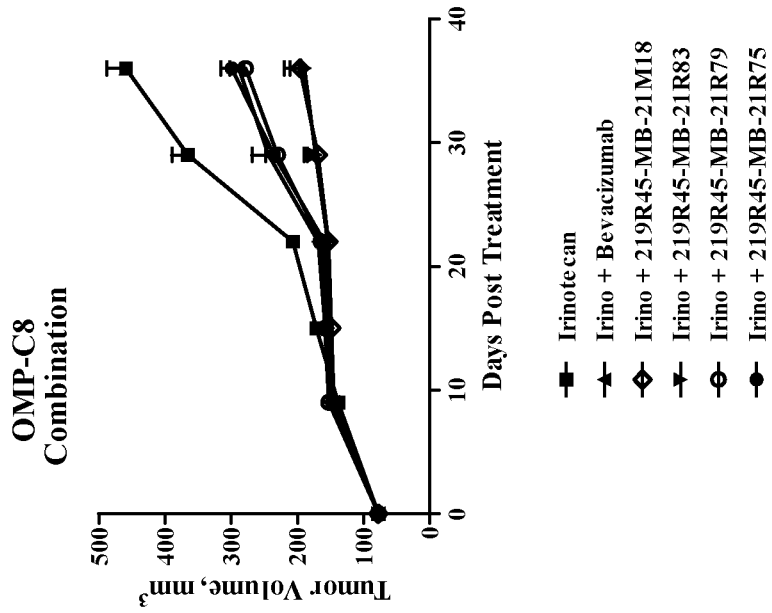
Figure 11A:
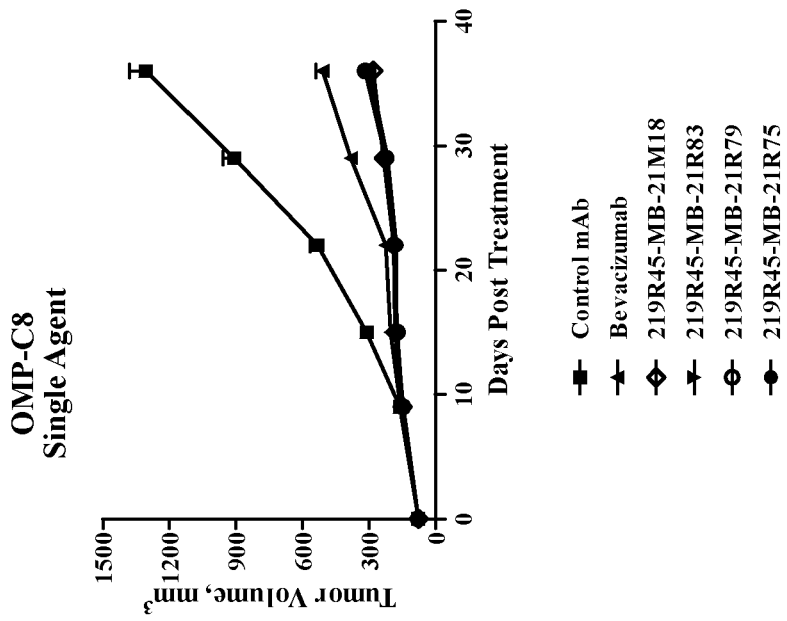

FIGS. 11A and 11B. Inhibition of colon tumor growth in vivo by anti-VEGF/anti-DLL4 bispecific antibodies. OMP-C8 colon tumor cells were injected subcutaneously into NOD/SCID mice. Mice were treated with control antibody (-■-), anti-VEGF antibody bevacizumab (-▲-), or anti-VEGF/anti-DLL4 bispecific antibodies 219R45-MB-21M18 (-◇-), 219R45-MB-21R75 (-●-), 219R45-MB-21R79 (-○-), or 219R45-MB-21R83 (-▼-). Mice were treated with antibodies as single agents (FIG. 11A) or in combination with irinotecan (FIG. 11B). Antibodies were administered intraperitoneally at a dose of 15 mg/kg once a week and irinotecan at a dose of 7.5 mg/kg one a week. Data are shown as tumor volume (mm$^3$) over days post-treatment.

DETAILED DESCRIPTION OF THE INVENTION

The present invention provides novel binding agents, including but not limited to polypeptides such as antibodies, that bind VEGF and/or DLL4 (e.g., a VEGF/DLL4 binding agent). Related polypeptides and polynucleotides, compositions comprising the VEGF/DLL4-binding agents, and methods of making the VEGF/DLL4-binding agents are also provided. Methods of using the novel VEGF/DLL4-binding agents, such as methods of inhibiting tumor growth, methods of treating cancer, methods of reducing tumorigenicity of a tumor, methods of reducing the frequency of cancer stem cells in a tumor, and/or methods of modulating angiogenesis, are further provided.

A monoclonal antibody that specifically binds human VEGF has been identified, 219R45. This antibody has a binding affinity for human VEGF of about 0.67 nM, and a binding affinity for mouse VEGF of about 23 nM. Several monoclonal antibodies that specifically bind human DLL4 have been identified, 21R79, 21R75 and 21R83. Antibody 21R79 has a binding affinity for human DLL4 of less than 0.1 nM. Bispecific antibodies that specifically bind human VEGF and human DLL4 have been produced, 219R45-MB-21M18, 219R45-MB-21R79, 219R45-MB-21R75, and 219R45-MB-21R83 (CDR sequences in FIG. 1). As used herein, the "MB" within an antibody name refers to "monovalent/bispecific". Bispecific antibody 219R45-MB-21M18 has a binding affinity for human VEGF of less than 1.0 nM and a binding affinity for human DLL4 of about 16 nM. Bispecific antibody 219R45-MB-21R79 has a binding affinity for human VEGF of less than 1.0 nM and a binding affinity for human DLL4 of less than 1.0 nM. Bispecific antibody 219R45-MB-21R75 has a binding affinity for human DLL4 of about 5 nM, while bispecific antibody 219R45-MB-21R83 has a binding affinity for human DLL4 of about 1 nM. Bispecific antibodies 219R45-MB-21M18 and 219R45-MB-21R79 bind mouse VEGF (Example 1, Table 3). Anti-VEGF/anti-DLL4 bispecific antibodies bind human VEGF and human DLL4 simultaneously (Example 2, FIG. 2). Anti-VEGF/anti-DLL4 bispecific antibodies inhibit VEGF-induced proliferation of HUVEC cells (Example 3, FIG. 3). Anti-VEGF/anti-DLL4 bispecific antibodies inhibit DLL4-induced Notch signaling (Example 4, FIG. 4). Anti-VEGF/anti-DLL4 bispecific antibodies inhibit tumor growth (Examples 5, 9, 11 and FIGS. 5, 9, 11). Anti-VEGF/anti-DLL4 bispecific antibodies inhibit tumorigenicity (Examples 6 and 10 and FIGS. 6, 10). Anti-VEGF/anti-DLL4 bispecific antibodies bind both VEGF and DLL4 in a bispecific ELISA (Example 7, FIG. 7). Anti-VEGF/anti-DLL4 bispecific antibodies are isolated and purified to a product comprising at least 90% heterodimeric antibody (Example 8, Table 7).

I. Definitions

To facilitate an understanding of the present invention, a number of terms and phrases are defined below.

The term "antibody" as used herein refers to an immunoglobulin molecule that recognizes and specifically binds a target, such as a protein, polypeptide, peptide, carbohydrate, polynucleotide, lipid, or combinations of the foregoing, through at least one antigen recognition site within the variable region of the immunoglobulin molecule. As used herein, the term encompasses intact polyclonal antibodies, intact monoclonal antibodies, single chain antibodies, antibody fragments (such as Fab, Fab', F(ab')2, and Fv fragments), single chain Fv (scFv) antibodies, multispecific antibodies such as bispecific antibodies, monospecific antibodies, monovalent antibodies, chimeric antibodies, humanized antibodies, human antibodies, fusion proteins comprising an antigen-binding site of an antibody, and any other modified immunoglobulin molecule comprising an antigen recognition site (i.e., antigen-binding site) as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1, and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins and radioisotopes.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site.

The term "variable region" of an antibody refers to the variable region of an antibody light chain, or the variable region of an antibody heavy chain, either alone or in combination. The variable regions of the heavy and light chains each consist of four framework regions (FR) connected by three complementarity determining regions (CDRs), also known as "hypervariable regions". The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, Sequences of Proteins of Immunological Interest, 5th Edition, National Institutes of Health, Bethesda, Md.), and (2) an approach based on crystallographic studies of antigen-antibody complexes (Al-Lazikani et al., 1997, J. Mol. Biol., 273:927-948). In addition, combinations of these two approaches are sometimes used in the art to determine CDRs.

The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (scFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and transgenic animals.

The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, Nature, 321:522-525; Riechmann et al., 1988, Nature, 332:323-327; Verhoeyen et al., 1988, Science, 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539.

The term "human antibody" as used herein refers to an antibody produced by a human or an antibody having an amino acid sequence corresponding to an antibody produced by a human. A human antibody may be made using any of the techniques known in the art. This definition of a human antibody specifically excludes a humanized antibody comprising non-human CDRs.

The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or binding capability, while the constant regions correspond to sequences in antibodies derived from another species (usually human).

The phrase "affinity-matured antibody" as used herein refers to an antibody with one or more alterations in one or more CDRs thereof that result in an improvement in the affinity of the antibody for antigen, compared to a parent antibody that does not possess those alterations(s). The definition also includes alterations in non-CDR residues made in conjunction with alterations to CDR residues. Preferred affinity-matured antibodies will have nanomolar or even picomolar affinities for the target antigen. Affinity-matured antibodies are produced by procedures known in the art. For example, Marks et al., 1992, Bio/Technology 10:779-783, describes affinity maturation by VH and VL domain shuffling. Random mutagenesis of CDR and/or framework residues is described by Barbas et al., 1994, PNAS, 91:3809-3813; Schier et al., 1995, Gene, 169:147-155; Yelton et al., 1995, J. Immunol. 155:1994-2004; Jackson et al., 1995, J. Immunol., 154:3310-9; and Hawkins et al., 1992, J. Mol. Biol., 226:889-896. Site-directed mutagenesis may also be used to obtain affinity-matured antibodies.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

The terms "heteromultimeric molecule" or "heteromultimer" or "heteromultimeric complex" or "heteromultimeric polypeptide" are used interchangeably herein to refer to a molecule comprising at least a first polypeptide and a second polypeptide, wherein the second polypeptide differs in amino acid sequence from the first polypeptide by at least one amino acid residue. The heteromultimeric molecule can comprise a "heterodimer" formed by the first and second polypeptide or can form higher order tertiary structures where additional polypeptides are present.

The terms "antagonist" and "antagonistic" as used herein refer to any molecule that partially or fully blocks, inhibits, reduces, or neutralizes a biological activity of a target and/or signaling pathway (e.g., the Notch pathway). The term "antagonist" is used herein to include any molecule that partially or fully blocks, inhibits, reduces, or neutralizes the activity of a protein. Suitable antagonist molecules specifically include, but are not limited to, antagonist antibodies or antibody fragments.

The terms "modulation" and "modulate" as used herein refer to a change or an alteration in a biological activity. Modulation includes, but is not limited to, stimulating or inhibiting an activity. Modulation may be an increase or a decrease in activity (e.g., a decrease in angiogenesis or an increase in angiogenesis), a change in binding characteristics, or any other change in the biological, functional, or immunological properties associated with the activity of a protein, pathway, or other biological point of interest.

The terms "selectively binds" or "specifically binds" mean that a binding agent or an antibody reacts or associates more frequently, more rapidly, with greater duration, with greater affinity, or with some combination of the above to the epitope, protein, or target molecule than with alternative substances, including unrelated proteins. In certain embodiments "specifically binds" means, for instance, that an antibody binds a protein with a $K_D$ of about 0.1 mM or less, but more usually less than about 1 µM. In certain embodiments, "specifically binds" means that an antibody binds a target at times with a $K_D$ of at least about 0.1 µM or less, at other times at least about 0.01 µM or less, and at other times at least about 1 nM or less. Because of the sequence identity between homologous proteins in different species, specific binding can include an antibody that recognizes a protein in more than one species (e.g., human VEGF and mouse VEGF). Likewise, because of homology within certain regions of polypeptide sequences of different proteins, specific binding can include an antibody (or other polypeptide or binding agent) that recognizes more than one protein (e.g., human VEGF-A and human VEGF-B). It is understood that, in certain embodiments, an antibody or binding moiety that specifically binds a first target may or may not specifically bind a second target. As such, "specific binding" does not necessarily require (although it can include) exclusive binding, i.e. binding to a single target. Thus, an antibody may, in certain embodiments, specifically bind more than one target. In certain embodiments, multiple targets may be bound by the same antigen-binding site on the antibody. For example, an antibody may, in certain instances, comprise two identical antigen-binding sites, each of which specifically binds the same epitope on two or more proteins. In certain alternative embodiments, an antibody may be multispecific and comprise at least two antigen-binding sites with differing specificities. By way of non-limiting example, a bispecific antibody may comprise one antigen-binding site that recognizes an epitope on one protein (e.g., human VEGF) and further comprise a second, different antigen-binding site that recognizes a different epitope on a second protein (e.g., human DLL4). Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because the polypeptides of this invention may be based upon antibodies, in certain embodiments, the polypeptides can occur as single chains or associated chains.

The terms "polynucleotide" and "nucleic acid" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

"Conditions of high stringency" may be identified by those that: (1) employ low ionic strength and high temperature for washing, for example 15 mM sodium chloride/1.5 mM sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 in 5×SSC (0.75M NaCl, 75 mM sodium citrate) at 42° C.; or (3) employ during hybridization 50% formamide in 5×SSC, 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 50% formamide, followed by a high-stringency wash consisting of 0.1×SSC containing EDTA at 55° C.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variations thereof. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 residues, at least about 60-80 residues in length or any integral value therebetween. In some embodiments, identity exists over a longer region than 60-80 residues, such as at least about 80-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. Preferably, conservative substitutions in the sequences of the polypeptides and antibodies of the invention do not abrogate the binding of the polypeptide or antibody containing the amino acid sequence, to the antigen to which the polypeptide or antibody binds. Methods of identifying nucleotide and amino acid conservative substitutions which do not eliminate antigen binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells, or compositions include those which have been purified to a degree that they are no longer in a form in which they are found in nature. In some embodiments, a polypeptide, antibody, polynucleotide, vector, cell, or composition which is isolated is substantially pure.

The term "substantially pure" as used herein refers to material which is at least 50% pure (i.e., free from contaminants), at least 90% pure, at least 95% pure, at least 98% pure, or at least 99% pure.

The terms "cancer" and "cancerous" as used herein refer to or describe the physiological condition in mammals in which a population of cells are characterized by unregulated cell growth. Examples of cancer include, but are not limited to, carcinoma, blastoma, sarcoma, and hematologic cancers such as lymphoma and leukemia.

The terms "tumor" and "neoplasm" as used herein refer to any mass of tissue that results from excessive cell growth or proliferation, either benign (noncancerous) or malignant (cancerous) including pre-cancerous lesions.

The term "metastasis" as used herein refers to the process by which a cancer spreads or transfers from the site of origin to other regions of the body with the development of a similar cancerous lesion at a new location. A "metastatic" or "metastasizing" cell is one that loses adhesive contacts with neighboring cells and migrates via the bloodstream or lymph from the primary site of disease to invade neighboring body structures.

The terms "cancer stem cell" and "CSC" and "tumor stem cell" and "tumor initiating cell" are used interchangeably herein and refer to cells from a cancer or tumor that: (1) have extensive proliferative capacity; 2) are capable of asymmetric cell division to generate one or more types of differentiated cell progeny wherein the differentiated cells have reduced proliferative or developmental potential; and (3) are capable of symmetric cell divisions for self-renewal or self-maintenance. These properties confer on the cancer stem cells the ability to form or establish a tumor or cancer upon serial transplantation into an immunocompromised host (e.g., a mouse) compared to the majority of tumor cells that fail to form tumors. Cancer stem cells undergo self-renewal versus differentiation in a chaotic manner to form tumors with abnormal cell types that can change over time as mutations occur.

The terms "cancer cell" and "tumor cell" refer to the total population of cells derived from a cancer or tumor or pre-cancerous lesion, including both non-tumorigenic cells, which comprise the bulk of the cancer cell population, and tumorigenic stem cells (cancer stem cells). As used herein, the terms "cancer cell" or "tumor cell" will be modified by the term "non-tumorigenic" when referring solely to those cells lacking the capacity to renew and differentiate to distinguish those tumor cells from cancer stem cells.

The term "tumorigenic" as used herein refers to the functional features of a cancer stem cell including the properties of self-renewal (giving rise to additional tumorigenic cancer stem cells) and proliferation to generate all other tumor cells (giving rise to differentiated and thus non-tumorigenic tumor cells).

The term "tumorigenicity" as used herein refers to the ability of a random sample of cells from the tumor to form palpable tumors upon serial transplantation into immunocompromised hosts (e.g., mice). This definition also includes enriched and/or isolated populations of cancer stem cells that form palpable tumors upon serial transplantation into immunocompromised hosts (e.g., mice).

The term "subject" refers to any animal (e.g., a mammal), including, but not limited to, humans, non-human primates, canines, felines, rodents, and the like, which is to be the recipient of a particular treatment. Typically, the terms "subject" and "patient" are used interchangeably herein in reference to a human subject.

The term "pharmaceutically acceptable" refers to a product or compound approved (or approvable) by a regulatory agency of the Federal government or a state government or listed in the U.S. Pharmacopeia or other generally recognized pharmacopeia for use in animals, including humans.

The terms "pharmaceutically acceptable excipient, carrier or adjuvant" or "acceptable pharmaceutical carrier" refer to an excipient, carrier or adjuvant that can be administered to a subject, together with at least one binding agent (e.g., an antibody) of the present disclosure, and which does not destroy the activity of the binding agent. The excipient, carrier or adjuvant should be nontoxic when administered with a binding agent in doses sufficient to deliver a therapeutic effect.

The terms "effective amount" or "therapeutically effective amount" or "therapeutic effect" refer to an amount of a binding agent, an antibody, polypeptide, polynucleotide, small organic molecule, or other drug effective to "treat" a disease or disorder in a subject or mammal. In the case of cancer, the therapeutically effective amount of a drug (e.g., an antibody) has a therapeutic effect and as such can reduce the number of cancer cells; decrease tumorigenicity, tumorigenic frequency or tumorigenic capacity; reduce the number or frequency of cancer stem cells; reduce the tumor size; reduce the cancer cell population; inhibit and/or stop cancer cell infiltration into peripheral organs including, for example, the spread of cancer into soft tissue and bone; inhibit and/or stop tumor or cancer cell metastasis; inhibit and/or stop tumor or cancer cell growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

The terms "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. In some embodiments, a subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer cells into soft tissue and bone; inhibition of or an absence of tumor or cancer cell metastasis; inhibition or an absence of cancer growth; relief of one or more symptoms associated with the specific cancer; reduced morbidity and mortality; improvement in quality of life; reduction in tumorigenicity; reduction in the number or frequency of cancer stem cells; or some combination of effects.

As used in the present disclosure and claims, the singular forms "a", "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided. It is also understood that wherever embodiments are described herein with the language "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. Antibodies

The present invention provides agents that specifically bind human VEGF proteins and/or human DLL4 proteins. These agents are referred to herein as "VEGF/DLL4-binding agents". The phrase "VEGF/DLL4-binding agent" encompasses agents that bind only VEGF, agents that bind only DLL4, and bispecific agents that bind both VEGF and DLL4. In certain embodiments, in addition to specifically binding VEGF and/or DLL4, the VEGF/DLL4-binding agents further specifically bind at least one additional target or antigen. In some embodiments, the VEGF/DLL4-binding agent is an antibody. In some embodiments, the VEGF/DLL4-binding agent is a polypeptide. In certain embodiments, the VEGF/DLL4-binding agent specifically binds human VEGF. In certain embodiments, the VEGF/DLL4-binding agent specifically binds human DLL4. In certain embodiments, the VEGF/DLL4-binding agent is a bispecific antibody. In certain embodiments, the VEGF/DLL4-binding agent is a bispecific antibody that specifically binds human VEGF and human DLL4. The full-length amino acid (aa) sequences for human VEGF (VEGF-A) and human DLL4 are known in the art and are provided herein as SEQ ID NO:27 (VEGF) and SEQ ID NO:23 (DLL4).

In certain embodiments, the VEGF/DLL4-binding agent or antibody binds VEGF and/or DLL4 with a dissociation constant ($K_D$) of about 1 µM or less, about 100 nM or less, about 40 nM or less, about 20 nM or less, about 10 nM or less, about 1 nM or less, or about 0.1 nM or less. In some embodiments, a VEGF/DLL4-binding agent or antibody binds VEGF and/or DLL4 with a $K_D$ of about 20 nM or less. In some embodiments, a VEGF/DLL4-binding agent or antibody binds VEGF and/or DLL4 with a $K_D$ of about 10 nM or less. In some embodiments, a VEGF/DLL4-binding agent or antibody binds VEGF and/or DLL4 with a $K_D$ of about 1 nM or less. In some embodiments, a VEGF/DLL4-binding agent or antibody binds VEGF and/or DLL4 with a $K_D$ of about 0.1 nM or less. In some embodiments, the VEGF/DLL4-binding agent binds both human VEGF and mouse VEGF with a $K_D$ of about 100 nM or less. In some embodiments, the VEGF/DLL4-binding agent binds both human VEGF and mouse VEGF with a $K_D$ of about 50 nM or less. In some embodiments, a VEGF/DLL4-binding agent binds both human DLL4 and mouse DLL4 with a $K_D$ of about 100 nM or less. In some embodiments, a VEGF/DLL4-binding agent binds both human DLL4 and mouse DLL4 with a $K_D$ of about 50 nM or less. In some embodiments, the dissociation constant of the binding agent (e.g., an antibody) to VEGF is the dissociation constant determined using a VEGF fusion protein comprising at least a portion of VEGF immobilized on a Biacore chip. In some embodiments, the dissociation constant of the binding agent (e.g., an antibody) to DLL4 is the dissociation constant determined using a DLL4-fusion protein comprising at least a portion of DLL4 immobilized on a Biacore chip.

In some embodiments, the VEGF/DLL4-binding agent is a bispecific antibody which comprises a first antigen-binding site that specifically binds VEGF and a second antigen-binding site that specifically binds DLL4. In some embodiments, a VEGF/DLL4-binding agent or antibody binds both VEGF and DLL4 with a $K_D$ of about 100 nM or less. In some embodiments, a VEGF/DLL4-binding agent or antibody binds both VEGF and DLL4 with a $K_D$ of about 50 nM or less. In some embodiments, a VEGF/DLL4-binding agent or antibody binds both VEGF and DLL4 with a $K_D$ of about 20 nM or less. In some embodiments, a VEGF/DLL4-binding agent or antibody binds both VEGF and DLL4 with a $K_D$ of about 10 nM or less. In some embodiments, a VEGF/DLL4-binding agent or antibody binds both VEGF and DLL4 with a $K_D$ of about 1 nM or less. In some embodiments, the affinity of one of the antigen-binding sites may be weaker than the affinity of the other antigen-binding site. For example, the $K_D$ of one antigen binding site may be about 1 nM and the $K_D$ of the second antigen-binding site may be about 10 nM. In some embodiments, the difference in affinity between the two antigen-binding sites may be about 2-fold or more, about 3-fold or more, about 5-fold or more, about 8-fold or more, about 10-fold or more, about 15-fold or more, about 20-fold or more, about 30-fold or more, about 50-fold or more, or about 100-fold or more. Modulation of the affinities of the two antigen-binding sites may affect the biological activity of the bispecific antibody. For example, decreasing the affinity of the antigen-binding site for DLL4 or VEGF, may have a desirable effect, for example decreased toxicity of the binding agent or increased therapeutic index.

By way of non-limiting example, the bispecific antibody may comprise (a) a first antigen-binding site that binds human VEGF with a $K_D$ between about 0.1 nM and about 1.0 nM, and (b) a second antigen-binding site that specifically binds human DLL4 with a $K_D$ between about 0.1 nM and about 20 nM, between about 0.5 nM and about 20 nM, between about 1.0 nM and 10 nM. In certain embodiments, the bispecific antibody comprises two identical light chains.

In certain embodiments, the VEGF/DLL4-binding agent (e.g., an antibody) binds VEGF and/or DLL4 with a half maximal effective concentration ($EC_{50}$) of about 104 or less, about 100 nM or less, about 40 nM or less, about 20 nM or less, about 10 nM or less, about 1 nM or less, or about 0.1 nM or less. In certain embodiments, a VEGF/DLL4-binding agent (e.g., an antibody) binds VEGF and/or DLL4 with a half maximal effective concentration ($EC_{50}$) of about 104 or less, about 100 nM or less, about 40 nM or less, about 20 nM or less, about 10 nM or less, about 1 nM or less, or about 0.1 nM or less.

In certain embodiments, the VEGF/DLL4-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In certain embodiments, the antibody is an IgA, IgD, IgE, IgG, or IgM antibody. In certain embodiments, the antibody is an IgG1 antibody. In certain embodiments, the antibody is an IgG2 antibody. In certain embodiments, the antibody is an antibody fragment comprising an antigen-binding site. In some embodiments, the antibody is a bispecific antibody. In some embodiments, the antibody is monovalent, monospecific, bivalent, or multispecific. In some embodiments, the antibody is conjugated to a cytotoxic moiety. In some embodiments, the antibody is isolated. In some embodiments, the antibody is substantially pure.

The VEGF/DLL4-binding agents (e.g., antibodies) of the present invention can be assayed for specific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, homogeneous time-resolved fluorescence assay (HTRF), and protein A immunoassay. Such assays are routine and well-known in the art (see, e.g., Ausubel et al., Editors, 1994-present, *Current Protocols in Molecular Biology*, John Wiley & Sons, Inc., New York, N.Y.).

For example, the specific binding of an antibody to human VEGF and/or human DLL4 may be determined using ELISA. An ELISA assay comprises preparing antigen, coating wells of a 96 well microtiter plate with antigen, adding the antibody or other binding agent conjugated to a detectable compound such as an enzymatic substrate (e.g. horseradish peroxidase or alkaline phosphatase) to the well, incubating for a period of time, and detecting the presence of the binding agent bound to the antigen. In some embodiments, the binding agent or antibody is not conjugated to a detectable compound, but instead a second antibody that recognizes the binding agent or antibody (e.g., an anti-Fc antibody) and is conjugated to a detectable compound is added to the well. In some embodiments, instead of coating the well with the antigen, the binding agent or antibody can be coated to the well and a second antibody conjugated to a detectable compound can be added following the addition of the antigen to the coated well. One of skill in the art would be knowledgeable as to the parameters that can be modified to increase the signal detected as well as other variations of ELISAs known in the art.

In another example, the specific binding of an antibody to human VEGF and/or human DLL4 may be determined using FACS. A FACS screening assay may comprise generating a cDNA construct that expresses an antigen as a fusion protein, transfecting the construct into cells, expressing the antigen on the surface of the cells, mixing the binding agent or antibody with the transfected cells, and incubating for a period of time. The cells bound by the binding agent or antibody may be identified by using a secondary antibody conjugated to a detectable compound (e.g., PE-conjugated anti-Fc antibody) and a flow cytometer. One of skill in the art would be knowledgeable as to the parameters that can be modified to optimize the signal detected as well as other variations of FACS that may enhance screening (e.g., screening for blocking antibodies).

The binding affinity of an antibody or other binding-agent to an antigen (e.g., VEGF or DLL4) and the off-rate of an antibody-antigen interaction can be determined by competitive binding assays. One example of a competitive binding assay is a radioimmunoassay comprising the incubation of labeled antigen (e.g., $^3$H or $^{125}$I), or fragment or variant thereof, with the antibody of interest in the presence of increasing amounts of unlabeled antigen followed by the detection of the antibody bound to the labeled antigen. The affinity of the antibody for the antigen and the binding off-rates can be determined from the data by Scatchard plot analysis. In some embodiments, Biacore kinetic analysis is used to determine the binding on and off rates of antibodies or agents that bind an antigen (e.g., VEGF or DLL4). Biacore kinetic analysis comprises analyzing the binding and dissociation of antibodies from chips with immobilized antigen (e.g., VEGF or DLL4) on their surface.

In certain embodiments, the invention provides a VEGF-binding agent (e.g., an antibody) that specifically binds human VEGF, wherein the VEGF-binding agent (e.g., an antibody) comprises one, two, three, four, five, and/or six of the CDRs of antibody 219R45 (see Table 1). In some embodiments, the VEGF-binding agent comprises one or more of the CDRs of 219R45, two or more of the CDRs of 219R45, three or more of the CDRs of 219R45, four or more of the CDRs of 219R45, five or more of the CDRs of 219R45, or all six of the CDRs of 219R45. In some embodiments, the VEGF-binding agent binds human VEGF and mouse VEGF.

TABLE 1

| 219R45 | |
|---|---|
| HC CDR1 | NYWMH (SEQ ID NO: 17) |
| HC CDR2 | DINPSNGRTSYKEKFKR (SEQ ID NO: 18) |
| HC CDR3 | HYDDKYYPLMDY (SEQ ID NO: 19) |
| LC CDR1 | RASESVDNYGISFMK (SEQ ID NO: 20) |
| LC CDR2 | AASNQGS (SEQ ID NO: 21) |
| LC CDR3 | QQSKEVPWTFGG (SEQ ID NO: 22) |

In certain embodiments, the invention provides a VEGF-binding agent (e.g., an antibody) that specifically binds human VEGF, wherein the VEGF-binding agent comprises a heavy chain CDR1 comprising NYWMH (SEQ ID NO:17), a heavy chain CDR2 comprising DINPSNGRT-SYKEKFKR (SEQ ID NO:18), and a heavy chain CDR3 comprising HYDDKYYPLMDY (SEQ ID NO:19). In some embodiments, the VEGF-binding agent further comprises a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In certain embodiments, the VEGF-binding agent comprises: (a) a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the invention provides a VEGF-binding agent (e.g., an antibody) that specifically binds human VEGF, wherein the VEGF-binding agent comprises: (a) a heavy chain CDR1 comprising NYWMH (SEQ ID NO:17), or a variant thereof comprising 1, 2, 3, or 4 amino acid substitutions; (b) a heavy chain CDR2 comprising DINPSNGRTSYKEKFKR (SEQ ID NO:18), or a variant thereof comprising 1, 2, 3, or 4 amino acid substitutions; (c) a heavy chain CDR3 comprising HYDDKYYPLMDY (SEQ ID NO:19), or a variant thereof comprising 1, 2, 3, or 4 amino acid substitutions; (d) a light chain CDR1 comprising RASESVDNYGISFMK (SEQ ID NO:20), or a variant thereof comprising 1, 2, 3, or 4 amino acid substitutions; (e) a light chain CDR2 comprising AASNQGS (SEQ ID NO:21), or a variant thereof comprising 1, 2, 3, or 4 amino acid substitutions; and (f) a light chain CDR3 comprising QQSKEVPWTFGG (SEQ ID NO:22), or a variant thereof comprising 1, 2, 3, or 4 amino acid substitutions. In certain embodiments, the amino acid substitutions are conservative substitutions.

In certain embodiments, the invention provides a VEGF-binding agent (e.g., an antibody) that specifically binds VEGF, wherein the VEGF-binding agent comprises a heavy chain variable region having at least about 80% sequence identity to SEQ ID NO:11, and a light chain variable region having at least 80% sequence identity to SEQ ID NO:12. In certain embodiments, the VEGF-binding agent comprises a heavy chain variable region having at least about 85%, at least about 90%, at least about 95%, at least about 97%, or at least about 99% sequence identity to SEQ ID NO:11. In certain embodiments, the VEGF-binding agent comprises a light chain variable region having at least about 85%, at least about 90%, at least about 95%, at least about 97%, or at least about 99% sequence identity to SEQ ID NO:12. In certain embodiments, the VEGF-binding agent comprises a heavy chain variable region having at least about 95% sequence identity to SEQ ID NO:11, and a light chain variable region having at least about 95% sequence identity to SEQ ID NO:12. In certain embodiments, the VEGF-binding agent comprises a heavy chain variable region comprising SEQ ID NO:11, and a light chain variable region comprising SEQ ID NO:12. In certain embodiments, the VEGF-binding agent comprises a heavy chain variable region consisting essentially of SEQ ID NO:11, and a light chain variable region consisting essentially of SEQ ID NO:12. In some embodiments, the VEGF-binding agent comprises a heavy chain comprising SEQ ID NO:49, and a light chain comprising SEQ ID NO:8. In some embodiments, the VEGF-binding antibody or other agent comprises a heavy chain comprising SEQ IDNO:7, and a light chain comprising SEQ ID NO:8.

In some embodiments, the VEGF-binding agent binds VEGF with a $K_D$ of about 10 nM or less. In some embodiments, the VEGF-binding agent binds VEGF with a $K_D$ of about 1 nM or less. In some embodiments, the VEGF-binding agent binds VEGF with a $K_D$ of about 0.1 nM or less. In some embodiments, the VEGF-binding agent binds VEGF with a $K_D$ of about 0.01 nM or less. In some embodiments, at least one amino acid residue in at least one CDR of the VEGF-binding agent is substituted with a different amino acid so that the affinity of the VEGF-binding agent for VEGF is altered. In some embodiments, the affinity of the VEGF-binding agent is increased. In some embodiments, the affinity of the VEGF-binding agent is decreased. In some embodiments, the VEGF-binding agent binds human VEGF. In some embodiments, the VEGF-binding agent binds human VEGF and mouse VEGF.

In certain embodiments, the VEGF-binding agent comprises the heavy chain variable region and light chain variable region of the 219R45 antibody. In certain embodiments, the VEGF-binding agent comprises the heavy chain and light chain of the 219R45 antibody (with or without the leader sequence). In certain embodiments, a VEGF-binding agent is the 219R45 antibody.

In certain embodiments, a VEGF-binding agent comprises, consists essentially of, or consists of, the antibody 219R45.

In certain embodiments, a VEGF-binding agent (e.g., an antibody) binds the same epitope, or essentially the same epitope, on VEGF as an antibody of the invention. In another embodiment, a VEGF-binding agent is an antibody that binds an epitope on VEGF that overlaps with the epitope on VEGF bound by an antibody of the invention. In certain embodiments, a VEGF-binding agent (e.g., an antibody) binds the same epitope, or essentially the same epitope, on VEGF as antibody 219R45. In another embodiment, the VEGF-binding agent is an antibody that binds an epitope on VEGF that overlaps with the epitope on VEGF bound by antibody 219R45.

In some embodiments, the VEGF-binding agent inhibits binding of VEGF to at least one VEGF receptor. In certain embodiments, the VEGF-binding agent inhibits binding of human VEGF to VEGFR-1 or VEGFR-2. In some embodiments, the VEGF-binding agent specifically binds VEGF and modulates angiogenesis. In some embodiments, the VEGF-binding agent specifically binds VEGF and inhibits angiogenesis. In some embodiments, the VEGF-binding agent specifically binds VEGF and inhibits tumor growth.

In certain embodiments, the invention provides a DLL4-binding agent (e.g., an antibody) that specifically binds human DLL4, wherein the DLL4-binding agent (e.g., an antibody) comprises one, two, three, four, five, and/or six of the CDRs of antibody 21R79 (see Table 2). In some embodiments, the DLL4-binding agent comprises one or more of the CDRs of 21R79, two or more of the CDRs of 21R79, three or more of the CDRs of 21R79, four or more of the CDRs of 21R79, five or more of the CDRs of 21R79, or all six of the CDRs of 21R79. In certain embodiments, the invention provides a DLL4-binding agent (e.g., an antibody) that specifically binds human DLL4, wherein the DLL4-binding agent (e.g., an antibody) comprises one, two, three, four, five, and/or six of the CDRs of antibody 21R75 (see Table 2). In some embodiments, the DLL4-binding agent comprises one or more of the CDRs of 21R75, two or more of the CDRs of 21R75, three or more of the CDRs of 21R75, four or more of the CDRs of 21R75, five or more of the CDRs of 21R75, or all six of the CDRs of 21R75. In certain embodiments, the invention provides a DLL4-binding agent (e.g., an antibody) that specifically binds human DLL4, wherein the DLL4-binding agent (e.g., an antibody) comprises one, two, three, four, five, and/or six of the CDRs of antibody 21R83 (see Table 2). In some embodiments, the DLL4-binding agent comprises one or more of the CDRs of 21R83, two or more of the CDRs of 21R83, three or more of the CDRs of 21R83, four or more of the CDRs of 21R83, five or more of the CDRs of 21R83, or all six of the CDRs of 21R83. In some embodiments, the DLL4-binding agent binds human DLL4 and mouse DLL4.

TABLE 2

| | 21R79 | 21R75 | 21R83 |
|---|---|---|---|
| HC CDR1 | TAYYIH (SEQ ID NO: 13) | TAYYIH (SEQ ID NO: 13) | TAYYIH (SEQ ID NO: 13) |
| HC CDR2 | YIANYNRATNYNQKFKG (SEQ ID NO: 14) | YIAGYKDATNYNQKFKG (SEQ ID NO: 59) | YISNYNRATNYNQKFKG (SEQ ID NO: 65) |
| HC CDR3 | RDYDYDVGMDY (SEQ ID NO: 16) | RDYDYDVGMDY (SEQ ID NO: 16) | RDYDYDVGMDY (SEQ ID NO: 16) |
| LC CDR1 | RASESVDNYGISFMK (SEQ ID NO: 20) | RASESVDNYGISFMK (SEQ ID NO: 20) | RASESVDNYGISFMK (SEQ ID NO: 20) |
| LC CDR2 | AASNQGS (SEQ ID NO: 21) | AASNQGS (SEQ ID NO: 21) | AASNQGS (SEQ ID NO: 21) |
| LC CDR3 | QQSKEVPWTFGG (SEQ ID NO: 22) | QQSKEVPWTFGG (SEQ ID NO: 22) | QQSKEVPWTFGG (SEQ ID NO: 22) |

In certain embodiments, the heavy chain CDR1 of the DLL4-binding antibody is a minimal HC CDR1 comprising AYYIH (SEQ ID NO:79).

In some embodiments, the binding agent is an antibody that binds human DLL4 and comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the invention provides a DLL4-binding agent (e.g., an antibody) that specifically binds human DLL4, wherein the DLL4-binding agent comprises a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16). In some embodiments, the DLL4-binding agent further comprises a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In certain embodiments, the DLL4-binding agent comprises: (a) a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the invention provides a DLL4-binding agent (e.g., an antibody) that specifically binds human DLL4, wherein the DLL4-binding agent comprises: (a) a heavy chain CDR1 comprising TAYYIH (SEQ ID NO:13), or a variant thereof comprising 1, 2, 3, or 4 amino acid substitutions; (b) a heavy chain CDR2 comprising YIANYNRATNYNQKFKG (SEQ ID NO:14), or a variant thereof comprising 1, 2, 3, or 4 amino acid substitutions; (c) a heavy chain CDR3 comprising RDYDYDVGMDY (SEQ ID NO:16), or a variant thereof comprising 1, 2, 3, or 4 amino acid substitutions; (d) a light chain CDR1 comprising RASESVDNYGISFMK (SEQ ID NO:20), or a variant thereof comprising 1, 2, 3, or 4 amino acid substitutions; (e) a light chain CDR2 comprising AASNQGS (SEQ ID NO:21), or a variant thereof comprising 1, 2, 3, or 4 amino acid substitutions; and (f) a light chain CDR3 comprising QQSKEVPWTFGG (SEQ ID NO:22), or a variant thereof comprising 1, 2, 3, or 4 amino acid substitutions. In certain embodiments, the amino acid substitutions are conservative substitutions.

In certain embodiments, the invention provides a DLL4-binding agent (e.g., an antibody) that specifically binds DLL4, wherein the DLL4-binding agent comprises a heavy chain variable region having at least about 80% sequence identity to SEQ ID NO:10, and a light chain variable region having at least 80% sequence identity to SEQ ID NO:12. In certain embodiments, the DLL4-binding agent comprises a heavy chain variable region having at least about 85%, at least about 90%, at least about 95%, at least about 97%, or at least about 99% sequence identity to SEQ ID NO:10. In certain embodiments, the DLL4-binding agent comprises a light chain variable region having at least about 85%, at least about 90%, at least about 95%, at least about 97%, or at least about 99% sequence identity to SEQ ID NO:12. In certain embodiments, the DLL4-binding agent comprises a heavy chain variable region having at least about 95% sequence identity to SEQ ID NO:10, and a light chain variable region having at least about 95% sequence identity to SEQ ID NO:12. In certain embodiments, the DLL4-binding agent comprises a heavy chain variable region comprising SEQ ID NO:10, and a light chain variable region comprising SEQ ID NO:12. In certain embodiments, the DLL4-binding agent comprises a heavy chain variable region consisting essentially of SEQ ID NO:10, and a light chain variable region consisting essentially of SEQ ID NO:12. In some embodiments, the DLL4-binding agent comprises a heavy chain comprising SEQ ID NO:48, and a light chain comprising SEQ ID NO:8. In some embodiments, the DLL4-binding antibody or other agent comprises a heavy chain comprising SEQ ID NO:6, and a light chain comprising SEQ ID NO:8. In some embodiments, the antibody is a bispecific antibody.

In certain embodiments, the invention provides a DLL4-binding agent (e.g., an antibody) that specifically binds human DLL4, wherein the DLL4-binding agent comprises a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16). In some embodiments, the DLL4-binding agent further comprises a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In certain embodiments, the DLL4-binding agent comprises: (a) a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the invention provides a DLL4-binding agent (e.g., an antibody) that specifically binds human DLL4, wherein the DLL4-binding agent comprises: (a) a heavy chain CDR1 comprising TAYYIH (SEQ ID NO:13), or a variant thereof comprising 1, 2, 3, or 4 amino acid substitutions; (b) a heavy chain CDR2 comprising YIAGYKDATNYNQKFKG (SEQ ID NO:59), or a variant thereof comprising 1, 2, 3, or 4 amino acid substitutions; (c) a heavy chain CDR3 comprising RDYDYDVGMDY (SEQ ID NO:16), or a variant thereof comprising 1, 2, 3, or 4 amino acid substitutions; (d) a light chain CDR1 comprising RASESVDNYGISFMK (SEQ ID NO:20), or a variant thereof comprising 1, 2, 3, or 4 amino acid substitutions; (e) a light chain CDR2 comprising AASNQGS (SEQ ID NO:21), or a variant thereof comprising 1, 2, 3, or 4 amino acid substitutions; and (f) a light chain CDR3 comprising QQSKEVPWTFGG (SEQ ID NO:22), or a variant thereof comprising 1, 2, 3, or 4 amino acid substitutions. In certain embodiments, the amino acid substitutions are conservative substitutions.

In certain embodiments, the invention provides a DLL4-binding agent (e.g., an antibody) that specifically binds DLL4, wherein the DLL4-binding agent comprises a heavy chain variable region having at least about 80% sequence identity to SEQ ID NO:58, and a light chain variable region having at least 80% sequence identity to SEQ ID NO:12. In certain embodiments, the DLL4-binding agent comprises a heavy chain variable region having at least about 85%, at least about 90%, at least about 95%, at least about 97%, or at least about 99% sequence identity to SEQ ID NO:58. In certain embodiments, the DLL4-binding agent comprises a light chain variable region having at least about 85%, at least about 90%, at least about 95%, at least about 97%, or at least about 99% sequence identity to SEQ ID NO:12. In certain embodiments, the DLL4-binding agent comprises a heavy chain variable region having at least about 95% sequence identity to SEQ ID NO:58, and a light chain variable region having at least about 95% sequence identity to SEQ ID NO:12. In certain embodiments, the DLL4-binding agent comprises a heavy chain variable region comprising SEQ ID NO:58, and a light chain variable region comprising SEQ ID NO:12. In certain embodiments, the DLL4-binding agent comprises a heavy chain variable region consisting essentially of SEQ ID NO:58, and a light chain variable region consisting essentially of SEQ ID NO:12. In some embodiments, the DLL4-binding agent comprises a heavy chain comprising SEQ ID NO:56, and a light chain comprising SEQ ID NO:8.

In certain embodiments, the invention provides a DLL4-binding agent (e.g., an antibody) that specifically binds human DLL4, wherein the DLL4-binding agent comprises a heavy chain CDR1 comprising TAYYIH (SEQ ID NO:13), a heavy chain CDR2 comprising YISNYN-RATNYNQKFKG (SEQ ID NO:65), and a heavy chain CDR3 comprising RDYDYDVGMDY (SEQ ID NO:16). In some embodiments, the DLL4-binding agent further comprises a light chain CDR1 comprising RASESVDNYGIS-FMK (SEQ ID NO:20), a light chain CDR2 comprising AASNQGS (SEQ ID NO:21), and a light chain CDR3 comprising QQSKEVPWTFGG (SEQ ID NO:22). In certain embodiments, the DLL4-binding agent comprises: (a) a heavy chain CDR1 comprising TAYYIH (SEQ ID NO:13), a heavy chain CDR2 comprising YISNYN-RATNYNQKFKG (SEQ ID NO:65), and a heavy chain CDR3 comprising RDYDYDVGMDY (SEQ ID NO:16), and (b) a light chain CDR1 comprising RASESVDNYGIS-FMK (SEQ ID NO:20), a light chain CDR2 comprising AASNQGS (SEQ ID NO:21), and a light chain CDR3 comprising QQSKEVPWTFGG (SEQ ID NO:22).

In certain embodiments, the invention provides a DLL4-binding agent (e.g., an antibody) that specifically binds human DLL4, wherein the DLL4-binding agent comprises: (a) a heavy chain CDR1 comprising TAYYIH (SEQ ID NO:13), or a variant thereof comprising 1, 2, 3, or 4 amino acid substitutions; (b) a heavy chain CDR2 comprising YISNYNRATNYNQKFKG (SEQ ID NO:65), or a variant thereof comprising 1, 2, 3, or 4 amino acid substitutions; (c) a heavy chain CDR3 comprising RDYDYDVGMDY (SEQ ID NO:16), or a variant thereof comprising 1, 2, 3, or 4 amino acid substitutions; (d) a light chain CDR1 comprising RASESVDNYGISFMK (SEQ ID NO:20), or a variant thereof comprising 1, 2, 3, or 4 amino acid substitutions; (e) a light chain CDR2 comprising AASNQGS (SEQ ID NO:21), or a variant thereof comprising 1, 2, 3, or 4 amino acid substitutions; and (f) a light chain CDR3 comprising QQSKEVPWTFGG (SEQ ID NO:22), or a variant thereof comprising 1, 2, 3, or 4 amino acid substitutions. In certain embodiments, the amino acid substitutions are conservative substitutions.

In certain embodiments, the invention provides a DLL4-binding agent (e.g., an antibody) that specifically binds DLL4, wherein the DLL4-binding agent comprises a heavy chain variable region having at least about 80% sequence identity to SEQ ID NO:64, and a light chain variable region having at least 80% sequence identity to SEQ ID NO:12. In certain embodiments, the DLL4-binding agent comprises a heavy chain variable region having at least about 85%, at least about 90%, at least about 95%, at least about 97%, or at least about 99% sequence identity to SEQ ID NO:64. In certain embodiments, the DLL4-binding agent comprises a light chain variable region having at least about 85%, at least about 90%, at least about 95%, at least about 97%, or at least about 99% sequence identity to SEQ ID NO:12. In certain embodiments, the DLL4-binding agent comprises a heavy chain variable region having at least about 95% sequence identity to SEQ ID NO:64, and a light chain variable region having at least about 95% sequence identity to SEQ ID NO:12. In certain embodiments, the DLL4-binding agent comprises a heavy chain variable region comprising SEQ ID NO:64, and a light chain variable region comprising SEQ ID NO:12. In certain embodiments, the DLL4-binding agent comprises a heavy chain variable region consisting essentially of SEQ ID NO:64, and a light chain variable region consisting essentially of SEQ ID NO:12. In some embodiments, the DLL4-binding agent comprises a heavy chain comprising SEQ ID NO:62, and a light chain comprising SEQ ID NO:8. In some embodiments, the agent is a bispecific antibody.

In some embodiments, the DLL4-binding agent is an antibody that comprises a heavy chain comprising SEQ ID NO:5, and a light chain comprising SEQ ID NO:8. In some embodiments, the antibody is a bispecific antibody.

In some embodiments, the DLL4-binding agent binds DLL4 with a $K_D$ of 25 nM or less. In some embodiments, the DLL4-binding agent binds DLL4 with a $K_D$ of 10 nM or less. In some embodiments, the DLL4-binding agent binds DLL4 with a $K_D$ of about 1 nM or less. In some embodiments, the DLL4-binding agent binds DLL4 with a $K_D$ of about 0.1 nM or less. In some embodiments, the DLL4-binding agent binds DLL4 with a $K_D$ of about 0.01 nM or less. In some embodiments, at least one amino acid residue in at least one CDR of the DLL4-binding agent is substituted with a different amino acid so that the affinity of the DLL4-binding agent for DLL4 is altered. In some embodiments, the affinity of the DLL4-binding agent is increased. In some embodiments, the affinity of the DLL4-binding agent is decreased.

In certain embodiments, the DLL4-binding agent comprises the heavy chain variable region and the light chain variable region of the 21R79 antibody. In certain embodiments, the DLL4-binding agent comprises the heavy chain and light chain of the 21R79 antibody (with or without the leader sequence). In certain embodiments, the DLL4-binding agent is the 21R79 antibody.

In certain embodiments, a DLL4-binding agent comprises, consists essentially of, or consists of, the antibody 21R79.

In certain embodiments, the DLL4-binding agent comprises the heavy chain variable region and the light chain variable region of the 21R75 antibody. In certain embodiments, the DLL4-binding agent comprises the heavy chain and light chain of the 21R75 antibody (with or without the leader sequence). In certain embodiments, the DLL4-binding agent is the 21R75 antibody.

In certain embodiments, a DLL4-binding agent comprises, consists essentially of, or consists of, the antibody 21R75.

In certain embodiments, the DLL4-binding agent comprises the heavy chain variable region and the light chain variable region of the 21R83 antibody. In certain embodiments, the DLL4-binding agent comprises the heavy chain and light chain of the 21R83 antibody (with or without the leader sequence). In certain embodiments, the DLL4-binding agent is the 21R83 antibody.

In certain embodiments, a DLL4-binding agent comprises, consists essentially of, or consists of, the antibody 21R83.

In some embodiments, a DLL4-binding agent binds an N-terminal fragment of human DLL4 (amino acids 1-191 of SEQ ID NO:24). In some embodiments, the DLL4-binding agent binds an epitope comprising amino acids 40-47 of SEQ ID NO:25. In some embodiments, the DLL4-binding agent binds an epitope comprising amino acids 113-120 of SEQ ID NO:25. In some embodiments, the DLL4-binding agent binds an epitope comprising amino acids 40-47 of SEQ ID NO:25 and amino acids 113-120 of SEQ ID NO:25.

In certain embodiments, a DLL4-binding agent (e.g., an antibody) binds the same epitope, or essentially the same epitope, on DLL4 as an antibody of the invention. In another embodiment, a DLL4-binding agent is an antibody that binds an epitope on DLL4 that overlaps with the epitope on DLL4 bound by an antibody of the invention. In certain embodiments, a DLL4-binding agent (e.g., an antibody) binds the same epitope, or essentially the same epitope, on DLL4 as antibody 21R79. In another embodiment, the DLL4-binding agent is an antibody that binds an epitope on DLL4 that overlaps with the epitope on DLL4 bound by antibody 21R79. In certain embodiments, a DLL4-binding agent (e.g., an antibody) binds the same epitope, or essentially the same epitope, on DLL4 as antibody 21R75. In another embodiment, the DLL4-binding agent is an antibody that binds an epitope on DLL4 that overlaps with the epitope on DLL4 bound by antibody 21R75. In certain embodiments, a DLL4-binding agent (e.g., an antibody) binds the same epitope, or essentially the same epitope, on DLL4 as antibody 21R83. In another embodiment, the DLL4-binding agent is an antibody that binds an epitope on DLL4 that overlaps with the epitope on DLL4 bound by antibody 21R83.

In some embodiments, the DLL4-binding agent inhibits binding of DLL4 to at least one Notch receptor. In certain embodiments, the Notch receptor is Notch1, Notch2, Notch3, or Notch4. In some embodiments, the DLL4-binding agent specifically binds DLL4 and inhibits DLL4 activity. In some embodiments, the DLL4-binding agent specifically binds DLL4 and inhibits Notch signaling. In some embodiments, the DLL4-binding agent specifically binds DLL4 and modulates angiogenesis. In some embodiments, the DLL4-binding agent specifically binds DLL4 and inhibits tumor growth. In some embodiments, the DLL4-binding agent specifically binds DLL4 and inhibits tumorigenicity. In some embodiments, the DLL4-binding agent specifically binds DLL4 and reduces the number or frequency of CSCs in a tumor.

In certain embodiments, the invention provides a VEGF/DLL4-binding agent that is a bispecific antibody. In some embodiments, the VEGF/DLL4 binding agent is a bispecific antibody comprising a first antigen-binding site that specifically binds human VEGF. In some embodiments, the VEGF/DLL4 binding agent is a bispecific antibody comprising a first antigen-binding site that specifically binds human VEGF and a second antigen-binding site that binds a tumor-associated target. In some embodiments, the VEGF/DLL4-binding agent is a bispecific antibody comprising: a first antigen-binding site that specifically binds human VEGF, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19). In some embodiments, the bispecific antibody further comprises: a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the VEGF/DLL4-binding agent is a bispecific antibody comprising: a first antigen-binding site that specifically binds human VEGF, wherein the first antigen-binding site comprises (a) a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In some embodiments, the VEGF/DLL4 binding agent is a bispecific antibody comprising a first heavy chain variable region having at least about 80% sequence identity to SEQ ID NO:11. In some embodiments, the bispecific antibody further comprises a light chain variable region having at least 80% sequence identity to SEQ ID NO:12. In certain embodiments, the bispecific VEGF/DLL4-binding agent comprises a first heavy chain variable region having at least about 85%, at least about 90%, at least about 95%, at least about 97%, or at least about 99% sequence identity to SEQ ID NO:11, and a light chain variable region having at least about 85%, at least about 90%, at least about 95%, at least about 97%, or at least about 99% sequence identity to SEQ ID NO:12.

In certain embodiments, the invention provides a VEGF/DLL4-binding agent that is a bispecific antibody. In some embodiments, the VEGF/DLL4 binding agent is a bispecific antibody comprising a first antigen-binding site that specifically binds human DLL4. In some embodiments, the VEGF/DLL4 binding agent is a bispecific antibody comprising a first antigen-binding site that specifically binds human DLL4 and a second antigen-binding site that binds a tumor-associated target. In some embodiments, the VEGF/DLL4-binding agent is a bispecific antibody comprising: a first antigen-binding site that specifically binds human DLL4, wherein the first antigen-binding site comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the VEGF/DLL4-binding agent is a bispecific antibody comprising: a first antigen-binding site that specifically binds human DLL4, wherein the first antigen-binding site comprises a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16). In some embodiments, the bispecific antibody comprises a first antigen-binding site comprising a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16). In some embodiments, the bispecific antibody comprises a first antigen-binding site comprising a heavy chain CDR1 comprising TAYYIH (SEQ ID NO:13), a heavy chain CDR2 comprising YISSYNGATNYNQKFKG (SEQ ID NO:15), and a heavy chain CDR3 comprising RDYDYDVGMDY (SEQ ID NO:16). In some embodiments, the bispecific antibody comprises a first antigen-binding site comprising a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16). In some embodiments, the bispecific antibody comprises a first antigen-binding site comprising a heavy chain CDR1 comprising TAYYIH (SEQ ID NO:13), a heavy chain CDR2 comprising YISNYNRATNYNQKFKG (SEQ ID NO:65), and a heavy chain CDR3 comprising RDYDYDVGMDY (SEQ ID NO:16). In some embodiments, the bispecific antibody further comprises: a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the VEGF/DLL4-binding agent is a bispecific antibody comprising: a first antigen-binding site that specifically binds human DLL4, wherein the first antigen-binding site comprises (a) a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16), and (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In some embodiments, the VEGF/DLL4 binding agent is a bispecific antibody comprising a first heavy chain variable region having at least about 80% sequence identity to SEQ ID NO:9, SEQ ID NO:10, SEQ ID NO:58, or SEQ ID NO:64. In some embodiments, the bispecific antibody further comprises a light chain variable region having at least 80% sequence identity to SEQ ID NO:12. In certain embodiments, the bispecific VEGF/DLL4-binding agent comprises a first heavy chain variable region having at least about 85%, at least about 90%, at least about 95%, at least about 97%, or at least about 99% sequence identity to SEQ ID NO:9, SEQ ID NO:10, SEQ ID NO:58, or SEQ ID NO:64; and/or a light chain variable region having at least about 85%, at least about 90%, at least about 95%, at least about 97%, or at least about 99% sequence identity to SEQ ID NO:12.

In certain embodiments, the invention provides a VEGF/DLL4-binding agent (e.g., a bispecific antibody) that specifically binds human VEGF and human DLL4. In some embodiments, the bispecific antibody comprises: a) a first antigen-binding site that specifically binds human VEGF, and b) a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); wherein the second antigen-binding site comprises a heavy chain CDR1 comprising TAYYIH (SEQ ID NO:13) or AYYIH (SEQ ID NO:79), a heavy chain CDR2 comprising YIX$_1$X$_2$YX$_3$X$_4$ATNYNQKFKG (SEQ ID NO:80), wherein X$_1$ is serine or alanine, X$_2$ is serine, asparagine, or glycine, X$_3$ is asparagine or lysine, and X$_4$ is glysine, arginine, or aspartic acid, and a heavy chain CDR3 comprising RDYDYDVGMDY (SEQ ID NO:16); and a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, a bispecific antibody comprises a first antigen-binding site that specifically binds human VEGF, and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

In some embodiments, the bispecific antibody comprises a first antigen-binding site that specifically binds human VEGF, and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody is 219R45-MB-21R79.

In some embodiments, the bispecific antibody comprises a first antigen-binding site that specifically binds human VEGF, and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YISSYNGATNYNQKFKG (SEQ ID NO:15), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody is 219R45-MB-21M18.

In some embodiments, the bispecific antibody comprises a first antigen-binding site that specifically binds human VEGF, and a second antigen-binding site that specifically binds human DLL4, wherein the first antigen-binding site which comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody is 219R45-MB-21R75.

In some embodiments, the bispecific antibody comprises a first antigen-binding site that specifically binds human VEGF, and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YISNYNRATNYNQKFKG (SEQ ID NO:65), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody is 219R45-MB-21R83.

In some embodiments, the VEGF/DLL4 binding agent (e.g., a bispecific antibody) comprises a first heavy chain variable region having at least about 80% sequence identity to SEQ ID NO:11, a second heavy chain variable region having at least about 80% sequence identity to SEQ ID NO:9, SEQ ID NO:10, SEQ ID NO:58, or SEQ ID NO:64, and a first and a second light chain variable region having at least 80% sequence identity to SEQ ID NO:12. In certain embodiments, the bispecific VEGF/DLL4-binding agent comprises a first heavy chain variable region having at least about 85%, at least about 90%, at least about 95%, at least about 97%, or at least about 99% sequence identity to SEQ ID NO:11; a second heavy chain variable region having at least about 85%, at least about 90%, at least about 95%, at least about 97%, or at least about 99% sequence identity to SEQ ID NO:9, SEQ ID NO:10, SEQ ID NO:58, or SEQ ID NO:64; and a first and a second light chain variable region having at least about 85%, at least about 90%, at least about 95%, at least about 97%, or at least about 99% sequence identity to SEQ ID NO:12. In certain embodiments, the bispecific VEGF/DLL4-binding agent comprises a first heavy chain variable region having at least about 95% sequence identity to SEQ ID NO:11, a second heavy chain variable region having at least about 95% sequence identity to SEQ ID NO:9, and a first and a second light chain variable region having at least about 95% sequence identity to SEQ ID NO:12. In certain embodiments, the bispecific VEGF/DLL4-binding agent comprises a first heavy chain variable region having at least about 95% sequence identity to SEQ ID NO:11, a second heavy chain variable region having at least about 95% sequence identity to SEQ ID NO:10, and a first and a second light chain variable region having at least about 95% sequence identity to SEQ ID NO:12. In certain embodiments, the bispecific VEGF/DLL4-binding agent comprises a first heavy chain variable region having at least about 95% sequence identity to SEQ ID NO:11, a second heavy chain variable region having at least about 95% sequence identity to SEQ ID NO:58, and a first and a second light chain variable region having at least about 95% sequence identity to SEQ ID NO:12. In certain embodiments, the bispecific VEGF/DLL4-binding agent comprises a first heavy chain variable region having at least about 95% sequence identity to SEQ ID NO:11, a second heavy chain variable region having at least about 95% sequence identity to SEQ ID NO:64, and a first and a second light chain variable region having at least about 95% sequence identity to SEQ ID NO:12. In certain embodiments, the bispecific VEGF/DLL4-binding agent comprises a first heavy chain variable region comprising SEQ ID NO:11, a second heavy chain variable region comprising SEQ ID NO:9, and a first and a second light chain variable region comprising SEQ ID NO:12. In certain embodiments, the bispecific VEGF/DLL4-binding agent comprises a first heavy chain variable region comprising SEQ ID NO:11, a second heavy chain variable region comprising SEQ ID NO:10, and a first and a second light chain variable region comprising SEQ ID NO:12. In certain embodiments, the bispecific VEGF/DLL4-binding agent comprises a first heavy chain variable region comprising SEQ ID NO:11, a second heavy chain variable region comprising SEQ ID NO:58, and a first and a second light chain variable region comprising SEQ ID NO:12. In certain embodiments, the bispecific VEGF/DLL4-binding agent comprises a first heavy chain variable region comprising SEQ ID NO:11, a second heavy chain variable region comprising SEQ ID NO:64, and a first and a second light chain variable region comprising SEQ ID NO:12. In certain embodiments, the bispecific VEGF/DLL4-binding agent comprises a first heavy chain variable region consisting essentially of SEQ ID NO:11, a second heavy chain variable region consisting essentially of SEQ ID NO:9, and a first and a second light chain variable region consisting essentially of SEQ ID NO:12. In certain embodiments, the bispecific VEGF/DLL4-binding agent comprises a first heavy chain variable region consisting essentially of SEQ ID NO:11, a second heavy chain variable region consisting essentially of SEQ ID NO:10, and a first and a second light chain variable region consisting essentially of SEQ ID NO:12. In certain embodiments, the bispecific VEGF/DLL4-binding agent comprises a first heavy chain variable region consisting essentially of SEQ ID NO:11, a second heavy chain variable region consisting essentially of SEQ ID NO:58, and a first and a second light chain variable region consisting essentially of SEQ ID NO:12. In certain embodiments, the bispecific VEGF/DLL4-binding agent comprises a first heavy chain variable region consisting essentially of SEQ ID NO:11, a second heavy chain variable region consisting essentially of SEQ ID NO:64, and a first and a second light chain variable region consisting essentially of SEQ ID NO:12.

In some embodiments, the VEGF/DLL4-binding agent is a bispecific antibody which comprises a heavy chain variable region from the anti-VEGF antibody 219R45. In some embodiments, the VEGF/DLL4-binding agent is a bispecific antibody which comprises a heavy chain variable region from the anti-DLL4 antibody 21M18. In some embodiments, the VEGF/DLL4-binding agent is a bispecific antibody which comprises a heavy chain variable region from the anti-DLL4 antibody 21R79. In some embodiments, the VEGF/DLL4-binding agent is a bispecific antibody which comprises a heavy chain variable region from the anti-DLL4 antibody 21R75. In some embodiments, the VEGF/DLL4-binding agent is a bispecific antibody which comprises a heavy chain variable region from the anti-DLL4 antibody 21R83. In some embodiments, the VEGF/DLL4-binding agent is a bispecific antibody which comprises a heavy chain variable region from the anti-VEGF antibody 219R45, a heavy chain variable region from the anti-DLL4 antibody 21R79 and two identical light chain variable regions. In some embodiments, the VEGF/DLL4-binding agent is a bispecific antibody which comprises a heavy chain variable region from the anti-VEGF antibody 219R45, a heavy chain variable region from the anti-DLL4 antibody 21M18 and two identical light chain variable regions. In some embodiments, the VEGF/DLL4-binding agent is a bispecific antibody which comprises a heavy chain variable region from the anti-VEGF antibody 219R45, a heavy chain variable region from the anti-DLL4 antibody 21R75 and two identical light chain variable regions. In some embodiments, the VEGF/DLL4-binding agent is a bispecific antibody which comprises a heavy chain variable region from the anti-VEGF antibody 219R45, a heavy chain variable region from the anti-DLL4 antibody 21R83 and two identical light chain variable regions.

In some embodiments, the VEGF/DLL4-binding agent is a bispecific antibody which comprises a first CH3 domain and a second CH3 domain, each of which is modified to promote formation of heteromultimers. In some embodiments, the first and second CH3 domains are modified using a knobs-into-holes technique. In some embodiments, the first and second CH3 domains comprise changes in amino acids that result in altered electrostatic interactions. In some embodiments, the first and second CH3 domains comprise changes in amino acids that result in altered hydrophobic/hydrophilic interactions.

In some embodiments, the VEGF/DLL4-binding agent is a bispecific antibody which comprises heavy chain constant regions selected from the group consisting of: (a) a first human IgG1 constant region, wherein the amino acids at positions 253 and 292 are substituted with glutamate or aspartate, and a second human IgG1 constant region, wherein the amino acids at positions 240 and 282 are substituted with lysine; (b) a first human IgG2 constant region, wherein the amino acids at positions 249 and 288 are substituted with glutamate or aspartate, and a second human IgG2 constant region wherein the amino acids at positions 236 and 278 are substituted with lysine; (c) a first human IgG3 constant region, wherein the amino acids at positions 300 and 339 are substituted with glutamate or aspartate, and a second human IgG3 constant region wherein the amino acids at positions 287 and 329 are substituted with lysine; and (d) a first human IgG4 constant region, wherein the amino acids at positions 250 and 289 are substituted with glutamate or aspartate, and a second IgG4 constant region wherein the amino acids at positions 237 and 279 are substituted with lysine.

In some embodiments, the VEGF/DLL4-binding agent is a bispecific antibody which comprises a first human IgG1 constant region with amino acid substitutions at positions 253 and 292, wherein the amino acids are glutamate or aspartate, and a second human IgG1 constant region with amino acid substitutions at positions 240 and 282, wherein the amino acids are lysine. In some embodiments, the VEGF/DLL4-binding agent is a bispecific antibody which comprises a first human IgG2 constant region with amino acid substitutions at positions 249 and 288, wherein the amino acids are glutamate or aspartate, and a second human IgG2 constant region with amino acid substitutions at positions 236 and 278, wherein the amino acids are lysine. In some embodiments, the VEGF/DLL4-binding agent is a bispecific antibody which comprises a first human IgG3 constant region with amino acid substitutions at positions 300 and 339, wherein the amino acids are glutamate or aspartate, and a second human IgG2 constant region with amino acid substitutions at positions 287 and 329, wherein the amino acids are lysine. In some embodiments, the VEGF/DLL4-binding agent is a bispecific antibody which comprises a first human IgG4 constant region with amino acid substitutions at positions 250 and 289, wherein the amino acids are glutamate or aspartate, and a second human IgG4 constant region with amino acid substitutions at positions 237 and 279, wherein the amino acids are lysine.

In some embodiments, the VEGF/DLL4-binding agent is a bispecific antibody which comprises a first human IgG2 constant region with amino acid substitutions at positions 249 and 288, wherein the amino acids are glutamate, and a second human IgG2 constant region with amino acid substitutions at positions 236 and 278, wherein the amino acids are lysine. In some embodiments, the VEGF/DLL4-binding agent is a bispecific antibody which comprises a first human IgG2 constant region with amino acid substitutions at positions 249 and 288, wherein the amino acids are asparate, and a second human IgG2 constant region with amino acid substitutions at positions 236 and 278, wherein the amino acids are lysine.

In some embodiments, the VEGF/DLL4-binding agent is a bispecific antibody which comprises a heavy chain of SEQ ID NO:7. In some embodiments, the VEGF/DLL4-binding agent is a bispecific antibody which comprises a heavy chain of SEQ ID NO:5. In some embodiments, the VEGF/DLL4-binding agent is a bispecific antibody which comprises a heavy chain of SEQ ID NO:56. In some embodiments, the VEGF/DLL4-binding agent is a bispecific antibody which comprises a heavy chain of SEQ ID NO:62. In some embodiments, the bispecific antibody further comprises a light chain of SEQ ID NO:12. In some embodiments, the VEGF/DLL4-binding agent is a bispecific antibody which comprises a heavy chain of SEQ ID NO:7, a heavy chain of SEQ ID NO:5, and two light chains of SEQ ID NO:8. In some embodiments, the VEGF/DLL4-binding agent is a bispecific antibody which comprises a heavy chain of SEQ ID NO:7, a heavy chain of SEQ ID NO:6, and two light chains of SEQ ID NO:8. In some embodiments, the VEGF/DLL4-binding agent is a bispecific antibody which comprises a heavy chain of SEQ ID NO:7, a heavy chain of SEQ ID NO:56, and two light chains of SEQ ID NO:8. In some embodiments, the VEGF/DLL4-binding agent is a bispecific antibody which comprises a heavy chain of SEQ ID NO:7, a heavy chain of SEQ ID NO:62, and two light chains of SEQ ID NO:8.

In some embodiments, the VEGF/DLL4-binding agent is a bispecific antibody which binds VEGF with a $K_D$ of about 50 nM or less, about 25 nM or less, about 10 nM or less, about 1 nM or less, or about 0.1 nM or less. In some embodiments, the VEGF/DLL4-binding agent is a bispecific antibody which binds DLL4 with a $K_D$ of about 50 nM or less, about 25 nM or less, about 10 nM or less, about 1 nM or less, or about 0.1 nM or less. In some embodiments, the VEGF/DLL4-binding agent is a bispecific antibody which binds VEGF with a $K_D$ of about 50 nM or less and binds DLL4 with a $K_D$ of about 50 nM or less. In some embodiments, the bispecific antibody binds VEGF with a $K_D$ of about 25 nM or less and binds DLL4 with a $K_D$ of about 25 nM or less. In some embodiments, the bispecific antibody binds VEGF with a $K_D$ of about 10 nM or less and binds DLL4 with a $K_D$ of about 10 nM or less. In some embodiments, the bispecific antibody binds VEGF with a $K_D$ of about 1 nM or less and binds DLL4 with a $K_D$ of about 1 nM or less.

In some embodiments, the VEGF/DLL4-binding agent is a bispecific antibody which comprises one antigen-binding site with a binding affinity that is weaker than the binding affinity of the second antigen-binding site. For example, in some embodiments, the bispecific antibody may bind VEGF with a $K_D$ ranging from about 0.1 nM to 1 nM and may bind DLL4 with a $K_D$ ranging from about 1 nM to 10 nM. Or the bispecific antibody may bind VEGF with a $K_D$ ranging from about 1 nM to 10 nM and may bind DLL4 with a $K_D$ ranging from about 0.1 nM to 1 nM. In some embodiments, the bispecific antibody may bind DLL4 with a $K_D$ ranging from about 0.1 nM to 1 nM and may bind VEGF with a $K_D$ ranging from about 1 nM to 10 nM. Or the bispecific antibody may bind DLL4 with a $K_D$ ranging from about 1 nM to 10 nM and may bind VEGF with a $K_D$ ranging from about 0.1 nM to 1 nM In some embodiments, the difference in affinity between the two antigen-binding sites may be about 2-fold or more, about 3-fold or more, about 5-fold or more, about 8-fold or more, about 10-fold or more, about 15-fold or more, about 30-fold or more, about 50-fold or more, or about 100-fold or more. In some embodiments, at least one amino acid residue in at least one CDR of the antigen-binding site for VEGF is substituted with a different amino acid so that the affinity of the VEGF-binding site is altered. In some embodiments, the affinity of the VEGF-binding site is increased. In some embodiments, the affinity of the VEGF-binding site is decreased. In some embodiments, at least one amino acid residue in at least one CDR of the antigen-binding site for DLL4 is substituted with a different amino acid so that the affinity of the DLL4-binding site is altered. In some embodiments, the affinity of the DLL4-binding site is increased. In some embodiments, the affinity of the DLL4-binding site is decreased. In some embodiments, the affinities of both the VEGF and DLL4 antigen-binding sites are altered.

The invention provides polypeptides, including but not limited to antibodies, that specifically bind VEGF and/or DLL4. In some embodiments, a polypeptide binds human VEGF. In some embodiments, a polypeptide binds human DLL4. In some embodiments, a polypeptide binds human VEGF and mouse VEGF. In some embodiments, a polypeptide binds human DLL4 and mouse DLL4.

In some embodiments, a VEGF-binding agent comprises a polypeptide comprising a sequence selected from the group consisting of: SEQ ID NO:3, SEQ ID NO:4, SEQ ID NO:7, SEQ ID NO:8, SEQ ID NO:11, SEQ ID NO:12, SEQ ID NO:47, and SEQ ID NO:49.

In some embodiments, a DLL4-binding agent comprises a polypeptide comprising a sequence selected from the group consisting of: SEQ ID NO:1, SEQ ID NO:2, SEQ ID NO:4, SEQ ID NO:5, SEQ NO ID:6, SEQ ID NO:8, SEQ ID NO:9, SEQ ID NO:10, SEQ ID NO:12, SEQ ID NO:46, SEQ ID NO:48, SEQ ID NO:56, SEQ ID NO:57, SEQ ID NO:58, SEQ ID NO:62, SEQ ID NO:63, and SEQ ID NO:64.

In some embodiments, a VEGF/DLL4-binding agent comprises a polypeptide comprising a sequence selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:46, SEQ ID NO:47, SEQ ID NO:48, SEQ ID NO:49, SEQ ID NO:56, SEQ ID NO:57, SEQ ID NO:58, SEQ ID NO:62, SEQ ID NO:63, and SEQ ID NO:64.

In some embodiments, a VEGF/DLL4-binding agent comprises a polypeptide comprising a sequence selected from the group consisting of: SEQ ID NO:1, SEQ ID NO:2, SEQ ID NO:5, SEQ ID NO:6, SEQ ID NO:9, SEQ ID NO:10, SEQ ID NO:46, SEQ ID NO:48, SEQ ID NO:56, SEQ ID NO:57, SEQ ID NO:58, SEQ ID NO:62, SEQ ID NO:63, and SEQ ID NO:64. In some embodiments, the VEGF/DLL4 binding agent further comprises a polypeptide comprising a sequence selected from the group consisting of: SEQ ID NO:3, SEQ ID NO:7, SEQ ID NO:11, SEQ ID NO:47, and SEQ ID NO:49. In some embodiments, the VEGF/DLL4 binding agent further comprises a polypeptide comprising a sequence selected from the group consisting of: SEQ ID NO:4, SEQ ID NO:8, and SEQ ID NO:12.

In some embodiments, a VEGF/DLL4-binding agent comprises a polypeptide comprising a sequence selected from the group consisting of: SEQ ID NO:3, SEQ ID NO:7, SEQ ID NO:11, SEQ ID NO:47, and SEQ ID NO:49. In some embodiments, the VEGF/DLL4 binding agent further comprises a polypeptide comprising a sequence selected from the group consisting of: SEQ ID NO:1, SEQ ID NO:2, SEQ ID NO:5, SEQ ID NO:6, SEQ ID NO:9, SEQ ID NO:10, SEQ ID NO:46, SEQ ID NO:48, SEQ ID NO:56, SEQ ID NO:57, SEQ ID NO:58, SEQ ID NO:62, SEQ ID NO:63, and SEQ ID NO:64. In some embodiments, the VEGF/DLL4 binding agent further comprises a polypeptide comprising a sequence selected from the group consisting of: SEQ ID NO:4, SEQ ID NO:8, and SEQ ID NO:12.

In certain embodiments, a VEGF/DLL4-binding agent (e.g., antibody) competes for specific binding to VEGF with an antibody that comprises a heavy chain variable region comprising SEQ ID NO:11 and a light chain variable region comprising SEQ ID NO:12. In certain embodiments, a VEGF/DLL4-binding agent competes with antibody 219R45 for specific binding to human VEGF. In some embodiments, a VEGF/DLL4-binding agent or antibody competes for specific binding to VEGF in an in vitro competitive binding assay. In some embodiments, the VEGF is human VEGF. In some embodiments, the VEGF is mouse VEGF.

In certain embodiments, a VEGF-DLL4-binding agent (e.g., an antibody) binds the same epitope, or essentially the same epitope, on VEGF as an antibody of the invention. In another embodiment, a VEGF/DLL4-binding agent is an antibody that binds an epitope on VEGF that overlaps with the epitope on VEGF bound by an antibody of the invention. In certain embodiments, a VEGF/DLL4-binding agent (e.g., an antibody) binds the same epitope, or essentially the same epitope, on VEGF as antibody 219R45. In another embodiment, the VEGF/DLL4-binding agent is an antibody that binds an epitope on VEGF that overlaps with the epitope on VEGF bound by antibody 219R45.

In certain embodiments, the VEGF/DLL4-binding agent is an agent that competes for specific binding to VEGF with the antibody 219R45 (e.g., in a competitive binding assay).

In certain embodiments, a VEGF/DLL4-binding agent (e.g., antibody) competes for specific binding to DLL4 with an antibody that comprises a heavy chain variable region comprising SEQ ID NO:9 SEQ ID NO:10, SEQ ID NO:58, or SEQ ID NO:64 and a light chain variable region comprising SEQ ID NO:12. In certain embodiments, a VEGF/DLL4-binding agent competes with antibody 21R79 for specific binding to human DLL4. In certain embodiments, a VEGF/DLL4-binding agent competes with antibody 21R75 for specific binding to human DLL4. In certain embodiments, a VEGF/DLL4-binding agent competes with antibody 21R83 for specific binding to human DLL4. In some embodiments, a VEGF/DLL4-binding agent or antibody competes for specific binding to DLL4 in an in vitro competitive binding assay. In some embodiments, the DLL4 is human DLL4. In some embodiments, the DLL4 is mouse DLL4.

In certain embodiments, a VEGF/DLL4-binding agent (e.g., an antibody) binds the same epitope, or essentially the same epitope, on DLL4 as an antibody of the invention. In another embodiment, a VEGF/DLL4-binding agent is an antibody that binds an epitope on DLL4 that overlaps with the epitope on DLL4 bound by an antibody of the invention. In certain embodiments, a VEGF/DLL4-binding agent binds the same epitope, or essentially the same epitope, on DLL4 as antibody 21R79. In certain embodiments, a VEGF/DLL4-binding agent binds the same epitope, or essentially the same epitope, on DLL4 as antibody 21R75. In certain embodiments, a VEGF/DLL4-binding agent binds the same epitope, or essentially the same epitope, on DLL4 as antibody 21R83. In another embodiment, the VEGF/DLL4-binding agent is an antibody that binds an epitope on DLL4 that overlaps with the epitope on DLL4 bound by antibody 21R79. In another embodiment, the VEGF/DLL4-binding agent is an antibody that binds an epitope on DLL4 that overlaps with the epitope on DLL4 bound by antibody 21R75. In another embodiment, the VEGF/DLL4-binding agent is an antibody that binds an epitope on DLL4 that overlaps with the epitope on DLL4 bound by antibody 21R83.

In certain embodiments, the VEGF/DLL4-binding agent is an agent that competes for specific binding to DLL4 with the antibody 21R79 (e.g., in a competitive binding assay). In certain embodiments, the VEGF/DLL4-binding agent is an agent that competes for specific binding to DLL4 with the antibody 21R75 (e.g., in a competitive binding assay). In certain embodiments, the VEGF/DLL4-binding agent is an agent that competes for specific binding to DLL4 with the antibody 21R83 (e.g., in a competitive binding assay). In certain embodiments, the VEGF/DLL4-binding agent is an agent that competes for specific binding to DLL4 with the antibody 21M18 (e.g., in a competitive binding assay).

In certain embodiments, the VEGF/DLL4-binding agent is an agent that competes for specific binding to VEGF and/or DLL4 with the bispecific antibody 219R45-MB-21M18 (e.g., in a competitive binding assay). In certain embodiments, the VEGF/DLL4-binding agent is an agent that competes for specific binding to VEGF and/or DLL4 with the bispecific antibody 219R45-MB-21M79 (e.g., in a competitive binding assay). In certain embodiments, the VEGF/DLL4-binding agent is an agent that competes for specific binding to VEGF and/or DLL4 with the bispecific antibody 219R45-MB-21M75 (e.g., in a competitive binding assay). In certain embodiments, the VEGF/DLL4-binding agent is an agent that competes for specific binding to VEGF and/or DLL4 with the bispecific antibody 219R45-MB-21M83 (e.g., in a competitive binding assay).

In certain embodiments, the VEGF/DLL4-binding agent (e.g., an antibody) described herein binds VEGF and modulates VEGF activity. In some embodiments, the VEGF/DLL4-binding agent is a VEGF antagonist and inhibits VEGF activity. In some embodiments, the VEGF/DLL4-binding agent is a VEGF antagonist and modulates angiogenesis. In some embodiments, the VEGF/DLL4-binding agent is a VEGF antagonist and inhibits angiogenesis. In some embodiments, the VEGF/DLL4-binding agent is a VEGF antagonist and inhibits tumor growth.

In certain embodiments, a VEGF/DLL4-binding agent (e.g., an antibody) described herein binds human DLL4 and modulates DLL4 activity. In some embodiments, a VEGF/DLL4-binding agent is a DLL4 antagonist and inhibits DLL4 activity. In some embodiments, a VEGF/DLL4-binding agent is a DLL4 antagonist and inhibits Notch activity. In some embodiments, a VEGF/DLL4-binding agent is a DLL4 antagonist and inhibits Notch signaling. In some embodiments, a VEGF/DLL4-binding agent is a DLL4 antagonist and modulates angiogenesis. In some embodiments, a VEGF/DLL4-binding agent is a DLL4 antagonist and promotes aberrant angiogenesis. In some embodiments, a VEGF/DLL4-binding agent is a DLL4 antagonist and inhibits tumor growth.

In certain embodiments, a VEGF/DLL4-binding agent (e.g., an antibody) described herein is a bispecific antibody that binds human VEGF and modulates VEGF activity. In certain embodiments, a VEGF/DLL4-binding agent (e.g., an antibody) described herein is a bispecific antibody that binds human DLL4 and modulates DLL4 activity. In certain embodiments, a VEGF/DLL4-binding agent (e.g., an antibody) described herein is a bispecific antibody that binds human VEGF and human DLL4 and modulates both VEGF and DLL4 activity. In some embodiments, the bispecific antibody is a VEGF antagonist and a DLL4 antagonist and inhibits both VEGF activity and DLL4 activity. In some embodiments, the bispecific antibody is a VEGF antagonist and a DLL4 antagonist and inhibits VEGF activity and Notch activity. In some embodiments, the bispecific antibody is a VEGF antagonist and a DLL4 antagonist and inhibits VEGF activity and Notch signaling. In some embodiments, the bispecific antibody is a VEGF antagonist and a DLL4 antagonist and modulates angiogenesis. In some embodiments, the bispecific antibody is a VEGF antagonist and a DLL4 antagonist and promotes aberrant angiogenesis. In some embodiments, the bispecific antibody is a VEGF antagonist and a DLL4 antagonist and inhibits angiogenesis. In some embodiments, the bispecific antibody is a VEGF antagonist and a DLL4 antagonist and inhibits tumor growth.

In certain embodiments, the VEGF/DLL4-binding agent (e.g., an antibody or a bispecific antibody) is an antagonist of VEGF. In some embodiments, the VEGF/DLL4-binding agent is an antagonist of VEGF and inhibits VEGF activity. In certain embodiments, the VEGF/DLL4-binding agent inhibits VEGF activity by at least about 10%, at least about 20%, at least about 30%, at least about 50%, at least about 75%, at least about 90%, or about 100%. In certain embodiments, a VEGF/DLL4-binding agent that inhibits human VEGF activity is antibody 219R45. In certain embodiments, a VEGF/DLL4-binding agent that inhibits human VEGF activity is a bispecific antibody comprising the antigen-binding site of 219R45. In certain embodiments, a VEGF/DLL4-binding agent that inhibits human VEGF activity is the bispecific antibody 219R45-MB-21M18. In certain embodiments, a VEGF/DLL4-binding agent that inhibits human VEGF activity is the bispecific antibody 219R45-MB-21R79. In certain embodiments, a VEGF/DLL4-binding agent that inhibits human VEGF activity is the bispecific antibody 219R45-MB-21R75. In certain embodiments, a VEGF/DLL4-binding agent that inhibits human VEGF activity is the bispecific antibody 219R45-MB-21R83.

In certain embodiments, the VEGF/DLL4-binding agent (e.g., an antibody) is an antagonist of DLL4. In some embodiments, the VEGF/DLL4-binding agent is an antagonist of DLL4 and inhibits DLL4 activity. In certain embodiments, the VEGF/DLL4-binding agent inhibits DLL4 activity by at least about 10%, at least about 20%, at least about 30%, at least about 50%, at least about 75%, at least about 90%, or about 100%. In certain embodiments, a VEGF/DLL4-binding agent that inhibits human DLL4 activity is antibody 21R79. In certain embodiments, a VEGF/DLL4-binding agent that inhibits human DLL4 activity is antibody 21R75. In certain embodiments, a VEGF/DLL4-binding agent that inhibits human DLL4 activity is antibody 21R83. In certain embodiments, a VEGF/DLL4-binding agent that inhibits human DLL4 activity is a bispecific antibody comprising the antigen-binding site of 21R79. In certain embodiments, a VEGF/DLL4-binding agent that inhibits human DLL4 activity is a bispecific antibody comprising the antigen-binding site of 21R75. In certain embodiments, a VEGF/DLL4-binding agent that inhibits human DLL4 activity is a bispecific antibody comprising the antigen-binding site of 21R83. In certain embodiments, a VEGF/DLL4-binding agent that inhibits human DLL4 activity is the bispecific antibody 219R45-MB-21M18. In certain embodiments, a VEGF/DLL4-binding agent that inhibits human DLL4 activity is the bispecific antibody 219R45-MB-21R79. In certain embodiments, a VEGF/DLL4-binding agent that inhibits human DLL4 activity is the bispecific antibody 219R45-MB-21R75. In certain embodiments, a VEGF/DLL4-binding agent that inhibits human DLL4 activity is the bispecific antibody 219R45-MB-21R83.

In certain embodiments, the VEGF/DLL4-binding agent (e.g., antibody) is an antagonist of Notch signaling. In certain embodiments, the VEGF/DLL4-binding agent inhibits Notch signaling by at least about 10%, at least about 20%, at least about 30%, at least about 50%, at least about 75%, at least about 90%, or about 100%. In certain embodiments, a VEGF/DLL4-binding agent that inhibits Notch signaling is antibody 21R79. In certain embodiments, a VEGF/DLL4-binding agent that inhibits Notch signaling is antibody 21R75. In certain embodiments, a VEGF/DLL4-binding agent that inhibits Notch signaling is antibody 21R83. In certain embodiments, a VEGF/DLL4-binding agent that inhibits Notch signaling is a bispecific antibody comprising the antigen-binding site of 21R79. In certain embodiments, a VEGF/DLL4-binding agent that inhibits Notch signaling is a bispecific antibody comprising the antigen-binding site of 21R75. In certain embodiments, a VEGF/DLL4-binding agent that inhibits Notch signaling is a bispecific antibody comprising the antigen-binding site of 21R83. In certain embodiments, a VEGF/DLL4-binding agent that inhibits Notch signaling is the bispecific antibody 219R45-MB-21M18. In certain embodiments, a VEGF/DLL4-binding agent that inhibits Notch signaling is the bispecific antibody 219R45-MB-21R79. In certain embodiments, a VEGF/DLL4-binding agent that inhibits Notch signaling is the bispecific antibody 219R45-MB-21R75. In certain embodiments, a VEGF/DLL4-binding agent that inhibits Notch signaling is the bispecific antibody 219R45-MB-21R83.

In certain embodiments, the VEGF/DLL4-binding agent (e.g., antibody) inhibits binding of VEGF to at least one receptor. In some embodiments, the VEGF/DLL4-binding agent inhibits binding of VEGF to VEGFR-1 or VEGFR-2. In certain embodiments, the VEGF/DLL4-binding agent inhibits binding of VEGF to at least one VEGF receptor by at least about 10%, at least about 25%, at least about 50%, at least about 75%, at least about 90%, or at least about 95%. In certain embodiments, a VEGF/DLL4-binding agent that inhibits binding of human VEGF to at least one VEGF receptor is antibody 219R45. In certain embodiments, a VEGF/DLL4-binding agent that inhibits binding of human VEGF to at least one VEGF receptor is a bispecific antibody comprising the antigen-binding site of 219R45. In certain embodiments, a VEGF/DLL4-binding agent that inhibits binding of human VEGF to at least one VEGF receptor is the bispecific antibody 219R45-MB-21M18. In certain embodiments, a VEGF/DLL4-binding agent that inhibits binding of human VEGF to at least one VEGF receptor is the bispecific antibody 219R45-MB-21R79. In certain embodiments, a VEGF/DLL4-binding agent that inhibits binding of human VEGF to at least one VEGF receptor is the bispecific antibody 219R45-MB-21R75. In certain embodiments, a VEGF/DLL4-binding agent that inhibits binding of human VEGF to at least one VEGF receptor is the bispecific antibody 219R45-MB-21R83.

In certain embodiments, the VEGF/DLL4-binding agent (e.g., antibody) inhibits binding of DLL4 protein to at least one Notch receptor. In some embodiments, the VEGF/DLL4-binding agent inhibits binding of DLL4 to Notch1, Notch2, Notch3, and/or Notch4. In certain embodiments, the VEGF/DLL4-binding agent inhibits binding of DLL4 to at least one Notch receptor by at least about 10%, at least about 25%, at least about 50%, at least about 75%, at least about 90%, or at least about 95%. In certain embodiments, a VEGF/DLL4-binding agent that inhibits binding of human DLL4 to at least one Notch receptor is antibody 21R79. In certain embodiments, a VEGF/DLL4-binding agent that inhibits binding of human DLL4 to at least one Notch receptor is antibody 21R75. In certain embodiments, a VEGF/DLL4-binding agent that inhibits binding of human DLL4 to at least one Notch receptor is antibody 21R83. In certain embodiments, a VEGF/DLL4-binding agent that inhibits binding of human DLL4 to at least one Notch receptor is a bispecific antibody comprising the antigen-binding site of 21R79. In certain embodiments, a VEGF/DLL4-binding agent that inhibits binding of human DLL4 to at least one Notch receptor is a bispecific antibody comprising the antigen-binding site of 21R75. In certain embodiments, a VEGF/DLL4-binding agent that inhibits binding of human DLL4 to at least one Notch receptor is a bispecific antibody comprising the antigen-binding site of 21R83. In certain embodiments, a VEGF/DLL4-binding agent that inhibits binding of human DLL4 to at least one Notch receptor is the bispecific antibody 219R45-MB-21M18. In certain embodiments, a VEGF/DLL4-binding agent that inhibits binding of human DLL4 to at least one Notch receptor is the bispecific antibody 219R45-MB-21R79. In certain embodiments, a VEGF/DLL4-binding agent that inhibits binding of human DLL4 to at least one Notch receptor is the bispecific antibody 219R45-MB-21R75. In certain embodiments, a VEGF/DLL4-binding agent that inhibits binding of human DLL4 to at least one Notch receptor is the bispecific antibody 219R45-MB-21R83.

In vivo and in vitro assays for determining whether a VEGF/DLL4-binding agent (or candidate VEGF/DLL4-binding agent) inhibits VEGF or affects angiogenesis are known in the art. In vitro assays of angiogenesis include but are not limited to, HUVEC proliferation assays, endothelial cell tube formation assays, sprouting (or sprout formation) assays, HUVEC cell migration assays, and invasion assays. In some embodiments, cells in the presence of VEGF and the presence of a VEGF/DLL4-binding agent are compared to cells in the presence of VEGF without the VEGF/DLL4-binding agent present, and evaluated for effects on angiogenesis (or biological effects associated with angiogenesis). In vivo assays of angiogenesis include, but are not limited to, matrigel plug assays, corneal micropocket assays, and chicken chorioallantoic membrane (CAM) assays.

In vivo and in vitro assays for determining whether a VEGF/DLL4-binding agent (or candidate VEGF/DLL4-binding agent) inhibits Notch activation or signaling are known in the art. For example, cell-based, luciferase reporter assays utilizing a TCF/Luc reporter vector containing multiple copies of the TCF-binding domain upstream of a firefly luciferase reporter gene may be used to measure Notch signaling levels in vitro (Gazit et al., 1999, Oncogene, 18; 5959-66; TOPflash, Millipore, Billerica, Mass.). In some embodiments, a cell-based, luciferase reporter assay utilizing a CBF/Luc reporter vector containing multiple copies of the CBF-binding domain upstream of a firefly luciferase report genes may be used. The level of Notch signaling in the presence of one or more Notch ligands (e.g., DLL4 expressed on the surface of transfected cells or soluble DLL4-Fc fusion protein) and in the presence of a VEGF/DLL4-binding agent is compared to the level of Notch signaling without the VEGF/DLL4-binding agent present.

In certain embodiments, the VEGF/DLL4-binding agents have one or more of the following effects: inhibit proliferation of tumor cells, inhibit tumor growth, reduce the tumorigenicity of a tumor, reduce the frequency of cancer stem cells in a tumor, trigger cell death of tumor cells, prevent metastasis of tumor cells, decrease survival of tumor cells, modulate angiogenesis, inhibit angiogenesis, inhibit productive angiogenesis, or promote aberrant angiogenesis.

In certain embodiments, the VEGF/DLL4-binding agents are capable of inhibiting tumor growth. In certain embodiments, the VEGF/DLL4-binding agents are capable of inhibiting tumor growth in vivo (e.g., in a xenograft mouse model, and/or in a human having cancer). In certain embodiments, tumor growth is inhibited at least about two-fold, about three-fold, about five-fold, about ten-fold, about 50-fold, about 100-fold, or about 1000-fold as compared to an untreated tumor.

In certain embodiments, the VEGF/DLL4-binding agents are capable of reducing the tumorigenicity of a tumor. In certain embodiments, the VEGF/DLL4-binding agent or antibody is capable of reducing the tumorigenicity of a tumor comprising cancer stem cells in an animal model, such as a mouse xenograft model. In certain embodiments, the VEGF/DLL4-binding agent or antibody is capable of reducing the tumorigenicity of a tumor by decreasing the number or frequency of cancer stem cells in the tumor. In certain embodiments, the number or frequency of cancer stem cells in a tumor is reduced by at least about two-fold, about three-fold, about five-fold, about ten-fold, about 50-fold, about 100-fold, or about 1000-fold. In certain embodiments, the reduction in the number or frequency of cancer stem cells is determined by limiting dilution assay using an animal model. Additional examples and guidance regarding the use of limiting dilution assays to determine a reduction in the number or frequency of cancer stem cells in a tumor can be found, e.g., in International Publication Number WO 2008/042236; U.S. Patent Publication No. 2008/0064049; and U.S. Patent Publication No. 2008/0178305.

In certain embodiments, the VEGF/DLL4-binding agents are capable of modulating angiogenesis. In certain embodiments, the VEGF/DLL4-binding agents are capable of modulating angiogenesis in vivo (e.g., in a xenograft mouse model, and/or in a human having cancer). In certain embodiments, VEGF/DLL4-binding agents are capable of inhibiting angiogenesis. In certain embodiments, VEGF/DLL4-binding agents are capable of promoting aberrant angiogenesis. In certain embodiments, VEGF/DLL4-binding agents are capable of inhibiting angiogenesis and/or promoting aberrant angiogenesis, leading to unproductive vascularization.

In certain embodiments, the VEGF/DLL4-binding agents described herein have a circulating half-life in mice, cynomolgus monkeys, or humans of at least about 2 hours, at least about 5 hours, at least about 10 hours, at least about 24 hours, at least about 3 days, at least about 1 week, or at least about 2 weeks. In certain embodiments, the VEGF/DLL4-binding agent is an IgG (e.g., IgG1 or IgG2) antibody that has a circulating half-life in mice, cynomolgus monkeys, or humans of at least about 2 hours, at least about 5 hours, at least about 10 hours, at least about 24 hours, at least about 3 days, at least about 1 week, or at least about 2 weeks. Methods of increasing (or decreasing) the half-life of agents such as polypeptides and antibodies are known in the art. For example, known methods of increasing the circulating half-life of IgG antibodies include the introduction of mutations in the Fc region which increase the pH-dependent binding of the antibody to the neonatal Fc receptor (FcRn) at pH 6.0 (see, e.g., U.S. Patent Publication Nos. 2005/0276799, 2007/0148164, and 2007/0122403). Known methods of increasing the circulating half-life of antibody fragments lacking the Fc region include such techniques as PEGylation.

In some embodiments, the VEGF/DLL4-binding agents are antibodies. Polyclonal antibodies can be prepared by any known method. In some embodiments, polyclonal antibodies are produced by immunizing an animal (e.g., a rabbit, rat, mouse, goat, donkey) with an antigen of interest (e.g., a purified peptide fragment, full-length recombinant protein, or fusion protein) by multiple subcutaneous or intraperitoneal injections. The antigen can be optionally conjugated to a carrier such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. After a sufficient period of time, polyclonal antibodies are recovered from the immunized animal, usually from blood or ascites. The polyclonal antibodies can be purified from serum or ascites according to standard methods in the art including, but not limited to, affinity chromatography, ion-exchange chromatography, gel electrophoresis, and dialysis.

In some embodiments, the VEGF/DLL4-binding agents are monoclonal antibodies. Monoclonal antibodies can be prepared using hybridoma methods known to one of skill in the art (see e.g., Kohler and Milstein, 1975, *Nature*, 256: 495-497). In some embodiments, using the hybridoma method, a mouse, hamster, or other appropriate host animal, is immunized as described above to elicit from lymphocytes the production of antibodies that specifically bind the immunizing antigen. In some embodiments, lymphocytes can be immunized in vitro. In some embodiments, the immunizing antigen can be a human protein or a portion thereof. In some embodiments, the immunizing antigen can be a mouse protein or a portion thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed specifically against a chosen antigen may be identified by a variety of methods including, but not limited to, immunoprecipitation, immunoblotting, and in vitro binding assays (e.g., flow cytometry, FACS, ELISA, and radioimmunoassay). The hybridomas can be propagated either in in vitro culture using standard methods (J. W. Goding, 1996, *Monoclonal Antibodies: Principles and Practice*, 3$^{rd}$ Edition, Academic Press, San Diego, Calif.) or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In certain embodiments, monoclonal antibodies can be made using recombinant DNA techniques as known to one skilled in the art. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using standard techniques. The isolated polynucleotides encoding the heavy and light chains are then cloned into suitable expression vectors which produce the monoclonal antibodies when transfected into host cells such as *E. coli*, simian COS cells, Chinese hamster ovary (CHO) cells, or myeloma cells that do not otherwise produce immunoglobulin proteins.

In certain other embodiments, recombinant monoclonal antibodies, or fragments thereof, can be isolated from phage display libraries expressing variable domains or CDRs of a desired species (see e.g., McCafferty et al., 1990, *Nature*, 348:552-554; Clackson et al., 1991, *Nature*, 352:624-628; and Marks et al., 1991, *J. Mol. Biol.*, 222:581-597).

The polynucleotide(s) encoding a monoclonal antibody can be modified, for example, by using recombinant DNA technology to generate alternative antibodies. In some embodiments, the constant domains of the light and heavy chains of, for example, a mouse monoclonal antibody can be substituted for those regions of, for example, a human antibody to generate a chimeric antibody, or for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

In some embodiments, a monoclonal antibody against VEGF and/or DLL4 is a humanized antibody. Typically, humanized antibodies are human immunoglobulins in which residues from the CDRs are replaced by residues from a CDR of a non-human species (e.g., mouse, rat, rabbit, hamster, etc.) that have the desired specificity, affinity, and/or binding capability using methods known to one skilled in the art. In some embodiments, the Fv framework region residues of a human immunoglobulin are replaced with the corresponding residues in an antibody from a non-human species that has the desired specificity, affinity, and/or binding capability. In some embodiments, a humanized antibody can be further modified by the substitution of additional residues either in the Fv framework region and/or within the replaced non-human residues to refine and optimize antibody specificity, affinity, and/or capability. In general, a humanized antibody will comprise substantially all of at least one, and typically two or three, variable domain regions containing all, or substantially all, of the CDRs that correspond to the non-human immunoglobulin whereas all, or substantially all, of the framework regions are those of a human immunoglobulin consensus sequence. In some embodiments, a humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see e.g., U.S. Pat. Nos. 5,225,539; 5,585,089; 5,693,761; and 5,693,762).

In certain embodiments, the VEGF/DLL4-binding agent is a human antibody. Human antibodies can be directly prepared using various techniques known in the art. In some embodiments, human antibodies may be generated from immortalized human B lymphocytes immunized in vitro or from lymphocytes isolated from an immunized individual. In either case, cells that produce an antibody directed against a target antigen can be generated and isolated (see, e.g., Cole et al., 1985, *Monoclonal Antibodies and Cancer Therapy*, Alan R. Liss, p. 77; Boemer et al., 1991, *J. Immunol.*, 147:86-95; and U.S. Pat. Nos. 5,750,373; 5,567,610; and 5,229,275). In some embodiments, the human antibody can be selected from a phage library, where that phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Alternatively, phage display technology can be used to produce human antibodies and antibody fragments in vitro, from immunoglobulin variable domain gene repertoires from unimmunized donors. Techniques for the generation and use of antibody phage libraries are also described in U.S. Pat. Nos. 5,969,108; 6,172,197; 5,885,793; 6,521,404; 6,544,731; 6,555,313; 6,582,915; 6,593,081; 6,300,064; 6,653,068; 6,706,484; and 7,264,963; and Rothe et al., 2008, *J. Mol. Bio.*, 376:1182-1200. Once antibodies are identified, affinity maturation strategies known in the art, including but not limited to, chain shuffling (Marks et al., 1992, *Bio/Technology*, 10:779-783) and site-directed mutagenesis, may be employed to generate high affinity human antibodies.

In some embodiments, human antibodies can be made in transgenic mice that contain human immunoglobulin loci. Upon immunization these mice are capable of producing the full repertoire of human antibodies in the absence of endogenous immunoglobulin production. This approach is described in U.S. Pat. Nos. 5,545,807; 5,545,806; 5,569,825; 5,625,126; 5,633,425; and 5,661,016.

This invention also encompasses bispecific antibodies. Bispecific antibodies are capable of specifically recognizing and binding at least two different antigens or epitopes. The different epitopes can either be within the same molecule (e.g., two epitopes on a single protein) or on different molecules (e.g., one epitope on a protein and one epitope on a second protein). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any binding agent (e.g., antibody) may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two binding agents (e.g., antibodies) in a common area (e.g., a tumor and/or tumor environment). In some embodiments, a bispecific antibody has the ability to concentrate the actions of two binding agents (e.g., antibodies) to a common target (e.g., a tumor or a tumor cell). In some embodiments, a bispecific antibody has the ability to target the actions of two binding agents (e.g., antibodies) to more than one biological pathway or function.

In certain embodiments, the bispecific antibody specifically binds VEGF and a second target. In certain embodiments, the bispecific antibody specifically binds DLL4 and a second target. In certain embodiments, the bispecific antibody specifically binds VEGF and DLL4. In some embodiments, the bispecific antibody specifically binds human VEGF and human DLL4. In some embodiments, the bispecific antibody is a monoclonal human or a humanized antibody. In some embodiments, the bispecific antibody inhibits angiogenesis and reduces cancer stem cell number or frequency. In some embodiments, the bispecific antibody inhibits blood vessel growth and inhibits blood vessel maturation. In some embodiments, the bispecific antibody prevents endothelial hyperproliferation. In some embodiments, the bispecific antibody has decreased toxicity and/or side effects. In some embodiments, the bispecific antibody has decreased toxicity and/or side effects as compared to a mixture of the two individual antibodies or the antibodies as single agents. In some embodiments, the bispecific antibody has an increased therapeutic index. In some embodiments, the bispecific antibody has an increased therapeutic index as compared to a mixture of the two individual antibodies or the antibodies as single agents.

In some embodiments, the bispecific antibody can specifically recognize and bind a first antigen target, (e.g., DLL4) as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the bispecific antibodies can be used to direct cytotoxic agents to cells which express a particular target antigen. These antibodies possess an antigen-binding site (e.g., to human DLL4) and a second site which binds a cytotoxic agent or a radionuclide chelator, such as EOTUBE, DPTA, DOTA, or TETA.

Techniques for making bispecific antibodies are known by those skilled in the art, see for example, Millstein et al., 1983, *Nature*, 305:537-539; Brennan et al., 1985, *Science*, 229:81; Suresh et al., 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; U.S. Pat. No. 5,731,168; International Publication No. WO 2009/089004; and U.S. Patent Publication No. 2011/0123532. In some embodiments, the bispecific antibodies comprise heavy chain constant regions with modifications in the amino acids which are part of the interface between the two heavy chains. In some embodiments, the bispecific antibodies can be generated using a "knobs-into-holes" strategy (see. e.g., U.S. Pat. No. 5,731,168; Ridgway et. al., 1996, *Prot. Engin.*, 9:617-621). At times the "knobs" and "holes" terminology is replaced with the terms "protuberances" and "cavities". In some embodiments, the bispecific antibodies may comprise variant hinge regions incapable of forming disulfide linkages between the heavy chains (see, e.g., WO 2006/028936). In some embodiments, the modifications may comprise changes in amino acids that result in altered electrostatic interactions. In some embodiments, the modifications may comprise changes in amino acids that result in altered hydrophobic/hydrophilic interactions.

Bispecific antibodies can be intact antibodies or antibody fragments comprising antigen-binding sites. Antibodies with more than two valencies are also contemplated. For example, trispecific antibodies can be prepared (Tutt et al., 1991, *J. Immunol.*, 147:60). Thus, in certain embodiments the antibodies to VEGF and/or DLL4 are multispecific.

In certain embodiments, the antibodies (or other polypeptides) described herein may be monospecific. In certain embodiments, each of the one or more antigen-binding sites that an antibody contains is capable of binding (or binds) a homologous epitope on different proteins.

In certain embodiments, the VEGF/DLL4-binding agent is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in and secreted from *E. coli* or other host cells, allowing for the production of large amounts of these fragments. In some embodiments, antibody fragments are isolated from antibody phage libraries as discussed herein. For example, methods can be used for the construction of Fab expression libraries (Huse et al., 1989, *Science*, 246:1275-1281) to allow rapid and effective identification of monoclonal Fab fragments with the desired specificity for VEGF and/or DLL4 or derivatives, fragments, analogs or homologs thereof. In some embodiments, antibody fragments are linear antibody fragments. In certain embodiments, antibody fragments are monospecific or bispecific. In certain embodiments, the VEGF/DLL4-binding agent is a scFv. Various techniques can be used for the production of single-chain antibodies specific to VEGF or DLL4 (see, e.g., U.S. Pat. No. 4,946,778).

It can further be desirable, especially in the case of antibody fragments, to modify an antibody in order to alter (e.g., increase or decrease) its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

Heteroconjugate antibodies are also within the scope of the present invention. Heteroconjugate antibodies are composed of two covalently joined antibodies. Such antibodies have, for example, been proposed to target immune cells to unwanted cells (see, e.g., U.S. Pat. No. 4,676,980). It is also contemplated that the heteroconjugate antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with the target (i.e., human VEGF or human DLL4). In this regard, the variable region may comprise or be derived from any type of mammal that can be induced to mount a humoral response and generate immunoglobulins against the desired antigen. As such, the variable region of the modified antibodies can be, for example, of human, murine, non-human primate (e.g. cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification and/or alteration. Although the CDRs may be derived from an antibody of the same class or even subclass as the antibody from which the framework regions are derived, it is envisaged that the CDRs may be derived from an antibody of different class and often from an antibody from a different species. It may not be necessary to replace all of the CDRs with all of the CDRs from the donor variable region to transfer the antigen binding capacity of one variable domain to another. Rather, it may only be necessary to transfer those residues that are required to maintain the activity of the antigen-binding site.

Alterations to the variable region notwithstanding, those skilled in the art will appreciate that the modified antibodies of this invention will comprise antibodies (e.g., full-length antibodies or immunoreactive fragments thereof) in which at least a fraction of one or more of the constant region domains has been deleted or otherwise altered so as to provide desired biochemical characteristics such as increased tumor localization or increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the modified antibodies will comprise domain deleted constructs or variants wherein the entire CH2 domain has been removed (ΔCH2 constructs). In some embodiments, the omitted constant region domain is replaced by a short amino acid spacer (e.g., 10 amino acid residues) that provides some of the molecular flexibility typically imparted by the absent constant region.

In some embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase cancer cell localization and/or tumor penetration. Similarly, it may be desirable to simply delete the part of one or more constant region domains that control a specific effector function (e.g. complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind a cell expressing a Fc receptor (FcR). There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In certain embodiments, the modified antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody thereby increasing cancer cell localization and/or tumor penetration. In other embodiments, the constant region modifications increase the serum half-life of the antibody. In other embodiments, the constant region modifications reduce the serum half-life of the antibody. In some embodiments, the constant region is modified to eliminate disulfide linkages or oligosaccharide moieties. Modifications to the constant region in accordance with this invention may easily be made using well known biochemical or molecular engineering techniques known to those of skill in the art.

In certain embodiments, a VEGF/DLL4-binding agent that is an antibody does not have one or more effector functions. For instance, in some embodiments, the antibody has no ADCC activity, and/or no complement-dependent cytotoxicity (CDC) activity. In certain embodiments, the antibody does not bind an Fc receptor, and/or complement factors. In certain embodiments, the antibody has no effector function.

The present invention further embraces variants and equivalents which are substantially homologous to the chimeric, humanized, and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another amino acid within the same general class such as, for example, one acidic amino acid with another acidic amino acid, one basic amino acid with another basic amino acid or one neutral amino acid by another neutral amino acid. What is intended by a conservative amino acid substitution is well known in the art and described herein.

Thus, the present invention provides methods for producing an antibody that binds VEGF and/or DLL4, including bispecific antibodies that specifically bind both VEGF and DLL4. In some embodiments, the method for producing an antibody that binds VEGF and/or DLL4 comprises using hybridoma techniques. In some embodiments, the method of generating an antibody that binds VEGF or DLL4 or a bispecific antibody that binds VEGF and DLL4 comprises screening a human phage library. The present invention further provides methods of identifying an antibody that binds VEGF and/or DLL4. In some embodiments, the antibody is identified by FACS screening for binding to VEGF or a portion thereof. In some embodiments, the antibody is identified by FACS screening for binding to DLL4 or a portion thereof. In some embodiments, the antibody is identified by FACS screening for binding to both VEGF and DLL4 or a portion thereof. In some embodiments, the antibody is identified by screening using ELISA for binding to VEGF. In some embodiments, the antibody is identified by screening using ELISA for binding to DLL4. In some embodiments, the antibody is identified by screening using ELISA for binding to VEGF and DLL4. In some embodiments, the antibody is identified by FACS screening for blocking of binding of human VEGF to a human VEGF receptor. In some embodiments, the antibody is identified by FACS screening for blocking of binding of human DLL4 to a human Notch receptor. In some embodiments, the antibody is identified by screening for inhibition or blocking of Notch signaling. In some embodiments, the antibody is identified by screening for inhibition or blocking of VEGF activity (e.g., induction of HUVEC proliferation). In some embodiments, the antibody is identified by screening for modulation of angiogenesis.

In some embodiments, a method of generating an antibody to human VEGF comprises immunizing a mammal with a polypeptide comprising amino acids 27-232 of human VEGF. In some embodiments, a method of generating an antibody to human VEGF comprises immunizing a mammal with a polypeptide comprising at least a portion of amino acids 27-232 of human VEGF. In some embodiments, the method further comprises isolating antibodies or antibody-producing cells from the mammal. In some embodiments, a method of generating a monoclonal antibody which binds VEGF comprises: immunizing a mammal with a polypeptide comprising at least a portion of amino acids 27-232 of human VEGF, and isolating antibody-producing cells from the immunized mammal. In some embodiments, the method further comprises fusing the antibody-producing cells with cells of a myeloma cell line to form hybridoma cells. In some embodiments, the method further comprises selecting a hybridoma cell expressing an antibody that binds VEGF. In certain embodiments, the mammal is a mouse. In some embodiments, the antibody is selected using a polypeptide comprising at least a portion of amino acids 27-232 of human VEGF.

In some embodiments, a method of generating an antibody to human DLL4 comprises immunizing a mammal with a polypeptide comprising amino acids 27-529 of human DLL4. In some embodiments, a method of generating an antibody to human DLL4 comprises immunizing a mammal with a polypeptide comprising at least a portion of amino acids 27-529 of human DLL4. In some embodiments, a method of generating a monoclonal antibody which binds DLL4 comprises: immunizing a mammal with a polypeptide comprising at least a portion of amino acids 27-529 of human DLL4, and isolating antibody producing cells from the immunized mammal. In some embodiments, the method further comprises fusing the antibody-producing cells with cells of a myeloma cell line to form hybridoma cells. In some embodiments, the method further comprises selecting a hybridoma cell expressing an antibody that binds DLL4. In certain embodiments, the mammal is a mouse. In some embodiments, the antibody is selected using a polypeptide comprising at least a portion of amino acids 27-529 of human DLL4.

In some embodiments, a method of generating an antibody to human VEGF comprises screening an antibody-expressing library for antibodies that bind human VEGF. In some embodiments, a method of generating an antibody human DLL4 comprises screening an antibody-expressing library for antibodies that bind human DLL4. In some embodiments, a method of generating an antibody to human VEGF and/or human DLL4 comprises screening an antibody-expressing library for bispecific antibodies that bind human VEGF and human DLL4. In some embodiments, the antibody-expressing library is a phage library. In some embodiments, the screening comprises panning. In some embodiments, the antibody-expressing library (e.g., a phage library) is screened using at least a portion of amino acids 27-232 of human VEGF. In some embodiments, antibodies identified in the first screening, are screened again using at least a portion of amino acids 27-529 of human DLL4 to identify a bispecific antibody that binds VEGF and DLL4. In some embodiments, the antibody-expressing library (e.g., a phage library) is screened using at least a portion of amino acids 27-529 of human DLL4. In some embodiments, antibodies identified in the first screening, are screened again using at least a portion of amino acids 27-232 of human VEGF to identify a bispecific antibody that binds VEGF and DLL4. In some embodiments, the antibody identified in the screening is a VEGF antagonist. In some embodiments, the antibody identified in the screening inhibits biological activities induced by VEGF. In some embodiments, the antibody identified in the screening is a DLL4 antagonist. In some embodiments, the antibody identified in the screening inhibits Notch signaling induced by DLL4. In some embodiments, the antibody identified in the screening binds both human VEGF and mouse VEGF. In some embodiments, the antibody identified in the screening binds both human DLL4 and mouse DLL4.

In certain embodiments, the antibodies described herein are isolated. In certain embodiments, the antibodies described herein are substantially pure.

In some embodiments of the present invention, the VEGF/DLL4-binding agents are polypeptides. The polypeptides can be recombinant polypeptides, natural polypeptides, or synthetic polypeptides comprising an antibody, or fragment thereof, that bind VEGF and/or DLL4. It will be recognized in the art that some amino acid sequences of the binding agents described herein can be varied without significant effect on the structure or function of the protein. Thus, the invention further includes variations of the polypeptides which show substantial activity or which include regions of an antibody, or fragment thereof, against human VEGF and/or DLL4. In some embodiments, amino acid sequence variations of VEGF/DLL4-binding polypeptides include deletions, insertions, inversions, repeats, and/or other types of substitutions.

In some embodiments, the polypeptides described herein are isolated. In some embodiments, the polypeptides described herein are substantially pure.

The polypeptides, analogs and variants thereof, can be further modified to contain additional chemical moieties not normally part of the polypeptide. The derivatized moieties can improve or otherwise modulate the solubility, the biological half-life, and/or absorption of the polypeptide. The moieties can also reduce or eliminate undesirable side effects of the polypeptides and variants. An overview for chemical moieties can be found in *Remington: The Science and Practice of Pharmacy*, 21$^{st}$ *Edition*, 2005, University of the Sciences, Philadelphia, Pa.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., 1984, *PNAS,* 81:5662-5066 and U.S. Pat. No. 4,588,585.

In some embodiments, a DNA sequence encoding a polypeptide of interest may be constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, or fragments thereof, against human VEGF and/or DLL4. For example, recombinant expression vectors can be replicable DNA constructs which have synthetic or cDNA-derived DNA fragments encoding a polypeptide chain of a VEGF/DLL4-binding agent, such as an anti-VEGF antibody or an anti-DLL4 antibody, or fragment thereof, operatively linked to suitable transcriptional and/or translational regulatory elements derived from mammalian, microbial, viral, or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In other embodiments, in situations where recombinant protein is expressed without a leader or transport sequence, it can include an N-terminal methionine residue. This residue can optionally be subsequently cleaved from the expressed recombinant protein to provide a final product.

The choice of an expression control sequence and an expression vector depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9, and their derivatives, and wider host range plasmids, such as M13 and other filamentous single-stranded DNA phages.

The VEGF/DLL4-binding agents (e.g., polypeptides) of the present invention can be expressed from one or more vectors. For example, in some embodiments, one heavy chain polypeptide is expressed by one vector, a second heavy chain polypeptide is expressed by a second vector and a light chain polypeptide is expressed by a third vector. In some embodiments, a first heavy chain polypeptide and a light chain polypeptide is expressed by one vector and a second heavy chain polypeptide is expressed by a second vector. In some embodiments, two heavy chain polypeptides are expressed by one vector and a light chain polypeptide is expressed by a second vector. In some embodiments, three polypeptides are expressed from one vector. Thus, in some embodiments, a first heavy chain polypeptide, a second heavy chain polypeptide, and a light chain polypeptide are expressed by a single vector.

Suitable host cells for expression of a VEGF/DLL4-binding polypeptide or antibody (or a VEGF or DLL4 protein to use as an antigen) include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described below. Cell-free translation systems may also be employed. Appropriate cloning and expression vectors for use with bacterial, fungal, yeast, and mammalian cellular hosts are described in Pouwels et al., 1985, *Cloning Vectors: A Laboratory Manual*, Elsevier, New York, N.Y. Additional information regarding methods of protein production, including antibody production, can be found, e.g., in U.S. Patent Publication No. 2008/0187954; U.S. Pat. Nos. 6,413,746; 6,660,501; and International Patent Publication No. WO 04/009823.

Various mammalian or insect cell culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants of these cell lines. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. Expression of recombinant proteins in baculovirus also offers a robust method for producing correctly folded and biologically functional proteins. Baculovirus systems for production of heterologous proteins in insect cells are well-known to those of skill in the art (see, e.g., Luckow and Summers, 1988, *Bio/Technology*, 6:47).

Thus, the present invention provides cells comprising the VEGF/DLL4-binding agents described herein. In some embodiments, the cells produce the VEGF/DLL4-binding agents described herein. In certain embodiments, the cells produce an antibody. In some embodiments, the cells produce a VEGF-binding agent, such as an anti-VEGF antibody. In some embodiments, the cells produce a bispecific antibody that binds VEGF. In some embodiments, the cells produce a DLL4-binding agent, such as an anti-DLL4 antibody. In some embodiments, the cells produce a bispecific antibody that binds DLL4. In certain embodiments, the cells produce a bispecific VEGF/DLL4-binding agent, such as a bispecific antibody that binds VEGF and DLL4. In certain embodiments, the cells produce antibody 219R45. In certain embodiments, the cells produce antibody 21R79. In certain embodiments, the cells produce antibody 21R75. In certain embodiments, the cells produce antibody 21R83. In certain embodiments, the cells produce a bispecific antibody which comprises an antigen-binding site from antibody 219R45. In certain embodiments, the cells produce a bispecific antibody which comprises an antigen-binding site from antibody 21R79. In certain embodiments, the cells produce a bispecific antibody which comprises an antigen-binding site from antibody 21R75. In certain embodiments, the cells produce a bispecific antibody which comprises an antigen-binding site from antibody 21R83. In certain embodiments, the cells produce a bispecific antibody which comprises an antigen-binding site from antibody 219R45 and an antigen-binding site from antibody 21R79. In certain embodiments, the cells produce a bispecific antibody which comprises an antigen-binding site from antibody 219R45 and an antigen-binding site from antibody 21M18. In certain embodiments, the cells produce a bispecific antibody which comprises an antigen-binding site from antibody 219R45 and an antigen-binding site from antibody 21R75. In certain embodiments, the cells produce a bispecific antibody which comprises an antigen-binding site from antibody 219R45 and an antigen-binding site from antibody 21R83. In certain embodiments, the cells produce the bispecific antibody 219R45-MB-21M18. In certain embodiments, the cells produce the bispecific antibody 219R45-MB-21R79. In certain embodiments, the cells produce the bispecific antibody 219R45-MB-21R75. In certain embodiments, the cells produce the bispecific antibody 219R45-MB-21R83.

The proteins produced by a transformed host can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column. Affinity chromatography used for purifying immunoglobulins can include Protein A, Protein G, and Protein L chromatography. Isolated proteins can be physically characterized using such techniques as proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose, or other types commonly employed in protein purification. In some embodiments, a cation exchange step can be employed. Suitable cation exchangers include various insoluble matrices comprising sulfopropyl or carboxymethyl groups. In some embodiments, a hydroxyapatite media can be employed, including but not limited to, ceramic hydroxyapatite (CHT). In certain embodiments, one or more reverse-phase HPLC steps employing hydrophobic RP-HPLC media, e.g., silica gel having pendant methyl or other aliphatic groups, can be employed to further purify a recombinant protein (e.g., a VEGF/DLL4-binding agent). Some or all of the foregoing purification steps, in various combinations, can be employed to provide a homogeneous recombinant protein.

In some embodiments, heterodimeric proteins such as bispecific antibodies are purified according the any of the methods described herein. In some embodiments, anti-VEGF/anti-DLL4 bispecific antibodies are isolated and/or purified using at least one chromatography step. In some embodiments, the at least one chromatography step comprises affinity chromatography. In some embodiments, the at least one chromatography step further comprises anion exchange chromatography. In some embodiments, the isolated and/or purified antibody product comprises at least 90% heterodimeric antibody. In some embodiments, the isolated and/or purified antibody product comprises at least 95%, 96%, 97%, 98% or 99% heterodimeric antibody. In some embodiments, the isolated and/or purified antibody product comprises about 100% heterodimeric antibody.

In some embodiments, recombinant protein produced in bacterial culture can be isolated, for example, by initial extraction from cell pellets, followed by one or more concentration, salting-out, aqueous ion exchange, or size exclusion chromatography steps. HPLC can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425; 2008/0177048; and 2009/0187005.

In certain embodiments, the VEGF/DLL4-binding agent is a polypeptide that is not an antibody. A variety of methods for identifying and producing non-antibody polypeptides that bind with high affinity to a protein target are known in the art. See, e.g., Skerra, 2007, *Curr. Opin. Biotechnol.*, 18:295-304; Hosse et al., 2006, *Protein Science,* 15:14-27; Gill et al., 2006, *Curr. Opin. Biotechnol.*, 17:653-658; Nygren, 2008, *FEBS J.*, 275:2668-76; and Skerra, 2008, *FEBS J.*, 275:2677-83. In certain embodiments, phage or mammalian cell display technology may be used to produce and/or identify a VEGF/DLL4-binding polypeptide that is not an antibody. In certain embodiments, the polypeptide comprises a protein scaffold of a type selected from the group consisting of protein A, protein G, a lipocalin, a fibronectin domain, an ankyrin consensus repeat domain, and thioredoxin.

In certain embodiments, the VEGF/DLL4-binding agents or antibodies can be used in any one of a number of conjugated (i.e. an immunoconjugate or radioconjugate) or non-conjugated forms. In certain embodiments, the antibodies can be used in a non-conjugated form to harness the subject's natural defense mechanisms including complement-dependent cytotoxicity and antibody-dependent cellular toxicity to eliminate malignant or cancer cells.

In some embodiments, the VEGF/DLL4-binding agent (e.g., an antibody or polypeptide) is conjugated to a cytotoxic agent. In some embodiments, the cytotoxic agent is a chemotherapeutic agent including, but not limited to, methotrexate, adriamicin, doxorubicin, melphalan, mitomycin C, chlorambucil, daunorubicin or other intercalating agents. In some embodiments, the cytotoxic agent is an enzymatically active toxin of bacterial, fungal, plant, or animal origin, or fragments thereof, including, but not limited to, diphtheria A chain, non-binding active fragments of diphtheria toxin, exotoxin A chain, ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the cytotoxic agent is a radioisotope to produce a radioconjugate or a radioconjugated antibody. A variety of radionuclides are available for the production of radioconjugated antibodies including, but not limited to, $^{90}Y$, $^{125}I$, $^{131}I$, $^{123}I$, $^{111}In$, $^{131}In$, $^{105}Rh$, $^{153}Sm$, $^{67}Cu$, $^{67}Ga$, $^{166}H$, $^{177}Lu$, $^{186}Re$ and $^{212}Bi$. Conjugates of an antibody and one or more small molecule toxins, such as calicheamicins, maytansinoids, trichothecenes, and CC1065, and the derivatives of these toxins that have toxin activity, can also be used. Conjugates of an antibody and cytotoxic agent can be made using a variety of bifunctional protein-coupling agents including, but not limited to, N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2, 4-dinitrobenzene).

III. Polynucleotides

In certain embodiments, the invention encompasses polynucleotides comprising polynucleotides that encode a polypeptide (or a fragment of a polypeptide) that specifically binds VEGF, DLL4, both VEGF and DLL4. The term "polynucleotides that encode a polypeptide" encompasses a polynucleotide which includes only coding sequences for the polypeptide, as well as a polynucleotide which includes additional coding and/or non-coding sequences. For example, in some embodiments, the invention provides a polynucleotide comprising a polynucleotide sequence that encodes an antibody to human VEGF or encodes a fragment of such an antibody (e.g., a fragment comprising the antigen-binding site). In some embodiments, the invention provides a polynucleotide comprising a polynucleotide sequence that encodes an antibody to human DLL4 or encodes a fragment of such an antibody (e.g., a fragment comprising the antigen-binding site). The polynucleotides of the invention can be in the form of RNA or in the form of DNA. DNA includes cDNA, genomic DNA, and synthetic DNA; and can be double-stranded or single-stranded, and if single-stranded can be the coding strand or non-coding (anti-sense) strand.

In certain embodiments, the polynucleotide comprises a polynucleotide encoding a polypeptide comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:46, SEQ ID NO:47, SEQ ID NO:48, SEQ ID NO:49, SEQ ID NO:56, SEQ ID NO:57, SEQ ID NO:58, SEQ ID NO:62, SEQ ID NO:63, and SEQ ID NO:64. In certain embodiments, the polynucleotide comprises a polynucleotide encoding a polypeptide comprising a sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:48, SEQ ID NO:49, SEQ ID NO:56, SEQ ID NO:58, SEQ ID NO:62, and SEQ ID NO: 64. In some embodiments, the polynucleotide comprises a polynucleotide sequence selected from the group consisting of SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:50, SEQ ID NO:51, SEQ ID NO:52, SEQ ID NO:53, SEQ ID NO:54, SEQ ID NO:55, SEQ ID NO:60, SEQ ID NO:61, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78.

In certain embodiments, the polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide comprising a sequence selected from the group consisting of SEQ ID NO:29, SEQ ID NO:30, SEQ ID NO:31, SEQ ID NO:32, SEQ ID NO:33, SEQ ID NO:34, SEQ ID NO:52, SEQ ID NO:53, SEQ ID NO:55, SEQ ID NO:60, SEQ ID NO:61, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78. In certain embodiments, the polynucleotide comprises a polynucleotide having a nucleotide sequence at least about 80% identical, at least about 85% identical, at least about 90% identical, at least about 95% identical, and in some embodiments, at least about 96%, 97%, 98% or 99% identical to a polynucleotide comprising a sequence selected from the group consisting of SEQ ID NO:35, SEQ ID NO:36, SEQ ID NO:37, SEQ ID NO:38, SEQ ID NO:39, SEQ ID NO:40, SEQ ID NO:50, SEQ ID NO:51, SEQ ID NO:54, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78. Also provided is a polynucleotide that comprises a polynucleotide that hybridizes to SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:50, SEQ ID NO:51, SEQ ID NO:52, SEQ ID NO:53, SEQ ID NO:54, SEQ ID NO:55, SEQ ID NO:60, SEQ ID NO:61, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, and SEQ ID NO:78. In certain embodiments, the hybridization is under conditions of high stringency.

In certain embodiments, the polynucleotides comprise the coding sequence for the mature polypeptide fused in the same reading frame to a polynucleotide which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains.

In certain embodiments, the polynucleotides comprise the coding sequence for the mature polypeptide fused in the same reading frame to a marker sequence that allows, for example, for purification of the encoded polypeptide. For example, the marker sequence can be a hexa-histidine tag supplied by a pQE-9 vector to provide for purification of the mature polypeptide fused to the marker in the case of a bacterial host, or the marker sequence can be a hemagglutinin (HA) tag derived from the influenza hemagglutinin protein when a mammalian host (e.g., COS-7 cells) is used. In some embodiments, the marker sequence is a FLAG-tag, a peptide of sequence DYKDDDDK (SEQ ID NO:45) which can be used in conjunction with other affinity tags.

The present invention further relates to variants of the hereinabove described polynucleotides encoding, for example, fragments, analogs, and/or derivatives.

In certain embodiments, the present invention provides polynucleotides comprising polynucleotides having a nucleotide sequence at least about 80% identical, at least about 85% identical, at least about 90% identical, at least about 95% identical, and in some embodiments, at least about 96%, 97%, 98% or 99% identical to a polynucleotide encoding a polypeptide comprising a VEGF/DLL4-binding agent (e.g., an antibody), or fragment thereof, described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference nucleotide sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations which produce silent substitutions, additions, or deletions, but does not alter the properties or activities of the encoded polypeptide. In some embodiments, a polynucleotide variant comprises silent substitutions that results in no change to the amino acid sequence of the polypeptide (due to the degeneracy of the genetic code). Polynucleotide variants can be produced for a variety of reasons, for example, to optimize codon expression for a particular host (i.e., change codons in the human mRNA to those preferred by a bacterial host such as E. coli). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, at least one polynucleotide variant is produced (without changing the amino acid sequence of the encoded polypeptide) to increase production of a heteromultimeric molecule. In some embodiments, at least one polynucleotide variant is produced (without changing the amino acid sequence of the encoded polypeptide) to increase production of a bispecific antibody.

In certain embodiments, the polynucleotides are isolated. In certain embodiments, the polynucleotides are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule.

IV. Methods of Use and Pharmaceutical Compositions

The binding agents (including polypeptides and antibodies) of the invention that bind (e.g., specifically bind) VEGF and/or DLL4 are useful in a variety of applications including, but not limited to, therapeutic treatment methods, such as the treatment of cancer. In certain embodiments, the agents are useful for inhibiting VEGF activity, inhibiting DLL4-induced Notch signaling, inhibiting tumor growth, reducing tumor volume, reducing the frequency of cancer stem cells in a tumor, reducing the tumorigenicity of a tumor, modulating angiogenesis, and/or inhibiting angiogenesis. The methods of use may be in vitro, ex vivo, or in vivo. In certain embodiments, a VEGF/DLL4-binding agent is an antagonist of human VEGF. In certain embodiments, a VEGF/DLL4-binding agent is an antagonist of human DLL4. In certain embodiments, a VEGF/DLL4-binding agent is an antagonist of both VEGF and DLL4.

In certain embodiments, the VEGF/DLL4-binding agents are used in the treatment of a disease associated with angiogenesis, i.e. increased angiogenesis and/or aberrant angiogenesis. In certain embodiments, the disease is a disease dependent upon angiogenesis. In certain embodiments, the VEGF/DLL4-binding agents are used in the treatment of disorders characterized by increased levels of stem cells and/or progenitor cells.

The present invention provides methods for inhibiting growth of a tumor using the VEGF/DLL4-binding agents or antibodies described herein. In certain embodiments, the method of inhibiting growth of a tumor comprises contacting a tumor cell with a VEGF/DLL4-binding agent (e.g., antibody) in vitro. For example, an immortalized cell line or a cancer cell line is cultured in medium to which is added an anti-VEGF antibody, an anti-DLL4 antibody, or an anti-VEGF/anti-DLL4 bispecific antibody to inhibit tumor cell growth. In some embodiments, tumor cells are isolated from a patient sample such as, for example, a tissue biopsy, pleural effusion, or blood sample and cultured in medium to which is added a VEGF/DLL4-binding agent to inhibit tumor cell growth.

In some embodiments, the method of inhibiting growth of a tumor comprises contacting a tumor or tumor cells with a VEGF/DLL4-binding agent (e.g., antibody) in vivo. In certain embodiments, contacting a tumor or tumor cell with a VEGF/DLL4-binding agent is undertaken in an animal model. For example, an anti-VEGF antibody, an anti-DLL4 antibody, or an anti-VEGF/anti-DLL4 bispecific antibody may be administered to an immunocompromised host animal (e.g., NOD/SCID mice) which has a tumor xenograft. In some embodiments, tumor cells and/or cancer stem cells are isolated from a patient sample such as, for example, a tissue biopsy, pleural effusion, or blood sample and injected into an immunocompromised host animal (e.g., NOD/SCID mice) that is then administered a VEGF/DLL4-binding agent to inhibit tumor cell growth. In some embodiments, the VEGF/DLL4-binding agent is administered at the same time or shortly after introduction of tumorigenic cells into the animal to prevent tumor growth ("preventative model"). In some embodiments, the VEGF/DLL4-binding agent is administered as a therapeutic after tumors have grown to a specified size ("therapeutic model"). In certain embodiments, the VEGF/DLL4-binding agent is a bispecific antibody that specifically binds human VEGF and human DLL4.

In certain embodiments, the method of inhibiting growth of a tumor comprises administering to a subject a therapeutically effective amount of a VEGF/DLL4-binding agent. In certain embodiments, the subject is a human. In certain embodiments, the subject has a tumor or has had a tumor which was removed. In certain embodiments, the tumor comprises cancer stem cells. In certain embodiments, the frequency of cancer stem cells in the tumor is reduced by administration of the VEGF/DLL4-binding agent. The invention also provides a method of reducing the frequency of cancer stem cells in a tumor, comprising contacting the tumor with an effective amount of a VEGF/DLL4-binding agent (e.g., an anti-VEGF/anti-DLL4 bispecific antibody). In some embodiments, a method of reducing the frequency of cancer stem cells in a tumor in a subject, comprises administering to the subject a therapeutically effective amount of a VEGF/DLL4-binding agent.

In some embodiments, the tumor is a solid tumor. In certain embodiments, the tumor is a tumor selected from the group consisting of colorectal tumor, colon tumor, pancreatic tumor, lung tumor, ovarian tumor, liver tumor, breast tumor, kidney tumor, prostate tumor, gastrointestinal tumor, melanoma, cervical tumor, bladder tumor, glioblastoma, and head and neck tumor. In certain embodiments, the tumor is a colorectal tumor or a colon tumor. In certain embodiments, the tumor is an ovarian tumor. In some embodiments, the tumor is a lung tumor. In certain embodiments, the tumor is a pancreatic tumor. In certain embodiments, the tumor is a breast tumor.

The present invention further provides methods for treating cancer comprising administering a therapeutically effective amount of a VEGF/DLL4-binding agent to a subject. In some embodiments, the VEGF/DLL4-binding agent binds VEGF, and inhibits or reduces growth of the cancer. In some embodiments, the VEGF/DLL4-binding agent binds DLL4, and inhibits or reduces growth of the cancer. In some embodiments, the VEGF/DLL4-binding agent is a bispecific antibody that binds VEGF and DLL4, and inhibits or reduces growth of the cancer. In some embodiments, the VEGF/DLL4-binding agent binds VEGF, interferes with VEGF/VEGF receptor interactions, and inhibits or reduces growth of the cancer. In some embodiments, the VEGF/DLL4-binding agent binds DLL4, interferes with DLL4/Notch interactions, and inhibits or reduces growth of the cancer. In some embodiments, the VEGF/DLL4-binding agent binds both VEGF and DLL4, interferes with VEGF/VEGF receptor interactions and with DLL4/Notch interactions, and inhibits or reduces growth of the cancer. In some embodiments, the VEGF/DLL4-binding agent binds DLL4, and reduces the frequency of cancer stem cells in the cancer.

The present invention provides methods of treating cancer comprising administering a therapeutically effective amount of a VEGF/DLL4-binding agent to a subject (e.g., a subject in need of treatment). In certain embodiments, the subject is a human. In certain embodiments, the subject has a cancerous tumor. In certain embodiments, the subject has had a tumor removed.

The subject's cancer/tumor, may, in some embodiments, be refractory to certain treatment(s). As a non-limiting example, the subject's cancer (or tumor) may be chemorefractory. In certain embodiments, the subject's cancer may be resistant to anti-VEGF therapy or anti-DLL4 therapy, or both.

In certain embodiments, the cancer is a cancer selected from the group consisting of colorectal cancer, pancreatic cancer, lung cancer, ovarian cancer, liver cancer, breast cancer, kidney cancer, prostate cancer, gastrointestinal cancer, melanoma, cervical cancer, bladder cancer, glioblastoma, and head and neck cancer. In certain embodiments, the cancer is ovarian cancer. In certain embodiments, the cancer is colorectal cancer or colon cancer. In certain embodiments, the cancer is pancreatic cancer. In certain embodiments, the cancer is breast cancer. In certain embodiments, the cancer is prostate cancer. In certain embodiments, the cancer is lung cancer. In some embodiments, the cancer is a hematologic cancer such as leukemia or lymphoma. In some embodiments, the leukemia or lymphoma is a B-cell leukemia or lymphoma. In some embodiments, the leukemia or lymphoma is a T-cell leukemia or lymphoma. In some embodiments the hematologic cancer is acute myelogenous leukemia, Hodgkin lymphoma, non-Hodgkins's lymphoma, acute lymphocytic leukemia, hairy cell leukemia, chronic lymphocytic leukemia, multiple myeloma, cutaneous T-cell lymphoma, or T-cell acute lymphoblastic leukemia.

The invention also provides methods of treating a disease or disorder in a subject, wherein the disease or disorder is associated with angiogenesis. In some embodiments, the disease or disorder is associated with aberrant angiogenesis. In some embodiments, the disease or disorder is associated with increased angiogenesis. Thus, the present invention provides methods for modulating angiogenesis in a subject, comprising administering to the subject a therapeutically effective amount of any of the VEGF/DLL4-binding agents described herein. In some embodiments, the VEGF/DLL4-binding agent is an antibody that binds human VEGF. In some embodiments, the VEGF/DLL4-binding agent is an antibody that binds human DLL4. In some embodiments, the VEGF/DLL4-binding agent is a bispecific antibody that binds human VEGF. In some embodiments, the VEGF/DLL4-binding agent is a bispecific antibody that binds human DLL4. In some embodiments, the VEGF/DLL4-binding agent is a bispecific antibody that binds human VEGF and human DLL4.

Methods of treating a disease or disorder in a subject, wherein the disease or disorder is characterized by an increased level of stem cells and/or progenitor cells are further provided. In some embodiments, the treatment methods comprise administering a therapeutically effective amount of a VEGF/DLL4-binding agent, polypeptide, or antibody to the subject.

In certain embodiments of any of the methods described herein, the VEGF/DLL4-binding agent is a bispecific antibody that specifically binds human VEGF and human DLL4. In some embodiments, the bispecific antibody comprises a first antigen-binding site that specifically binds human VEGF and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises a first antigen-binding site that specifically binds human VEGF and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YIANYNRATNYNQKFKG (SEQ ID NO:14), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises a first antigen-binding site that specifically binds human VEGF and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YISSYN-GATNYNQKFKG (SEQ ID NO:15), and a heavy chain CDR3 comprising RDYDYDVGMDY (SEQ ID NO:16); and wherein both the first and second antigen-binding sites comprise a light chain CDR1 comprising RASESVDNYG-ISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises a first antigen-binding site that specifically binds human VEGF and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and second antigen-binding site which comprises a heavy chain CDR1 comprising TAYYIH (SEQ ID NO:13), a heavy chain CDR2 comprising YIAGYKDATNYNQKFKG (SEQ ID NO:59), and a heavy chain CDR3 comprising RDYDYDVGMDY (SEQ ID NO:16); and wherein both the first and second antigen-binding sites comprise a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22). In some embodiments, the bispecific antibody comprises a first antigen-binding site that specifically binds human VEGF and a second antigen-binding site that specifically binds human DLL4, wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19), and the second antigen-binding site comprises a heavy chain CDR1 comprising TAYYIH (SEQ ID NO:13), a heavy chain CDR2 comprising YISNYN-RATNYNQKFKG (SEQ ID NO:65), and a heavy chain CDR3 comprising RDYDYDVGMDY (SEQ ID NO:16); and wherein both the first and second antigen-binding sites comprise a light chain CDR1 comprising RASESVDNYG-ISFMK (SEQ ID NO:20), a light chain CDR2 comprising AASNQGS (SEQ ID NO:21), and a light chain CDR3 comprising QQSKEVPWTFGG (SEQ ID NO:22).

In certain embodiments of any of the methods described herein, the VEGF/DLL4 bispecific antibody comprises a first heavy chain variable region having at least about 80% sequence identity to SEQ ID NO:11, a second heavy chain variable region having at least about 80% sequence identity to SEQ ID NO:9, SEQ ID NO:10, SEQ ID NO:58, or SEQ ID NO:64, and a first and a light chain variable region having at least 80% sequence identity to SEQ ID NO:12. In some embodiments, the VEGF/DLL4 bispecific antibody comprises a first heavy chain variable region having at least about 80% sequence identity to SEQ ID NO:11, a second heavy chain variable region having at least about 80% sequence identity to SEQ ID NO:9, and a first and a second light chain variable region having at least 80% sequence identity to SEQ ID NO:12. In some embodiments, the VEGF/DLL4 bispecific antibody comprises a first heavy chain variable region having at least about 80% sequence identity to SEQ ID NO:11, a second heavy chain variable region having at least about 80% sequence identity to SEQ ID NO:10, and a first and a second light chain variable region having at least 80% sequence identity to SEQ ID NO:12. In some embodiments, the VEGF/DLL4 bispecific antibody comprises a first heavy chain variable region having at least about 80% sequence identity to SEQ ID NO:11, a second heavy chain variable region having at least about 80% sequence identity to SEQ ID NO:58, and a first and a second light chain variable region having at least 80% sequence identity to SEQ ID NO:12. In some embodiments, the VEGF/DLL4 bispecific antibody comprises a first heavy chain variable region having at least about 80% sequence identity to SEQ ID NO:11, a second heavy chain variable region having at least about 80% sequence identity to SEQ ID NO:64, and a first and a second light chain variable region having at least 80% sequence identity to SEQ ID NO:12.

In some embodiments of any of the methods described herein, the VEGF/DLL4-binding agent is an antibody. In some embodiments, the VEGF/DLL4-binding agent is an anti-VEGF antibody. In some embodiments, the anti-VEGF antibody is antibody 219R45. In some embodiments, the VEGF/DLL4-binding agent is an anti-DLL4 antibody. In some embodiments, the anti-DLL4 antibody is antibody 21R79. In some embodiments, the anti-DLL4 antibody is antibody 21R75. In some embodiments, the anti-DLL4 antibody is antibody 21R83. In some embodiments, the VEGF/DLL4-binding agent is a bispecific antibody comprising an antigen-binding site from antibody 219R45. In some embodiments, the VEGF/DLL4-binding agent is a bispecific antibody comprising an antigen-binding site from antibody 21R79. In some embodiments, the VEGF/DLL4-binding agent is a bispecific antibody comprising an antigen-binding site from antibody 21R75. In some embodiments, the VEGF/DLL4-binding agent is a bispecific antibody comprising an antigen-binding site from antibody 21R83. In some embodiments, the VEGF/DLL4-binding agent is a bispecific antibody comprising a first antigen-binding site from antibody 219R45 and a second antigen-binding site from antibody 21R79. In some embodiments, the VEGF/DLL4-binding agent is a bispecific antibody comprising a first antigen-binding site from antibody 219R45 and a second antigen-binding site from antibody 21M18. In some embodiments, the VEGF/DLL4-binding agent is a bispecific antibody comprising a first antigen-binding site from antibody 219R45 and a second antigen-binding site from antibody 21R75. In some embodiments, the VEGF/DLL4-binding agent is a bispecific antibody comprising a first antigen-binding site from antibody 219R45 and a second antigen-binding site from antibody 21R83. In some embodiments, the VEGF/DLL4-binding agent is the bispecific antibody 219R45-MB-21M18. In some embodiments, the VEGF/DLL4-binding agent is the bispecific antibody 219R45-MB-21R79. In some embodiments, the VEGF/DLL4-binding agent is the bispecific antibody 219R45-MB-21R75. In some embodiments, the VEGF/DLL4-binding agent is the bispecific antibody 219R45-MB-21R83.

The present invention further provides pharmaceutical compositions comprising the binding agents described herein. In certain embodiments, the pharmaceutical compositions further comprise a pharmaceutically acceptable vehicle. These pharmaceutical compositions find use in inhibiting tumor growth and/or treating cancer in a subject (e.g., a human patient).

In certain embodiments, the invention provides pharmaceutical compositions comprising bispecific antibodies, wherein at least about 90%, at least about 95%, at least about 98%, at least about 99% of the antibodies in the composition are bispecific antibodies or heterodimeric antibodies. In certain embodiments, the bispecific antibodies are IgG (e.g., IgG2 or IgG1) antibodies. In certain embodiments, less than about 10%, less than about 5%, less than about 2% or less than about 1% of the total antibodies in the compositions are monospecific antibodies or homodimeric antibodies. In certain embodiments, the antibodies in the composition are at least about 98% heterodimeric.

In certain embodiments, formulations are prepared for storage and use by combining a purified antibody or agent of the present invention with a pharmaceutically acceptable vehicle (e.g., a carrier or excipient). Suitable pharmaceutically acceptable vehicles include, but are not limited to, non-toxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, 21st Edition, 2005, University of the Sciences, Philadelphia, Pa.).

The pharmaceutical compositions of the present invention can be administered in any number of ways for either local or systemic treatment. Administration can be topical by epidermal or transdermal patches, ointments, lotions, creams, gels, drops, suppositories, sprays, liquids, and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present invention, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol and cellulose acetate.

The VEGF/DLL4-binding agents or antibodies described herein can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions as described in *Remington: The Science and Practice of Pharmacy*, 21st Edition, 2005, University of the Sciences in Philadelphia, Pa.

In certain embodiments, pharmaceutical formulations include a VEGF/DLL4-binding agent (e.g., an antibody) of the present invention complexed with liposomes. Methods to produce liposomes are known to those of skill in the art. For example, some liposomes can be generated by reverse phase evaporation with a lipid composition comprising phosphatidylcholine, cholesterol, and PEG-derivatized phosphatidylethanolamine (PEG-PE). Liposomes can be extruded through filters of defined pore size to yield liposomes with the desired diameter.

In certain embodiments, sustained-release preparations can be produced. Suitable examples of sustained-release preparations include semi-permeable matrices of solid hydrophobic polymers containing a VEGF/DLL4-binding agent (e.g., an antibody), where the matrices are in the form of shaped articles (e.g., films or microcapsules). Additional examples of sustained-release matrices include polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(-)-3-hydroxybutyric acid.

In certain embodiments, in addition to administering a VEGF/DLL4-binding agent (e.g., an antibody), the method or treatment further comprises administering at least one additional therapeutic agent. An additional therapeutic agent can be administered prior to, concurrently with, and/or subsequently to, administration of the VEGF/DLL4-binding agent. Pharmaceutical compositions comprising a VEGF/DLL4-binding agent and the additional therapeutic agent(s) are also provided. In some embodiments, the at least one additional therapeutic agent comprises 1, 2, 3, or more additional therapeutic agents.

Combination therapy with at least two therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of at least one of the agents. Combination therapy may decrease the likelihood that resistant cancer cells will develop. In some embodiments, combination therapy comprises a therapeutic agent that primarily affects (e.g., inhibits or kills) non-tumorigenic cells and a therapeutic agent that primarily affects (e.g., inhibits or kills) tumorigenic CSCs.

Useful classes of therapeutic agents include, for example, antitubulin agents, auristatins, DNA minor groove binders, DNA replication inhibitors, alkylating agents (e.g., platinum complexes such as cisplatin, mono(platinum), bis(platinum) and tri-nuclear platinum complexes and carboplatin), anthracyclines, antibiotics, antifolates, antimetabolites, chemotherapy sensitizers, duocarmycins, etoposides, fluorinated pyrimidines, ionophores, lexitropsins, nitrosoureas, platinols, purine antimetabolites, puromycins, radiation sensitizers, steroids, taxanes, topoisomerase inhibitors, vinca alkaloids, or the like. In certain embodiments, the second therapeutic agent is an alkylating agent, an antimetabolite, an antimitotic, a topoisomerase inhibitor, or an angiogenesis inhibitor. In some embodiments, the second therapeutic agent is a platinum complex such as carboplatin or cisplatin. In some embodiments, the additional therapeutic agent is a platinum complex in combination with a taxane.

Therapeutic agents that may be administered in combination with the VEGF/DLL4-binding agents include chemotherapeutic agents. Thus, in some embodiments, the method or treatment involves the administration of an anti-VEGF-binding agent or antibody of the present invention in combination with a chemotherapeutic agent or cocktail of multiple different chemotherapeutic agents. In some embodiments, the method or treatment involves the administration of an anti-DLL4-binding agent or antibody of the present invention in combination with a chemotherapeutic agent or cocktail of multiple different chemotherapeutic agents. In some embodiments, the method or treatment involves the administration of a bispecific antibody of the present invention that binds VEGF and DLL4 in combination with a chemotherapeutic agent or cocktail of multiple different chemotherapeutic agents.

Chemotherapeutic agents useful in the instant invention include, but are not limited to, alkylating agents such as thiotepa and cyclophosphamide (CYTOXAN); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytosine arabinoside, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenishers such as folinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2', 2"-trichlorotriethylamine; urethan; vindesine; dacarbazine; mannomustine; mitobronitol; mitolactol; pipobroman; gacytosine; arabinoside (Ara-C); taxoids, e.g. paclitaxel (TAXOL) and docetaxel (TAXOTERE); chlorambucil; gemcitabine; 6-thioguanine; mercaptopurine; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; ibandronate; CPT11; topoisomerase inhibitor RFS 2000; difluoromethylornithine (DMFO); retinoic acid; esperamicins; capecitabine (XELODA); and pharmaceutically acceptable salts, acids or derivatives of any of the above. Chemotherapeutic agents also include anti-hormonal agents that act to regulate or inhibit hormone action on tumors such as anti-estrogens including, for example, tamoxifen, raloxifene, aromatase inhibiting 4(5)-imidazoles, 4-hydroxytamoxifen, trioxifene, keoxifene, LY117018, onapristone, and toremifene (FARESTON); and anti-androgens such as flutamide, nilutamide, bicalutamide, leuprolide, and goserelin; and pharmaceutically acceptable salts, acids or derivatives of any of the above. In certain embodiments, the second therapeutic agent is cisplatin. In certain embodiments, the second therapeutic agent is carboplatin. In certain embodiments, the second therapeutic agent is paclitaxel.

In certain embodiments, the chemotherapeutic agent is a topoisomerase inhibitor. Topoisomerase inhibitors are chemotherapeutic agents that interfere with the action of a topoisomerase enzyme (e.g., topoisomerase I or II). Topoisomerase inhibitors include, but are not limited to, doxorubicin HCl, daunorubicin citrate, mitoxantrone HCl, actinomycin D, etoposide, topotecan HCl, teniposide (VM-26), and irinotecan, as well as pharmaceutically acceptable salts, acids, or derivatives of any of these. In certain embodiments, the second therapeutic agent is irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Anti-metabolites include, but are not limited to, gemcitabine, fluorouracil, capecitabine, methotrexate sodium, raltitrexed, pemetrexed, tegafur, cytosine arabinoside, thioguanine, 5-azacytidine, 6-mercaptopurine, azathioprine, 6-thioguanine, pentostatin, fludarabine phosphate, and cladribine, as well as pharmaceutically acceptable salts, acids, or derivatives of any of these. In certain embodiments, the second therapeutic agent is gemcitabine.

In certain embodiments, the chemotherapeutic agent is an antimitotic agent, including, but not limited to, agents that bind tubulin. In some embodiments, the agent is a taxane. In certain embodiments, the agent is paclitaxel or docetaxel, or a pharmaceutically acceptable salt, acid, or derivative of paclitaxel or docetaxel. In certain embodiments, the agent is paclitaxel (TAXOL), docetaxel (TAXOTERE), albumin-bound paclitaxel (ABRAXANE), DHA-paclitaxel, or PG-paclitaxel. In certain alternative embodiments, the antimitotic agent comprises a vinca alkaloid, such as vincristine, binblastine, vinorelbine, or vindesine, or pharmaceutically acceptable salts, acids, or derivatives thereof. In some embodiments, the antimitotic agent is an inhibitor of kinesin Eg5 or an inhibitor of a mitotic kinase such as Aurora A or Plk1. In certain embodiments, where the chemotherapeutic agent administered in combination with a VEGF/DLL4-binding agent is an anti-mitotic agent, the cancer or tumor being treated is breast cancer or a breast tumor.

In some embodiments, a second therapeutic agent comprises an agent such as a small molecule. For example, treatment can involve the combined administration of a VEGF/DLL4-binding agent (e.g. an antibody) of the present invention with a small molecule that acts as an inhibitor against additional tumor-associated proteins including, but not limited to, EGFR, ErbB2, HER2, and/or VEGF. In certain embodiments, the second therapeutic agent is a small molecule that inhibits a cancer stem cell pathway. In some embodiments, the second therapeutic agent is a small molecule inhibitor of the Notch pathway. In some embodiments, the second therapeutic agent is a small molecule inhibitor of the Wnt pathway. In some embodiments, the second therapeutic agent is a small molecule inhibitor of the BMP pathway. In some embodiments, the second therapeutic agent is a small molecule that inhibits β-catenin signaling.

In some embodiments, a second therapeutic agent comprises a biological molecule, such as an antibody. For example, treatment can involve the combined administration of a VEGF/DLL4-binding agent (e.g. an antibody) of the present invention with other antibodies against additional tumor-associated proteins including, but not limited to, antibodies that bind EGFR, ErbB2, HER2, and/or VEGF. In certain embodiments, the second therapeutic agent is an antibody that is an anti-cancer stem cell marker antibody. In some embodiments, the second therapeutic agent is an antibody that binds a component of the Notch pathway. In some embodiments, the second therapeutic agent is an antibody that binds a component of the Wnt pathway. In certain embodiments, the second therapeutic agent is an antibody that inhibits a cancer stem cell pathway. In some embodiments, the second therapeutic agent is an antibody inhibitor of the Notch pathway. In some embodiments, the second therapeutic agent is an antibody inhibitor of the Wnt pathway. In some embodiments, the second therapeutic agent is an antibody inhibitor of the BMP pathway. In some embodiments, the second therapeutic agent is an antibody that inhibits β-catenin signaling. In certain embodiments, the second therapeutic agent is an antibody that is an angiogenesis inhibitor or modulator (e.g., an anti-VEGF or VEGF receptor antibody). In certain embodiments, the second therapeutic agent is bevacizumab (AVASTIN), trastuzumab (HERCEPTIN), panitumumab (VECTIBIX), or cetuximab (ERBITUX). Combined administration can include co-administration, either in a single pharmaceutical formulation or using separate formulations, or consecutive administration in either order but generally within a time period such that all active agents can exert their biological activities simultaneously.

Furthermore, treatment with a VEGF/DLL4-binding agent described herein can include combination treatment with other biologic molecules, such as one or more cytokines (e.g., lymphokines, interleukins, tumor necrosis factors, and/or growth factors) or can be accompanied by surgical removal of tumors, cancer cells, or any other therapy deemed necessary by a treating physician.

In certain embodiments, the treatment involves the administration of a VEGF/DLL4-binding agent (e.g. an antibody) of the present invention in combination with radiation therapy. Treatment with a VEGF/DLL4-binding agent can occur prior to, concurrently with, or subsequent to administration of radiation therapy. Dosing schedules for such radiation therapy can be determined by the skilled medical practitioner.

It will be appreciated that the combination of a VEGF/DLL4-binding agent and an additional therapeutic agent may be administered in any order or concurrently. Treatment with a VEGF/DLL4-binding agent (e.g., an antibody) can occur prior to, concurrently with, or subsequent to administration of chemotherapies. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically by the skilled practitioner. Preparation and dosing schedules for such chemotherapy are also described in *The Chemotherapy Source Book*, 4$^{th}$ Edition, 2008, M. C. Perry, Editor, Lippincott, Williams & Wilkins, Philadelphia, Pa.

In some embodiments, the VEGF/DLL4-binding agent will be administered to patients that have previously undergone treatment with a second therapeutic agent. In certain other embodiments, the VEGF/DLL4-binding agent and a second therapeutic agent will be administered substantially simultaneously or concurrently. For example, a subject may be given a VEGF/DLL4-binding agent (e.g., an antibody) while undergoing a course of treatment with a second therapeutic agent (e.g., chemotherapy). In certain embodiments, a VEGF/DLL4-binding agent will be administered within 1 year of the treatment with a second therapeutic agent. In certain alternative embodiments, a VEGF/DLL4-binding agent will be administered within 10, 8, 6, 4, or 2 months of any treatment with a second therapeutic agent. In certain other embodiments, a VEGF/DLL4-binding agent will be administered within 4, 3, 2, or 1 weeks of any treatment with a second therapeutic agent. In some embodiments, a VEGF/DLL4-binding agent will be administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of an VEGF/DLL4-binding agent (e.g., an antibody) of the present invention depends on the type of disease to be treated, the severity and course of the disease, the responsiveness of the disease, whether the VEGF/DLL4-binding agent or antibody is administered for therapeutic or preventative purposes, previous therapy, the patient's clinical history, and so on, all at the discretion of the treating physician. The VEGF/DLL4-binding agent or antibody can be administered one time or as a series of treatments spread over several days to several months, or until a cure is effected or a diminution of the disease state is achieved (e.g., reduction in tumor size). Optimal dosing schedules can be calculated from measurements of drug accumulation in the body of the patient and will vary depending on the relative potency of an individual antibody or agent. The administering physician can determine optimum dosages, dosing methodologies, and repetition rates. In certain embodiments, dosage of a VEGF/DLL4-binding agent or antibody is from about 0.01 μg to about 100 mg/kg of body weight, from about 0.1 µg to about 100 mg/kg of body weight, from about 1 µg to about 100 mg/kg of body weight, from about 1 mg to about 100 mg/kg of body weight, about 1 mg to about 80 mg/kg of body weight from about 10 mg to about 100 mg/kg of body weight, from about 10 mg to about 75 mg/kg of body weight, or from about 10 mg to about 50 mg/kg of body weight. In certain embodiments, the dosage of the antibody or other VEGF/DLL4-binding agent is from about 0.1 mg to about 20 mg/kg of body weight. In certain embodiments, dosage can be given once or more daily, weekly, monthly, or yearly. In certain embodiments, the antibody or other VEGF/DLL4-binding agent is given once every week, once every two weeks, once every three weeks, or once every month.

In some embodiments, a VEGF/DLL4-binding agent (e.g., an antibody) may be administered at an initial higher "loading" dose, followed by one or more lower doses. In some embodiments, the frequency of administration may also change. In some embodiments, a dosing regimen may comprise administering an initial dose, followed by additional doses (or "maintenance" doses) once a week, once every two weeks, once every three weeks, or once every month. For example, a dosing regimen may comprise administering an initial loading dose, followed by a weekly maintenance dose of, for example, one-half of the initial dose. Or a dosing regimen may comprise administering an initial loading dose, followed by maintenance doses of, for example one-half of the initial dose every other week. Or a dosing regimen may comprise administering three initial doses for 3 weeks, followed by maintenance doses of, for example, the same amount every other week. Or a dosing regimen may comprise administering an initial dose followed by additional doses every 3 weeks or once a month. The treating physician can estimate repetition rates for dosing based on measured residence times and concentrations of the drug in bodily fluids or tissues. The progress of therapy can be monitored by conventional techniques and assays.

As is known to those of skill in the art, administration of any therapeutic agent may lead to side effects and/or toxicities. In some cases, the side effects and/or toxicities are so severe as to preclude administration of the particular agent at a therapeutically effective dose. In some cases, drug therapy must be discontinued, and other agents may be tried. However, many agents in the same therapeutic class often display similar side effects and/or toxicities, meaning that the patient either has to stop therapy, or if possible, suffer from the unpleasant side effects associated with the therapeutic agent.

Side effects from therapeutic agents may include, but are not limited to, hives, skin rashes, itching, nausea, vomiting, decreased appetite, diarrhea, chills, fever, fatigue, muscle aches and pain, headaches, low blood pressure, high blood pressure, hypokalemia, low blood counts, bleeding, and cardiac problems.

Thus, one aspect of the present invention is directed to methods of treating cancer in a patient comprising administering an anti-VEGF/anti-DLL4 bispecific antibody using an intermittent dosing regimen, which may reduce side effects and/or toxicities associated with administration of the anti-VEGF/anti-DLL4 bispecific antibody. As used herein, "intermittent dosing" refers to a dosing regimen using a dosing interval of more than once a week, e.g., dosing once every 2 weeks, once every 3 weeks, once every 4 weeks, etc. In some embodiments, a method for treating cancer in a human patient comprises administering to the patient an effective dose of an anti-VEGF/anti-DLL4 bispecific antibody according to an intermittent dosing regimen. In some embodiments, a method for treating cancer in a human patient comprises administering to the patient an effective dose of an anti-VEGF/anti-DLL4 bispecific antibody according to an intermittent dosing regimen, and increasing the therapeutic index of the anti-VEGF/anti-DLL4 bispecific antibody. In some embodiments, the intermittent dosing regimen comprises administering an initial dose of an anti-VEGF/anti-DLL4 bispecific antibody to the patient, and administering subsequent doses of the anti-VEGF/anti-DLL4 bispecific antibody about once every 2 weeks. In some embodiments, the intermittent dosing regimen comprises administering an initial dose of an anti-VEGF/anti-DLL4 bispecific antibody to the patient, and administering subsequent doses of the anti-VEGF/anti-DLL4 bispecific antibody about once every 3 weeks. In some embodiments, the intermittent dosing regimen comprises administering an initial dose of an anti-VEGF/anti-DLL4 bispecific antibody to the patient, and administering subsequent doses of the anti-VEGF/anti-DLL4 bispecific antibody about once every 4 weeks.

In some embodiments, the subsequent doses in an intermittent dosing regimen are about the same amount or less than the initial dose. In other embodiments, the subsequent doses are a greater amount than the initial dose. As is known by those of skill in the art, doses used will vary depending on the clinical goals to be achieved. In some embodiments, the initial dose is about 0.25 mg/kg to about 20 mg/kg. In some embodiments, the initial dose is about 0.5, 1, 2, 3, 4, 5, 6, 7, 8, 9, 10, 11, 12, 13, 14, 15, 16, 17, 18, 19, or 20 mg/kg. In certain embodiments, the initial dose is about 0.5 mg/kg. In certain embodiments, the initial dose is about 1 mg/kg. In certain embodiments, the initial dose is about 2.5 mg/kg. In certain embodiments, the initial dose is about 5 mg/kg. In certain embodiments, the initial dose is about 7.5 mg/kg. In certain embodiments, the initial dose is about 10 mg/kg. In certain embodiments, the initial dose is about 12.5 mg/kg. In certain embodiments, the initial dose is about 15 mg/kg. In certain embodiments, the initial dose is about 20 mg/kg. In some embodiments, the subsequent doses are about 0.25 mg/kg to about 15 mg/kg. In certain embodiments, the subsequent doses are about 0.5, 1, 2, 3, 4, 5, 6, 7, 8, 9, 10, 11, 12, 13, 14 or 15 mg/kg. In certain embodiments, the subsequent doses are about 0.5 mg/kg. In certain embodiments, the subsequent doses are about 1 mg/kg. In certain embodiments, the subsequent doses are about 2.5 mg/kg. In certain embodiments, the subsequent doses are about 5 mg/kg. In some embodiments, the subsequent doses are about 7.5 mg/kg. In some embodiments, the subsequent doses are about 10 mg/kg. In some embodiments, the subsequent doses are about 12.5 mg/kg.

In some embodiments, the intermittent dosing regimen comprises: (a) administering to the patient an initial dose of an anti-VEGF/anti-DLL4 bispecific antibody of about 2.5 mg/kg and (b) administering subsequent doses of about 2.5 mg/kg once every 2 weeks. In some embodiments, the intermittent dosing regimen comprises: (a) administering to the patient an initial dose of an anti-VEGF/anti-DLL4 bispecific antibody of about 5 mg/kg and (b) administering subsequent doses of about 5 mg/kg once every 2 weeks. In some embodiments, the intermittent dosing regimen comprises: (a) administering to the patient an initial dose of an anti-VEGF/anti-DLL4 bispecific antibody of about 2.5 mg/kg and (b) administering subsequent doses of about 2.5 mg/kg once every 3 weeks. In some embodiments, the intermittent dosing regimen comprises: (a) administering to the patient an initial dose of an anti-VEGF/anti-DLL4 bispecific antibody of about 5 mg/kg and (b) administering subsequent doses of about 5 mg/kg once every 3 weeks. In some embodiments, the intermittent dosing regimen comprises: (a) administering to the patient an initial dose of an anti-VEGF/anti-DLL4 bispecific antibody of about 2.5 mg/kg and (b) administering subsequent doses of about 2.5 mg/kg once every 4 weeks. In some embodiments, the intermittent dosing regimen comprises: (a) administering to the patient an initial dose of an anti-VEGF/anti-DLL4 bispecific antibody of about 5 mg/kg and (b) administering subsequent doses of about 5 mg/kg once every 4 weeks. In certain embodiments, the initial dose and the maintenance doses are different, for example, the initial dose is about 5 mg/kg and the subsequent doses are about 2.5 mg/kg. In certain embodiments, an intermittent dosing regimen may comprise a loading dose, for example, the initial dose is about 20 mg/kg and the subsequent doses are about 2.5 mg/kg or about 5 mg/kg administered once every 2 weeks, once every 3 weeks, or once every 4 weeks.

Another aspect of the present invention is directed to methods for reducing toxicity of an anti-VEGF/anti-DLL4 bispecific antibody in a human patient comprises administering to the patient the anti-VEGF/anti-DLL4 bispecific antibody using an intermittent dosing regimen. Another aspect of the present invention is directed to methods for reducing side effects of an anti-VEGF/anti-DLL4 bispecific antibody in a human patient comprises administering to the patient the anti-VEGF/anti-DLL4 bispecific antibody using an intermittent dosing regimen. Another aspect of the present invention is directed to methods for increasing the therapeutic index of an anti-VEGF/anti-DLL4 bispecific antibody in a human patient comprises administering to the patient the anti-VEGF/anti-DLL4 bispecific antibody using an intermittent dosing regimen.

The choice of delivery method for the initial and subsequent doses is made according to the ability of the animal or human patient to tolerate introduction of the anti-VEGF/anti-DLL4 bispecific antibody into the body. Thus, in any of the aspects and/or embodiments described herein, the administration of the anti-VEGF/anti-DLL4 bispecific antibody may be by intravenous injection or intravenously. In some embodiments, the administration is by intravenous infusion. In any of the aspects and/or embodiments described herein, the administration of the anti-VEGF/anti-DLL4 bispecific antibody may be by a non-intravenous route.

V. Kits Comprising VEGF/DLL4-Binding Agents

The present invention provides kits that comprise the VEGF/DLL4-binding agents (e.g., antibodies) described herein and that can be used to perform the methods described herein. In certain embodiments, a kit comprises at least one purified antibody against VEGF and/or DLL4 in one or more containers. In some embodiments, the kits contain all of the components necessary and/or sufficient to perform a detection assay, including all controls, directions for performing assays, and any necessary software for analysis and presentation of results. One skilled in the art will readily recognize that the disclosed VEGF/DLL4-binding agents of the present invention can be readily incorporated into one of the established kit formats which are well known in the art.

Further provided are kits comprising a VEGF/DLL4-binding agent (e.g., an anti-VEGF/anti-DLL4 bispecific antibody), as well as at least one additional therapeutic agent. In certain embodiments, the second (or more) therapeutic agent is a chemotherapeutic agent. In certain embodiments, the second (or more) therapeutic agent is an angiogenesis inhibitor.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, may be practiced without departing from the scope of the present disclosure.

EXAMPLES

Example 1

Binding Affinities of Anti-VEGF/Anti-DLL4 Antibodies

The $K_D$s of parental antibodies anti-VEGF 219R45 (IgG format), anti-DLL4 21R79 (IgG format), anti-DLL4 21M18 (IgG format) and bispecific antibodies 219R45-MB-21M18 and 219R45-MB-21R79 were determined using a Biacore 2000 system from Biacore LifeSciences (GE Healthcare). Recombinant human DLL4-Fc or mouse DLL4-Fc proteins were immobilized on CM5 carboxyl chips using standard amine-based chemistry (NHS/EDC) and blocked with ethanolamine. Recombinant human $VEGF_{165}$ or mouse $VEGF_{165}$ were biotinylated and immobilized on streptavidin chips. The antibodies were serially diluted 2-fold from 100 nM to 0.78 nM in HBS-P (0.01M HEPES pH7.4, 0.15M NaCl, 0.005% v/v Polysorbate 20). For each antibody, all 8 dilutions were sequentially injected over a specific chip. Kinetic data were collected over time and were fit using the simultaneous global fit equation to yield affinity constants ($K_D$ values) for each bispecific antibody.

TABLE 3

| Antibody | hVEGF (nM) | mVEGF (nM) | hDLL4 (nM) | mDLL4 (nM) |
| --- | --- | --- | --- | --- |
| 219R45 | 0.67 | 22.9 | NB | NB |
| 21M18 | NB | NB | <0.1 | NB |
| 21R79 | NB | NB | <0.1 | NB |
| 219R45-MB-21M18 | 0.36 | 25.5 | 16 | NB |
| 219R45-MB-21R79 | 0.68 | 12.5 | 0.53 | NB |

As shown in Table 3, bispecific antibody 219R45-MB-21M18 had an affinity constant ($K_D$) for human VEGF of 0.36 nM and a $K_D$ for human DLL4 of 16 nM. Bispecific antibody 219R45-MB-21R79 had a $K_D$ for human VEGF of 0.68 nM and a $K_D$ for human DLL4 of 0.53 nM. Both bispecific antibodies demonstrated weaker binding to mouse VEGF as compared to human VEGF and neither antibody bound mouse DLL4. Thus, both bispecific antibodies demonstrated similar binding affinity to human VEGF and 219R45-MB-21R79 demonstrated approximately 30-fold stronger binding to human DLL4 than 219R45-MB-21M18. Furthermore, bispecific antibody 219R45-MB-21R79 had a similar binding affinity to human VEGF despite the fact the bispecific antibody is monovalent for VEGF as compared to the bivalent parental antibody.

Several additional anti-DLL4 antibodies were identified that had binding affinities intermediate to the $K_D$s of 21M18 and 21R79. Two of these anti-DLL4 antibodies were used to produce anti-VEGF/anti-DLL4 bispecific antibodies 219R45-MB-21R75 and 219R45-MB-21R83. Using the Biacore 2000 system as described above, the $K_D$s of the bispecific antibodies 219R45-MB-21R75 and 219R45-MB- 21R83 to human DLL4 were determined. A comparison of the binding affinity to human DLL4 of these four anti-VEGF/anti-DLL4 bispecific antibodies is shown in Table 4.

The CDRs for anti-VEGF/anti-DLL4 bispecific antibodies 219R45-MB-21M18, 219R45-MB-21R79, 219R45-MB-21R75, and 219R45-MB-21R83 are shown in FIG. 1A. The heavy chain and light chain variable region SEQ ID NOs are shown in FIG. 1B and the heavy chain and light chain SEQ ID NOs (with and without signal sequence) are shown in FIG. 1C.

Anti-VEGF/anti-DLL4 bispecific antibody 219R45-MB-21M18 comprises a (a) heavy chain encoded by the DNA comprising SEQ ID NO:75 deposited with American Type Culture Collection (ATCC), 10801 University Boulevard, Manassas, Va., USA, under the conditions of the Budapest Treaty on Sep. 21, 2012 and assigned designation number PTA-13233, (b) a heavy chain encoded by the DNA comprising SEQ ID NO:33 deposited with ATCC under the conditions of the Budapest Treaty on Sep. 21, 2012 and assigned designation number PTA-13236, and (c) a light chain encoded by the DNA comprising SEQ ID NO:34 deposited with ATCC under the conditions of the Budapest Treaty on Sep. 21, 2012 and assigned designation number PTA-13235.

Anti-VEGF/anti-DLL4 bispecific antibody 219R45-MB-21R79 comprises a (a) heavy chain encoded by the DNA comprising SEQ ID NO:31 deposited with ATCC under the conditions of the Budapest Treaty on Sep. 21, 2012 and assigned designation number PTA-13232, (b) a heavy chain encoded by the DNA comprising SEQ ID NO:33 deposited with ATCC under the conditions of the Budapest Treaty on Sep. 21, 2012 and assigned designation number PTA-13236, and (c) a light chain encoded by the DNA comprising SEQ ID NO:34 deposited with ATCC under the conditions of the Budapest Treaty on Sep. 21, 2012 and assigned designation number PTA-13235.

Anti-VEGF/anti-DLL4 bispecific antibody 219R45-MB-21R83 comprises (a) a heavy chain encoded by the DNA comprising SEQ ID NO:72 deposited with ATCC under the conditions of the Budapest Treaty on Oct. 24, 2012 and assigned designation number PTA-13278, (b) a heavy chain encoded by the DNA comprising SEQ ID NO:33 deposited with ATCC under the conditions of the Budapest Treaty on Sep. 21, 2012 and assigned designation number PTA-13236, and (c) a light chain encoded by the DNA comprising SEQ ID NO:34 deposited with ATCC under the conditions of the Budapest Treaty on Sep. 21, 2012 and assigned designation number PTA-13235.

Anti-VEGF/anti-DLL4 bispecific antibody 219R45-MB-21R75 comprises (a) a heavy chain encoded by the DNA comprising SEQ ID NO:74 deposited with ATCC under the conditions of the Budapest Treaty on Sep. 21, 2012 and assigned designation number PTA-13234, (b) a heavy chain encoded by the DNA comprising SEQ ID NO:33 deposited with ATCC under the conditions of the Budapest Treaty on Sep. 21, 2012 and assigned designation number PTA-13236, and (c) a light chain encoded by the DNA comprising SEQ ID NO:34 deposited with ATCC under the conditions of the Budapest Treaty on Sep. 21, 2012 and assigned designation number PTA-13235.

TABLE 4

| Antibody | Heavy chain CDR2 | hDLL4 (nM) |
| --- | --- | --- |
| 219R45-MB-21M18 | YISSYNGATNYNQKFKG (SEQ ID NO: 15) | 16.00 |
| 219R45-MB-21R79 | YIANYNRATNYNQKFKG (SEQ ID NO: 14) | 0.53 |
| 219R45-MB-21R75 | YIAGYKDATNYNQKFKG (SEQ ID NO: 59) | 5.10 |
| 219R45-MB-21R83 | YISNYNRATNYNQKFKG (SEQ ID NO: 65) | 1.30 |

Example 2

HTRF Assay for Simultaneous Binding of Bispecific Antibodies to Human VEGF and Human DLL4

To characterize the binding capabilities of certain antibodies and/or antibody mixtures to both VEGF and DLL4, homogeneous time resolved fluorescence (HTRF) assays were performed. Antibodies tested were anti-VEGF/anti-DLL4 bispecific antibodies 219R45-MB-21M18 and 219R45-MB-21R79, parental antibodies 219R45 (anti-VEGF), 21M18 (anti-DLL4), 21R79 (anti-DLL4), a combination of 219R45 and 21M18, or a combination of 219R45 and 21R79. The antibodies or antibody mixtures were serially diluted 2-fold from 3000 nM to 2.9 nM in binding buffer (1× PBS, 0.1% gelatin, 0.1% Polysorbate 20, 400 mM potassium fluoride) and placed in a white 96-well plate. An equal volume of solution containing 4 µg/ml of d2-labeled hDLL4-Fc and 21.4 ng/ml Europium crypate-labeled hVEGF$_{165}$ was added to each well for a final volume of 100 µl (final concentrations of acceptor and donor fluorophores were 2 µg/ml and 10.7 ng/ml, respectively). The assay plates were incubated for 2 hours to overnight and read on a SpectraMax M5e Microplate reader (Molecular Devices, Sunnyvale, Calif.) at an excitation wavelength of 314 nm.

As shown in FIG. 2, anti-VEGF/anti-DLL4 bispecific antibodies 219R45-MB-21M18 and 219R45-MB-21R79, were able to bind both hVEGF and hDLL4 simultaneously. Importantly, neither of the combinations of the parental antibodies (i.e., 219R45 and 21M18 or 219R45 and 21R79) was able to bind VEGF and DLL4 simultaneously. These results clearly demonstrate that the anti-VEGF/anti-DLL4 bispecific antibodies 219R45-MB-21M18 and 219R45-MB-21R79 are capable of functioning differently than just a mixture of the two individual antibodies.

Example 3

Inhibition of HUVEC Proliferation by Anti-VEGF/Anti-DLL4 Bispecific Antibodies

HUVEC cells were obtained from Lonza (Walkersville, Md.) and cultured in growth media (M199, 10% heat-inactivated FBS (HI-FBS), 50 µg/ml EGS, 1X heparin, 1 mM L-glutamine). For the HUVEC proliferation assay, a 96-well plate was pre-coated with 50 µl of 10 µg/ml rat tail collagen type I solution (collagen I in 0.02N acetic acid) and incubated at 4° C. overnight. After incubation, the plate was thoroughly aspirated to remove unbound collagen I solution and washed once with 200 µl DPBS. The HUVEC cells were removed from the surface of the growth flasks using an endothelial cell subclone reagent and centrifuged at 1200 rpm for 5 minutes at 4° C. The cells were resuspended in starvation/assay medium (M199 and 2% HI-FBS, 1× heparin, 5 U/ml heparin-glutamine) at a density of $10^5$ cells/ml. The cells were seeded into the collagen-coated assay plate at 5000 cells/well, 50 ul/well. The cells were incubated for 3 hours at 37° C., washed one time, refed with 100 ul assay media, and incubated overnight at 37° C. The next day, bispecific antibodies 219R45-MB-21M18, 219R45-MB-21R79, parental antibody 219R45, or control antibody LZ1 were prepared in a mixture with human VEGF (R&D Biosystems, Minneapolis, Minn.). The antibodies were serially diluted 5-fold from 2004 to 0.25 nM in assay buffer in combination with hVEGF (final concentration 5 ng/ml). The mixture was pre-incubated at 37° C. for 2 hours. The medium was removed from the assay plate, and 100 µl of the antibody/hVEGF mixture was added to each well. After 3-4 days incubation, medium was removed and a fresh aliquot of the antibody/hVEGF mixture was added to each well and allowed to incubate for another 4 days. On day 7, 20 µl of Alamar Blue reagent (Invitrogen, Carlsbad, Calif.) was added to each well and incubated at 37° C. for 5-6 hours. The plate was read with a SpectraMax M5e Microplate reader (Molecular Devices, Sunnyvale CA) using a excitation wavelength of 539 nm and an emission wavelength of 590 nm.

As shown in FIG. 3, anti-VEGF/anti-DLL4 bispecific antibodies 219R45-MB-21M18 and 219R45-MB-21R79, as well as parental anti-VEGF antibody 219R45 inhibited HUVEC proliferation. These results demonstrated that the bispecific antibodies were capable of inhibiting VEGF-induced proliferation of HUVEC cells.

Example 4

Inhibition of DLL4-Induced Notch Signaling by Bispecific Antibodies

Human PC3 cells were transfected with an expression vector encoding a full-length human Notch2 receptor and a firefly luciferase reporter vector (8× CBF-luciferase reporter) that is responsive to Notch signaling. The cells were also transfected with a Renilla luciferase reporter (Promega, Madison, Wis.) as an internal control for transfection efficiency. Purified human DLL4 protein was coated onto 96-well plates at 100 ng/well and Notch2-expressing PC3-luc cells were added to the wells. Anti-VEGF/anti-DLL4 bispecific antibodies 219R45-MB-21M18, 219R45-MB-21R79, parental anti-DLL4 antibodies 21M18, 21R79 or a control antibody LZ1 were serially diluted 5-fold from 20 ug/ml to 0.064 ug/ml, added to the appropriate wells, and incubated overnight. Luciferase activity was determined using a dual luciferase assay kit (Promega, Madison, Wis.) with firefly luciferase activity normalized to Renilla luciferase activity.

As shown in FIG. 4, anti-VEGF/anti-DLL4 bispecific antibody 219R45-MB-21R79 and parental anti-DLL4 antibodies 21M18 and 21R79 inhibited DLL4-induced Notch signaling. Bispecific antibody 219R45-MB-21M18 inhibited DLL4-induced Notch signaling only at high antibody concentrations. These results demonstrated that bispecific antibody 219R45-MB-21R79, and to a lesser extent bispecific antibody 219R45-MB-21M18, were capable of inhibiting DLL4-induced Notch signaling. Thus, in combination with the results presented in Example 3, the anti-VEGF/anti-DLL4 bispecific antibodies 219R45-MB-21R79 and 219R45-MB-21M18 have demonstrated the ability to inhibit both VEGF-induced and DLL4-induced signaling and/or proliferation functions.

Example 5

Inhibition of Tumor Growth In Vivo by a Bispecific Antibody in a Human Skin Graft Model A human skin graft model has been reported which comprises a human skin graft and human tumor cells. A human skin graft is established and then human tumor cells are implanted into the skin graft, allowing the tumor cells to grow in an environment with human stroma and vasculature (Tahtis et al., 2003, Mol. Cancer Ther. 2:229-737). Human skin samples were obtained from neonatal foreskin tissue and grafted onto the lateral flank of NOD-SCID mice. After establishment of the skin graft, luciferase-labeled OMP-C8 colon tumor cells (20,000 cells) were injected intradermally into the human skin. Tumor growth was monitored by bioluminescence imaging using an IVIS imaging system (Caliper Life Sciences, Mountain View, Calif.). Tumors were allowed to grow until they reached $1.2 \times 10^6$ photons per second. Tumor-bearing mice (n=6 mice/group) were randomized and treated with control Ab, anti-hDLL4 antibody 21M18, anti-VEGF antibody bevacizumab, or anti-VEGF/anti-DLL4 bispecific antibody 219R45-MB-21M18. Animals were treated once a week and antibodies were administered intraperitoneally at a dose of 25 mg/kg. Tumor growth was monitored by bioluminescence imaging on the indicated days.

As shown in FIG. 5, both anti-hDLL4 antibody 21M18 and anti-VEGF antibody bevacizumab inhibited tumor growth in this human skin graft/human tumor model. Furthermore, bispecific anti-VEGF/anti-DLL4 bispecific antibody 219R45-MB-21M18 was more effective than either the anti-DLL4 antibody or the anti-VEGF antibody alone. These data demonstrate the utility of simultaneously targeting DLL4 and VEGF with a bispecific antibody.

Example 6

Tumorigenicity of OMP-PN8 Pancreatic Tumor Cells After Treatment with Anti-VEGF/Anti-DLL4 Bispecific Antibodies Mice bearing OMP-PN8 pancreatic tumors were treated with control antibody (15 mg/kg), anti-hDLL4 antibody 21M18 (15 mg/kg), anti-VEGF antibody bevacizumab (15 mg/kg), or anti-VEGF/anti-DLL4 bispecific antibodies 219R45-MB-21M18 or 219R45-MB-21R79 (30 mg/kg) with or without gemcitabine (70 mg/kg). Following four weeks of treatment, tumors were harvested, processed to single cell suspensions and the human tumor cells were purified by immunomagnetic depletion of murine cells. 90 human tumor cells from each treatment group were transferred to a new cohort of mice (n=10 mice/group). Tumors were allowed to grow for 55 days without any treatment and tumor volumes were measured with electronic calipers.

FIG. 6 shows the tumor volume from the individual mice in each group. Cells isolated from mice treated with anti-hDLL4 antibody 21M18 had greatly decreased tumorigenicity, 5 out of 10 mice had tumors, as compared to cells isolated from mice treated with control antibody where 9 out of 10 mice had tumors. The reduction in tumor growth frequency indicates a reduction in cancer stem cell frequency. In contrast, bevacizumab treatment resulted in no reduction of tumor growth frequency, 10 out of 10 mice had tumors. Similar to bevacizumab, treatment with gemcitabine as a single agent had no effect on tumor growth frequency as 10 out of 10 mice had tumors. The anti-VEGF/anti-DLL4 bispecific antibodies 219R45-MB-21M18 and 219R45-MB-21R79 both reduced tumor growth frequency (5 out of 10 mice had tumors and 4 out of 10 mice had tumors, respectively). Combination treatment with gemcitabine appeared to have no effect on tumor growth frequency. These data indicate that targeting DLL4 reduces cancer stem cell frequency while targeting VEGF alone does not. Importantly, these data indicate that the anti-CSC activity of the anti-DLL4 antibody is retained in a bispecific antibody.

Example 7

Bispecific Antibody ELISA

VEGF (ATGEN, South Korea) was coated onto Nunc maxisorb plates at 2 ug/ml (100 µl/well) and incubated overnight at 2-8° C. Bispecific antibodies 219R45-MB-21M18, 219R45-MB-21R79, 219R45-MB-21R75, and 219R45-MB-21R83 were diluted in blocking buffer (1× PBS, 0.1% gelatin, 0.1% Polysorbate-20, pH 7.4) containing 2 µg/ml biotin-DLL4-hFc. The antibodies were serially diluted 3-fold from 500 ng/ml to 0.008 ng/ml. The antibody samples were incubated for 2 hours in blocking buffer containing the biotin-DLL4-hFc. After incubation, the antibody samples were transferred to the VEGF-coated assay plate (100 ul/well) and incubated for 2 hours. Streptavidin-HRP (Jackson ImmunoResearch, West Grove, Pa.) was added to each well and incubated for 1 hr. TMB substrate was added to the wells with a 10 minute color development and the reaction was stopped with 2M sulfuric acid. Absorbance was read at 450-650 nm and the data analyzed using the 4-parameter fit within the Softmax Pro analysis program (Molecular Devices, Sunnyvale, Calif.).

FIG. 7 shows the titration curves of bispecific antibodies 219R45-MB-21M18 (open circles), 219R45-MB-21R79 (open squares), 219R45-MB-21R75 (open triangles), and 219R45-MB-21R83 (open diamonds) in comparison to a reference anti-VEGF/anti-DLL4 bispecific antibody (solid circles). Relative potencies for the bispecific antibodies as compared to the reference bispecific antibody are shown in Table 5.

TABLE 5

| Antibody | Relative Potency (%) |
| --- | --- |
| 219R45-MB-21M18 | 67 |
| 219R45-MB-21R79 | 501 |
| 219R45-MB-21R75 | 422 |
| 219R45-MB-21R83 | 222 |

Bispecific antibody 219R45-MB-21R79 was the most potent, about 7-fold more potent than 219R45-MB-21M18, which reflected the higher affinity of the 21R79 antigen-binding site.

Example 8

Bispecific Antibody Production

Bispecific antibodies were produced using a GS-CHO cell line. CHOK1SV cells (Lonza Biologics) were transfected via electroporation with the gene(s) of interest coupled with glutamine synthetase (GS) as the selectable marker. Transfectants and subclones were screened for antibody productivity and the high producers were selected for scaled-up production. Cells were grown using a fed-batch process and fed-batch bioreactors. Accumulated antibody in harvested cell culture fluid (HCCF) was isolated and purified using chromatography techniques.

Bispecific antibody cell lines 219R45-MB-21M18.010.017 and 219R45-MB-21R79.017.003 were cultured in 5 L stirred tank bioreactors for 14 days. Cell line 219R45-MB-21M18.010.017 produced a final antibody titer of 3.0 g/L and cell line 219R45-MB-21R79.017.003 produced a final antibody titer of 0.8 g/L. Cell lines 219R45-MB-21R75.101 and 219R45-MB-21R83.113 were cultured in 25 L WAVE bioreactor systems (GE Healthcare) using a fed-batch process that achieved final antibody titers of 0.4 g/L. Bispecific antibody cell lines 219R45-MB-21M18AG.138.007, 219R45-MB-21M18AG.038.009, 219R45-MB-21M18AG.142.002, 219R45-MB-21R79AG.072.014 and 219R45-MB-21R83AG.129.003 were cultured in 5 L stirred tank bioreactors for 14-15 days. Cell line 219R45-MB-21M18AG.138.007 produced a final antibody titer of 1.0 g/L after 14 days. Cell line 219R45-MB-21M18AG.038.009 produced a final antibody titer of 1.6 g/L after 14 days. Cell line 219R45-MB-21M18AG.142.002 produced a final antibody titer of 2.6 g/L after 14 days. Cell line 219R45-MB-21R79AG.072.014 produced a final antibody titer of 2.1 g/L after 15 days. Cell line 219R45-MB-21M18AG.038.009 produced a final antibody titer of 2.4 g/L after 15 days. Culture fluid was harvested by filtration from each of these four cell lines and subjected to Protein A affinity chromatography. The Protein A column was washed with a series of buffers and the antibodies were eluted using a low pH elution buffer. Initial characterization of the purity of the bispecific antibodies was performed using size exclusion chromatography (SEC-HPLC) and isoelectric focusing (IEF).

Size exclusion chromatography (SEC) was used to determine the purity of the antibody product. SEC is a well known chromatographic method in which molecules (e.g., antibodies) in solution are separated by their size. SEC may be used to distinguish an antibody product from aggregate and/or impurities, and to determine the percentage of the antibody product as compared to the total mixture. As used herein, SEC does not distinguish between a homomeric antibody and a heterodimeric bispecific antibody.

Imaged capillary isoelectric focusing (icIEF) was used to determine identity and purity of the bispecific antibody heterodimers. Using icIEF, the charge isoforms of an antibody are separated according to their pI and the result is a "fingerprint" of the antibody's charge distribution. The icIEF method can also serve as a determination of purity by separating the bispecific antibody heterodimers by their distinct pI from any homodimer products or impurities.

Bispecific antibody samples were analyzed by icIEF on a ProteinSimple ICE280 instrument (ProteinSimple, Santa Clara, Calif.). For this analysis, a protein mixture is introduced into a capillary, high voltage is applied across the capillary and ampholytes establish a linear pH gradient along the length of the capillary. Under the influence of the electric field, the pI markers and the protein mixture both migrate the length of the capillary until a pH value is reached where the net charge is zero. Once focused, the ICE280 instrument uses whole-column imaging detection with a 280-nm UV camera to monitor the pattern of protein isoforms within the capillary. The resulting electropherogram is calibrated using internal pI markers and integrated to establish the respective percentage areas of the different charged isoforms of the protein mixture. The charge profiles from several anti-VEGF/anti-DLL4 bispecific antibodies are shown in FIG. 8. For this experiment, Protein A eluates were diluted with MilliQ water to a concentration of 6.6 mg/ml. A total of 18 µl of the sample was mixed with 100 µL of 8M urea, 70 µl of 0.5% methylcellulose, 8 µL of 3-10 Pharmalyte, 2 µl of high pI marker and 2 µl of low pI marker to a final volume of 200 µl. Table 6 shows the percentage of antibody product from cell lines 219R45-MB-21M18.010.017, 219R45-MB-21R79.017.002, 219R45-MB-21R75.101, 219R45-MB-21R83.113, 219R45-MB- 21M18.138.007, 219R45-MB-21M18AG.038.009, 219R45-MB-21M18AG.142.002, 219R45-MB-21R79AG.072.014, and 219R45-MB-21R83AG.129.003 after Protein A affinity chromatography as determined by SEC-HPLC. Table 6 also shows the percentage of heterodimeric antibodies from cell lines 219R45-MB-21M18.010.017, 219R45-MB-21R79.017.002, 219R45-MB-21R75.101, 219R45-MB-21R83.113, 219R45-MB-21M18.138.007, 219R45-MB-21M18AG.038.009, 219R45-MB-21M18AG.142.002, 219R45-MB-21R79AG.072.014, and 219R45-MB-21R83AG.129.003 after Protein A affinity chromatography as analyzed by icIEF.

TABLE 6

| Cell Line | Antibody Titer (g/L) | Purity by SEC (%) | Purity by IEF (% heterodimer) |
| --- | --- | --- | --- |
| 219R45-MB-21M18.010.017 | 3.0 | 73.9 | 47.2 |
| 219R45-MB-21R79.017.002 | 0.8 | 79.3 | 72.5 |
| 219R45-MB-21R75.101 | 0.4 | 91.2 | 84.9 |
| 219R45-MB-21R83.113 | 0.4 | 91.8 | 91.4 |
| 219R45-MB-21M18.138.007 | 1.0 | 92.6 | 95.8 |
| 219R45-MB-21M18AG.038.009 | 1.6 | 89.6 | 89.0 |
| 219R45-MB-21M18AG.142.002 | 2.6 | 91.2 | 84.6 |
| 219R45-MB-21R79AG.072.014 | 2.1 | 87.8 | 84.9 |
| 219R45-MB-21R83AG.129.003 | 2.4 | 89.4 | 90.5 |

The purity of the bispecific antibody product can be increased further by additional chromatography steps. After Protein A affinity chromatography, the eluate fraction was held at a low pH for no less than 60 minutes at room temperature for viral inactivation. The antibody solution (Protein A column eluate, pH adjusted) was loaded onto a strong anion-exchange column. Product- and process-related impurities bound to the anion exchange chromatography resin and the flow-through fraction (antibody product) was collected. In some cases, purity was further improved by use of a multi-modal chromatography resin such as ceramic hydroxyapatite. In some cases, buffer exchange of the antibody product was undertaken using ultrafiltration and diafiltration techniques, after which excipients were added. The formulated antibody was sterile filtered into sterile containers and stored refrigerated or frozen. Purity of the bispecific antibodies was re-assessed using SEC-HPLC and IEF.

TABLE 7

| Cell Line | Purity by SEC (%) | Purity by IEF (% heterodimer) |
| --- | --- | --- |
| 219R45-MB-21M18.010.017 | 98.9 | 98.5 |
| 219R45-MB-21R79.017.002 | 95.1 | 99.3 |
| 219R45-MB-21R75.101 | 97.2 | 98.2 |
| 219R45-MB-21R83.113 | 95.3 | 91.4 |
| 219R45-MB-21M18.138.007 | 98.1 | 100 |
| 219R45-MB-21M18AG.142.002 | 99.6 | 100 |
| 219R45-MB-21R79AG.072.014 | 98.2 | 100 |
| 219R45-MB-21R83AG.129.003 | 998.6 | 100 |

As shown in Table 7, the purification of the anti-VEGF/anti-DLL4 bispecific antibodies with additional chromatography steps after Protein A resulted in isolation of antibody products that were 95% to about 99% pure as analyzed by SEC. Analysis by IEF determined that purified anti-VEGF/anti-DLL4 bispecific antibody from cell line 219R45-MB-21M18.010.017 was 98.5% heterodimeric, anti-VEGF/anti-DLL4 bispecific antibody from cell line 219R45-MB-21R79.017.002 was 99.3% heterodimeric, anti-VEGF/anti-DLL4 bispecific antibody from cell line 219R45-MB-21R75.101 was 98.2% heterodimeric, anti-VEGF/anti-DLL4 bispecific antibody from cell line 219R45-MB-21R83.113 was 91.4% heterodimeric, anti-VEGF/anti-DLL4 bispecific antibody from cell line 219R45-MB-21M18.138.007 was 100% heterodimeric, anti-VEGF/anti-DLL4 bispecific antibody from cell line 219R45-MB-21M18AG.142.002 was 100% heterodimeric, anti-VEGF/anti-DLL4 bispecific antibody from cell line 219R45-MB-21R79AG.072.014 was 100% heterodimeric, and anti-VEGF/anti-DLL4 bispecific antibody from cell line 219R45-MB-21R83AG.129.003 was 100% heterodimeric. These results demonstrated that the anion-exchange chromatography step greatly increased the percentage of heterodimeric antibodies as compared to purification with Protein A chromatography alone. The addition of a multi-modal chromatography step such as ceramic hydroxyapatite can also improve monomeric purity (as determined by SEP-HPLC).

Example 9

Inhibition of OMP-C8 Colon Tumor Growth In Vivo Tumor Recurrence Model

Single cell suspensions of OMP-C8 colon tumor xenografts (20,000 cells) were injected subcutaneously into the flanks of 6-8 week old NOD/SCID mice. Tumors were allowed to grow for 33 days until they reached an average volume of 240 mm$^3$ The mice were randomized (n=10 per group) and treated with anti-hDLL4 antibody 21M18, anti-VEGF antibody bevacizumab, a combination of antibodies 21M18 and bevacizumab, anti-VEGF/anti-DLL4 bispecific antibody 219R45-MB-21M18, anti-VEGF/anti-DLL4 bispecific antibody 219R45-MB-21R79, or control antibody, all in combination with irinotecan. Antibodies and irinotecan were dosed weekly by injection into the intraperitoneal cavity. Antibodies 21M18 and bevacizumab were dosed at 7.5 mg/kg, bispecific antibodies 219R45-MB-21M18 and 219R45-MB-21R79 were dosed at 15 mg/kg, and irinotecan was dosed at 45 mg/kg. Irinotecan was dosed for four weeks, at which time, it was discontinued and the administration of the antibodies continued. Tumor growth was monitored and tumor volumes were measured with electronic calipers at the indicated time points. Data are expressed as mean±S.E.M.

As shown in FIG. 9, anti-hDLL4 antibody 21M18 continued to inhibit tumor growth after treatment with irinotecan was stopped. In contrast, anti-VEGF antibody bevacizumab was not able to inhibit regrowth of the tumor after irinotecan had been stopped. The combination of anti-DLL4 antibody 21M18 and anti-VEGF antibody bevacizumab resulted in greater inhibition of tumor regrowth than either agent alone. Furthermore, the anti-VEGF/anti-DLL4 bispecific antibody 219R45-MB-21M18 was more effective at inhibiting tumor regrowth than the mixture of the two antibodies.

Example 10

Reduction in Tumorigenicity of OMP-C8 Colon Tumors

Single cell suspensions of OMP-C8 colon tumor xenografts (20,000 cells) were injected subcutaneously into the flanks of 6-8 week old NOD/SCID mice. Tumors were allowed to grow for 33 days until they reached an average volume of 300 mm$^3$. The mice were randomized (n=5 per group) and treated with anti-DLL4 antibody 21M18, anti- VEGF antibody bevacizumab, a combination of antibodies 21M18 and bevacizumab, anti-VEGF/anti-DLL4 bispecific antibody 219R45-MB-21M18, anti-VEGF/anti-DLL4 bispecific antibody 219R45-MB-21R79, or control antibody, either in combination with irinotecan or without irinotecan. Antibodies and irinotecan were dosed weekly by injection into the intraperitoneal cavity. Antibodies 21M18 and bevacizumab were dosed at 7.5 mg/kg, bispecific antibodies 219R45-MB-21M18 and 219R45-MB-21R79 were dosed at 15 mg/kg, and irinotecan was dosed at 45 mg/kg. Tumors were harvested after 4 weeks, processed into single cell suspensions, and the human tumor cells were isolated. 150 tumor cells from each experimental group were injected subcutaneously into a new cohort of mice (n=10 per group) and tumors were allowed to grow without treatment. Tumor growth was monitored and tumor volumes were measured with electronic calipers.

Individual tumor volumes at day 68 are shown in FIG. 10. Anti-DLL4 antibody 21M18, the combination of 21M18 with anti-VEGF antibody bevacizumab, bispecific antibodies 219R45-MB-21M18 and 219R45-MB-21R79, and irinotecan all reduced tumor growth frequency as single agents. In contrast, anti-VEGF bevacizumab as a single agent had no effect on tumor growth frequency as compared to the control antibody. In the groups treated with a combination of irinotecan and antibodies, the bispecific antibody 219R45-MB-21M18 had the greatest effect in reducing tumor growth frequency.

Example 11

Inhibition of OMP-C8 Colon Tumor Growth In Vivo

Single cell suspensions of OMP-C8 colon tumor xenografts (50,000 cells) were injected subcutaneously into the flanks of 6-8 week old NOD/SCID mice. Tumors were allowed to grow for 21 days until they reached an average volume of 80 mm$^3$. The mice were randomized (n=8 per group) and treated with anti-DLL4 antibody 21M18, anti-VEGF antibody bevacizumab, anti-VEGF/anti-DLL4 bispecific antibodies 219R45-MB-21M18, 219R45-MB-21R75, 219R45-MB-21R79, 219R45-MB-21R83, or control antibody, either alone or in combination with irinotecan. Antibodies and irinotecan were dosed weekly by injection into the intraperitoneal cavity. Bevacizumab and bispecific antibodies 219R45-MB-21M18, 219R45-MB-21R75, 219R45-MB-21R79, and 219R45-MB-21R83 were dosed at 15 mg/kg, and irinotecan was dosed at 7.5 mg/kg. Tumor growth was monitored and tumor volumes were measured with electronic calipers at the indicated time points. Data are expressed as mean±S.E.M.

As single agents, all four anti-VEGF/anti-DLL4 bispecific antibodies showed enhanced anti-tumor activity relative to anti-VEGF antibody bevacizumab (FIG. 11A). In combination with irinotecan, treatment with anti-VEGF/anti-DLL4 bispecific antibodies 219R45-MB-21M18 and 219R45-MB-21R83 resulted in the greatest inhibition of tumor growth (FIG. 11B).

Following the treatment phase, tumor sections were prepared and analyzed by hematoxylin and eosin (H&E) staining. The tumors treated with 219R45-MB-21M18 and 219R45-MB-21R83 in combination with irinotecan showed dark pink staining regions providing evidence of extensive calcification. This is characteristic of highly necrotic tumor tissue.

Example 12

Non-GLP Toxicity Study of Bispecific Antibodies in Cynomolgus Monkeys

A non-GLP toxicity study in cynomolgus monkeys was initiated to evaluate and compare the toxicity profile of some of the bispecific antibodies. The animals were dosed with 0 mg/kg (control), 5 mg/kg (low dose), or 30 mg/kg (high dose) of anti-DLL4/anti-VEGF bispecific antibody (219R45-MB-21M18, 219R45-MB-21R83, or 219R45-MB-21R79) every 2 weeks via IV infusion. 3 males and 3 females were dosed in each group. After 15 weeks, mean body weights were lower in animals receiving the high dose of 219R45-MB-21R79 than in animals that received the high dose of either 219R45-MB-21R18 or 219R45-MB-21R83. In addition, mean serum albumin levels were lower in animals that received 219R45-MB-21R79 than in those that received either 219R45-MB-21R18 or 219R45-MB-21R83. Although preliminary in nature, these early data suggest that 219R45-MB-21R18 and 219R45-MB-21R83 may have a superior toxicity profile compared to 219R45-MB-21R79.

It is understood that the examples and embodiments described herein are for illustrative purposes only and that various modifications or changes in light thereof will be suggested to persons skilled in the art and are to be included within the spirit and purview of this application.

All publications, patents, patent applications, internet sites, and accession numbers/database sequences including both polynucleotide and polypeptide sequences cited herein are hereby incorporated by reference herein in their entirety for all purposes to the same extent as if each individual publication, patent, patent application, internet site, or accession number/database sequence was specifically and individually indicated to be so incorporated by reference.

```
SEQUENCES
21M18 Heavy chain with signal sequence (underlined)
(SEQ ID NO: 1)
MKHLWFFLLLVAAPRWVLSQVQLVQSGAEVKKPGASVKISCKASGYSFTAYYIHWVKQAP

GQGLEWIGYISSYNGATNYNQKFKGRVTFTTDTSTSTAYMELRSLRSDDTAVYYCARDYD

YDVGMDYWGQGTLVTVSSASTKGPSVFPLAPCSRSTSESTAALGCLVKDYFPEPVTVSWN

SGALTSGVHTFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVEGFYPSDIAVEWESNGQPENNYKTTPPMLDSDGS

FFLYSELTVDKSRWQQGNVFSCSVMHEALHNHYTQKSLSLSPGK
```

21R79 Heavy chain with signal sequence (underlined)
(SEQ ID NO: 2)
MKHLWFFLLLVAAPRWVLSQVQLVQSGAEVKKPGASVKISCKASGYSFTAYYIHWVKQAP

GQGLEWIGYIANYNRATNYNQKFKGRVTFTTDTSTSTAYMELRSLRSDDTAVYYCARDYD

YDVGMDYWGQGTLVTVSSASTKGPSVFPLAPCSRSTSESTAALGCLVKDYFPEPVTVSWN

SGALTSGVHTFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVEGFYPSDIAVEWESNGQPENNYKTTPPMLDSDGS

FFLYSELTVDKSRWQQGNVFSCSVMHEALHNHYTQKSLSLSPGK

219R45 Heavy chain with signal sequence (underlined)
(SEQ ID NO: 3)
MKHLWFFLLLVAAPRWVLSQVQLVQSGAEVKKPGASVKVSCKASGYTFTNYWMHWVRQAP

GQGLEWMGDINPSNGRTSYKEKFKRRVTLSVDKSSSTAYMELSSLRSEDTAVYFCTIHYD

DKYYPLMDYWGQGTLVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAPIEKTISKTKG

QPREPQVYTLPPSREKMTKNQVSLTCLVKGFYPSDIAVEWESNGQPENNYKTTPPMLKSD

GSFFLYSKLTVDKSRWQQGNVFSCSVMHEALHNHYTQKSLSLSPGK

Light chain with signal sequence (underlined)
(SEQ ID NO: 4)
MVLQTQVFISLLLWISGAYGDIVMTQSPDSLAVSLGERATISCRASESVDNYGISFMKWF

QQKPGQPPKLLIYAASNQGSGVPDRFSGSGSGTDFTLTISSLQAEDVAVYYCQQSKEVPW

TFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGEC

21M18 Heavy chain without predicted signal sequence
(SEQ ID NO: 5)
QVQLVQSGAEVKKPGASVKISCKASGYSFTAYYIHWVKQAPGQGLEWIGYISSYNGATNY

NQKFKGRVTFTTDTSTSTAYMELRSLRSDDTAVYYCARDYDYDVGMDYWGQGTLVTVSSA

STKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQ

VSLTCLVEGFYPSDIAVEWESNGQPENNYKTTPPMLDSDGSFFLYSELTVDKSRWQQGNV

FSCSVMHEALHNHYTQKSLSLSPGK

21R79 Heavy chain without predicted signal sequence
(SEQ ID NO: 6)
QVQLVQSGAEVKKPGASVKISCKASGYSFTAYYIHWVKQAPGQGLEWIGYIANYNRATNY

NQKFKGRVTFTTDTSTSTAYMELRSLRSDDTAVYYCARDYDYDVGMDYWGQGTLVTVSSA

STKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQ

-continued

```
VSLTCLVEGFYPSDIAVEWESNGQPENNYKTTPPMLDSDGSFFLYSELTVDKSRWQQGNV

FSCSVMHEALHNHYTQKSLSLSPGK

219R45 Heavy chain without predicted signal sequence
(SEQ ID NO: 7)
QVQLVQSGAEVKKPGASVKVSCKASGYTFTNYWMHWVRQAPGQGLEWMGDINPSNGRTSY

KEKFKRRVTLSVDKSSSTAYMELSSLRSEDTAVYFCTIHYDDKYYPLMDYWGQGTLVTVS

SASTKGPSVFPLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYTLPPSREKMTK

NQVSLTCLVKGFYPSDIAVEWESNGQPENNYKTTPPMLKSDGSFFLYSKLTVDKSRWQQG

NVFSCSVMHEALHNHYTQKSLSLSPGK

Light chain without predicted signal sequence
(SEQ ID NO: 8)
DIVMTQSPDSLAVSLGERATISCRASESVDNYGISFMKWFQQKPGQPPKLLIYAASNQGS

GVPDRFSGSGSGTDFTLTISSLQAEDVAVYYCQQSKEVPWTFGGGTKVEIKRTVAAPSVI

FPPSDEQLKSGTASVVCLLNNFYPREAKVQWKVDNALQSGNSQESVTEQDSKDSTYSLSS

TLTLSKADYEKHKVYACEVTHQGLSSPVTKSFNRGEC

21M18 Heavy chain variable region
(SEQ ID NO: 9)
QVQLVQSGAEVKKPGASVKISCKASGYSFTAYYIHWVKQAPGQGLEWIGYISSYNGATNY

NQKFKGRVTFTTDTSTSTAYMELRSLRSDDTAVYYCARDYDYDVGMDYWGQGTLVTVSS

21R79 Heavy chain variable region
(SEQ ID NO: 10)
QVQLVQSGAEVKKPGASVKISCKASGYSFTAYYIHWVKQAPGQGLEWIGYIANYNRATNY

NQKFKGRVTFTTDTSTSTAYMELRSLRSDDTAVYYCARDYDYDVGMDYWGQGTLVTVSS

219R45 Heavy chain variable region
(SEQ ID NO: 11)
QVQLVQSGAEVKKPGASVKVSCKASGYTFTNYWMHWVRQAPGQGLEWMGDINPSNGRTSY

KEKFKRRVTLSVDKSSSTAYMELSSLRSEDTAVYFCTIHYDDKYYPLMDYWGQGTLVTVSS

Light chain variable region
(SEQ ID NO: 12)
DIVMTQSPDSLAVSLGERATISCRASESVDNYGISFMKWFQQKPGQPPKLLIYAASNQGS

GVPDRFSGSGSGTDFTLTISSLQAEDVAVYYCQQSKEVPWTFGGGTKVEIK

21R75, 21R79, 21R83, and 21M18 Heavy chain CDR1
(SEQ ID NO: 13)
TAYYIH

Alternative 21R75, 21R79, 21R83, and 21M18 Heavy chain CDR1
(SEQ ID NO: 79)
AYYIH 21R79 Heavy chain CDR2
(SEQ ID NO: 14)
YIANYNRATNYNQKFKG 21M18 Heavy chain CDR2
(SEQ ID NO: 15)
YISSYNGATNYNQKFKG 21R75, 21R79, 21R83, and 21M18 Heavy chain CDR3
(SEQ ID NO: 16)
RDYDYDVGMDY 219R45 Heavy chain CDR1
(SEQ ID NO: 17)
NYWMH
```

-continued

219R45 Heavy chain CDR2
(SEQ ID NO: 18)
DINPSNGRTSYKEKFKR

219R45 Heavy chain CDR3
(SEQ ID NO: 19)
HYDDKYYPLMDY

Light chain CDR1
(SEQ ID NO: 20)
RASESVDNYGISFMK

Light chain CDR2
(SEQ ID NO: 21)
AASNQGS

Light chain CDR3
(SEQ ID NO: 22)
QQSKEVPWTFGG

Human DLL4 with signal sequence (underlined)
(SEQ ID NO: 23)
MAAASRSASGWALLLLVALWQQRAAGSGVFQLQLQEFINERGVLASGRPCEPGCRTFFRV

CLKHFQAVVSPGPCTFGTVSTPVLGTNSFAVRDDSSGGGRNPLQLPFNFTWPGTFSLIIE

AWHAPGDDLRPEALPPDALISKIAIQGSLAVGQNWLLDEQTSTLTRLRYSYRVICSDNYY

GDNCSRLCKKRNDHFGHYVCQPDGNLSCLPGWTGEYCQQPICLSGCHEQNGYCSKPAECL

CRPGWQGRLCNECIPHNGCRHGTCSTPWQCTCDEGWGGLFCDQDLNYCTHHSPCKNGATC

SNSGQRSYTCTCRPGYTGVDCELELSECDSNPCRNGGSCKDQEDGYHCLCPPGYYGLHCE

HSTLSCADSPCFNGGSCRERNQGANYACECPPNFTGSNCEKKVDRCTSNPCANGGQCLNR

GPSRMCRCRPGFTGTYCELHVSDCARNPCAHGGTCHDLENGLMCTCPAGFSGRRCEVRTS

IDACASSPCFNRATCYTDLSTDTFVCNCPYGFVGSRCEFPVG

Human DLL4 without predicted signal sequence
(SEQ ID NO: 24)
SGVFQLQLQEFINERGVLASGRPCEPGCRTFFRVCLKHFQAVVSPGPCTFGTVSTPVLGT

NSFAVRDDSSGGGRNPLQLPFNFTWPGTFSLIIEAWHAPGDDLRPEALPPDALISKIAIQ

GSLAVGQNWLLDEQTSTLTRLRYSYRVICSDNYYGDNCSRLCKKRNDHFGHYVCQPDGNL

SCLPGWTGEYCQQPICLSGCHEQNGYCSKPAECLCRPGWQGRLCNECIPHNGCRHGTCST

PWQCTCDEGWGGLFCDQDLNYCTHHSPCKNGATCSNSGQRSYTCTCRPGYTGVDCELELS

ECDSNPCRNGGSCKDQEDGYHCLCPPGYYGLHCEHSTLSCADSPCFNGGSCRERNQGANY

ACECPPNFTGSNCEKKVDRCTSNPCANGGQCLNRGPSRMCRCRPGFTGTYCELHVSDCAR

NPCAHGGTCHDLENGLMCTCPAGFSGRRCEVRTSIDACASSPCFNRATCYTDLSTDTFVC

NCPYGFVGSRCEFPVG

Human DLL4 N-Terminal Region
(SEQ ID NO: 25)
SGVFQLQLQEFINERGVLASGRPCEPGCRTFFRVCLKHFQAVVSPGPCTFGTVSTPVLGT

NSFAVRDDSSGGGRNPLQLPFNFTWPGTFSLIIEAWHAPGDDLRPEALPPDALISKIAIQ

GSLAVGQN

Human DLL4 DSL Domain
(SEQ ID NO: 26)
WLLDEQTSTLTRLRYSYRVICSDNYYGDNCSRLCKKRNDHFGHYVCQPDGNLSCLPGWTG

EYC

Human VEGF-A with signal sequence (underlined)
(SEQ ID NO: 27)
MNFLLSWVHWSLALLLYLHHAKWSQAAPMAEGGGQNHHEVVKFMDVYQRSYCHPIETLVD

IFQEYPDEIEYIFKPSCVPLMRCGGCCNDEGLECVPTEESNITMQIMRIKPHQGQHIGEM

SFLQHNKCECRPKKDRARQEKKSVRGKGKGQKRKRKKSRYKSWSVYVGARCCLMPWSLPG

PHPCGPCSERRKHLFVQDPQTCKCSCKNTDSRCKARQLELNERTCRCDKPRR

Human VEGF-A without predicted signal sequence
(SEQ ID NO: 28)
APMAEGGGQNHHEVVKFMDVYQRSYCHPIETLVDIFQEYPDEIEYIFKPSCVPLMRCGGC

CNDEGLECVPTEESNITMQIMRIKPHQGQHIGEMSFLQHNKCECRPKKDRARQEKKSVRG

KGKGQKRKRKKSRYKSWSVYVGARCCLMPWSLPGPHPCGPCSERRKHLFVQDPQTCKCSC

KNTDSRCKARQLELNERTCRCDKPRR

21M18 Heavy chain nucleotide sequence (13B Version 1)
(SEQ ID NO: 29)
ATGAAGCACCTGTGGTTCTTTCTGCTGCTGGTGGCCGCTCCCAGATGGGTGCTGTCCCAG

GTGCAGCTGGTGCAGTCTGGCGCCGAAGTGAAGAAACCTGGCGCCTCCGTGAAGATCTCC

TGCAAGGCCTCCGGCTACTCCTTCACCGCTTACTACATCCACTGGGTCAAGCAGGCCCCT

GGGCAGGGCCTGGAATGGATCGGCTACATCTCCTCCTACAACGGCGCCACCAACTACAAC

CAGAAATTCAAGGGCCGCGTGACCTTCACCACCGACACCTCCACCTCCACCGCCTACATG

GAACTGCGGTCCCTGCGGAGCGACGACACCGCCGTGTACTACTGCGCCAGAGACTACGAC

TACGACGTGGGCATGGACTACTGGGGCCAGGGCACCCTGGTCACCGTGTCCTCTGCCTCC

ACCAAGGGCCCATCCGTGTTCCCTCTGGCCCCTTGCTCCCGGTCCACCTCTGAGTCTACC

GCCGCTCTGGGCTGCCTGGTGAAGGACTACTTCCCTGAGCCTGTGACCGTGTCCTGGAAC

TCTGGCGCCCTGACCTCTGGCGTGCACACCTTCCCTGCCGTGCTGCAGTCCTCCGGCCTG

TACTCCCTGTCTAGCGTGGTGACCGTGCCTTCCTCCAACTTCGGCACCCAGACCTACACC

TGTAACGTGGACCACAAGCCTTCCAACACCAAGGTGGACAAGACCGTGGAGCGGAAGTGC

TGCGTGGAGTGCCCTCCTTGTCCTGCTCCTCCTGTGGCTGGCCCTTCTGTGTTCCTGTTC

CCTCCAAAGCCTAAGGACACCCTGATGATCTCCCGGACCCCTGAAGTGACCTGCGTGGTG

GTGGACGTGTCCCACGAGGACCCTGAGGTGCAGTTCAATTGGTACGTGGACGGCGTGGAG

GTGCACAACGCCAAGACCAAGCCTCGGGAGGAACAGTTCAACTCCACCTTCCGGGTGGTG

TCTGTGCTGACCGTGGTGCACCAGGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGATATCGCCGTGGAGTGGGAGTCT

AACGGCCAGCCTGAGAACAACTACAAGACCACCCCTCCTATGCTGGACTCCGACGGCTCC

TTCTTCCTGTACTCCGAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCCCTG

TCTCCTGGCAAGTAG

21R79 Heavy chain nucleotide sequence (13B Version 1)
(SEQ ID NO: 30)
ATGAAGCACCTGTGGTTCTTTCTGCTGCTGGTGGCCGCTCCCAGATGGGTGCTGTCCCAG

GTGCAGCTGGTGCAGTCTGGCGCCGAAGTGAAGAAACCTGGCGCCTCCGTGAAGATCTCC

TGCAAGGCCTCCGGCTACTCCTTCACCGCCTACTACATCCACTGGGTGAAACAGGCACCA

GGCCAGGGACTGGAATGGATCGGCTATATCGCCAACTACAACCGGGCCACCAACTACAAC

CAGAAATTCAAGGGCCGCGTGACCTTCACCACCGACACCTCCACCTCCACAGCCTACATG

GAACTGCGGTCCCTGCGGAGCGACGACACCGCCGTGTACTACTGCGCCAGAGACTACGAC

TACGACGTGGGCATGGACTACTGGGGCCAGGGCACCCTGGTGACAGTGTCCTCCGCCTCC

-continued

```
ACCAAGGGCCCCTCCGTGTTCCCTCTGGCCCCTTGCTCCCGGTCCACCTCTGAGTCTACC

GCCGCTCTGGGCTGCCTGGTGAAGGACTACTTCCCTGAGCCTGTGACCGTGTCCTGGAAC

TCTGGCGCCCTGACCTCTGGCGTGCACACCTTCCCTGCCGTGCTGCAGTCCTCCGGCCTG

TACTCCCTGTCTAGCGTGGTGACCGTGCCTTCCTCCAACTTCGGCACCCAGACCTACACC

TGTAACGTGGACCACAAGCCTTCCAACACCAAGGTGGACAAGACCGTGGAGCGGAAGTGC

TGCGTGGAGTGCCCCTCCTTGTCCTGCTCCTCCTGTGGCTGGCCCTTCTGTGTTCCTGTTC

CCTCCAAAGCCTAAGGACACCCTGATGATCTCCCGGACCCCTGAAGTGACCTGCGTGGTG

GTGGACGTGTCCCACGAGGACCCTGAGGTGCAGTTCAATTGGTACGTGGACGGCGTGGAG

GTGCACAACGCCAAGACCAAGCCTCGGGAGGAACAGTTCAACTCCACCTTCCGGGTGGTG

TCTGTGCTGACCGTGGTGCACCAGGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGATATCGCCGTGGAGTGGGAGTCT

AACGGCCAGCCTGAGAACAACTACAAGACCACCCCTCCTATGCTGGACTCCGACGGCTCC

TTCTTCCTGTACTCCGAACTGACCGTGGACAAGTCCCGGTGGCAGCAGGGCAACGTGTTC

TCCTGCTCCGTGATGCACGAGGCCCTGCACAACCACTACACCCAGAAGTCCCTGTCCCTG

TCTCCTGGCAAGTAG

21R79 Heavy chain nucleotide sequence (13B Version 2)
(SEQ ID NO: 31)
ATGAAGCACCTATGGTTCTTTCTATTATTAGTGGCCGCTCCCCGTTGGGTGTTATCGCAG

GTTCAGCTAGTTCAGTCTGGAGCGGAAGTTAAGAAACCTGGAGCATCCGTGAAAATAAGT

TGCAAGGCATCCGGTTACTCGTTCACCGCATACTATATCCACTGGGTTAAACAGGCACCA

GGACAGGGACTTGAATGGATCGGATATATCGCTAATTATAATAGAGCTACAAACTATAAC

CAAAAATTCAAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGACATCGCCGTTGAGTGGGAGTCT

AACGGACAGCCGGAGAACAACTACAAGACTACGCCTCCAATGCTGGACTCCGACGGCTCC

TTCTTCCTGTACTCCGAACTGACCGTGGACAAGTCCCGGTGGCAGCAGGGCAACGTGTTC
```

-continued

TCATGCTCCGTAATGCACGAAGCCTTGCACAATCACTACACTCAAAAGTCCCTATCCTTA

TCTCCTGGCAAGTAG

219R45 Heavy chain nucleotide sequence (13A Version 1)
(SEQ ID NO: 32)
ATGAAGCATCTGTGGTTTTTCCTGTTGCTCGTGGCGGCACCCAGATGGGTGTTGTCCCAA

GTGCAGCTGGTCCAGAGCGGGGCTGAGGTGAAGAAACCCGGAGCAAGCGTAAAAGTATCG

TGTAAGGCCTCGGGGTACACGTTTACAAACTACTGGATGCATTGGGTGCGGCAGGCTCCG

GGACAGGGGTTGGAATGGATGGGTGACATTAACCCCTCAAATGGCAGAACATCATATAAG

GAAAAGTTCAAACGCCGCGTCACACTCTCCGTGGACAAGTCAAGCTCGACTGCGTACATG

GAACTTTCGTCGCTGAGGTCGGAGGACACGGCAGTGTACTTTTGCACCATCCATTATGAT

GACAAGTATTACCCTCTGATGGATTATTGGGGTCAGGGTACGTTGGTCACCGTCTCCAGC

GCGTCGACGAAAGGTCCCTCGGTATTTCCCCTCGCCCCTGCTCGAGGTCGACATCCGAA

TCAACAGCTGCCCTCGGCTGCCTGGTCAAAGACTACTTCCCAGAGCCGGTAACGGTGTCG

TGGAACTCGGGAGCGCTTACGTCCGGAGTCCACACATTTCCGGCGGTACTGCAATCCTCG

GGACTGTATTCGTTGTCGTCAGTGGTGACTGTCCCGTCCTCCAATTTCGGGACTCAGACC

TATACGTGCAACGTCGACCACAAACCCTCAAACACCAAGGTGGATAAGACAGTGGAGCGC

AAGTGCTGCGTGGAGTGTCCCCCGTGTCCGGCACCCCCTGTCGCCGGACCCTCAGTCTTT

TTGTTTCCGCCGAAGCCCAAAGATACACTCATGATCTCAAGAACGCCCGAGGTAACATGC

GTGGTGGTCGATGTAAGCCACGAGGATCCAGAAGTACAATTCAATTGGTATGTAGACGGG

GTCGAGGTCCATAACGCAAAGACGAAACCGAGGGAAGAGCAGTTCAATTCGACTTTCCGG

GTGGTGTCGGTGCTTACAGTCGTACATCAGGACTGGTTGAACGGGAAGGAGTACAAGTGT

AAAGTATCGAATAAGGGCCTTCCAGCGCCGATTGAAAAGACCATCTCCAAGACCAAAGGA

CAGCCACGAGAGCCGCAAGTCTATACGCTTCCTCCCAGCCGAGAAAAGATGACTAAAAAC

CAGGTATCGCTTACGTGTCTCGTCAAGGGTTTCTACCCTTCGGACATCGCGGTGGAATGG

GAGAGCAATGGACAACCGGAAAACAACTACAAGACGACACCGCCTATGTTGAAAAGCGAT

GGATCGTTTTTCCTCTATTCGAAACTCACGGTCGATAAGTCACGGTGGCAGCAGGGGAAT

GTGTTCTCCTGTTCAGTGATGCACGAGGCGCTCCACAATCACTATACCCAGAAAAGCCTG

TCACTTTCCCCGGGAAAATGA

219R45 Heavy chain nucleotide sequence (13A Version 2)
(SEQ ID NO: 33)
ATGAAGCACCTCTGGTTCTTCCTGCTCCTCGTGGCTGCTCCTCGGTGGGTCCTCTCCCAA

GTGCAGCTGGTCCAGAGCGGGGCTGAGGTGAAGAAACCCGGAGCTTCCGTCAAAGTCTCC

TGTAAGGCTTCCGGATACACCTTTACCAACTATTGGATGCACTGGGTGCGGCAGGCTCCT

GGACAAGGGCTGGAATGGATGGGAGACATCAATCCTTCCAATGGCAGAACCTCCTACAAG

GAAAAATTCAAACGGCGGGTCACACTCTCCGTGGACAAGTCTAGCTCCACAGCTTACATG

GAACTCTCCTCCCTGCGGTCCGAAGACACAGCTGTCTACTTCTGCACCATCCACTACGAC

GACAAGTACTACCCTCTGATGGACTACTGGGGCCAGGGAACCCTGGTCACCGTGTCCAGC

GCTTCCACAAAAGGACCCTCCGTCTTTCCCCTCGCCCCTGCTCCCGGTCCACATCCGAA

TCAACAGCTGCCCTCGGCTGCCTGGTCAAAGACTACTTCCCAGAGCCTGTCACAGTGTCC

TGGAACTCCGGAGCTCTCACATCCGGAGTCCACACATTTCCTGCTGTGCTCCAATCCTCC

GGACTGTATTCCCTCTCCTCCGTGGTGACAGTGCCTTCCTCCAATTTCGGGACACAGACC

TATACATGCAACGTGGACCACAAACCCTCCAACACCAAAGTCGATAAGACAGTGGAGCGC

-continued
```
AAGTGCTGCGTGGAGTGTCCCCCTTGTCCTGCTCCCCCTGTGGCTGGACCTTCCGTCTTT

CTGTTTCCTCCTAAACCTAAAGACACCCTCATGATCTCCCGGACCCCCGAGGTCACATGC

GTGGTCGTCGATGTGAGCCACGAGGACCCCGAAGTCCAATTTAATTGGTATGTGGACGGG

GTGGAGGTCCATAACGCTAAGACCAAACCTAGGGAAGAGCAGTTCAATTCCACTTTCCGG

GTGGTGTCCGTGCTGACCGTCGTTCATCAGGACTGGCTCAACGGGAAAGAATACAAATGC

AAAGTCTCTAATAAGGGCCTCCCTGCTCCTATTGAAAAAACAATTTCCAAAACAAAAGGA

CAACCTCGGGAGCCTCAAGTCTACACACTGCCACCTTCCCGGGAAAAAATGACAAAAAAT

CAAGTCTCCCTCACATGTCTCGTCAAGGGATTCTACCCTTCCGACATTGCTGTGGAATGG

GAATCCAATGGACAACCTGAAAACAACTACAAGACAACACCTCCTATGCTCAAAAGCGAT

GGGTCCTTTTTCCTCTATTCCAAACTCACAGTCGATAAGTCTCGGTGGCAGCAGGGGAAT

GTGTTCTCCTGTTCCGTGATGCACGAGGCTCTCCACAATCACTATACCCAGAAAAGCCTG

TCCCTCTCCCCTGGAAAATGA

Light chain nucleotide sequence
(SEQ ID NO: 34)
ATGGTGCTGCAGACCCAGGTGTTCATCTCCCTGCTGCTGTGGATCTCCGGCGCCTACGGC

GACATCGTGATGACCCAGTCCCCAGACTCCCTGGCTGTGTCTCTGGGAGAGCGGGCCACC

ATCTCTTGCAGAGCCTCCGAGTCCGTGGACAACTACGGCATCTCCTTCATGAAGTGGTTC

CAGCAGAAGCCCGGCCAGCCCCCAAAGCTGCTGATCTACGCCGCCTCCAACCAGGGATCT

GGCGTGCCCGACCGGTTCTCTGGATCCGGCTCTGGCACCGACTTTACCCTGACCATCAGC

TCCCTGCAGGCCGAGGACGTGGCCGTGTACTACTGCCAGCAGTCCAAAGAGGTGCCCTGG

ACCTTCGGCGGAGGCACCAAGGTGGAAATCAAGCGGACCGTGGCCGCTCCCTCCGTGTTC

ATCTTCCCACCCTCCGACGAGCAGCTGAAGTCCGGAACCGCCTCCGTCGTGTGCCTGCTG

AACAACTTCTACCCCCGCGAGGCCAAGGTGCAGTGGAAGGTGGACAACGCCCTGCAGTCC

GGCAACTCCCAGGAATCCGTCACCGAGCAGGACTCCAAGGACAGCACCTACTCCCTGTCC

TCCACCCTGACCCTGTCCAAGGCCGACTACGAGAAGCACAAGGTGTACGCCTGCGAAGTG

ACCCACCAGGGCCTGTCCAGCCCCGTGACCAAGTCCTTCAACCGGGGCGAGTGTTAG

21M18 Heavy chain variable region nucleotide sequence
(SEQ ID NO: 35)
CAGGTGCAGCTGGTGCAGTCTGGCGCCGAAGTGAAGAAACCTGGCGCCTCCGTGAAGATC

TCCTGCAAGGCCTCCGGCTACTCCTTCACCGCTTACTACATCCACTGGGTCAAGCAGGCC

CCTGGGCAGGGCCTGGAATGGATCGGCTACATCTCCTCCTACAACGGCGCCACCAACTAC

AACCAGAAATTCAAGGGCCGCGTGACCTTCACCACCGACACCTCCACCTCCACCGCCTAC

ATGGAACTGCGGTCCCTGCGGAGCGACGACACCGCCGTGTACTACTGCGCCAGAGACTAC

GACTACGACGTGGGCATGGACTACTGGGGCCAGGGCACCCTGGTCACCGTGTCCTCT

21R79 Heavy chain variable region nucleotide sequence (13B)
(SEQ ID NO: 36)
CAGGTGCAGCTGGTGCAGTCTGGCGCCGAAGTGAAGAAACCTGGCGCCTCCGTGAAGATC

TCCTGCAAGGCCTCCGGCTACTCCTTCACCGCCTACTACATCCACTGGGTGAAACAGGCA

CCAGGCCAGGGACTGGAATGGATCGGCTATATCGCCAACTACAACCGGGCCACCAACTAC

AACCAGAAATTCAAGGGCCGCGTGACCTTCACCACCGACACCTCCACCTCCACAGCCTAC

ATGGAACTGCGGTCCCTGCGGAGCGACGACACCGCCGTGTACTACTGCGCCAGAGACTAC

GACTACGACGTGGGCATGGACTACTGGGGCCAGGGCACCCTGGTGACAGTGTCCTCC
```

-continued

21R79 Heavy chain variable region nucleotide sequence
(13B Version 2)
(SEQ ID NO: 37)
CAGGTTCAGCTAGTTCAGTCTGGAGCGGAAGTTAAGAAACCTGGAGCATCCGTGAAAATA

AGTTGCAAGGCATCCGGTTACTCGTTCACCGCATACTATATCCACTGGGTTAAACAGGCA

CCAGGACAGGGACTTGAATGGATCGGATATATCGCTAATTATAATAGAGCTACAAACTAT

AACCAAAAATTCAAAGGACGCGTGACTTTCACAACTGACACCTCAACCTCGACAGCATAC

ATGGAATTACGGTCCCTACGGTCTGACGACACTGCCGTTTACTATTGCGCTAGAGATTAT

GATTATGATGTTGGAATGGACTATTGGGGCCAGGGAACACTGGTGACAGTGTCTCT

219R45 Heavy chain variable region nucleotide sequence
(13A version 1)
(SEQ ID NO: 38)
CAAGTGCAGCTGGTCCAGAGCGGGGCTGAGGTGAAGAAACCCGGAGCAAGCGTAAAGTA

TCGTGTAAGGCCTCGGGGTACACGTTTACAAACTACTGGATGCATTGGGTGCGGCAGGCT

CCGGGACAGGGGTTGGAATGGATGGGTGACATTAACCCCTCAAATGGCAGAACATCATAT

AAGGAAAAGTTCAAACGCCGCGTCACACTCTCCGTGGACAAGTCAAGCTCGACTGCGTAC

ATGGAACTTTCGTCGCTGAGGTCGGAGGACACGGCAGTGTACTTTTGCACCATCCATTAT

GATGACAAGTATTACCCTCTGATGGATTATTGGGGTCAGGGTACGTTGGTCACCGTCTCC

AGC

219R45 Heavy chain variable region nucleotide sequence
(13A Version 2)
(SEQ ID NO: 39)
CAAGTGCAGCTGGTCCAGAGCGGGGCTGAGGTGAAGAAACCCGGAGCTTCCGTCAAAGTC

TCCTGTAAGGCTTCCGGATACACCTTTACCAACTATTGGATGCACTGGGTGCGGCAGGCT

CCTGGACAAGGGCTGGAATGGATGGGAGACATCAATCCTTCCAATGGCAGAACCTCCTAC

AAGGAAAAATTCAAACGGCGGGTCACACTCTCCGTGGACAAGTCTAGCTCCACAGCTTAC

ATGGAACTCTCCTCCCTGCGGTCCGAAGACACAGCTGTCTACTTCTGCACCATCCACTAC

GACGACAAGTACTACCCTCTGATGGACTACTGGGGCCAGGGAACCCTGGTCACCGTGTCC

AGC

Light chain variable region nucleotide sequence
(SEQ ID NO: 40)
GACATCGTGATGACCCAGTCCCCAGACTCCCTGGCTGTGTCTCTGGGAGAGCGGGCCACC

ATCTCTTGCAGAGCCTCCGAGTCCGTGGACAACTACGGCATCTCCTTCATGAAGTGGTTC

CAGCAGAAGCCCGGCCAGCCCCCAAAGCTGCTGATCTACGCCGCCTCCAACCAGGGATCT

GGCGTGCCCGACCGGTTCTCTGGATCCGGCTCTGGCACCGACTTTACCCTGACCATCAGC

TCCCTGCAGGCCGAGGACGTGGCCGTGTACTACTGCCAGCAGTCCAAAGAGGTGCCCTGG

ACCTTCGGCGGAGGCACCAAGGTGGAAATCAAG

Human IgG1 Heavy chain constant region
(SEQ ID NO: 41)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

```
Human IgG2 Heavy chain constant region
(SEQ ID NO: 42)
ASTKGPSVFPLAPCSRSTSESTAALGCLVKDYFPEPVTVSWNSGALTSGVHTFPAVLQSS

GLYSLSSVVTVPSSNFGTQTYTCNVDHKPSNTKVDKTVERKCCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGK

Human IgG3 Heavy chain constant region
(SEQ ID NO: 43)
ASTKGPSVFPLAPCSRSTSGGTAALGCLVKDYFPEPVTVSWNSGALTSGVHTFPAVLQSS

GLYSLSSVVTVPSSSLGTQTYTCNVNHKPSNTKVDKRVELKTPLGDTTHTCPRCPEPKSC

DTPPPCPRCPEPKSCDTPPPCPRCPEPKSCDTPPPCPRCPAPELLGGPSVFLFPPKPKDT

LMISRTPEVTCVVVDVSHEDPEVQFKWYVDGVEVHNAKTKPREEQYNSTFRVVSVLTVLH

QDWLNGKEYKCKVSNKALPAPIEKTISKTKGQPREPQVYTLPPSREEMTKNQVSLTCLVK

GFYPSDIAVEWESSGQPENNYNTTPPMLDSDGSFFLYSKLTVDKSRWQQGNIFSCSVMHE

ALHNRFTQKSLSLSPGK

Human IgG4 Heavy chain constant region
(SEQ ID NO: 44)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

FLAG peptide
(SEQ ID NO: 45)
DYKDDDDK

Parental 21R79 Heavy chain with signal sequence underlined
unmodified chain
(SEQ ID NO: 46)
MKHLWFFLLLVAAPRWVLSQVQLVQSGAEVKKPGASVKISCKASGYSFTAYYIHWVKQAP

GQGLEWIGYIANYNRATNYNQKFKGRVTFTTDTSTSTAYMELRSLRSDDTAVYYCARDYD

YDVGMDYWGQGTLVTVSSASTKGPSVFPLAPCSRSTSESTAALGCLVKDYFPEPVTVSWN

SGALTSGVHTFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGK

Parental 219R45 Heavy chain with signal sequence underlined
(SEQ ID NO :47)
MKHLWFFLLLVAAPRWVLSQVQLVQSGAEVKKPGASVKVSCKASGYTFTNYWMHWVRQAP

GQGLEWMGDINPSNGRTSYKEKFKRRVTLSVDKSSSTAYMELSSLRSEDTAVYFCTIHYD

DKYYPLMDYWGQGTLVTVSSASTKGPSVFPLAPCSRSTSESTAALGCLVKDYFPEPVTVS

WNSGALTSGVHTFPAVLQSSGLYSLSSVVTVPSSNFGTQTYTCNVDHKPSNTKVDKTVER

KCCVECPPCPAPPVAGPSVFLFPPKPKDTLMISRTPEVTCVVVDVSHEDPEVQFNWYVDG

VEVHNAKTKPREEQFNSTFRVVSVLTVVHQDWLNGKEYKCKVSNKGLPAPIEKTISKTKG
```

-continued

QPREPQVYTLPPSREEMTKNQVSLTCLVKGFYPSDIAVEWESNGQPENNYKTTPPMLDSD

GSFFLYSKLTVDKSRWQQGNVFSCSVMHEALHNHYTQKSLSLSPGK

Parental 21R79 Heavy chain without predicted signal sequence
(SEQ ID NO: 48)
QVQLVQSGAEVKKPGASVKISCKASGYSFTAYYIHWVKQAPGQGLEWIGYIANYNRATNY

NQKFKGRVTFTTDTSTSTAYMELRSLRSDDTAVYYCARDYDYDVGMDYWGQGTLVTVSSA

STKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQ

VSLTCLVKGFYPSDIAVEWESNGQPENNYKTTPPMLDSDGSFFLYSKLTVDKSRWQQGNV

FSCSVMHEALHNHYTQKSLSLSPGK

Parental 219R45 Heavy chain without signal sequence
(SEQ ID NO: 49)
QVQLVQSGAEVKKPGASVKVSCKASGYTFTNYWMHWVRQAPGQGLEWMGDINPSNGRTSY

KEKFKRRVTLSVDKSSSTAYMELSSLRSEDTAVYFCTIHYDDKYYPLMDYWGQGTLVTVS

SASTKGPSVFPLAPCSRSTSESTAALGCLVKDYFPEPVTVSWNSGALTSGVHTFPAVLQS

SGLYSLSSVVTVPSSNFGTQTYTCNVDHKPSNTKVDKTVERKCCVECPPCPAPPVAGPSV

FLFPPKPKDTLMISRTPEVTCVVVDVSHEDPEVQFNWYVDGVEVHNAKTKPREEQFNSTF

RVVSVLTVVHQDWLNGKEYKCKVSNKGLPAPIEKTISKTKGQPREPQVYTLPPSREEMTK

NQVSLTCLVKGFYPSDIAVEWESNGQPENNYKTTPPMLDSDGSFFLYSKLTVDKSRWQQG

NVFSCSVMHEALHNHYTQKSLSLSPGK

Parental 21R79 Heavy chain variable region nucleotide sequence
(SEQ ID NO: 50)
CAAGTGCAGCTCGTGCAGTCAGGGGCGGAGGTCAAGAAGCCGGGAGCATCGGTCAAAATC

TCGTGTAAGGCCTCGGGGTACTCCTTTACTGCGTATTACATCCATTGGGTAAAGCAGGCG

CCAGGGCAGGGATTGGAGTGGATTGGGTATATCGCCAATTACAATCGCGCGACGAACTAT

AACCAGAAATTCAAGGGAAGGGTGACCTTCACAACGGATACATCGACATCGACGGCCTAC

ATGGAACTTCGCAGCCTGCGATCAGATGACACGCGGGTATACTATTGCGCAAGAGATTAC

GACTATGATGTGGGAATGGACTATTGGGGTCAAGGTACTCTGGTCACAGTCTCCTCC

Parental 219R45 Heavy chain variable region nucleotide sequence
(SEQ ID NO: 51)
CAGGTACAGCTCGTGCAATCGGGGGCAGAGGTCAAAAAGCCCGGTGCGTCGGTAAAGGTC

AGCTGCAAAGCGTCAGGTTATACATTCACGAATTACTGGATGCATTGGGTCAGACAGGCC

CCTGGACAAGGGCTTGAATGGATGGGAGATATCAATCCGTCGAACGGACGGACTAGCTAT

AAGGAGAAGTTTAAGAGGCGCGTAACACTGTCGGTGGACAAATCGTCCTCAACGGCCTAC

ATGGAGTTGTCATCCCTGCGGTCGGAAGATACGGCGGTCTACTTCTGTACTATCCACTAT

GACGATAAGTACTACCCGCTTATGGACTACTGGGGTCAGGGAACATTGGTAACCGTGAGC

AGC

Parental 21R79 Heavy chain nucleotide sequence with signal
sequence
(SEQ ID NO: 52)
ATGAAACACTTGTGGTTTTTCCTCTTGCTCGTGGCAGCTCCTCGGTGGGTACTTTCACAA

GTGCAGCTCGTGCAGTCAGGGGCGGAGGTCAAGAAGCCGGGAGCATCGGTCAAAATCTCG

TGTAAGGCCTCGGGGTACTCCTTTACTGCGTATTACATCCATTGGGTAAAGCAGGCGCCA

GGGCAGGGATTGGAGTGGATTGGGTATATCGCCAATTACAATCGCGCGACGAACTATAAC

-continued

```
CAGAAATTCAAGGGAAGGGTGACCTTCACAACGGATACATCGACATCGACGGCCTACATG

GAACTTCGCAGCCTGCGATCAGATGACACGGCGGTATACTATTGCGCAAGAGATTACGAC

TATGATGTGGGAATGGACTATTGGGGTCAAGGTACTCTGGTCACAGTCTCCTCCGCCAGC

ACCAAGGGCCCTAGCGTCTTCCCTCTGGCTCCCTGCAGCAGGAGCACCAGCGAGAGCACA

GCCGCCCTGGGCTGCCTGGTCAAGGACTACTTCCCCGAACCGGTGACGGTGTCGTGGAAC

TCAGGCGCTCTGACCAGCGGCGTGCACACCTTCCCAGCTGTCCTACAGTCCTCAGGACTC

TACTCCCTCAGCAGCGTGGTGACCGTGCCCTCCAGCAACTTCGGCACCCAGACCTACACC

TGCAACGTAGATCACAAGCCCAGCAACACCAAGGTGGACAAGACAGTTGAGCGCAAATGT

TGTGTCGAGTGCCCACCGTGCCCAGCACCACCTGTGGCAGGACCGTCAGTCTTCCTCTTC

CCCCCAAAACCCAAGGACACCCTCATGATCTCCCGGACCCCTGAGGTCACGTGCGTGGTG

GTGGACGTGAGCCACGAAGACCCCGAGGTCCAGTTCAACTGGTACGTGGACGGCGTGGAG

GTGCATAATGCCAAGACAAAGCCACGGGAGGAGCAGTTCAACAGCACGTTCCGTGTGGTC

AGCGTCCTCACCGTTGTGCACCAGGACTGGCTGAACGGCAAGGAGTACAAGTGCAAGGTC

TCCAACAAAGGCCTCCCAGCCCCCATCGAGAAAACCATCTCCAAAACCAAAGGGCAGCCC

CGAGAACCACAGGTGTACACCCTGCCCCCATCCCGGGAGGAGATGACCAAGAACCAGGTC

AGCCTGACCTGCCTGGTCAAAGGCTTCTACCCCAGCGACATCGCCGTGGAGTGGGAGAGC

AATGGGCAGCCGGAGAACAACTACAAGACCACACCTCCCATGCTGGACTCCGACGGCTCC

TTCTTCCTCTACAGCAAGCTCACCGTGGACAAGAGCAGGTGGCAGCAGGGGAACGTCTTC

TCATGCTCCGTGATGCATGAGGCTCTGCACAACCACTACACGCAGAAGAGCCTCTCCCTG

TCTCCGGGTAAA
```

Parental 219R45 Heavy chain nucleotide sequence with signal sequence
(SEQ ID NO: 53)
```
ATGAAACACCTCTGGTTCTTTTTGCTCCTGGTGGCAGCTCCCCGATGGGTGCTTAGCCAG

GTACAGCTCGTGCAATCGGGGCAGAGGTCAAAAAGCCCGGTGCGTCGGTAAAGGTCAGC

TGCAAAGCGTCAGGTTATACATTCACGAATTACTGGATGCATTGGGTCAGACAGGCCCCT

GGACAAGGGCTTGAATGGATGGGAGATATCAATCCGTCGAACGGACGGACTAGCTATAAG

GAGAAGTTTAAGAGGCGCGTAACACTGTCGGTGGACAAATCGTCCTCAACGGCCTACATG

GAGTTGTCATCCCTGCGGTCGGAAGATACGGCGGTCTACTTCTGTACTATCCACTATGAC

GATAAGTACTACCCGCTTATGGACTACTGGGGTCAGGGAACATTGGTAACCGTGAGCAGC

GCGTCCACAAAGGGCCCTAGCGTCTTCCCTCTGGCTCCCTGCAGCAGGAGCACCAGCGAG

AGCACAGCCGCCCTGGGCTGCCTGGTCAAGGACTACTTCCCCGAACCGGTGACGGTGTCG

TGGAACTCAGGCGCTCTGACCAGCGGCGTGCACACCTTCCCAGCTGTCCTACAGTCCTCA

GGACTCTACTCCCTCAGCAGCGTGGTGACCGTGCCCTCCAGCAACTTCGGCACCCAGACC

TACACCTGCAACGTAGATCACAAGCCCAGCAACACCAAGGTGGACAAGACAGTTGAGCGC

AAATGTTGTGTCGAGTGCCCACCGTGCCCAGCACCACCTGTGGCAGGACCGTCAGTCTTC

CTCTTCCCCCCAAAACCCAAGGACACCCTCATGATCTCCCGGACCCCTGAGGTCACGTGC

GTGGTGGTGGACGTGAGCCACGAAGACCCCGAGGTCCAGTTCAACTGGTACGTGGACGGC

GTGGAGGTGCATAATGCCAAGACAAAGCCACGGGAGGAGCAGTTCAACAGCACGTTCCGT

GTGGTCAGCGTCCTCACCGTTGTGCACCAGGACTGGCTGAACGGCAAGGAGTACAAGTGC

AAGGTCTCCAACAAAGGCCTCCCAGCCCCCATCGAGAAAACCATCTCCAAAACCAAAGGG

CAGCCCCGAGAACCACAGGTGTACACCCTGCCCCCATCCCGGGAGGAGATGACCAAGAAC
```

-continued

CAGGTCAGCCTGACCTGCCTGGTCAAAGGCTTCTACCCCAGCGACATCGCCGTGGAGTGG

GAGAGCAATGGGCAGCCGGAGAACAACTACAAGACCACACCTCCCATGCTGGACTCCGAC

GGCTCCTTCTTCCTCTACAGCAAGCTCACCGTGGACAAGAGCAGGTGGCAGCAGGGGAAC

GTCTTCTCATGCTCCGTGATGCATGAGGCTCTGCACAACCACTACACGCAGAAGAGCCTC

TCCCTGTCTCCGGGTAAA

Parental 21R79 and 219R45 light chain variable region
nucleotide sequence
(SEQ ID NO: 54)
GACATCGTGATGACCCAGTCCCCTGACTCCCTGGCTGTGTCCCTGGGCGAGAGGGCCACC

ATCTCCTGCAGAGCCAGCGAATCCGTCGATAATTATGGCATTTCCTTTATGAAGTGGTTC

CAGCAGAAACCAGGACAGCCTCCTAAGCTGCTCATTTACGCTGCATCCAACCAAGGGTCC

GGGGTCCCTGACAGGTTCTCCGGCAGCGGGTCCGGAACAGATTTCACTCTCACCATCAGC

AGCCTGCAGGCTGAAGATGTGGCTGTCTATTACTGTCAGCAAAGCAAGGAGGTGCCTTGG

ACATTCGGAGGAGGGACCAAGGTGGAAATCAAA

Parental 21R79 and 219R45 light chain nucleotide sequence
(SEQ ID NO: 55)
ATGGTGCTCCAGACCCAGGTCTTCATTTCCCTGCTGCTCTGGATCAGCGGAGCCTACGGG

GACATCGTGATGACCCAGTCCCCTGACTCCCTGGCTGTGTCCCTGGGCGAGAGGGCCACC

ATCTCCTGCAGAGCCAGCGAATCCGTCGATAATTATGGCATTTCCTTTATGAAGTGGTTC

CAGCAGAAACCAGGACAGCCTCCTAAGCTGCTCATTTACGCTGCATCCAACCAAGGGTCC

GGGGTCCCTGACAGGTTCTCCGGCAGCGGGTCCGGAACAGATTTCACTCTCACCATCAGC

AGCCTGCAGGCTGAAGATGTGGCTGTCTATTACTGTCAGCAAAGCAAGGAGGTGCCTTGG

ACATTCGGAGGAGGGACCAAGGTGGAAATCAAACGTACGGTGGCTGCCCCCTCCGTCTTC

ATCTTCCCCCCCAGCGATGAGCAGCTGAAAAGCGGCACTGCCAGCGTGGTGTGCCTGCTG

AATAACTTCTATCCCCGGGAGGCCAAAGTGCAGTGGAAGGTGGATAACGCCCTCCAAAGC

GGCAACTCCCAGGAGAGCGTCACAGAGCAGGACAGCAAGGACAGCACCTACAGCCTCAGC

AGCACCCTGACCCTGAGCAAAGCCGACTACGAGAAACACAAAGTCTACGCCTGCGAAGTC

ACCCATCAGGGCCTGAGCAGCCCCGTCACAAAGAGCTTCAACAGGGGCGAGTGTTGA

21R75 Heavy chain without predicted signal sequence
(SEQ ID NO: 56)
QVQLVQSGAEVKKPGASVKISCKASGYSFTAYYIHWVKQAPGQGLEWIGYIAGYKDATNY

NQKFKGRVTFTTDTSTSTAYMELRSLRSDDTAVYYCARDYDYDVGMDYWGQGTLVTVSSA

STKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQ

VSLTCLVEGFYPSDIAVEWESNGQPENNYKTTPPMLDSDGSFFLYSELTVDKSRWQQGNV

FSCSVMHEALHNHYTQKSLSLSPGK

21R75 Heavy chain with predicted signal sequence (underlined)
(SEQ ID NO: 57)
MKHLWFFLLLVAAPRWVLSQVQLVQSGAEVKKPGASVKISCKASGYSFTAYYIHWVKQAP

GQGLEWIGYIAGYKDATNYNQKFKGRVTFTTDTSTSTAYMELRSLRSDDTAVYYCARDYD

YDVGMDYWGQGTLVTVSSASTKGPSVFPLAPCSRSTSESTAALGCLVKDYFPEPVTVSWN

SGALTSGVHTFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVEGFYPSDIAVEWESNGQPENNYKTTPPMLDSDGS

FFLYSELTVDKSRWQQGNVFSCSVMHEALHNHYTQKSLSLSPGK

21R75 Heavy chain variable region
(SEQ ID NO: 58)
QVQLVQSGAEVKKPGASVKISCKASGYSFTAYYIHWVKQAPGQGLEWIGYIAGYKDATNY

NQKFKGRVTFTTDTSTSTAYMELRSLRSDDTAVYYCARDYDYDVGMDYWGQGTLVTVSS

21R75 Heavy chain CDR2
(SEQ ID NO: 59)
YIAGYKDATNYNQKFKG

21R75 Heavy chain nucleotide sequence with signal sequence
(13B Version 1)
(SEQ ID NO: 60)
<u>ATGAAGCACCTGTGGTTCTTTCTGCTGCTGGTGGCCGCTCCCAGATGGGTGCTGTCCCAG</u>

GTGCAGCTGGTGCAGTCTGGCGCCGAAGTGAAGAAACCTGGCGCCTCCGTGAAGATCTCC

TGCAAGGCCTCCGGCTACTCCTTCACCGCCTACTACATCCACTGGGTCAAGCAGGCCCCT

GGACAGGGCCTGGAATGGATCGGCTATATCGCCGGCTACAAGGACGCCACCAACTACAAC

CAGAAATTCAAGGGCAGAGTGACCTTCACCACCGACACCTCCACCTCTACCGCCTACATG

GAACTGCGGTCCCTGCGGAGCGACGACACCGCCGTGTACTACTGCGCCAGAGACTACGAC

TACGACGTGGGCATGGACTACTGGGGCCAGGGCACACTCGTGACCGTGTCCTCTGCTTCC

ACCAAGGGCCCCTCCGTGTTTCCTCTGGCCCCTTGCTCCAGATCCACCTCCGAGTCTACC

GCCGCTCTGGGCTGCCTCGTGAAGGACTACTTCCCCGAGCCCGTGACAGTGTCTTGGAAC

TCTGGCGCCCTGACCTCCGGCGTGCACACCTTTCCAGCTGTGCTGCAGTCCTCCGGCCTG

TACTCCCTGTCCTCCGTCGTGACTGTGCCCTCCTCCAACTTCGGCACCCAGACCTACACC

TGTAACGTGGACCACAAGCCCTCCAACACCAAGGTGGACAAGACCGTGGAACGGAAGTGC

TGCGTGGAATGCCCCCCTTGTCCTGCCCCTCCTGTGGCTGGCCCTAGCGTGTTCCTGTTC

CCCCCAAAGCCCAAGGACACCCTGATGATCTCCCGGACCCCCGAAGTGACCTGCGTGGTG

GTGGATGTGTCCCACGAGGACCCCGAGGTGCAGTTCAATTGGTACGTGGACGGCGTGGAA

GTGCACAACGCCAAGACCAAGCCCAGAGAGGAACAGTTCAACTCCACCTTCCGGGTGGTG

TCCGTGCTGACCGTGGTGCATCAGGACTGGCTGAACGGCAAAGAGTACAAGTGCAAGGTG

TCCAACAAGGGCCTGCCTGCCCCCATCGAAAAGACCATCTCTAAGACCAAGGGACAGCCC

CGCGAGCCCCAGGTGTACACACTGCCTCCATCCCGGGAAGAGATGACCAAGAACCAGGTG

TCCCTGACCTGTCTGGTGGAAGGCTTCTACCCCTCCGATATCGCCGTGGAATGGGAGTCC

AACGGCCAGCCCGAGAACAACTACAAGACCACCCCCCCCATGCTGGACTCCGACGGCTCA

TTCTTCCTGTACAGCGAGCTGACAGTGGACAAGTCCCGGTGGCAGCAGGGCAACGTGTTC

TCCTGCTCCGTGATGCACGAGGCCCTGCACAACCACTACACCCAGAAGTCCCTGTCCCTG

AGCCCCGGCAAG

21R75 Heavy chain nucleotide sequence with signal sequence
(13B Version 1T)
(SEQ ID NO: 77)
<u>ATGAAGCACCTGTGGTTCTTTCTGCTGCTGGTGGCCGCTCCCAGATGGGTGCTGTCTCAG</u>

GTGCAGCTGGTGCAGTCTGGCGCCGAAGTGAAGAAACCTGGCGCCTCCGTGAAGATCTCC

TGCAAGGCCTCCGGCTACTCCTTCACCGCCTACTACATCCACTGGGTCAAGCAGGCCCCT

GGACAGGGCCTGGAATGGATCGGCTATATCGCCGGCTACAAGGACGCCACCAACTACAAC

CAGAAATTCAAGGGCAGAGTGACCTTCACCACCGACACCTCCACCTCTACCGCCTACATG

```
GAACTGCGGTCCCTGCGGAGCGACGACACCGCCGTGTACTACTGCGCCAGAGACTACGAC

TACGACGTGGGCATGGACTACTGGGGCCAGGGCACACTCGTGACCGTGTCCTCTGCTTCC

ACCAAGGGCCCCTCCGTGTTTCCTCTGGCCCCTTGCTCCAGATCCACCTCCGAGTCTACC

GCCGCTCTGGGCTGCCTCGTGAAGGACTACTTCCCCGAGCCCGTGACAGTGTCTTGGAAC

TCTGGCGCCCTGACCTCCGGCGTGCACACCTTTCCAGCTGTGCTGCAGTCCTCCGGCCTG

TACTCCCTGTCCTCCGTCGTGACTGTGCCCTCCTCCAACTTCGGCACCCAGACCTACACC

TGTAACGTGGACCACAAGCCCTCCAACACCAAGGTGGACAAGACCGTGGAACGGAAGTGC

TGCGTGGAATGCCCCCCTTGTCCTGCCCCTCCTGTGGCTGGCCCTAGCGTGTTCCTGTTC

CCCCCAAAGCCCAAGGACACCCTGATGATCTCCCGGACCCCCGAAGTGACCTGCGTGGTG

GTGGATGTGTCCCACGAGGACCCCGAGGTGCAGTTCAATTGGTACGTGGACGGCGTGGAA

GTGCACAACGCCAAGACCAAGCCCAGAGAGGAACAGTTCAACTCCACCTTCCGGGTGGTG

TCCGTGCTGACCGTGGTGCATCAGGACTGGCTGAACGGCAAAGAGTACAAGTGCAAGGTG

TCCAACAAGGGCCTGCCTGCCCCCATCGAAAAGACCATCTCTAAGACCAAGGGACAGCCC

CGCGAGCCCCAGGTGTACACACTGCCTCCATCCCGGGAAGAGATGACCAAGAACCAGGTG

TCCCTGACCTGTCTGGTGGAAGGCTTCTACCCCTCCGATATCGCCGTGGAATGGGAGTCC

AACGGCCAGCCCGAGAACAACTACAAGACCACCCCCCCCATGCTGGACTCCGACGGCTCA

TTCTTCCTGTACAGCGAGCTGACAGTGGACAAGTCCCGGTGGCAGCAGGGCAACGTGTTC

TCCTGCTCCGTGATGCACGAGGCCCTGCACAACCACTACACCCAGAAGTCCCTGTCCCTG

AGCCCCGGCAAG

21R75 Heavy chain nucleotide sequence with signal sequence
(13B Version S1-2)
(SEQ ID NO: 61)
ATGAAGCACCTGTGGTTCTTTCTGCTGCTGGTGGCCGCTCCCAGATGGGTGCTGTCCCAG

GTTCAGCTAGTTCAGTCTGGAGCGGAAGTTAAGAAACCTGGAGCATCCGTGAAAATAAGT

TGCAAGGCATCCGGTTACTCGTTCACCGCATACTATATCCACTGGGTTAAACAGGCACCA

GGACAGGGACTTGAATGGATCGGATATATCGCTGGATATAAAGATGCTACAAACTATAAC

CAAAAATTCAAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCAGCCGGGAAGAAATGACCAAGAACCAGGTG

TCCCTGACCTGTCTGGTGGAGGGCTTCTACCCTTCCGACATCGCCGTTGAGTGGGAGTCT
```

-continued
```
AACGGACAGCCGGAGAACAACTACAAGACTACGCCTCCAATGCTGGACTCCGACGGCTCC

TTCTTCCTGTACTCCGAACTGACCGTGGACAAGTCCCGGTGGCAGCAGGGCAACGTGTTC

TCATGCTCCGTAATGCACGAAGCCTTGCACAATCACTACACTCAAAAGTCCCTATCCTTA

TCTCCTGGCAAG

21R83 Heavy chain without predicted signal sequence
(SEQ ID NO: 62)
QVQLVQSGAEVKKPGASVKISCKASGYSFTAYYIHWVKQAPGQGLEWIGYISNYNRATNY

NQKFKGRVTFTTDTSTSTAYMELRSLRSDDTAVYYCARDYDYDVGMDYWGQGTLVTVSSA

STKGPSVFPLAPCSRSTSESTAALGCLVKDYFPEPVTVSWNSGALTSGVHTFPAVLQSSG

LYSLSSVVTVPSSNFGTQTYTCNVDHKPSNTKVDKTVERKCCVECPPCPAPPVAGPSVFL

FPPKPKDTLMISRTPEVTCVVVDVSHEDPEVQFNWYVDGVEVHNAKTKPREEQFNSTFRV

VSVLTVVHQDWLNGKEYKCKVSNKGLPAPIEKTISKTKGQPREPQVYTLPPSREEMTKNQ

VSLTCLVEGFYPSDIAVEWESNGQPENNYKTTPPMLDSDGSFFLYSELTVDKSRWQQGNV

FSCSVMHEALHNHYTQKSLSLSPGK

21R83 Heavy chain with predicted signal sequence (underlined)
(SEQ ID NO: 63)
MKHLWFFLLLVAAPRWVLSQVQLVQSGAEVKKPGASVKISCKASGYSFTAYYIHWVKQAP

GQGLEWIGYISNYNRATNYNQKFKGRVTFTTDTSTSTAYMELRSLRSDDTAVYYCARDYD

YDVGMDYWGQGTLVTVSSASTKGPSVFPLAPCSRSTSESTAALGCLVKDYFPEPVTVSWN

SGALTSGVHTFPAVLQSSGLYSLSSVVTVPSSNFGTQTYTCNVDHKPSNTKVDKTVERKC

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVEGFYPSDIAVEWESNGQPENNYKTTPPMLDSDGS

FFLYSELTVDKSRWQQGNVFSCSVMHEALHNHYTQKSLSLSPGK

21R83 Heavy chain variable region
(SEQ ID NO: 64)
QVQLVQSGAEVKKPGASVKISCKASGYSFTAYYIHWVKQAPGQGLEWIGYISNYNRATNY

NQKFKGRVTFTTDTSTSTAYMELRSLRSDDTAVYYCARDYDYDVGMDYWGQGTLVTVSS

21R83 Heavy chain CDR2
(SEQ ID NO: 65)
YISNYNRATNYNQKFKG

21R83 Heavy chain nucleotide sequence with signal sequence
underlined (13B Version 1)
(SEQ ID NO: 66)
ATGAAGCACCTGTGGTTCTTTCTGCTGCTGGTGGCCGCTCCCAGATGGGTGCTGTCCCAG

GTGCAGCTGGTGCAGTCTGGCGCCGAAGTGAAGAAACCTGGCGCCTCCGTGAAGATCTCC

TGCAAGGCCTCCGGCTACTCCTTCACCGCCTACTACATCCACTGGGTCAAGCAGGCCCCT

GGACAGGGCCTGGAATGGATCGGCTACATCTCCAACTACAACCGGGCCACCAATTACAAC

CAGAAATTCAAGGGCCGCGTGACCTTCACCACCGACACCTCTACCTCTACCGCCTACATG

GAACTGCGGTCCCTGCGGAGCGACGACACCGCCGTGTACTACTGCGCCAGAGACTACGAC

TACGACGTGGGCATGGACTACTGGGGCCAGGGCACACTCGTGACCGTGTCTAGCGCTTCC

ACCAAGGGCCCCTCCGTGTTTCCTCTGGCCCCTTGCTCCAGATCCACCTCCGAGTCTACC

GCCGCTCTGGGCTGCCTCGTGAAGGACTACTTCCCCGAGCCCGTGACAGTGTCCTGGAAC

TCTGGCGCTCTGACCTCCGGCGTGCACACCTTTCCAGCTGTGCTGCAGTCCTCCGGCCTG

TACTCCCTGTCCTCCGTCGTGACTGTGCCCTCCTCCAACTTCGGCACCCAGACCTACACC

TGTAACGTGGACCACAAGCCCTCCAACACCAAGGTGGACAAGACCGTGGAACGGAAGTGC
```

```
TGCGTGGAATGCCCCCCTTGTCCTGCCCCTCCTGTGGCTGGCCCTAGCGTGTTCCTGTTC

CCCCCAAAGCCCAAGGACACCCTGATGATCTCCCGGACCCCCGAAGTGACCTGCGTGGTG

GTGGATGTGTCCCACGAGGACCCCGAGGTGCAGTTCAATTGGTACGTGGACGGCGTGGAA

GTGCACAACGCCAAGACCAAGCCCAGAGAGGAACAGTTCAACTCCACCTTCCGGGTGGTG

TCCGTGCTGACCGTGGTGCATCAGGACTGGCTGAACGGCAAAGAGTACAAGTGCAAGGTG

TCCAACAAGGGCCTGCCTGCCCCCATCGAAAAGACCATCTCTAAGACCAAGGGACAGCCC

CGCGAGCCCCAGGTGTACACACTGCCTCCATCCCGGGAAGAGATGACCAAGAACCAGGTG

TCCCTGACCTGTCTGGTGGAAGGCTTCTACCCCTCCGATATCGCCGTGGAATGGGAGTCC

AACGGCCAGCCCGAGAACAACTACAAGACCACCCCCCCCATGCTGGACTCCGACGGCTCA

TTCTTCCTGTACAGCGAGCTGACAGTGGACAAGTCCCGGTGGCAGCAGGGCAACGTGTTC

TCCTGCTCCGTGATGCACGAGGCCCTGCACAACCACTACACCCAGAAGTCCCTGTCCCTG

AGCCCCGGCAAG

21R83 Heavy chain nucleotide sequence with signal sequence
underlined (13B Version 1T)
(SEQ ID NO: 78)
ATGAAGCACCTGTGGTTCTTTCTGCTGCTGGTGGCCGCTCCCAGATGGGTGCTGTCTCAG

GTGCAGCTGGTGCAGTCTGGCGCCGAAGTGAAGAAACCTGGCGCCTCCGTGAAGATCTCC

TGCAAGGCCTCCGGCTACTCCTTCACCGCCTACTACATCCACTGGGTCAAGCAGGCCCCT

GGACAGGGCCTGGAATGGATCGGCTACATCTCCAACTACAACGGGCCACCAATTACAAC

CAGAAATTCAAGGGCCGCGTGACCTTCACCACCGACACCTCTACCTCTACCGCCTACATG

GAACTGCGGTCCCTGCGGAGCGACGACACCGCCGTGTACTACTGCGCCAGAGACTACGAC

TACGACGTGGGCATGGACTACTGGGGCCAGGGCACACTCGTGACCGTGTCTAGCGCTTCC

ACCAAGGGCCCCTCCGTGTTTCCTCTGGCCCCTTGCTCCAGATCCACCTCCGAGTCTACC

GCCGCTCTGGGCTGCCTCGTGAAGGACTACTTCCCCGAGCCCGTGACAGTGTCCTGGAAC

TCTGGCGCTCTGACCTCCGGCGTGCACACCTTTCCAGCTGTGCTGCAGTCCTCCGGCCTG

TACTCCCTGTCCTCCGTCGTGACTGTGCCCTCCTCCAACTTCGGCACCCAGACCTACACC

TGTAACGTGGACCACAAGCCCTCCAACACCAAGGTGGACAAGACCGTGGAACGGAAGTGC

TGCGTGGAATGCCCCCCTTGTCCTGCCCCTCCTGTGGCTGGCCCTAGCGTGTTCCTGTTC

CCCCCAAAGCCCAAGGACACCCTGATGATCTCCCGGACCCCCGAAGTGACCTGCGTGGTG

GTGGATGTGTCCCACGAGGACCCCGAGGTGCAGTTCAATTGGTACGTGGACGGCGTGGAA

GTGCACAACGCCAAGACCAAGCCCAGAGAGGAACAGTTCAACTCCACCTTCCGGGTGGTG

TCCGTGCTGACCGTGGTGCATCAGGACTGGCTGAACGGCAAAGAGTACAAGTGCAAGGTG

TCCAACAAGGGCCTGCCTGCCCCCATCGAAAAGACCATCTCTAAGACCAAGGGACAGCCC

CGCGAGCCCCAGGTGTACACACTGCCTCCATCCCGGGAAGAGATGACCAAGAACCAGGTG

TCCCTGACCTGTCTGGTGGAAGGCTTCTACCCCTCCGATATCGCCGTGGAATGGGAGTCC

AACGGCCAGCCCGAGAACAACTACAAGACCACCCCCCCCATGCTGGACTCCGACGGCTCA

TTCTTCCTGTACAGCGAGCTGACAGTGGACAAGTCCCGGTGGCAGCAGGGCAACGTGTTC

TCCTGCTCCGTGATGCACGAGGCCCTGCACAACCACTACACCCAGAAGTCCCTGTCCCTG

AGCCCCGGCAAG

21R75 Heavy chain nucleotide sequence with signal sequence
underlined (13B Version S1-2)
(SEQ ID NO: 67)
ATGAAGCACCTGTGGTTCTTTCTGCTGCTGGTGGCCGCTCCCAGATGGGTGCTGTCCCAG

GTTCAGCTAGTTCAGTCTGGAGCGGAAGTTAAGAAACCTGGAGCATCCGTGAAAATAAGT
```

-continued

```
TGCAAGGCATCCGGTTACTCGTTCACCGCATACTATATCCACTGGGTTAAACAGGCACCA

GGACAGGGACTTGAATGGATCGGATATATCGCTGGATATAAAGATGCTACAAACTATAAC

CAAAAATTCAAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGACATCGCCGTTGAGTGGGAGTCT

AACGGACAGCCGGAGAACAACTACAAGACTACGCCTCCAATGCTGGACTCCGACGGCTCC

TTCTTCCTGTACTCCAACTGACCGTGGACAAGTCCCGGTGGCAGCAGGGCAACGTGTTC

TCATGCTCCGTAATGCACGAAGCCTTGCACAATCACTACACTCAAAAGTCCCTATCCTTA

TCTCCTGGCAAG

21R75 Heavy chain variable region nucleotide sequence
(13B Version 1)
(SEQ ID NO: 68)
CAGGTGCAGCTGGTGCAGTCTGGCGCCGAAGTGAAGAAACCTGGCGCCTCCGTGAAGATC

TCCTGCAAGGCCTCCGGCTACTCCTTCACCGCCTACTACATCCACTGGGTCAAGCAGGCC

CCTGGACAGGGCCTGGAATGGATCGGCTATATCGCCGGCTACAAGGACGCCACCAACTAC

AACCAGAAATTCAAGGGCAGAGTGACCTTCACCACCGACACCTCCACCTCTACCGCCTAC

ATGGAACTGCGGTCCCTGCGGAGCGACGACACCGCCGTGTACTACTGCGCCAGAGACTAC

GACTACGACGTGGGCATGGACTACTGGGGCCAGGGCACACTCGTGACCGTGTCCTCT

21R75 Heavy chain variable region nucleotide sequence
(13B Version 2)
(SEQ ID NO: 69)
CAGGTTCAGCTAGTTCAGTCTGGAGCGGAAGTTAAGAAACCTGGAGCATCCGTGAAAATA

AGTTGCAAGGCATCCGGTTACTCGTTCACCGCATACTATATCCACTGGGTTAAACAGGCA

CCAGGACAGGGACTTGAATGGATCGGATATATCGCTGGATATAAAGATGCTACAAACTAT

AACCAAAAATTCAAAGGACGCGTGACTTTCACAACTGACACCTCAACCTCGACAGCATAC

ATGGAATTACGGTCCCTACGGTCTGACGACACTGCCGTTTACTATTGCGCTAGAGATTAT

GATTATGATGTTGGAATGGACTATTGGGGCCAGGGAACACTGGTGACAGTGTCTTCT

21R83 Heavy chain variable region nucleotide sequence
(13B Version 1)
(SEQ ID NO: 70)
CAGGTGCAGCTGGTGCAGTCTGGCGCCGAAGTGAAGAAACCTGGCGCCTCCGTGAAGATC

TCCTGCAAGGCCTCCGGCTACTCCTTCACCGCCTACTACATCCACTGGGTCAAGCAGGCC
```

CCTGGACAGGGCCTGGAATGGATCGGCTACATCTCCAACTACAACCGGGCCACCAATTAC

AACCAGAAATTCAAGGGCCGCGTGACCTTCACCACCGACACCTCTACCTCTACCGCCTAC

ATGGAACTGCGGTCCCTGCGGAGCGACGACACCGCCGTGTACTACTGCGCCAGAGACTAC

GACTACGACGTGGGCATGGACTACTGGGGCCAGGGCACACTCGTGACCGTGTCTAGC

21R75 Heavy chain variable region nucleotide sequence
(13B Version 2)
(SEQ ID NO: 71)
CAGGTTCAGCTAGTTCAGTCTGGAGCGGAAGTTAAGAAACCTGGAGCATCCGTGAAAATA

AGTTGCAAGGCATCCGGTTACTCGTTCACCGCATACTATATCCACTGGGTTAAACAGGCA

CCAGGACAGGGACTTGAATGGATCGGATATATCGCTGGATATAAAGATGCTACAAACTAT

AACCAAAAATTCAAGGACGCGTGACTTTCACAACTGACACCTCAACCTCGACAGCATAC

ATGGAATTACGGTCCCTACGGTCTGACGACACTGCCGTTTACTATTGCGCTAGAGATTAT

GATTATGATGTTGGAATGGACTATTGGGGCCAGGGAACACTGGTGACAGTGTCTTCT

21R83 Heavy chain nucleotide sequence with signal sequence
underlined (13B Version 2)
(SEQ ID NO: 72)
<u>ATGAAGCACCTATGGTTCTTTCTATTATTAGTGGCCGCTCCCCGTTGGGTGTTATCGCAG</u>

GTTCAGCTAGTTCAGTCTGGAGCGGAAGTTAAGAAACCTGGAGCATCCGTGAAAATAAGT

TGCAAGGCATCCGGTTACTCGTTCACCGCATACTATATCCACTGGGTTAAACAGGCACCA

GGACAGGGACTTGAATGGATCGGATATATCTCCAATTATAATAGAGCTACAAACTATAAC

CAAAAATTCAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGACATCGCCGTTGAGTGGGAGTCT

AACGGACAGCCGGAGAACAACTACAAGACTACGCCTCCAATGCTGGACTCCGACGGCTCC

TTCTTCCTGTACTCCGAACTGACCGTGGACAAGTCCCGGTGGCAGCAGGGCAACGTGTTC

TCATGCTCCGTAATGCACGAAGCCTTGCACAATCACTACACTCAAAAGTCCCTATCCTTA

TCTCCTGGCAAGTAG

21R83 Heavy chain variable region nucleotide sequence
(13B Version 2)
(SEQ ID NO: 73)
CAGGTTCAGCTAGTTCAGTCTGGAGCGGAAGTTAAGAAACCTGGAGCATCCGTGAAAATA

AGTTGCAAGGCATCCGGTTACTCGTTCACCGCATACTATATCCACTGGGTTAAACAGGCA

-continued

CCAGGACAGGGACTTGAATGGATCGGATATATCTCCAATTATAATAGAGCTACAAACTAT

AACCAAAAATTCAAAGGACGCGTGACTTTCACAACTGACACCTCAACCTCGACAGCATAC

ATGGAATTACGGTCCCTACGGTCTGACGACACTGCCGTTTACTATTGCGCTAGAGATTAT

GATTATGATGTTGGAATGGACTATTGGGGCCAGGGAACACTGGTGACAGTGTCTTCT

21R75 Heavy chain nucleotide sequence with signal sequence
underlined (13B Version 2)
(SEQ ID NO: 74)
<u>ATGAAGCACCTATGGTTCTTTCTATTATTAGTGGCCGCTCCCCGTTGGGTGTTATCGCAG</u>

GTTCAGCTAGTTCAGTCTGGAGCGGAAGTTAAGAAACCTGGAGCATCCGTGAAAATAAGT

TGCAAGGCATCCGGTTACTCGTTCACCGCATACTATATCCACTGGGTTAAACAGGCACCA

GGACAGGGACTTGAATGGATCGGATATATCGCTGGATATAAAGATGCTACAAACTATAAC

CAAAAATTCAAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGACATCGCCGTTGAGTGGGAGTCT

AACGGACAGCCGGAGAACAACTACAAGACTACGCCTCCAATGCTGGACTCCGACGGCTCC

TTCTTCCTGTACTCCGAACTGACCGTGGACAAGTCCCGGTGGCAGCAGGGCAACGTGTTC

TCATGCTCCGTAATGCACGAAGCCTTGCACAATCACTACACTCAAAAGTCCCTATCCTTA

TCTCCTGGCAAGTAG

21M18 Heavy chain nucleotide sequence (version 2)
(SEQ ID NO: 75)
ATGAAGCACCTATGGTTCTTTCTATTATTAGTGGCCGCTCCCCGTTGGGTGTTATCGCAG

GTTCAGCTAGTTCAGTCTGGAGCGGAAGTTAAGAAACCTGGAGCATCCGTGAAAATAAGT

TGCAAGGCATCCGGTTACTCGTTCACCGCATACTATATCCACTGGGTTAAACAGGCACCA

GGACAGGGACTTGAATGGATCGGATATATCTCCTCTTATAATGGAGCTACAAACTATAAC

CAAAAATTCAAAGGACGCGTGACTTTCACAACTGACACCTCAACCTCGACAGCATACATG

GAATTACGGTCCCTACGGTCTGACGACACTGCCGTTTACTATTGCGCTAGAGATTATGAT

TATGATGTTGGAATGGACTATTGGGGCCAGGGAACACTGGTGACAGTGTCTTCTGCATCC

ACTAAGGGACCATCCGTGTTCCCTTTGGCCCCTTGCTCTCGTTCGACCTCTGAATCGACT

GCCGCTCTGGGATGCCTCGTGAAAGATTACTTCCCTGAGCCTGTGACCGTTTCCTGGAAC

TCGGGCGCCCTAACCTCTGGCGTGCACACATTCCCTGCCGTGCTACAGTCTTCTGGCCTA

-continued

```
TACTCTTTATCTTCGGTTGTTACCGTACCTTCTTCTAACTTCGGAACCCAAACTTACACC

TGTAACGTAGACCACAAGCCTTCGAACACCAAGGTGGACAAGACTGTTGAGCGAAAGTGC

TGCGTTGAGTGCCCTCCATGTCCTGCACCTCCTGTGGCTGGCCCTTCTGTGTTCCTGTTC

CCTCCAAACCTAAGGACACTCTAATGATCTCTCGGACTCCTGAGGTGACTTGCGTGGTT

GTGGACGTGTCCCACGAGGACCCTGAGGTGCAGTTCAATTGGTACGTGGACGGAGTCGAG

GTGCACAATGCAAAGACCAAGCCTCGGGAGGAACAGTTCAACTCCACCTTCCGGGTGGTT

TCTGTGTTGACCGTTGTGCACCAAGACTGGCTGAACGGCAAAGAATACAAGTGCAAGGTG

TCCAACAAGGGCCTGCCTGCCCCTATCGAAAAGACCATCAGCAAGACCAAGGGCCAGCCT

CGCGAGCCTCAGGTGTACACCCTGCCTCCCAGCCGGGAAGAAATGACCAAGAACCAGGTG

TCCCTGACCTGTCTGGTGGAGGGCTTCTACCCTTCCGACATCGCCGTTGAGTGGGAGTCT

AACGGACAGCCGGAGAACAACTACAAGACTACGCCTCCAATGCTGGACTCCGACGGCTCC

TTCTTCCTGTACTCCGAACTGACCGTGGACAAGTCCCGGTGGCAGCAGGGCAACGTGTTC

TCATGCTCCGTAATGCACGAAGCCTTGCACAATCACTACACTCAAAAGTCCCTATCCTTA

TCTCCTGGCAAGTAG
```

21M18 Heavy chain variable region (version 2)
(SEQ ID NO: 76)
```
CAGCTAGTTCAGTCTGGAGCGGAAGTTAAGAAACCTGGAGCATCCGTGAAAATAAGTTGC

AAGGCATCCGGTTACTCGTTCACCGCATACTATATCCACTGGGTTAAACAGGCACCAGGA

CAGGGACTTGAATGGATCGGATATATCTCCTCTTATAATGGAGCTACAAACTATAACCAA

AAATTCAAAGGACGCGTGACTTTCACAACTGACACCTCAACCTCGACAGCATACATGGAA

TTACGGTCCCTACGGTCTGACGACACTGCCGTTTACTATTGCGCTAGAGATTATGATTAT

GATGTTGGAATGGACTATTGGGGCCAGGGAACACTGGTGACAGTGTCTTCT
```

Anti-DLL4 heavy chain CDR2 consensus sequence
(SEQ ID NO: 80):
YIX$_1$X$_2$YX$_3$X$_4$ATNYNQKFKG, where X$_1$ is serine or alanine, X$_2$ is
serine, asparagine, or glycine, X$_3$ is asparagine or lysine,
and X$_4$ is lysine, arginine, or aspartic acid

---

What is claimed is:

1. An isolated antibody that specifically binds human vascular endothelial growth factor (VEGF), comprising:
   (a) a heavy chain having the sequence of SEQ ID NO:49 or SEQ ID NO:7; and
   (b) a light chain having the sequence of SEQ ID NO:4 that lacks signal sequence MVLQTQVFISLLLWISGAYG (amino acid residues 1-20 of SEQ ID NO:4).

2. The antibody of claim 1, comprising:
   (a) a heavy chain variable region having at least 90% sequence identity to SEQ ID NO:11; and
   (b) a light chain variable region having at least 90% sequence identity to SEQ ID NO:12.

3. The antibody of claim 1, which is a bispecific antibody.

4. The antibody of claim 1, which is a humanized antibody.

5. The antibody of claim 1, which is an antibody fragment comprising an antigen-binding site.

6. A pharmaceutical composition comprising the antibody of claim 1 and a pharmaceutically acceptable carrier.

7. A method of inhibiting growth of a tumor in a subject, comprising administering to the subject a therapeutically effective amount of the antibody of claim 1.

8. The method of claim 7, wherein the tumor is a colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, or head and neck tumor.

9. A method of treating cancer in a subject, comprising administering to the subject a therapeutically effective amount of the antibody of claim 1.

10. The method of claim 9, wherein the cancer is colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, head and neck cancer, lymphoma, or leukemia.

11. A method of inhibiting growth of a tumor or treating cancer in a subject, comprising administering to the subject a therapeutically effective amount of an isolated antibody that specifically binds human VEGF, comprising:
   (a) a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19); and
   (b) a light chain CDR1 comprising RASESVDNYGISFMK (SEQ ID NO:20), a light chain CDR2 comprising AASNQGS (SEQ ID NO:21), and a light chain CDR3 comprising QQSKEVPWTFGG (SEQ ID NO:22).

12. The method of claim 11, wherein the tumor is a colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, or head and neck tumor.

13. The method of claim 11, wherein the cancer is colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, head and neck cancer, lymphoma, or leukemia.

14. The method of claim 11, wherein the antibody comprises:
   (a) a heavy chain variable region having at least 95% sequence identity to SEQ ID NO:11; and
   (b) a light chain variable region having at least 95% sequence identity to SEQ ID NO:12.

15. The method of claim 11, wherein the antibody comprises:
   (a) a heavy chain variable region comprising the sequence of SEQ ID NO:11; and
   (b) a light chain variable region comprising the sequence of SEQ ID NO:12.

16. A method of inhibiting growth of a tumor or treating cancer in a subject, comprising administering to the subject a therapeutically effective amount of a modified immunoglobulin molecule, comprising:
   (a) a first antigen-binding site that specifically binds human VEGF, and
   (b) a second antigen-binding site that specifically binds human delta-like ligand 4 (DLL4);
   wherein the first antigen-binding site comprises a heavy chain CDR1 comprising NYWMH (SEQ ID NO:17), a heavy chain CDR2 comprising DINPSNGRTSYKEKFKR (SEQ ID NO:18), and a heavy chain CDR3 comprising HYDDKYYPLMDY (SEQ ID NO:19);
   wherein the second antigen-binding site comprises a heavy chain CDR1 comprising TAYYIH (SEQ ID NO:13) or AYYIH (SEQ ID NO:79), a heavy chain CDR2 comprising YIANYNRATNYNQKFKG (SEQ ID NO:14), YISSYNGATNYNQKFKG (SEQ ID NO:15), YIAGYKDATNYNQKFKG (SEQ ID NO:59), or YISNYNRATNYNQKFKG (SEQ ID NO:65), and a heavy chain CDR3 comprising RDYDYDVGMDY (SEQ ID NO:16); and
   wherein both the first and second-antigen binding sites comprise a light chain having at least 95% sequence identity to SEQ ID NO:4 that lacks signal sequence MVLQTQVFISLLLWISGAYG (amino acid residues 1-20 of SEQ ID NO:4).

17. The method of claim 16, wherein the tumor is a colorectal tumor, colon tumor, ovarian tumor, pancreatic tumor, lung tumor, liver tumor, breast tumor, kidney tumor, prostate tumor, gastrointestinal tumor, melanoma, cervical tumor, bladder tumor, glioblastoma, or head and neck tumor.

18. The method of claim 16, wherein the cancer is colorectal cancer, colon cancer, ovarian cancer, pancreatic cancer, lung cancer, liver cancer, breast cancer, kidney cancer, prostate cancer, gastrointestinal cancer, melanoma, cervical cancer, bladder cancer, glioblastoma, head and neck cancer, lymphoma, or leukemia.

19. The method of claim 16, wherein both the first and second antigen-binding sites of the modified immunoglobulin molecule comprise a light chain comprising SEQ ID NO:4 that lacks signal sequence MVLQTQVFISLLLWISGAYG (amino acid residues 1-20 of SEQ ID NO:4).

20. The method of claim 16, wherein modified immunoglobulin molecule comprises a heavy chain of SEQ ID NO:7, a heavy chain of SEQ ID NO:62, and two light chains of SEQ ID NO:4 that lacks signal sequence MVLQTQVFISLLLWISGAYG (amino acid residues 1-20 of SEQ ID NO:4).

* * * * *